United States Patent
Parham et al.

(10) Patent No.: US 12,035,625 B2
(45) Date of Patent: Jul. 9, 2024

(54) MATERIALS FOR ORGANIC ELECTROLUMINESCENT DEVICES

(71) Applicant: Merck Patent GmbH, Darmstadt (DE)

(72) Inventors: Amir Parham, Frankfurt am Main (DE); Christian Eickhoff, Mannheim (DE); Rouven Linge, Darmstadt (DE); Jens Kaiser, Frankfurt am Main (DE); Amel Mekic, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 371 days.

(21) Appl. No.: 17/294,571

(22) PCT Filed: Nov. 11, 2019

(86) PCT No.: PCT/EP2019/080844
§ 371 (c)(1),
(2) Date: May 17, 2021

(87) PCT Pub. No.: WO2020/099307
PCT Pub. Date: May 22, 2020

(65) Prior Publication Data
US 2022/0006030 A1   Jan. 6, 2022

(30) Foreign Application Priority Data
Nov. 15, 2018 (EP) .................................... 18206493

(51) Int. Cl.
| | | |
|---|---|---|
| *H10K 85/60* | (2023.01) | |
| *C07D 487/14* | (2006.01) | |
| *C07D 491/153* | (2006.01) | |
| *C07D 495/04* | (2006.01) | |
| *C07D 495/14* | (2006.01) | |
| *C07D 495/22* | (2006.01) | |
| *C09K 11/06* | (2006.01) | |
| *H10K 50/11* | (2023.01) | |
| *H10K 50/15* | (2023.01) | |
| *H10K 50/16* | (2023.01) | |
| *H10K 50/18* | (2023.01) | |
| *H10K 101/10* | (2023.01) | |

(52) U.S. Cl.
CPC ....... *H10K 85/6576* (2023.02); *C07D 487/14* (2013.01); *C07D 491/153* (2013.01); *C07D 495/04* (2013.01); *C07D 495/14* (2013.01); *C07D 495/22* (2013.01); *C09K 11/06* (2013.01); *H10K 85/615* (2023.02); *H10K 85/622* (2023.02); *H10K 85/636* (2023.02); *H10K 85/654* (2023.02); *H10K 85/657* (2023.02); *H10K 85/6572* (2023.02); *H10K 85/6574* (2023.02); *C09K 2211/1018* (2013.01); *H10K 50/11* (2023.02); *H10K 50/15* (2023.02); *H10K 50/16* (2023.02); *H10K 50/18* (2023.02); *H10K 2101/10* (2023.02)

(58) Field of Classification Search
CPC .................................................. H10K 85/6576
See application file for complete search history.

(56) References Cited

U.S. PATENT DOCUMENTS

| | | |
|---|---|---|
| 2002/0155215 A1 | 10/2002 | Miyashita et al. |
| 2011/0248247 A1 | 10/2011 | Matsumoto et al. |
| 2012/0223633 A1 | 9/2012 | Yoshinaga et al. |
| 2018/0205022 A1 | 7/2018 | Dyatkin et al. |

FOREIGN PATENT DOCUMENTS

| | | |
|---|---|---|
| CN | 1212114 A | 3/1999 |
| CN | 103842339 A | 6/2014 |
| KR | 10-2018-0097955 A | 9/2018 |
| WO | 98/24271 A1 | 6/1998 |
| WO | 2005/053051 A1 | 6/2005 |
| WO | 2009/030981 A2 | 3/2009 |
| WO | 2010/151006 A1 | 12/2010 |
| WO | 2015/192939 A1 | 12/2015 |
| WO | 2017/016632 A1 | 2/2017 |

OTHER PUBLICATIONS

International Preliminary Report on Patentability received for PCT Patent Application No. PCT/EP2019/080844, dated May 27, 2021, 11 pages (6 pages of English Translation and 5 pages of Original Document).
International Search Report and Written Opinion received for PCT Patent Application No. PCT/EP2019/080844, dated Jan. 15, 2020, 15 pages (6 pages of English Translation and 9 pages of Original Document).
Pommerehne et al., "Efficient two layer leds on a polymer blend basis," Advance Materials, vol. 7, Issue 6, Jun. 1995, pp. 551-554.
Yumiao et al., "The Applications of Carbazole and Carbazole-Related Compounds in Blue Emitting Organic Light-Emitting Diodes," Progress in Chemistry, vol. 27, No. 10, Dec. 31, 2015, pp. 1384-1399.

*Primary Examiner* — William D Young
(74) *Attorney, Agent, or Firm* — Faegre Drinker Biddle & Reath LLP

(57) ABSTRACT

The invention relates to compounds of formula (1) which are suitable for use in electronic devices, and to electronic devices, in particular organic electroluminescent devices, containing said compounds. X is, identically or differently in each occurrence, CR or N, or two adjacent X stand for a group of the following formula (2), wherein the dashed bonds mark the bonding of said group in formula (1), with the stipulation that the compound of formula (1) contains one or two groups of formula (2); $X^1$ is, identically or differently in each occurrence, CR or N; Y is, identically or differently in each occurrence, CR or N; $Z^1$, $Z^2$, $Z^3$ are, identically or differently in each occurrence, O, S, N—Ar or $CR_2$.

15 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2019/080844, filed Nov. 11, 2019, which claims benefit of European Application No. 18206493.1, filed Nov. 15, 2018, both of which are incorporated herein by reference in their entirety.

The present invention relates to materials for use in electronic devices, and to electronic devices, in particular organic electroluminescent devices, containing these materials.

The emitting materials employed in organic electroluminescent devices (OLEDs) are frequently phosphorescent organometallic complexes. In general, there is still a need for improvement, for example with respect to efficiency, operating voltage and lifetime, in OLEDs, in particular also in OLEDs which exhibit triplet emission (phosphorescence). The properties of phosphorescent OLEDs are not determined only by the triplet emitters employed. In particular, the other materials used, such as matrix materials, are also of particular importance here. Improvements to these materials can therefore also lead to improvements in the OLED properties.

The object of the present invention is the provision of compounds which are suitable for use in an OLED, in particular as matrix material for phosphorescent emitters, but also as electron-transport materials, hole-blocking materials, hole-transport materials, electron-blocking materials or as fluorescent emitters. A further object of the present invention is to provide further organic semiconductors for organic electroluminescent devices in order thus to provide the person skilled in the art with a greater possible choice of materials for the production of OLEDs.

Surprisingly, it has been found that certain compounds, described in greater detail below, achieve this object and are highly suitable for use in OLEDs. The OLEDs here have, in particular, a long lifetime, high efficiency and a low operating voltage. The present invention therefore relates to these compounds and to electronic devices, in particular organic electroluminescent devices, which contain compounds of this type.

The present invention relates to a compound of the formula (1),

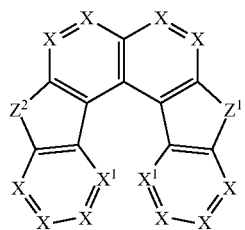

formula (1)

where the following applies to the symbols used:

X is on each occurrence, identically or differently, CR or N or two adjacent X stand for a group of the following formula (2),

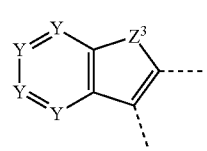

formula (2)

where the dashed bonds denote the linking of this group in the formula (1), with the proviso that the compound of the formula (1) contains one or two groups of the formula (2);

$X^1$ is on each occurrence, identically or differently, CR or N;

Y is on each occurrence, identically or differently, CR or N;

$Z^1$, $Z^2$, $Z^3$ are on each occurrence, identically or differently, O, S, N—Ar or $CR_2$;

Ar is on each occurrence, identically or differently, an aromatic or heteroaromatic ring system having 5 to 40 aromatic ring atoms, which may be substituted by one or more radicals R;

R is on each occurrence, identically or differently, H, D, F, Cl, Br, I, $N(Ar')_2$, $N(R^1)_2$, OAr', SAr', CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 C atoms or an alkenyl or alkynyl group having 2 to 20 C atoms or a branched or cyclic alkyl group having 3 to 20 C atoms, where the alkyl, alkenyl or alkynyl group may in each case be substituted by one or more radicals $R^1$, where one or more non-adjacent $CH_2$ groups may be replaced by $Si(R^1)_2$, C=O, $NR^1$, O, S or $CONR^1$, or an aromatic or heteroaromatic ring system having 5 to 60 aromatic ring atoms, preferably having 5 to 40 aromatic ring atoms, which may in each case be substituted by one or more radicals $R^1$; two radicals R may also form an aliphatic, heteroaliphatic, aromatic or heteroaromatic ring system with one another;

Ar' is on each occurrence, identically or differently, an aromatic or heteroaromatic ring system having 5 to 40 aromatic ring atoms, which may be substituted by one or more radicals $R^1$;

$R^1$ is on each occurrence, identically or differently, H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 C atoms or an alkenyl or alkynyl group having 2 to 20 C atoms or a branched or cyclic alkyl group having 3 to 20 C atoms, where the alkyl, alkenyl or alkynyl group may in each case be substituted by one or more radicals $R^2$, where one or more non-adjacent $CH_2$ groups may be replaced by $Si(R^2)_2$, C=O, $NR^2$, O, S or $CONR^2$ and where one or more H atoms in the alkyl, alkenyl or alkynyl group may be replaced by D, F, C, Br, I or CN, or an aromatic or heteroaromatic ring system having 5 to 40 aromatic ring atoms, which may in each case be substituted by one or more radicals $R^2$ two or more radicals $R^1$ may form an aliphatic ring system with one another;

$R^2$ is on each occurrence, identically or differently, H, D, F, CN or an aliphatic, aromatic or heteroaromatic organic radical, in particular a hydrocarbon radical, having 1 to 20 C atoms, in which, in addition, one or more H atoms may be replaced by F.

An aryl group in the sense of this invention contains 6 to 40 C atoms, a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (anellated) aryl or heteroaryl group, for example naphthalene, anthracene, phenanthrene, quinoline, isoquinoline, etc. By contrast, aromatic groups that are linked to one another by a single bond, such as, for example, biphenyl, are not referred to as an aryl or heteroaryl group, but instead as an aromatic ring system.

An aromatic ring system in the sense of this invention contains 6 to 60 C atoms, preferably 6 to 40 C atoms, in the ring system. A heteroaromatic ring system in the sense of this invention contains 2 to 60 C atoms, preferably 2 to 40 C atoms, and at least one heteroatom in the ring system, with the proviso that the sum of C atoms and heteroatoms is at least 5. The heteroatoms are preferably selected from N, O and/or S. In the sense of this invention, an aromatic or heteroaromatic ring system is intended to be taken to mean a system which does not necessarily contain only aryl or heteroaryl groups, but instead in which, in addition, a plurality of aryl or heteroaryl groups may be connected by a non-aromatic unit, such as, for example, a C, N or O atom. This is likewise intended to be taken to mean systems in which two or more aryl or heteroaryl groups are linked directly to one another, such as, for example, biphenyl, terphenyl, bipyridine or phenylpyridine. Thus, for example, systems such as fluorene, 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are connected, for example, by a short alkyl group. Preferred aromatic or heteroaromatic ring systems are simple aryl or heteroaryl groups as well as groups in which two or more aryl or heteroaryl groups are linked directly to one another, for example biphenyl or bipyridine, as well as fluorene or spirobifluorene.

For the purposes of the present invention, an aliphatic hydrocarbon radical or an alkyl group or an alkenyl or alkynyl group, which may contain 1 to 40 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group $OR^1$ having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cyclo-heptyloxy, n-octyloxy, cyclooctyloxy, 2-ethylhexyloxy, pentafluoroethoxy and 2,2,2-trifluoroethoxy. A thioalkyl group $SR^1$ having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynyl-thio, pentynylthio, hexynylthio, heptynylthio or octynylthio. In general, alkyl, alkoxy or thioalkyl groups in accordance with the present invention can be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, C or CN, particularly preferably F or CN.

An aromatic or heteroaromatic ring system having 5-60 aromatic ring atoms, which may also in each case be substituted by the above-mentioned radicals $R^2$ or a hydrocarbon radical and which can be linked via any desired positions on the aromatic or heteroaromatic ring system, is taken to mean, in particular, groups derived from benzene, naphthalene, anthracene, benzanthracene, phenanthrene, pyrene, chry-sene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimida-zole, phenanthrimidazole, pyridimidazole, pyrazinimidazole, quinoxalinimidazole, oxazole, benzoxazole, naphthoxazole, anthroxazole, phen-anthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraaza-perylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combination of these systems.

For the purposes of the present description, the formulation that two or more radicals may form an aliphatic ring with one another is intended to be taken to mean, inter alia, that the two radicals are linked to one another by a chemical bond with formal elimination of two hydrogen atoms. This is illustrated by the following scheme:

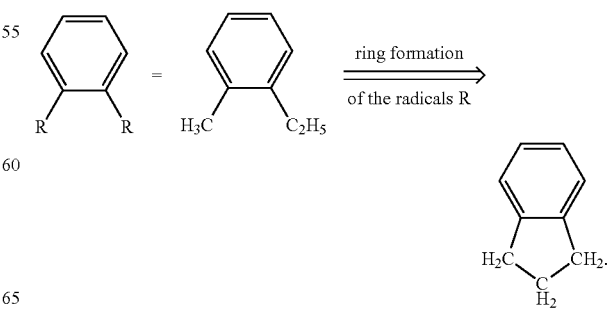

Furthermore, however, the above-mentioned formulation is also intended to be taken to mean that, in the case where one of the two radicals represents hydrogen, the second radical is bonded at the position at which the hydrogen was bonded, with formation of a ring. This is intended to be illustrated by the following scheme:

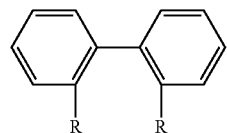

=

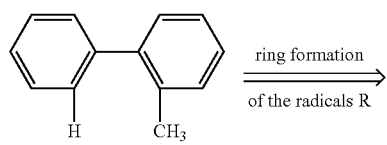

ring formation of the radicals R

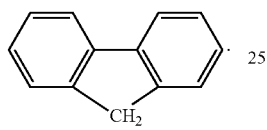

Depending on the position of the bonding of the group of the formula (2), different isomers arise, which are represented below by the formulae (3) to (8),

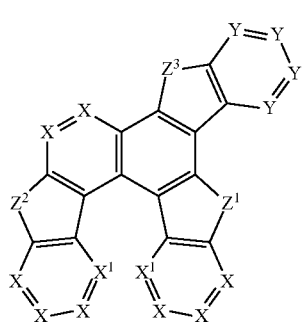

formula (3)

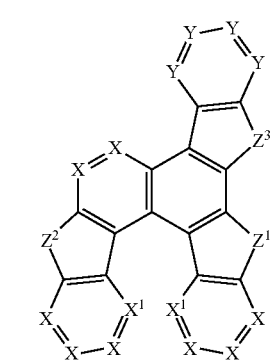

formula (4)

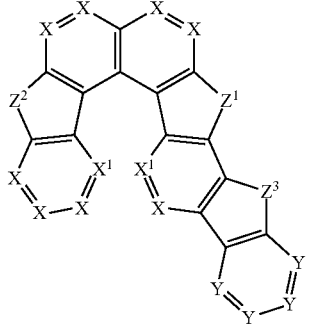

formula (5)

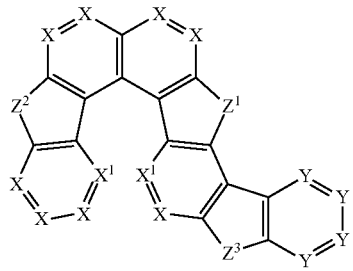

formula (6)

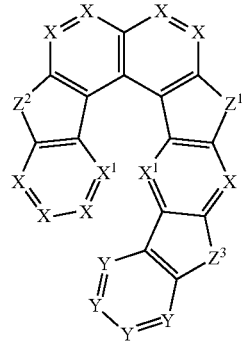

formula (7)

formula (8)

where the symbols used have the meanings given above.

In a preferred embodiment of the invention, the compound of the formula (1) contains precisely one group of the formula (2).

In a preferred embodiment of the invention, the symbol $X^1$ in formula (1) and formulae (3) to (8) stands for CH.

In a preferred embodiment of the invention, a maximum of one symbol Y in the group of the formula (2) stands for N, and the other symbols Y stand, identically or differently, for CR. Particularly preferably, all symbols Y in formula (2) stand for CR. The radicals R on Y preferably do not form an aromatic or heteroaromatic ring system with one another. The group of the formula (2) is then a group of the following formula (2a),

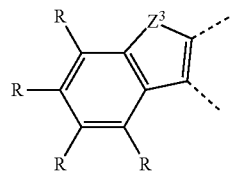

formula (2a)

where the symbols used have the meanings given above, and the radicals R preferably do not form an aromatic or heteroaromatic ring system with one another.

In still a further preferred embodiment of the invention, a maximum of two symbols X stand for N, particularly preferably a maximum of one symbol X. Very particularly preferably, the symbols X that do not stand for a group of the formula (2) stand, identically or differently on each occurrence, for CR. In a particularly preferred embodiment of the invention, the symbols Y stand, identically or differently on each occurrence, for CR, so that this is preferably a group of the formula (2a), and the symbols X that do not stand for a group of the formula (2) stand, identically or differently on each occurrence, for CR, and the symbols $X^1$ stand for CH.

Preference is therefore given to the structures of the following formulae (3a) to (8a),

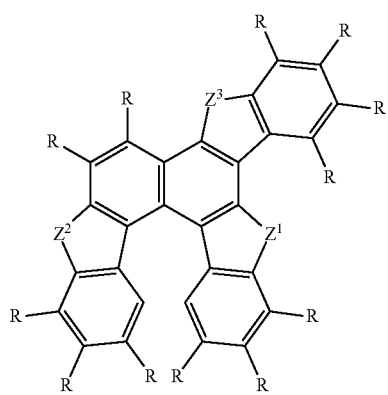

formula (3a)

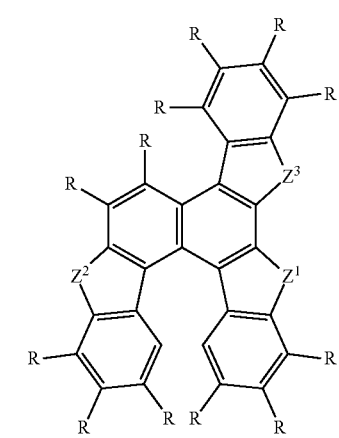

formula (4a)

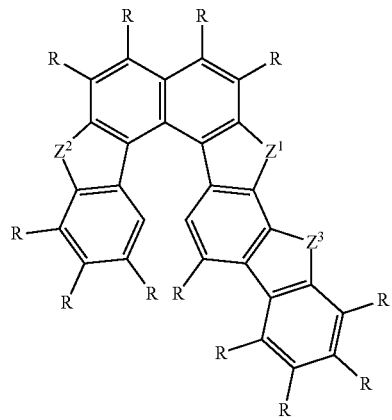

formula (5a)

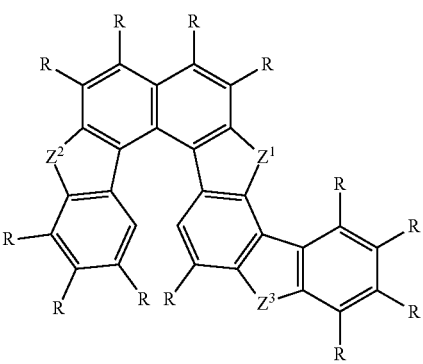

formula (6a)

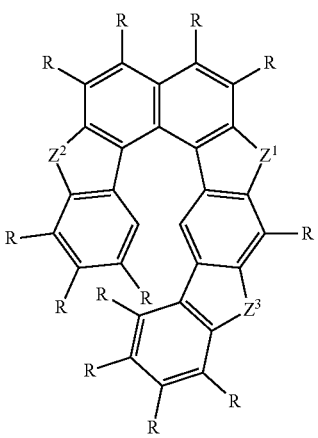

formula (7a)

formula (8a)

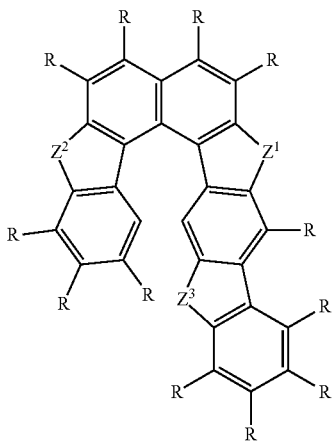

where the symbols used have the meanings given above.

Particular preference is given to the structures of the following formulae (3b) to (8b), formula (3b)

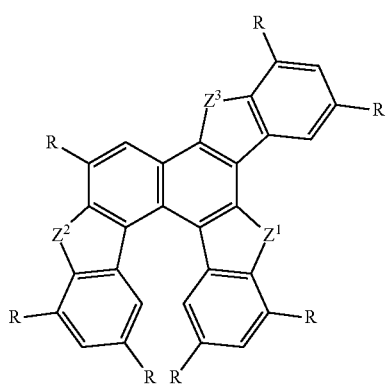

formula (4b)

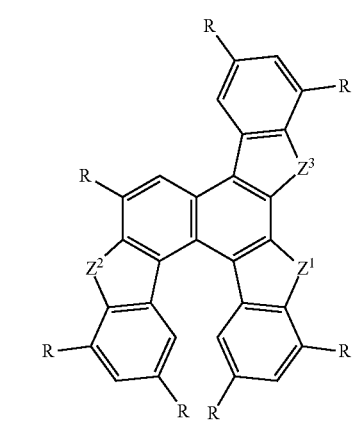

formula (5b)

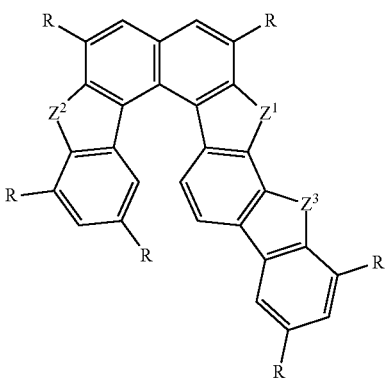

formula (6b)

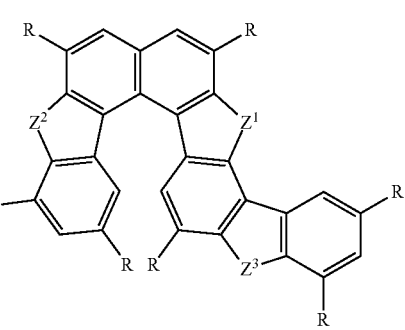

formula (7b)

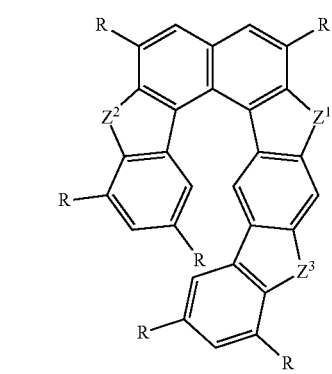

formula (8b)

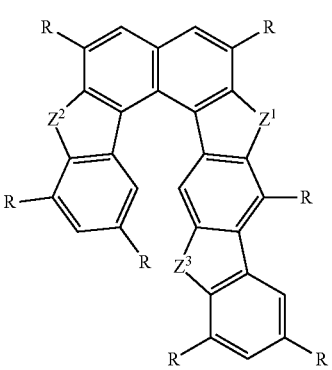

where the symbols used have the meanings given above.

In a preferred embodiment of the invention, in total a maximum of three radicals R, particularly preferably a maximum of two radicals R and very particularly preferably a maximum of one radical R in the compound of the formula (1) or the preferred structures shown above and below stand for a group other than hydrogen.

Very particular preference is given to the structures of the following formulae (3c) to (8c), formula (3c)
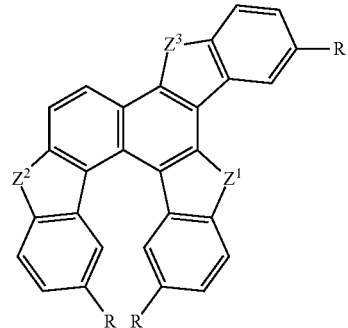

formula (4c)
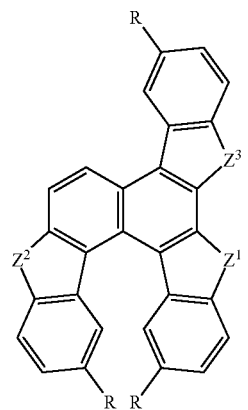

formula (5c)
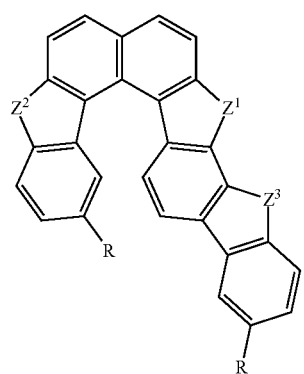

formula (6c)
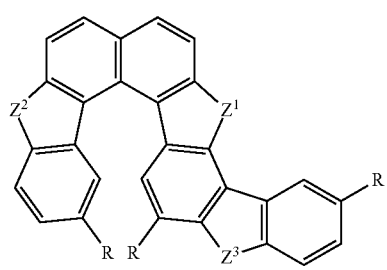

formula (7c)
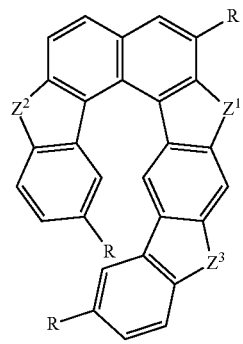

formula (8c)
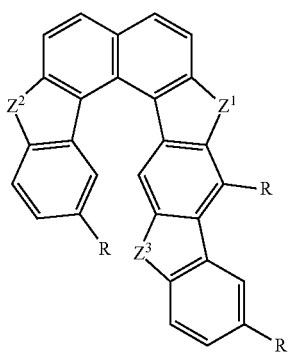

where the symbols used have the meanings given above.

Particular preference is given to the structures of the formulae (3b) and (4b) or (3c) and (4c).

$Z^1$, $Z^2$ and $Z^3$ are selected, independently of one another, from the group consisting of O, S, N—Ar and $CR_2$, preferably from the group consisting of O, S and N—Ar. Suitable combinations $Z^1$, $Z^2$ and $Z^3$ here are the combinations shown in the following table, where each of these combinations can be employed for each of the structures of the formulae (1), (3), (4), (5), (6), (7), (8), (3a), (4a), (5a), (6a), (7a), (8a), (3b), (4b), (5b), (6b), (7b), (8b), (3c), (4c), (5c), (6c), (7c) and (8c):

| $Z^1$ | $Z^2$ | $Z^3$ |
|---|---|---|
| O | O | O |
| O | O | S |
| O | O | N—Ar |
| O | O | $CR_2$ |
| O | S | O |
| O | S | S |
| O | S | N—Ar |
| O | S | $CR_2$ |
| O | N—Ar | O |
| O | N—Ar | S |
| O | N—Ar | N—Ar |
| O | N—Ar | $CR_2$ |
| O | $CR_2$ | O |
| O | $CR_2$ | S |
| O | $CR_2$ | N—Ar |
| O | $CR_2$ | $CR_2$ |
| S | O | O |
| S | O | S |
| S | O | N—Ar |
| S | O | $CR_2$ |
| S | S | O |
| S | S | S |
| S | S | N—Ar |
| S | S | $CR_2$ |
| S | N—Ar | O |

| $Z^1$ | $Z^2$ | $Z^3$ |
|---|---|---|
| S | N—Ar | S |
| S | N—Ar | N—Ar |
| S | N—Ar | $CR_2$ |
| S | $CR_2$ | O |
| S | $CR_2$ | S |
| S | $CR_2$ | N—Ar |
| S | $CR_2$ | $CR_2$ |
| N—Ar | O | O |
| N—Ar | O | S |
| N—Ar | O | N—Ar |
| N—Ar | O | $CR_2$ |
| N—Ar | S | O |
| N—Ar | S | S |
| N—Ar | S | N—Ar |
| N—Ar | S | $CR_2$ |
| N—Ar | N—Ar | O |
| N—Ar | N—Ar | S |
| N—Ar | N—Ar | N—Ar |
| N—Ar | N—Ar | $CR_2$ |
| N—Ar | $CR_2$ | O |
| N—Ar | $CR_2$ | S |
| N—Ar | $CR_2$ | N—Ar |
| N—Ar | $CR_2$ | $CR_2$ |
| $CR_2$ | O | O |
| $CR_2$ | O | S |
| $CR_2$ | O | N—Ar |
| $CR_2$ | O | $CR_2$ |
| $CR_2$ | S | O |
| $CR_2$ | S | S |
| $CR_2$ | S | N—Ar |
| $CR_2$ | S | $CR_2$ |
| $CR_2$ | N—Ar | O |
| $CR_2$ | N—Ar | S |
| $CR_2$ | N—Ar | N—Ar |
| $CR_2$ | N—Ar | $CR_2$ |
| $CR_2$ | $CR_2$ | O |
| $CR_2$ | $CR_2$ | S |
| $CR_2$ | $CR_2$ | N—Ar |
| $CR_2$ | $CR_2$ | $CR_2$ |

In an embodiment of the invention, $Z^1$ and $Z^2$ are selected identically. It is preferred if $Z^1$ and $Z^2$=O or $Z^1$ and $Z^2$=S and the same time $Z^3$=NAr. In a further embodiment of the invention, two of the symbols $Z^1$, $Z^2$ and $Z^3$ stand for NAr and the third of the symbols stands for S.

If the compound according to the invention is employed as matrix material for phosphorescent emitters, it is preferred if at least one of the symbols $Z^1$, $Z^2$ and/or $Z^3$ stands for N—Ar. In this case, it is particularly preferred if $Z^3$ stands for N—Ar. Particular preference is therefore given to the compounds of the following formulae (3d) to (8d),

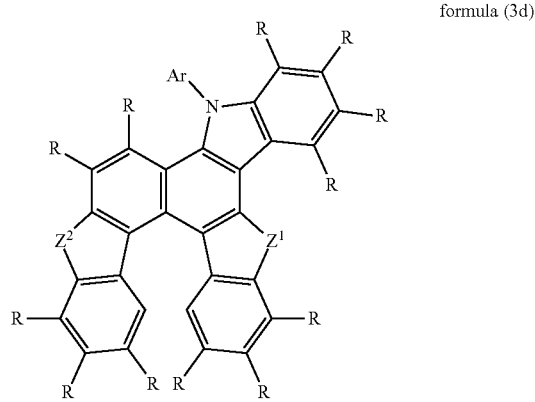

formula (3d)

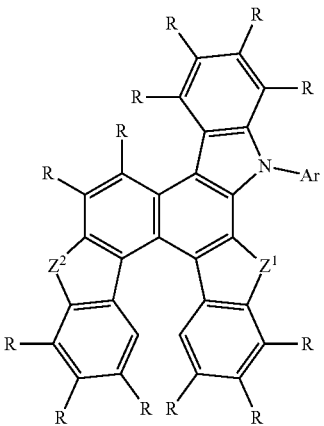

formula (4d)

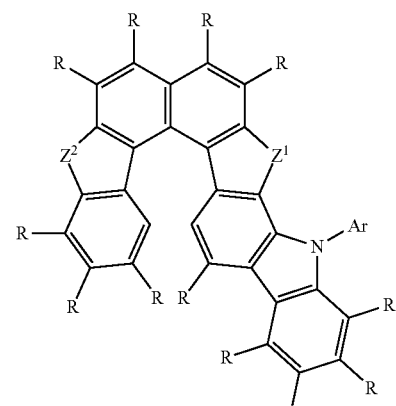

formula (5d)

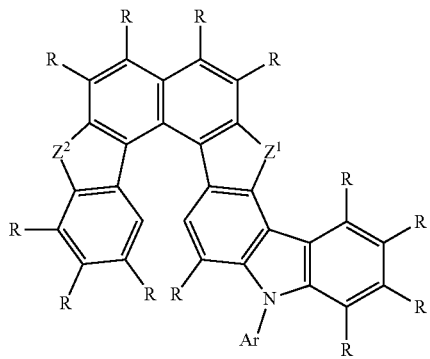

formula (6d)

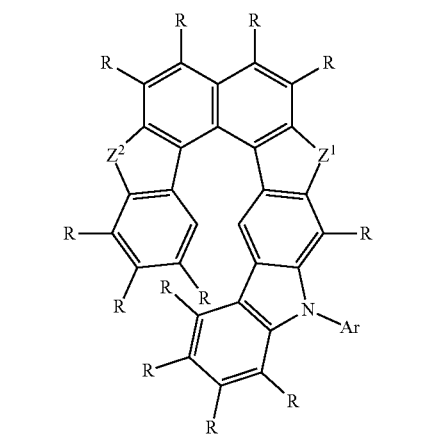

formula (7d)

formula (8d)

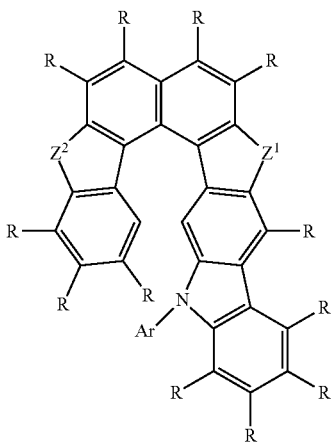

where the symbols used have the meanings given above.

Very particular preference is given to the structures of the following formulae (3e) to (8e), formula (3e)

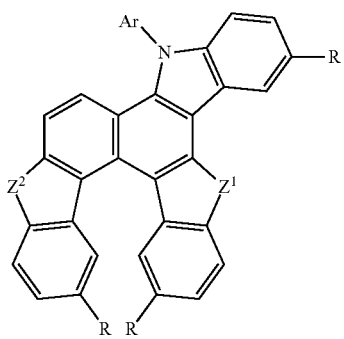

formula (4e)

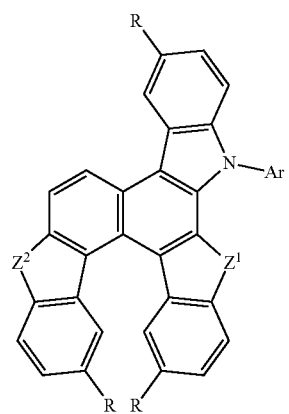

formula (5e)

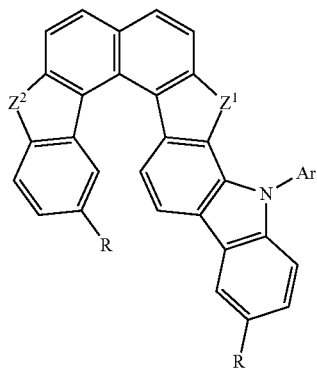

formula (6e)

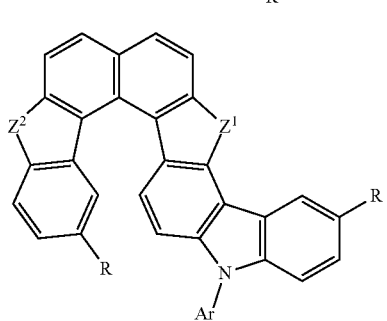

formula (7e)

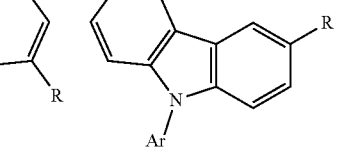

formula (8e)

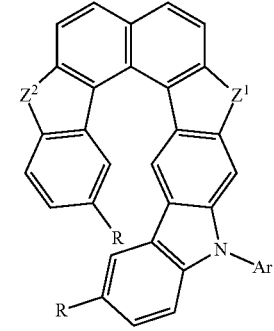

where the symbols used have the meanings given above.

Preferred substituents Ar, R, Ar', $R^1$ and $R^2$ are described below. In a particularly preferred embodiment of the invention, the preferences given below for Ar, R, Ar', $R^1$ and $R^2$ occur simultaneously and apply to the structures of the formula (1) and to all preferred embodiments mentioned above.

In a preferred embodiment of the invention, Ar is on each occurrence, identically or differently, an aromatic or heteroaromatic ring system having 6 to 30 aromatic ring atoms, which may be substituted by one or more radicals R, where the radicals R are preferably non-aromatic radicals. Ar is particularly preferably on each occurrence, identically or differently, an aromatic or heteroaromatic ring system having 6 to 24 aromatic ring atoms, in particular having 6 to 13 aromatic ring atoms, which may be substituted by one or more, preferably non-aromatic radicals R. If Ar stands for a heteroaryl group, in particular for triazine, pyrimidine, quinazoline or carbazole, aromatic or heteroaromatic substituents R may also be preferred on this heteroaryl group. It may furthermore be preferred if Ar is substituted by a group $N(Ar')_2$, so that the substituent Ar overall represents a triarylamine or triheteroarylamine group.

Suitable aromatic or heteroaromatic ring system Ar are selected on each occurrence, identically or differently, from phenyl, biphenyl, in particular ortho-, meta- or para-biphenyl, terphenyl, in particular ortho-, meta-, para- or branched terphenyl, quaterphenyl, in particular ortho-, meta-, para- or branched quaterphenyl, fluorene, which can be linked via the 1-, 2-, 3- or 4-position, spirobifluorene, which can be linked via the 1-, 2-, 3- or 4-position, naphthalene, which can be linked via the 1- or 2-position, indole, benzofuran, benzothiophene, carbazole, which can be linked via the 1-, 2-, 3- or 4-position, dibenzofuran, which can be linked via the 1-, 2-, 3- or 4-position, dibenzothiophene, which can be linked via the 1-, 2-, 3- or 4-position, indenocarbazole, indolocarbazole, pyridine, pyrimidine, pyrazine, pyridazine, triazine, quinoline, quinazoline, benzimidazole, phenanthrene, triphenylene or a combination of two or three of these groups, which may in each case be substituted by one or more radicals R, preferably non-aromatic radicals R. If Ar stands for a heteroaryl group, in particular for triazine, pyrimidine or quinazoline, aromatic or heteroaromatic radicals R may also be preferred on this heteroaryl group.

Ar here is preferably selected on each occurrence, identically or differently, from the groups of the following formulae Ar-1 to Ar-81,

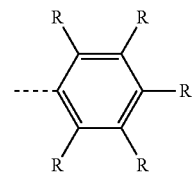
Ar-1

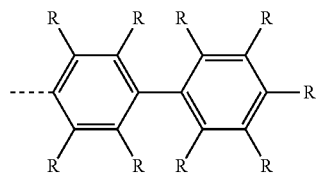
Ar-2

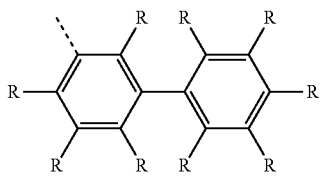
Ar-3

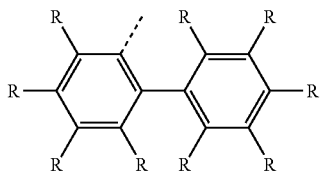
Ar-4

-continued

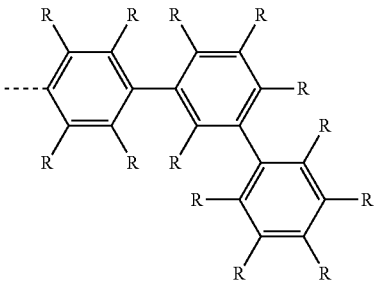
Ar-5

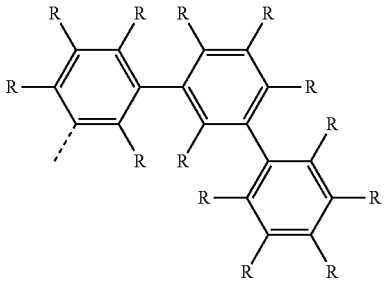
Ar-6

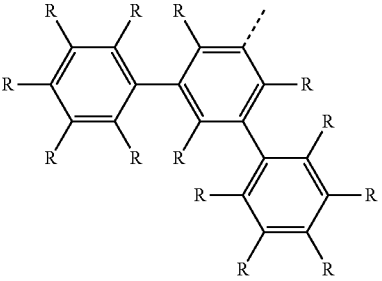
Ar-7

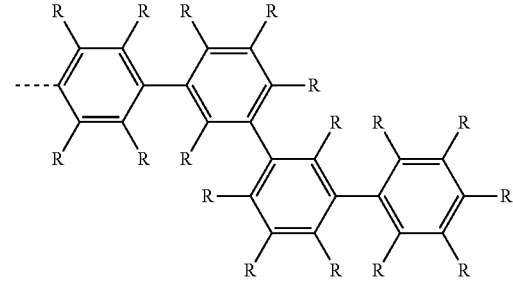
Ar-8

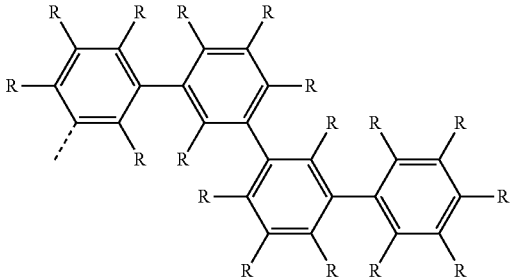
Ar-9

Ar-10
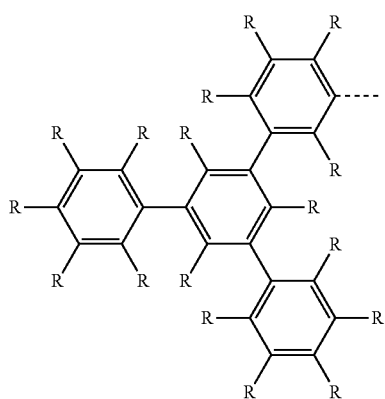
Ar-11
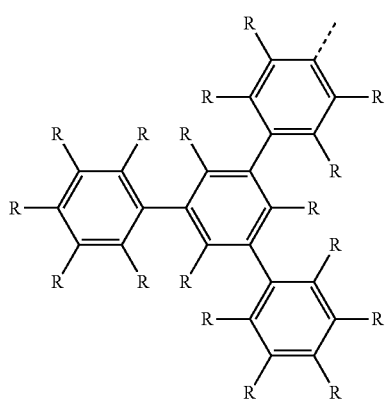
Ar-12
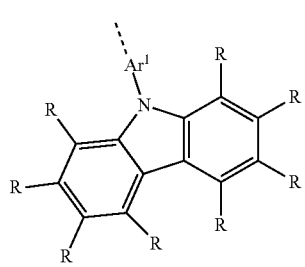
Ar-13
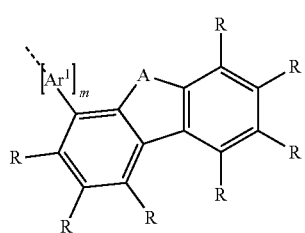
Ar-14
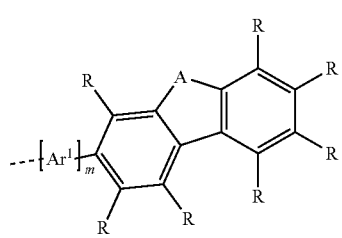
Ar-15
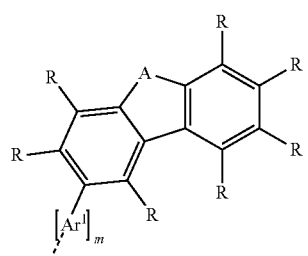
Ar-16
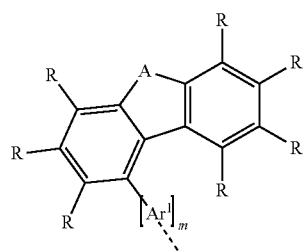
Ar-17
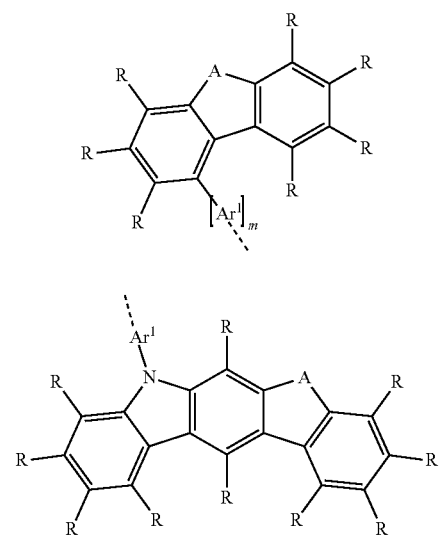
Ar-18
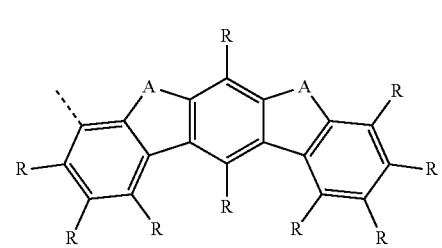
Ar-19
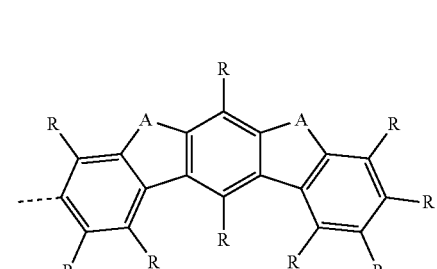
Ar-20
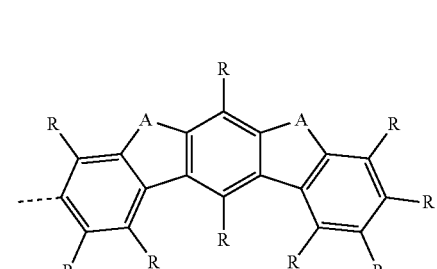

Ar-21 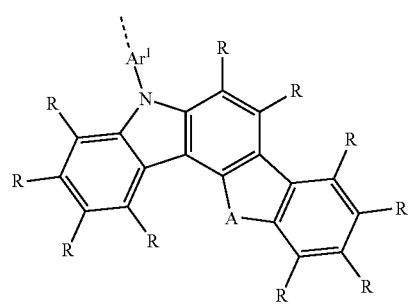
Ar-22 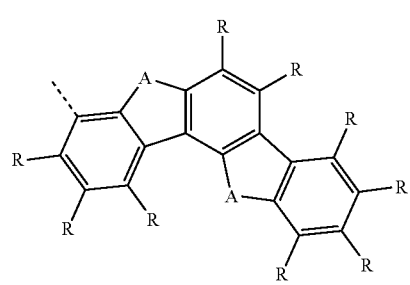
Ar-23 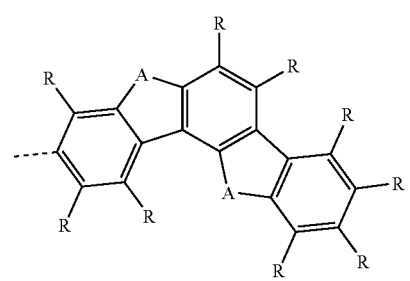
Ar-24 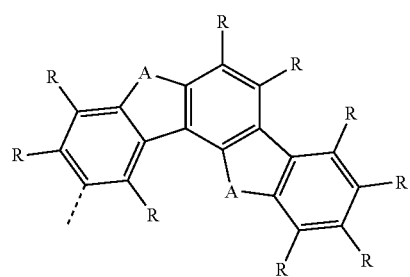
Ar-25 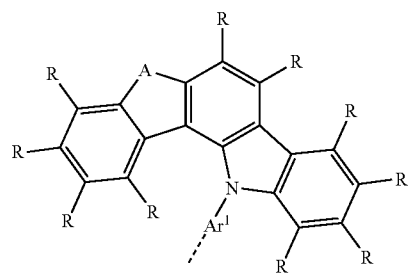
Ar-26 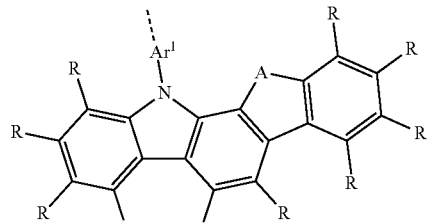
Ar-27 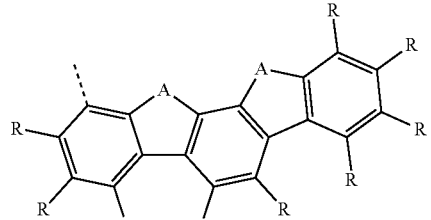
Ar-28 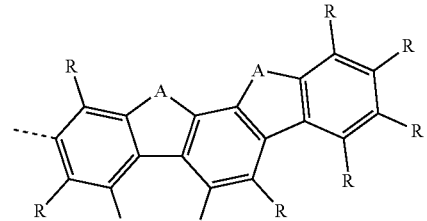
Ar-29 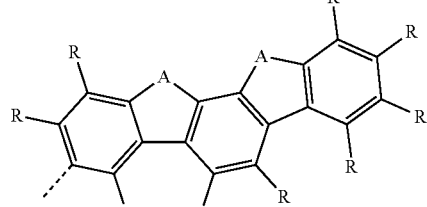
Ar-30 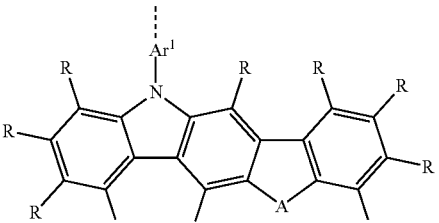
Ar-31 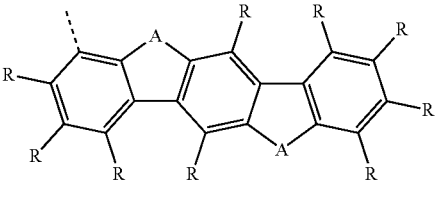
Ar-32 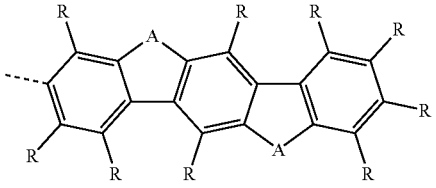

Ar-33
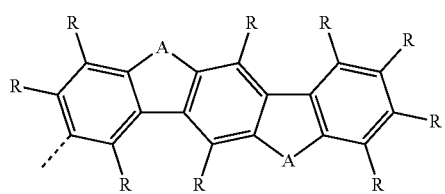
Ar-34
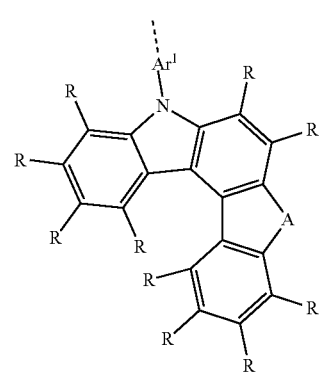
Ar-35
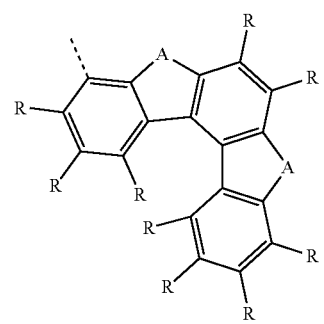
Ar-36
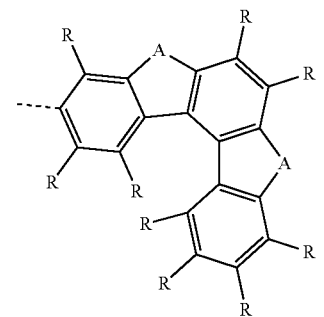
Ar-37
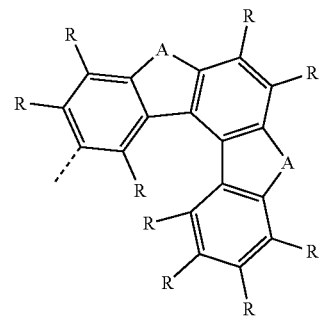
Ar-38
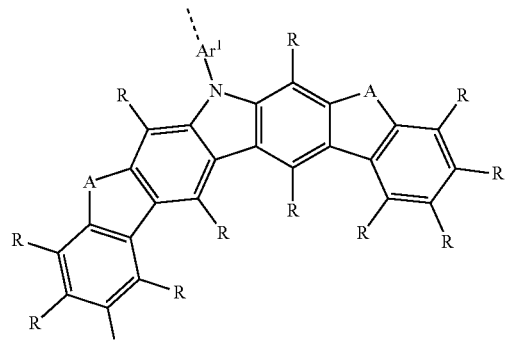
Ar-39
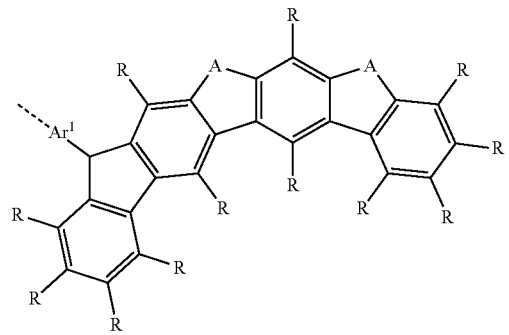
Ar-40
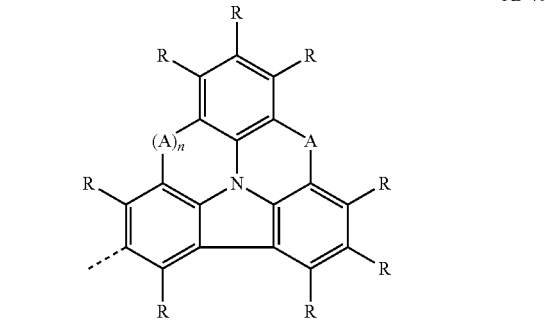
Ar-41
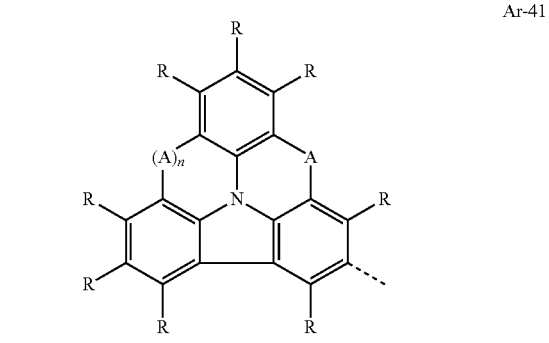

-continued
Ar-42
Ar-43
Ar-44
Ar-45
Ar-46
-continued
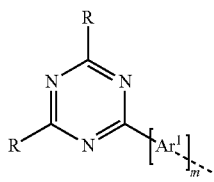
Ar-47
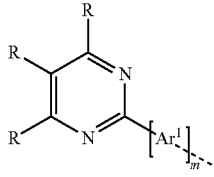
Ar-48
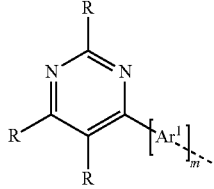
Ar-49
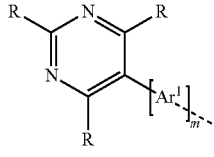
Ar-50
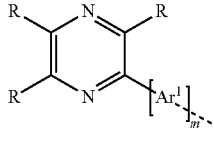
Ar-51
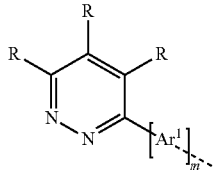
Ar-52
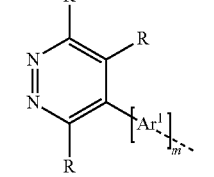
Ar-53
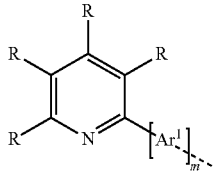
Ar-54

-continued
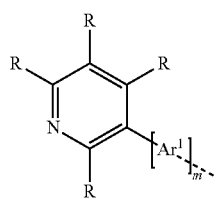
Ar-55
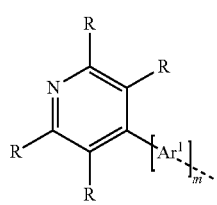
Ar-56
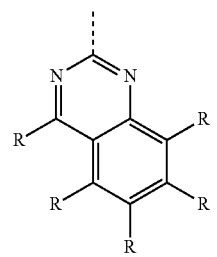
Ar-57
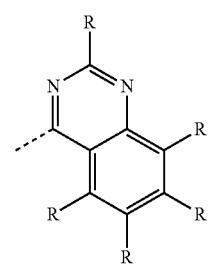
Ar-58
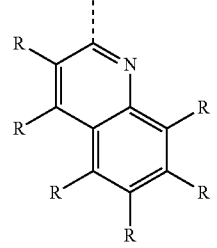
Ar-59
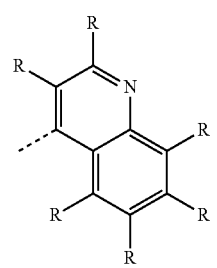
Ar-60
-continued
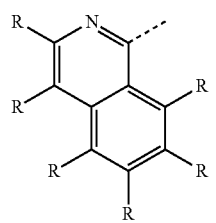
Ar-61
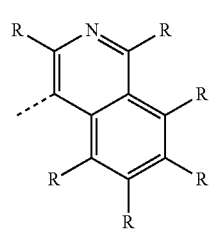
Ar-62
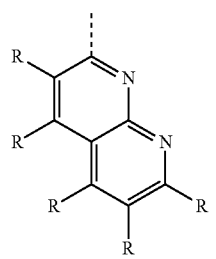
Ar-63
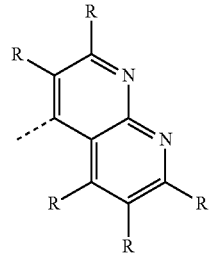
Ar-64
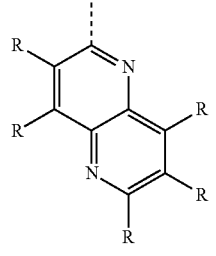
Ar-65
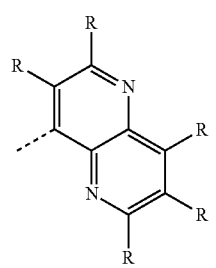
Ar-66

Ar-67
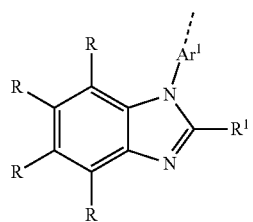
Ar-68
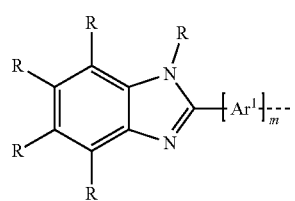
Ar-69
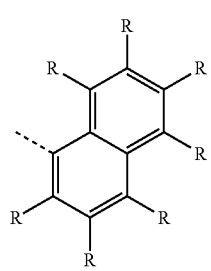
Ar-70
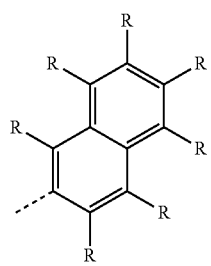
Ar-71
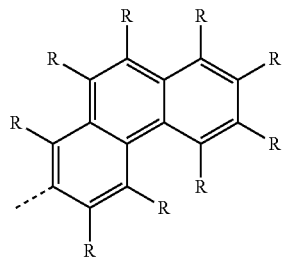
Ar-72
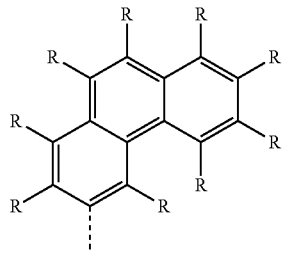
Ar-73
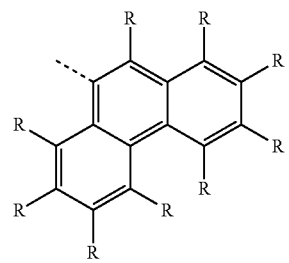
Ar-74
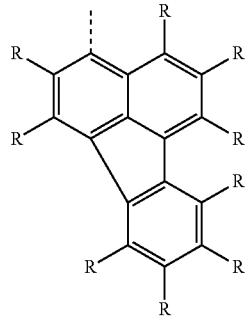
Ar-75
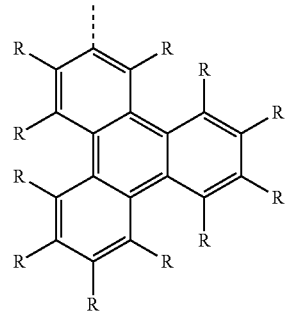
Ar-76
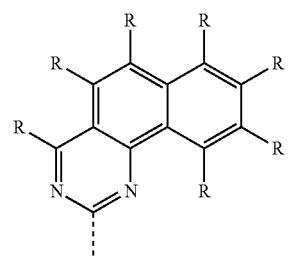
Ar-77
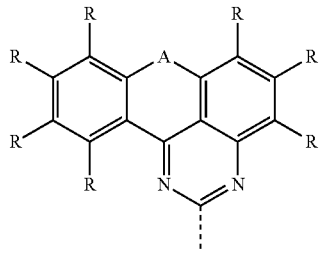

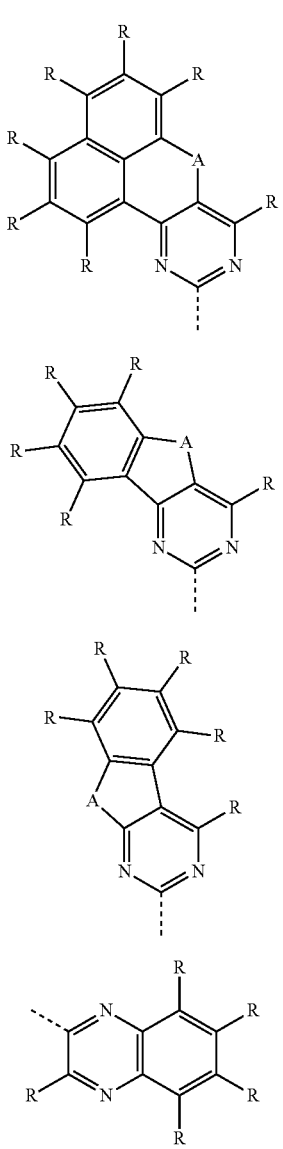

where R is the meanings given above, the dashed bond represents the bond to the nitrogen atom and furthermore:

Ar¹ is on each occurrence, identically or differently, a divalent aromatic or heteroaromatic ring system having 6 to 18 aromatic ring atoms, which may in each case be substituted by one or more radicals R;

A is on each occurrence, identically or differently, $CR_2$, NR, O or S;

n is 0 or 1, where n=0 means that no group A is bonded at this position and instead radicals R are bonded to the corresponding carbon atoms;

m is 0 or 1, where m=0 means that the group Ar¹ is not present and that's the corresponding aromatic or heteroaromatic group is bonded directly to the nitrogen atom.

In a preferred embodiment of the invention, R is selected on each occurrence, identically or differently, from the group consisting of H, D, F, $N(Ar')_2$, CN, $OR^1$, a straight-chain alkyl group having 1 to 10 C atoms or an alkenyl group having 2 to 10 C atoms or a branched or cyclic alkyl group having 3 to 10 C atoms, where the alkyl or alkenyl group may in each case be substituted by one or more radicals $R^1$, but is preferably unsubstituted, and where one or more non-adjacent $CH_2$ groups may be replaced by O, or an aromatic or heteroaromatic ring system having 6 to 30 aromatic ring atoms, which may in each case be substituted by one or more radicals $R^1$, where the radicals $R^1$ are then preferably non-aromatic radicals; two radicals R may also form an aliphatic ring system with one another. R is particularly preferably selected on each occurrence, identically or differently, from the group consisting of H, $N(Ar')_2$, a straight-chain alkyl group having 1 to 6 C atoms, in particular having 1, 2, 3 or 4 C atoms, or a branched or cyclic alkyl group having 3 to 6 C atoms, where the alkyl group may in each case be substituted by one or more radicals $R^1$, but is preferably unsubstituted, or an aromatic or heteroaromatic ring system having 6 to 24 aromatic ring atoms, which may in each case be substituted by one or more radicals $R^1$, preferably non-aromatic radicals $R^1$. R is very particularly preferably selected on each occurrence, identically or differently, from the group consisting of H or an aromatic or heteroaromatic ring system having 6 to 24 aromatic ring atoms, preferably having 6 to 13 aromatic ring atoms, which may in each case be substituted by one or more radicals $R^1$, preferably non-aromatic radicals $R^1$. It may furthermore be preferred if R stands for a triarylamine or triheteroarylamine group, which may be substituted by one or more radicals $R^1$. This group is an embodiment of an aromatic or heteroaromatic ring system, where a plurality of aryl or heteroaryl groups may then be linked to one another by a nitrogen atom. If R stands for a triarylamine or triheteroarylamine group, this group preferably has 18 to 30 aromatic ring atoms and may be substituted by one or more radicals $R^1$, preferably non-aromatic radicals $R^1$.

If $Z^1$, $Z^2$ and/or $Z^3$ stand for $CR_2$, the substituents R that are bonded to this carbon atom are preferably selected, identically or differently on each occurrence, from the group consisting of a linear alkyl group having 1 to 10 C atoms or a branched or cyclic alkyl group having 3 to 10 C atoms or an aromatic or heteroaromatic ring system having 5 to 24 aromatic ring atoms, which may also be substituted by one or more radicals $R^1$. R very particularly preferably stands for a methyl group or for a phenyl group. The radicals R here may also form a ring system with one another, which leads to a spiro system.

In a further preferred embodiment of the invention, Ar' is an aromatic or heteroaromatic ring system having 6 to 30 aromatic ring atoms, which may be substituted by one or more radicals $R^1$. In a particularly preferred embodiment of the invention, Ar' is an aromatic or heteroaromatic ring system having 6 to 24 aromatic ring atoms, in particular having 6 to 13 aromatic ring atoms, which may be substituted by one or more, preferably non-aromatic, radicals $R^1$.

In a further preferred embodiment of the invention, $R^1$ is selected, identically or differently on each occurrence, from the group consisting of H, D, F, CN, $OR^2$, a straight-chain alkyl group having 1 to 10 C atoms or an alkenyl group having 2 to 10 C atoms or a branched or cyclic alkyl group having 3 to 10 C atoms, where the alkyl or alkenyl group may in each case be substituted by one or more radicals $R^2$ and where one or more non-adjacent $CH_2$ groups may be replaced by O, or an aromatic or heteroaromatic ring system having 6 to 30 aromatic ring atoms, which may in each case be substituted by one or more radicals $R^2$, two or more radicals $R^1$ may form an aliphatic ring system with one another. In a particularly preferred embodiment of the invention, $R^1$ is selected, identically or differently on each occurrence, from the group consisting of H, a straight-chain alkyl group having 1 to 6 C atoms, in particular having 1, 2, 3 or 4 C atoms, or a branched or cyclic alkyl group having 3 to 6 C atoms, where the alkyl group may be substituted by one or more radicals $R^2$, but is preferably unsubstituted, or an aromatic or heteroaromatic ring system having 6 to 24 aromatic ring atoms, preferably having 6 to 13 aromatic ring atoms, which may in each case be substituted by one or more, preferably non-aromatic radicals $R^2$, but is preferably unsubstituted.

In a further preferred embodiment of the invention, $R^2$ is, identically or differently on each occurrence, H, F, an alkyl group having 1 to 4 C atoms or an aryl group having 6 to 10 C atoms, which may be substituted by an alkyl group having 1 to 4 C atoms, but is preferably unsubstituted.

Suitable aromatic or heteroaromatic ring systems R, if R stands for an aromatic or heteroaromatic ring system, or Ar' are selected from phenyl, biphenyl, in particular ortho-, meta- or para-biphenyl, terphenyl, in particular ortho-, meta-, para- or branched terphenyl, quaterphenyl, in particular ortho-, meta-, para- or branched quaterphenyl, fluorene, which can be linked via the 1-, 2-, 3- or 4-position, spirobifluorene, which can be linked via the 1-, 2-, 3- or 4-position, naphthalene, which can be linked via the 1- or 2-position, indole, benzofuran, benzothiophene, carbazole, which can be linked via the 1-, 2-, 3- or 4-position, dibenzofuran, which can be linked via the 1-, 2-, 3- or 4-position, dibenzothiophene, which can be linked via the 1-, 2-, 3- or 4-position, indenocarbazole, indolocarbazole, pyridine, pyrimidine, pyrazine, pyridazine, triazine, quinoline, quinazoline, benzimidazole, phenanthrene, triphenylene or a combination of two or three of these groups, which may in each case be substituted by one or more radicals $R^1$. If R or Ar' stands for a heteroaryl group, in particular for triazine, pyrimidine, quinazoline or carbazole, aromatic or heteroaromatic radicals $R^1$ may also be preferred on this heteroaryl group.

The groups R, if they stand for an aromatic or heteroaromatic ring system, or Ar' are preferably selected from the groups of the following formulae R-1 to R-81,

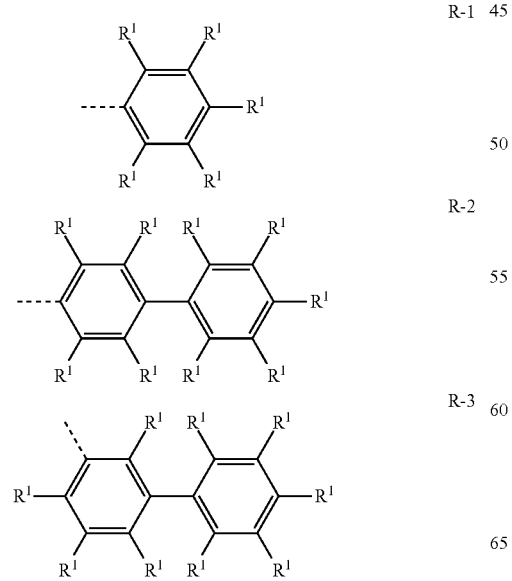

R-1

R-2

R-3

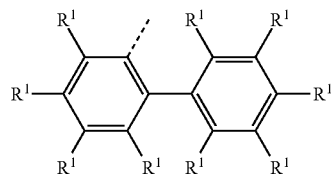

R-4

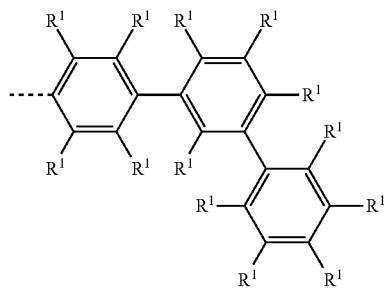

R-5

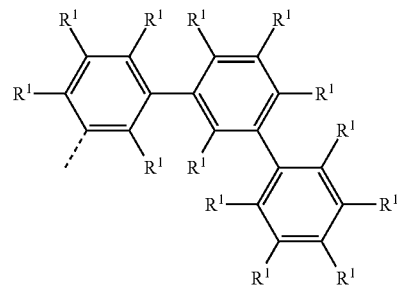

R-6

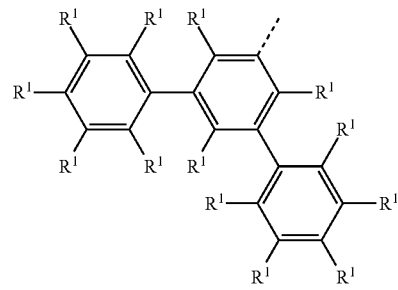

R-7

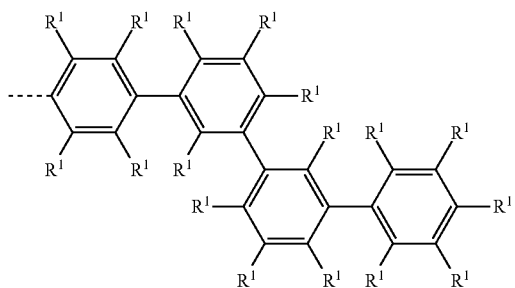

R-8

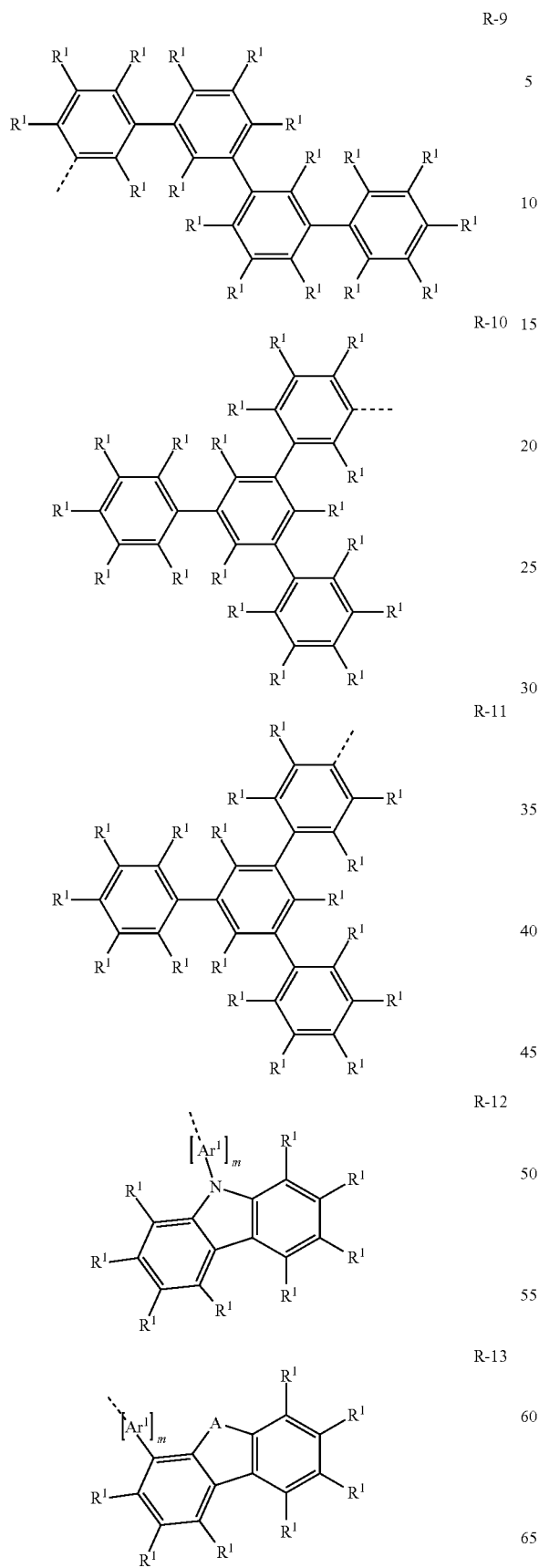
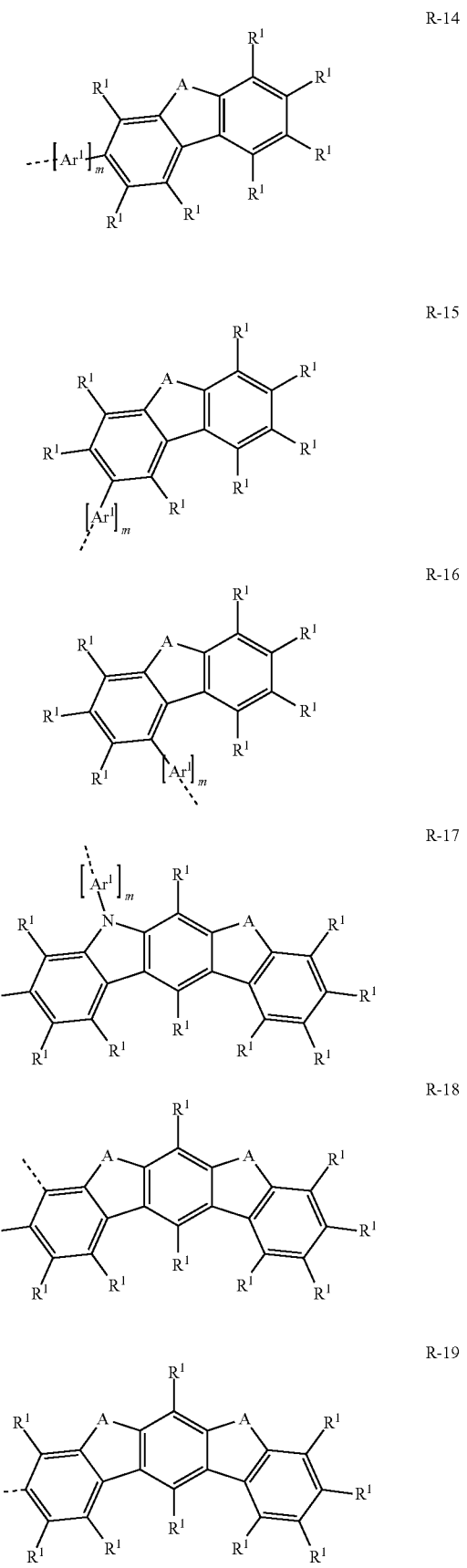

R-20
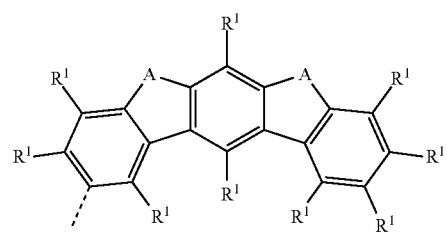
R-21
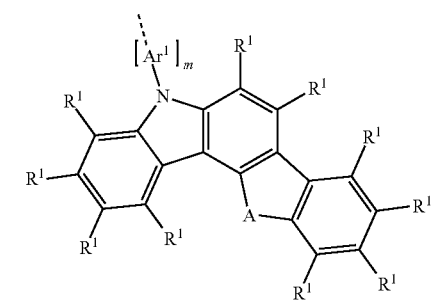
R-22
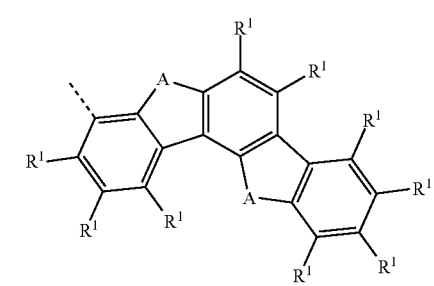
R-23
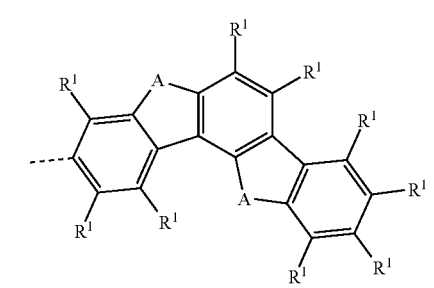
R-24
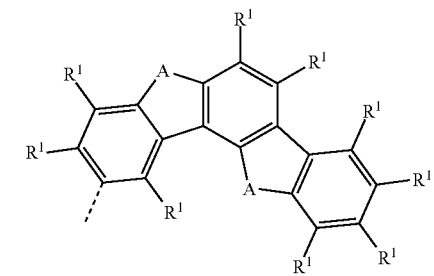
R-25
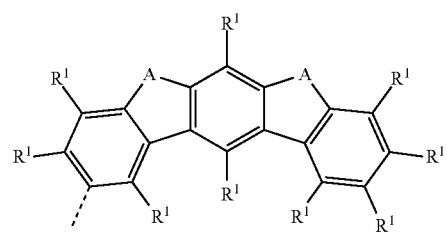
R-26
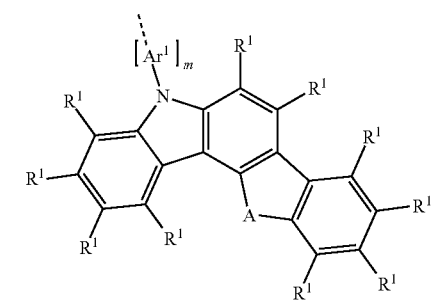
R-27
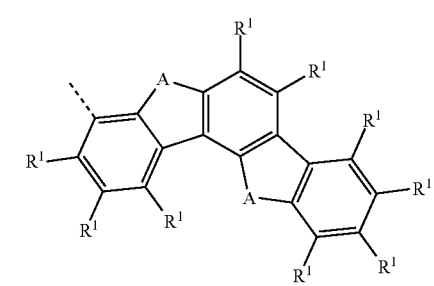
R-28
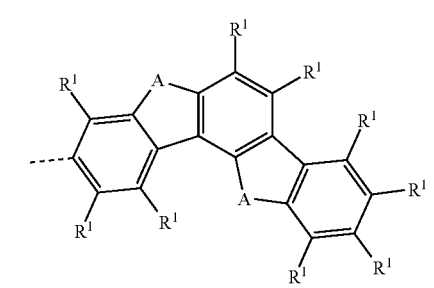
R-29
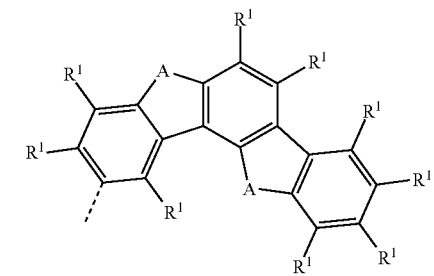
R-30
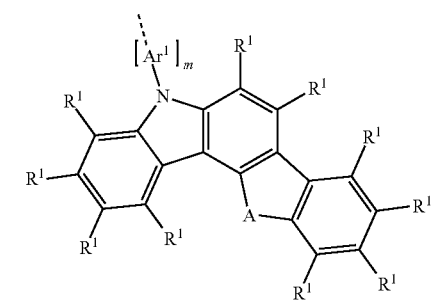

R-31
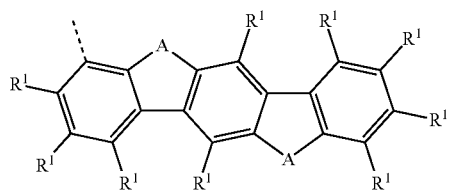
R-32
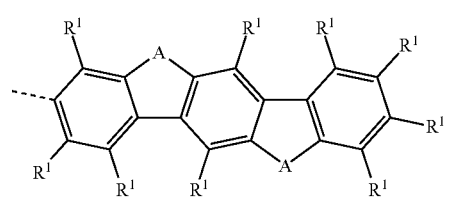
R-33
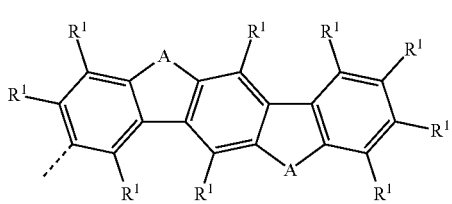
R-34
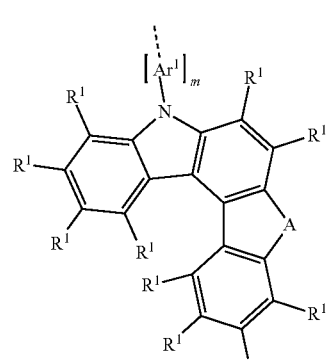
R-35
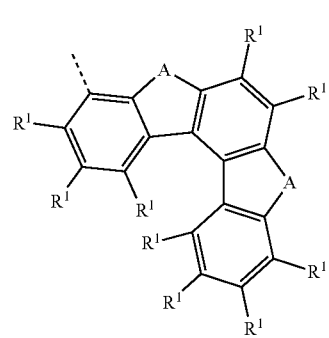
R-36
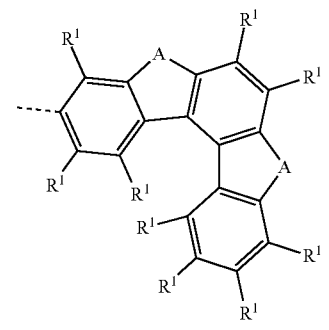
R-37
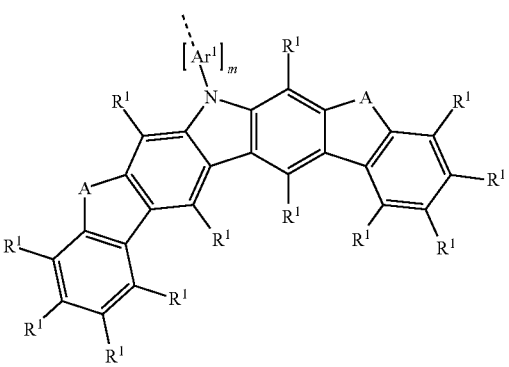
R-38
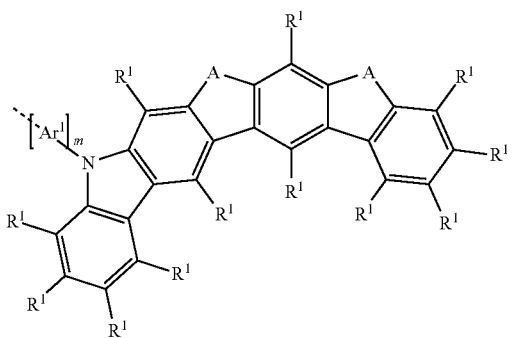
R-39
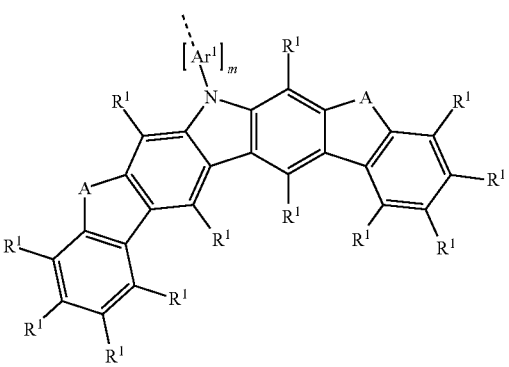
R-40
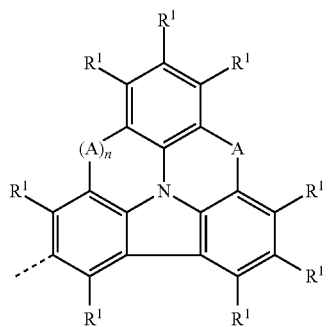

-continued
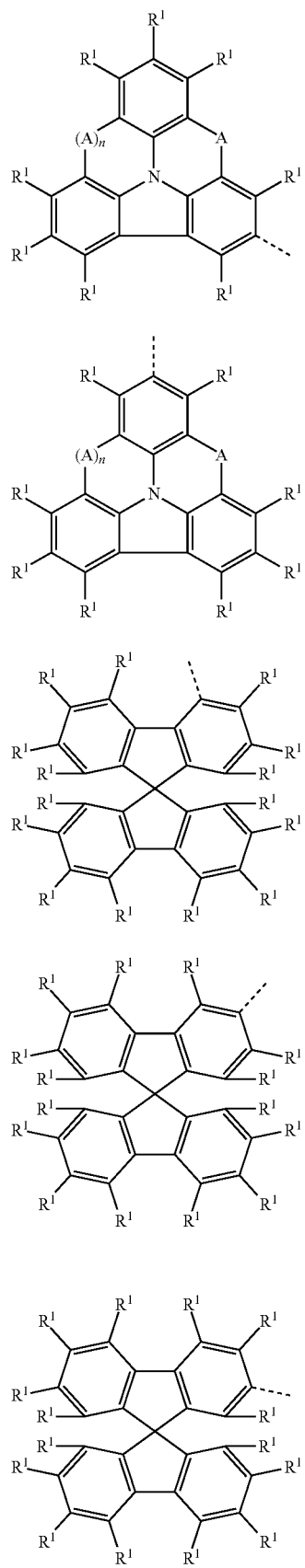
R-41
R-42
R-43
R-44
R-45
-continued
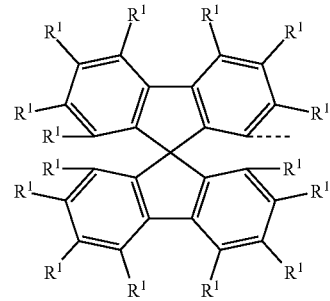
R-46
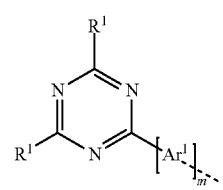
R-47
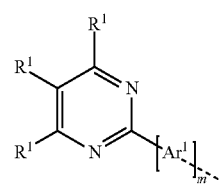
R-48
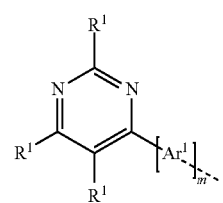
R-49
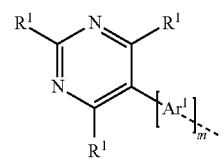
R-50
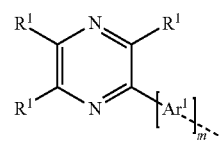
R-51
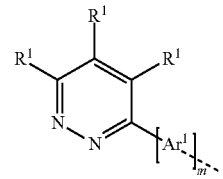
R-52
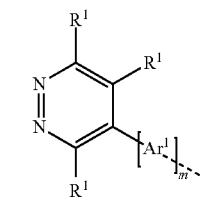
R-53

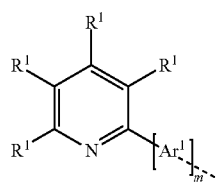 R-54
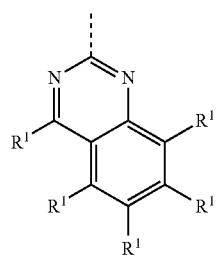 R-55
R-56
R-57
R-58
R-59
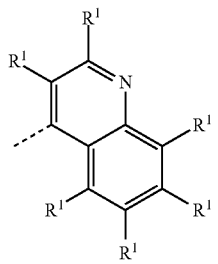 R-60
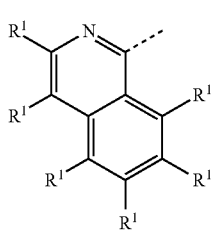 R-61
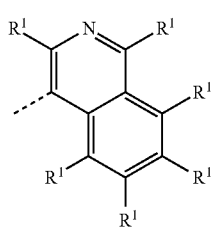 R-62
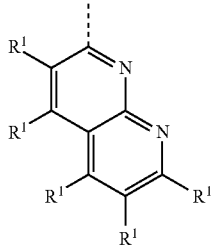 R-63
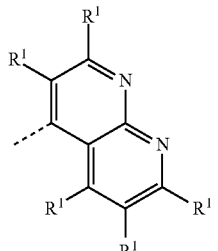 R-64
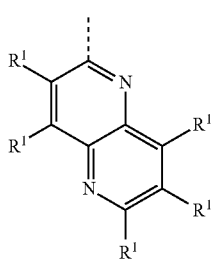 R-65

R-66 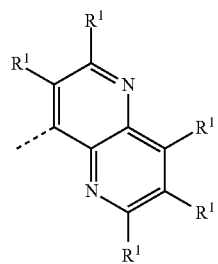
R-67 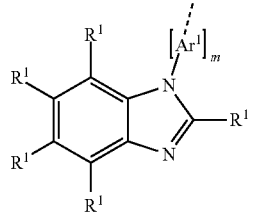
R-68 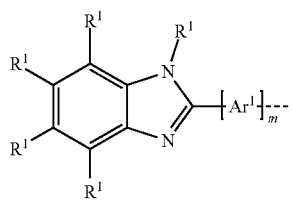
R-69 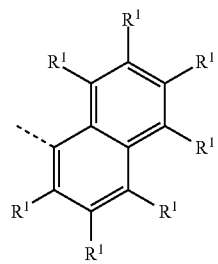
R-70 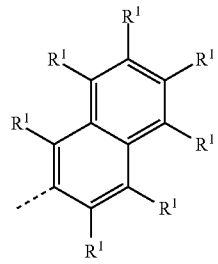
R-71 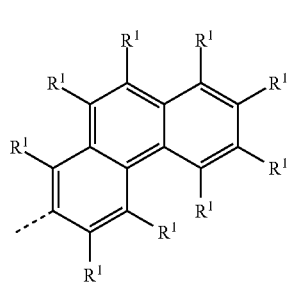
R-72 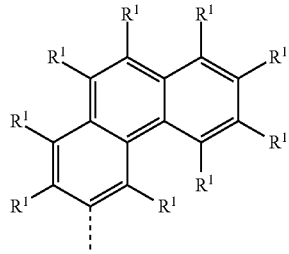
R-73 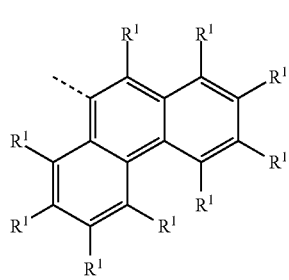
R-74 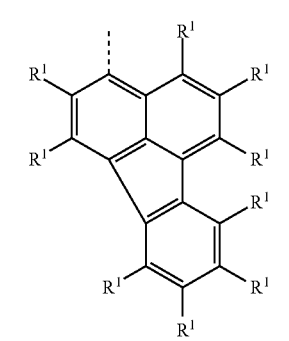
R-75 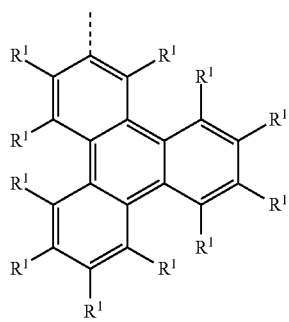
R-76 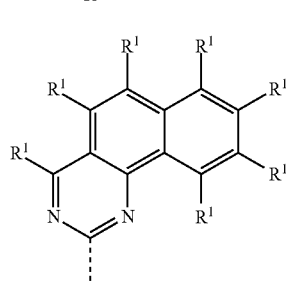

-continued

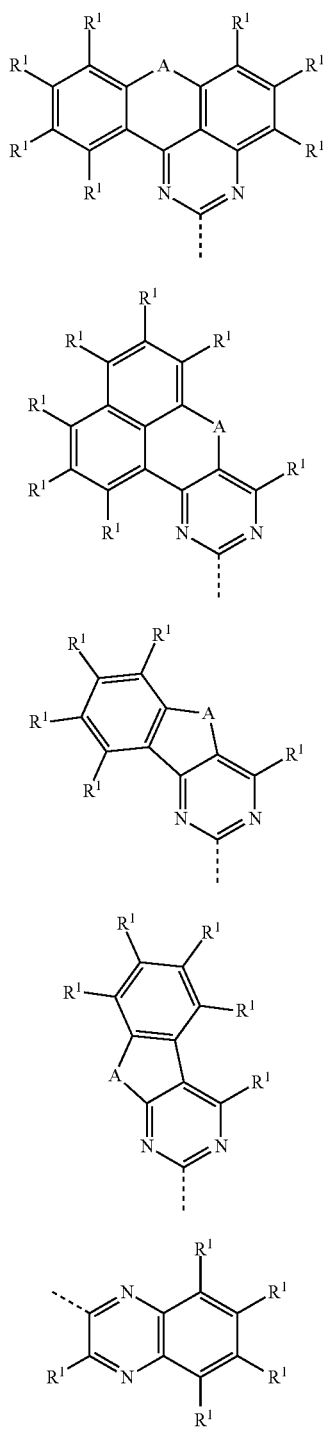

where R¹ has the meanings given above, the dashed bond represents the bond to a carbon atom of the basic structure in formula (1) and (2) or in the preferred embodiments or to the nitrogen atom in the group N(Ar')₂ and furthermore:

Ar¹ is on each occurrence, identically or differently, a divalent aromatic or heteroaromatic ring system having 6 to 18 aromatic ring atoms, which may in each case be substituted by one or more radicals R¹;

A is on each occurrence, identically or differently, C(R¹)₂, NR¹, O or S;

n is 0 or 1, where n=0 means that no group A is bonded at this position and instead radicals R¹ are bonded to the corresponding carbon atoms;

m is 0 or 1, where m=0 means that the group Ar¹ is not present and that the corresponding aromatic or heteroaromatic group is bonded directly to a carbon atom of the basic structure in formula (1) or in the preferred embodiments or to the nitrogen atom in the group N(Ar')₂; with the proviso that m=1 for structures (R-12), (R-17), (R-21), (R-25), (R-26), (R-30), (R-34), (R-38) and (R-39) if these groups are embodiments of Ar'.

If the above-mentioned groups Ar-1 to Ar-81 for Ar or R-1 to R-81 for R, R' or Ar' contain a plurality of groups A, all combinations from the definition of A come into consideration for this. Preferred embodiments are then those in which one group A stands for NR or NR¹ and the other group A stands for C(R)₂ or C(R¹)₂ or in which both groups A stand for NR or NR¹ or in which both groups A stand for O. In a particularly preferred embodiment of the invention, at least one group A in groups Ar, R or Ar' that contain a plurality of groups A stands for C(R)₂ or C(R¹)₂ or for NR or NR¹.

If A stands for NR or NR¹ in the groups Ar-1 to Ar-81 or R-1 to R-81, the substituent R or R¹ that is bonded to the nitrogen atom preferably stands for an aromatic or heteroaromatic ring system having 5 to 24 aromatic ring atoms, which may also be substituted by one or more radicals R¹ or R². In a particularly preferred embodiment, this substituent R or R¹ stands, identically or differently on each occurrence, for an aromatic or heteroaromatic ring system having 6 to 24 aromatic ring atoms, preferably having 6 to 12 aromatic ring atoms, which contains no condensed aryl groups or heteroaryl groups in which two or more aromatic or heteroaromatic 6-membered ring groups are condensed directly onto one another, and which may in each case also be substituted by one or more radicals R¹ or R². Particular preference is given to phenyl, biphenyl, terphenyl and quaterphenyl having linking patterns as shown above for Ar-1 to Ar-11 or R-1 to R-11, where these structures may be substituted by one or more radicals R¹ or R², but are preferably unsubstituted.

If A stands for CR₂ or C(R¹)₂ in the groups Ar-1 to Ar-81 or R-1 to R-81, the substituents R or R¹ that are bonded to this carbon atom preferably stand, identically or differently on each occurrence, for a linear alkyl group having 1 to 10 C atoms or for a branched or cyclic alkyl group having 3 to 10 C atoms or for an aromatic or heteroaromatic ring system having 5 to 24 aromatic ring atoms, which may also be substituted by one or more radicals R¹ or R². R or R¹ very particularly preferably stands for a methyl group or for a phenyl group. The radicals R or R¹ may also form a ring system with one another, which leads to a spiro system.

Further suitable groups Ar, R or Ar' are groups of the formula —Ar⁴—N(Ar²)(Ar³), where Ar², Ar³ and Ar⁴ stand, identically or differently on each occurrence, for an aromatic or heteroaromatic ring system having 5 to 24 aromatic ring atoms, which may in each case be substituted by one or more radicals R¹. For Ar, such a group arises through the group Ar being substituted by a group N(Ar')₂. The total number of aromatic ring atoms of Ar², Ar³ and Ar⁴ here is a maximum of 60 and preferably a maximum of 40.

Ar⁴ and Ar² may also be connected to one another and/or Ar² and Ar³ may also be connected to one another by a group selected from C(R¹)₂, NR¹, O or S. The linking of Ar⁴ and Ar² to one another or of Ar² and Ar³ to one another preferably takes place in each case ortho to the position of the linking to the nitrogen atom. In a preferred embodiment of the invention, none of the groups Ar², Ar³ or Ar⁴ are linked to one another.

Ar⁴ is preferably an aromatic or heteroaromatic ring system having 6 to 24 aromatic ring atoms, in particular having 6 to 12 aromatic ring atoms, which may in each case be substituted by one or more radicals R¹. Ar⁴ is particularly preferably selected from the group consisting of ortho-, meta- or para-phenylene or ortho-, meta- or para-biphenyl, which may in each case be substituted by one or more radicals R¹, but are preferably unsubstituted. Ar⁴ is very particularly preferably an unsubstituted phenylene group. This applies, in particular, if Ar⁴ is connected to Ar² by a single bond.

Ar² and Ar³, identically or differently on each occurrence, are preferably an aromatic or heteroaromatic ring system having 6 to 24 aromatic ring atoms, which may in each case be substituted by one or more radicals R¹. Particularly preferred groups Ar² or Ar³ are selected, identically or differently on each occurrence, from the group consisting of benzene, ortho-, meta- or para-biphenyl, ortho-, meta-, para- or branched terphenyl, ortho-, meta-, para- or branched quaterphenyl, 1-, 2-, 3- or 4-fluorenyl, 1-, 2-, 3- or 4-spirobifluorenyl, 1- or 2-naphthyl, indole, benzofuran, benzothiophene, 1-, 2-, 3- or 4-carbazole, 1-, 2-, 3- or 4-dibenzofuran, 1-, 2-, 3- or 4-dibenzothiophene, indenocarbazole, indolocarbazole, 2-, 3- or 4-pyridine, 2-, 4- or 5-pyrimidine, pyrazine, pyridazine, triazine, phenanthrene, triphenylene or combinations of two, three or four of these groups, which may in each case be substituted by one or more radicals R¹. Ar² and Ar³ particularly preferably stand, identically or differently on each occurrence, for an aromatic ring system having 6 to 24 aromatic ring atoms, which may be substituted by one or more radicals R¹, in particular selected from the group consisting of benzene, biphenyl, in particular ortho-, meta- or para-biphenyl, terphenyl, in particular ortho-, meta-, para- or branched terphenyl, quaterphenyl, in particular ortho-, meta-, para- or branched quaterphenyl, fluorene, in particular 1-, 2-, 3- or 4-fluorene, or spirobifluorene, in particular 1-, 2-, 3- or 4-spirobifluorene.

The alkyl groups in compounds according to the invention that are processed by vacuum evaporation preferably have not more than five C atoms, particularly preferably not more than 4 C atoms, very particularly preferably not more than 1 C atom. For compounds that are processed from solution, suitable compounds are also those that are substituted by alkyl groups, in particular branched alkyl groups, having up to 10 C atoms or that are substituted by oligoarylene groups, for example ortho-, meta-, para- or branched terphenyl or quaterphenyl groups.

If the compounds of the formula (1) or the preferred embodiments are used as matrix material for a phosphorescent emitter or in a layer which is directly adjacent to a phosphorescent layer, it is furthermore preferred if the compound contains no condensed aryl or heteroaryl groups in which more than two six-membered rings are condensed directly onto one another. In particular, it is preferred that the radicals Ar, R, Ar', R¹ and R² contain no condensed aryl or heteroaryl groups in which two or more six-membered rings are condensed directly onto one another. An exception therefrom is formed by phenanthrene and triphenylene, which, owing to their high triplet energy, may be preferred in spite of the presence of condensed aromatic six-membered rings.

The preferred embodiments mentioned above can be combined with one another as desired within the restrictions defined in Claim 1. In a particularly preferred embodiment of the invention, the above-mentioned preferences apply simultaneously.

Examples of preferred compounds in accordance with the above-mentioned embodiments are the compounds shown in the following table.

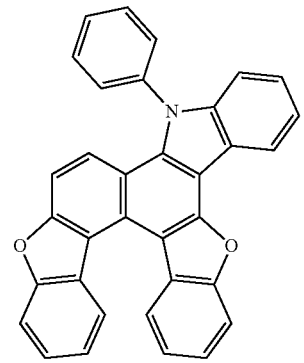

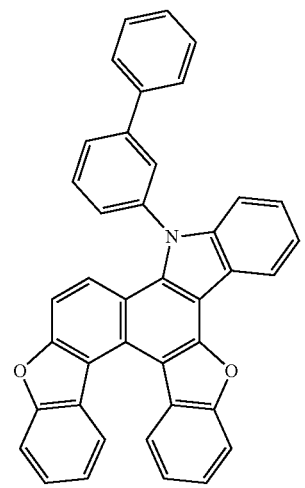

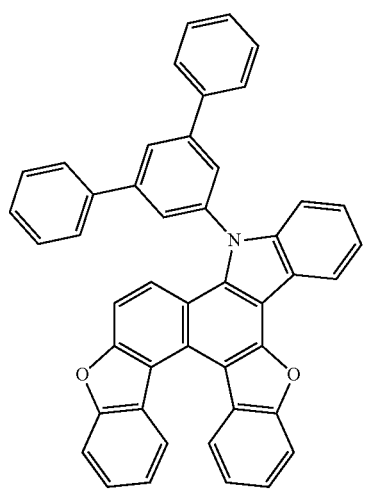

51
-continued
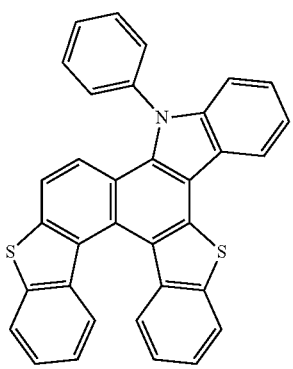
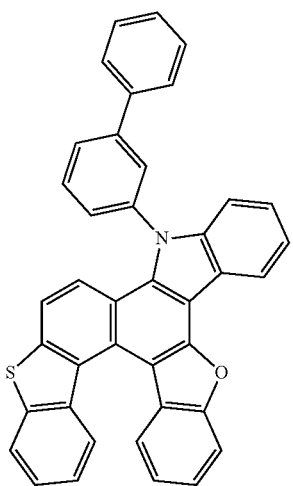
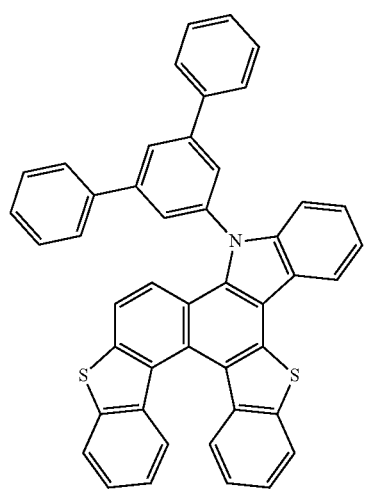
52
-continued
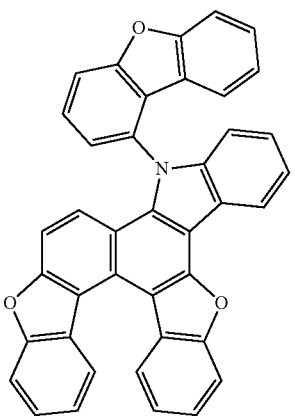
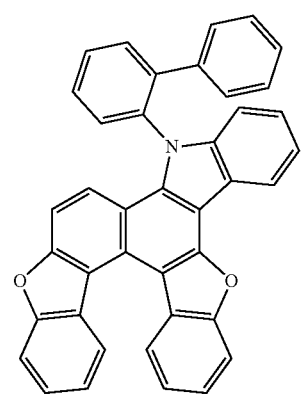
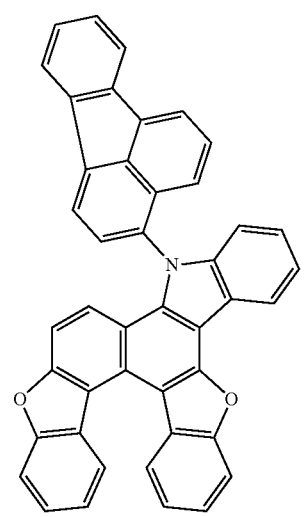
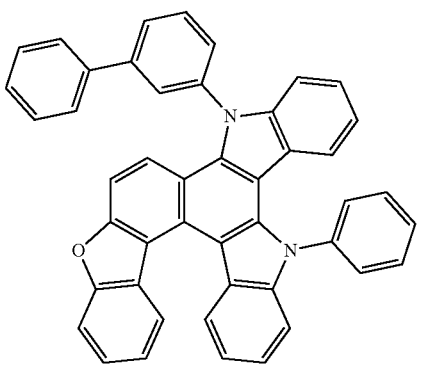

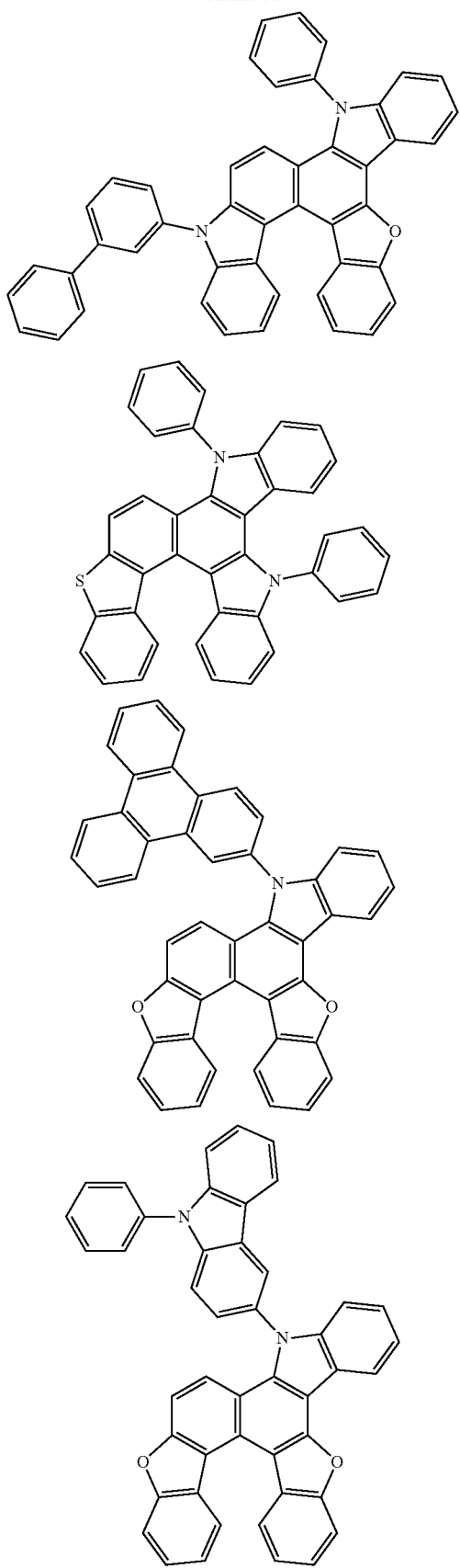
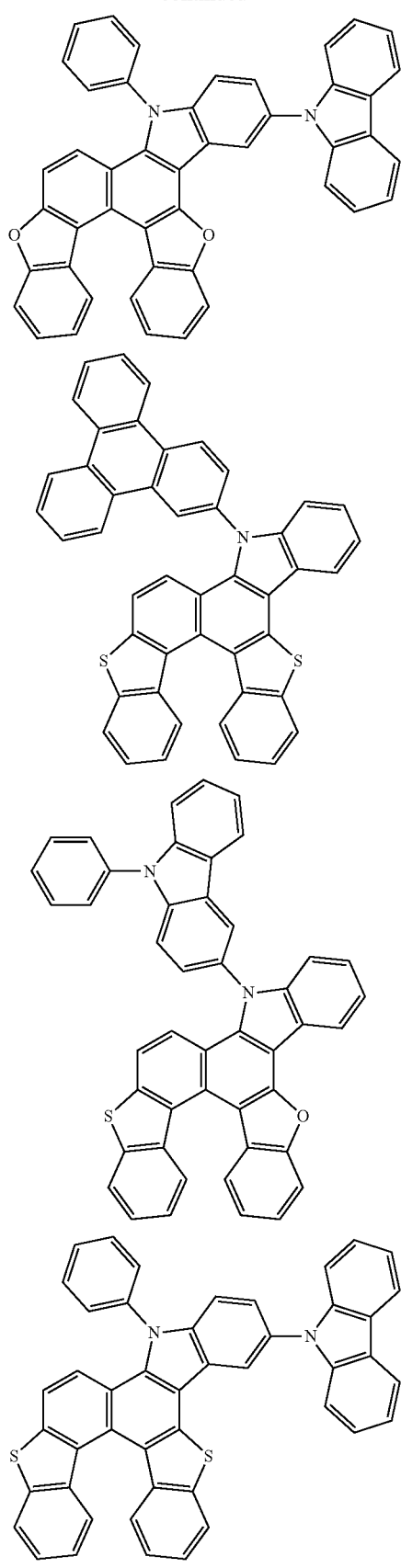

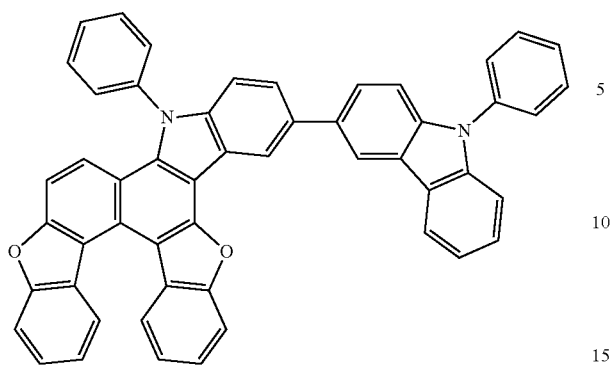
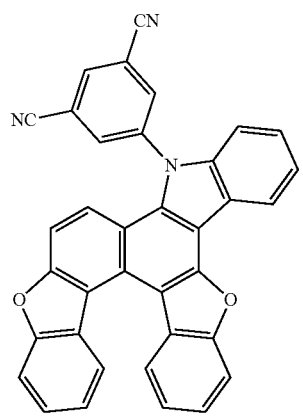
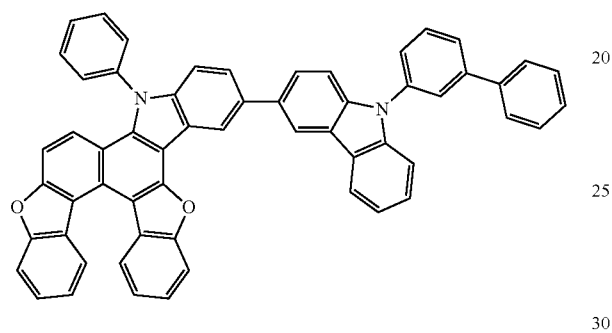
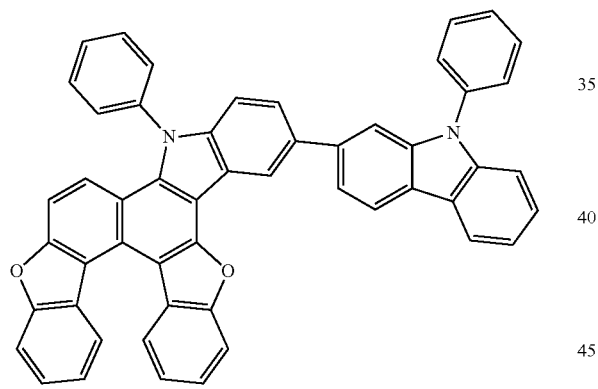
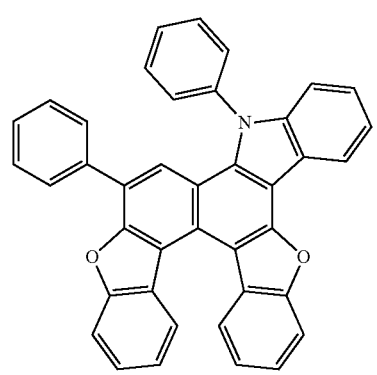
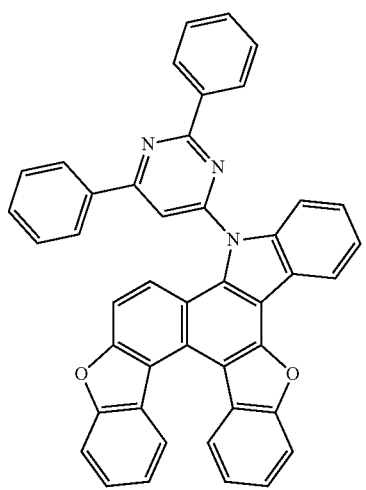

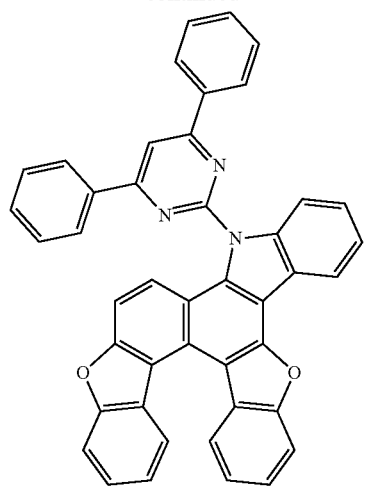
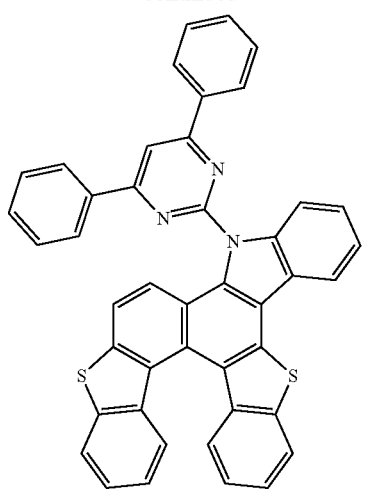
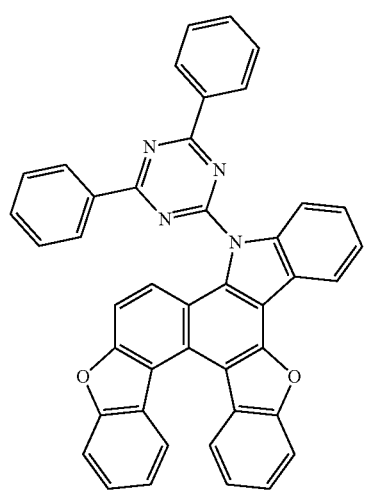
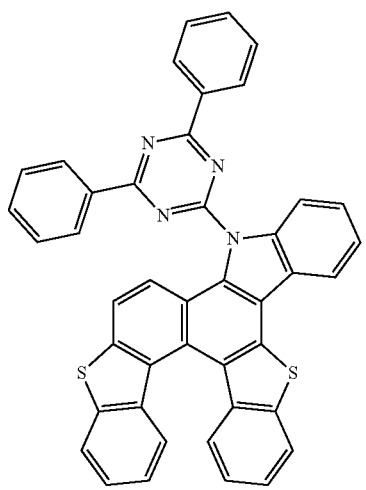
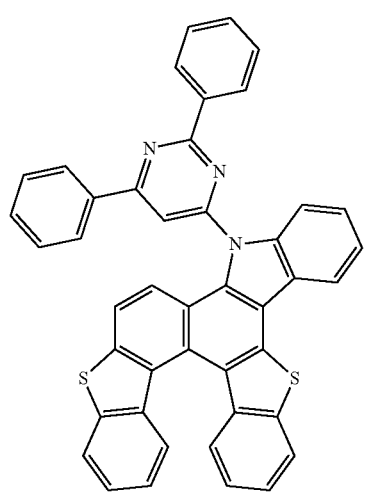
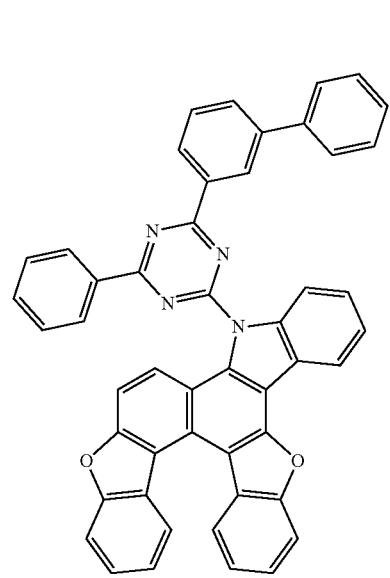

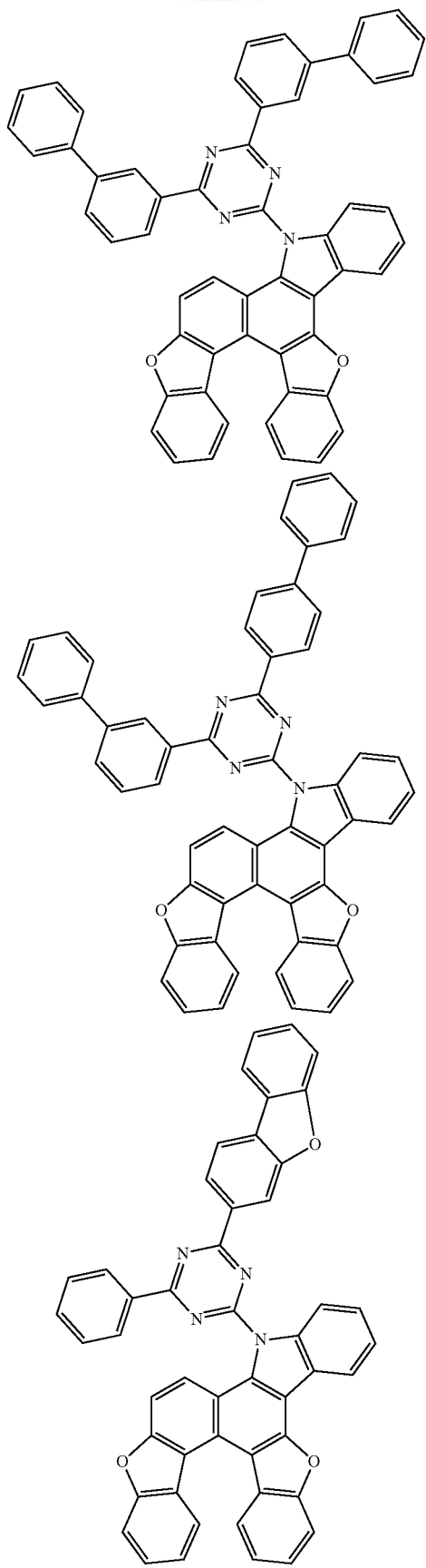
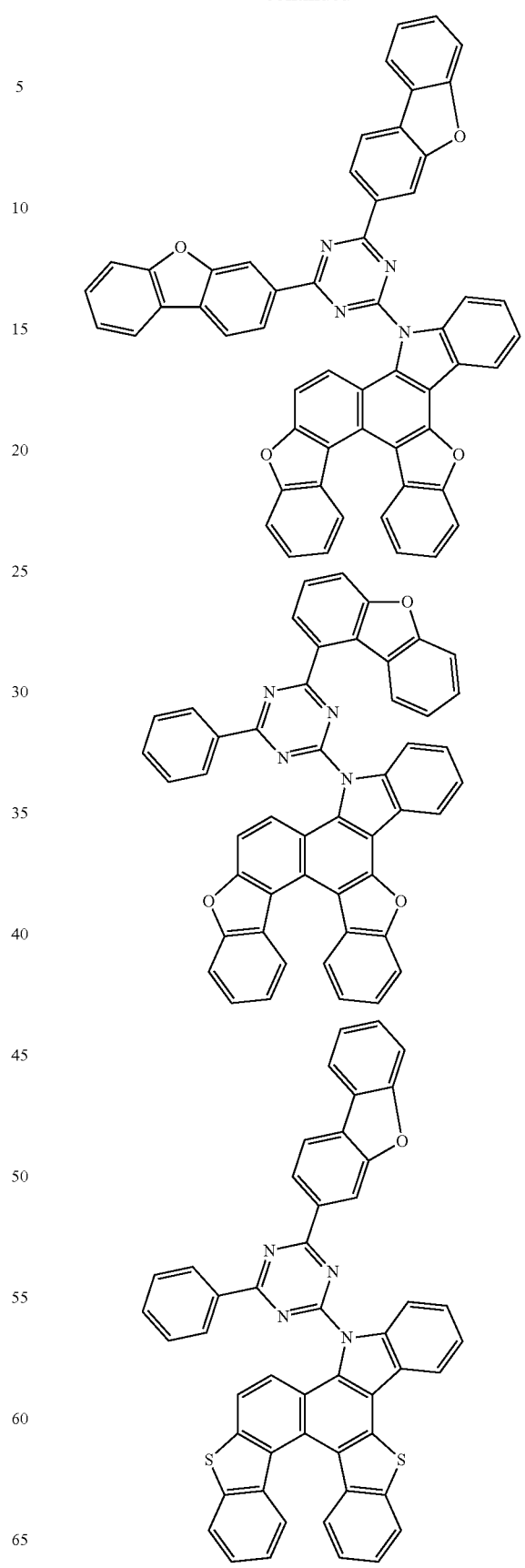

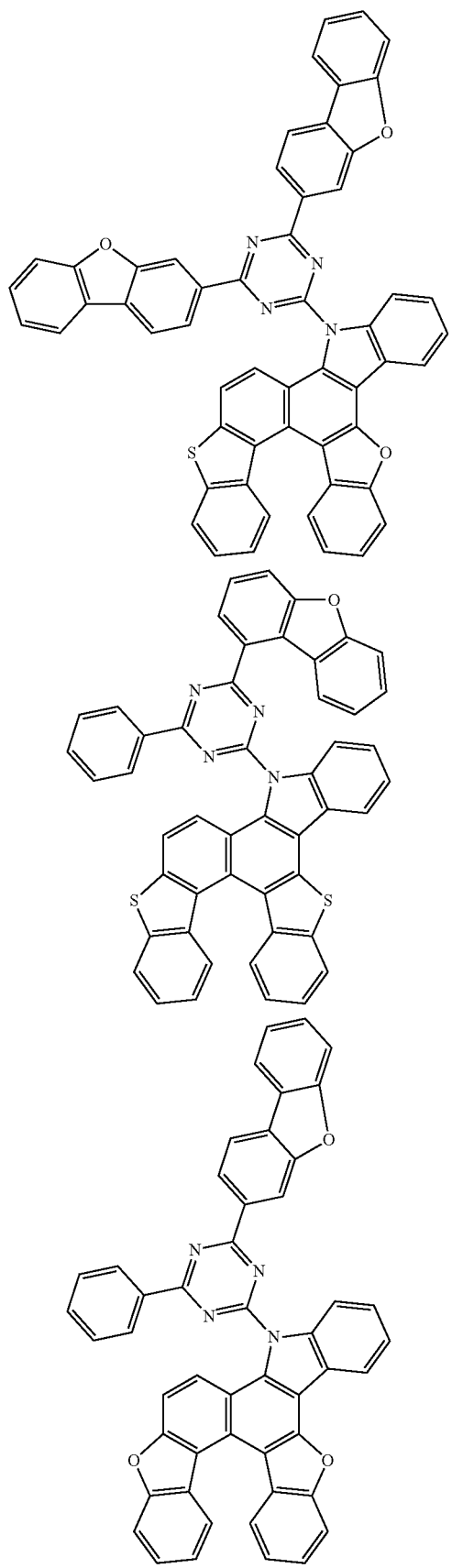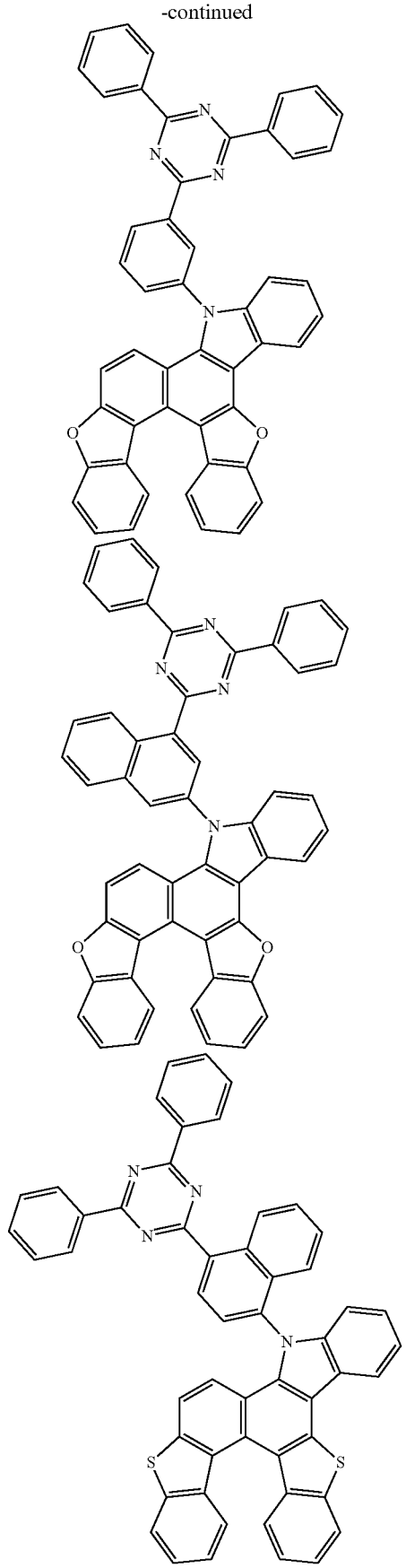

63
-continued
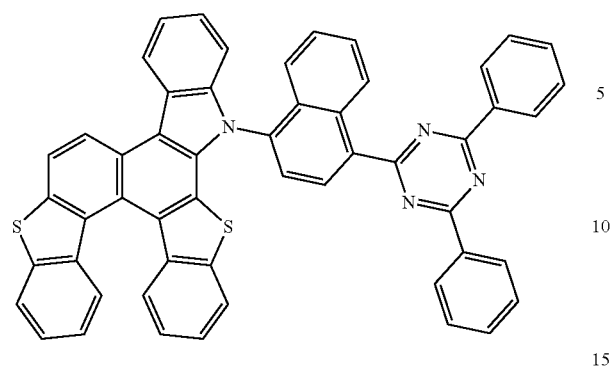
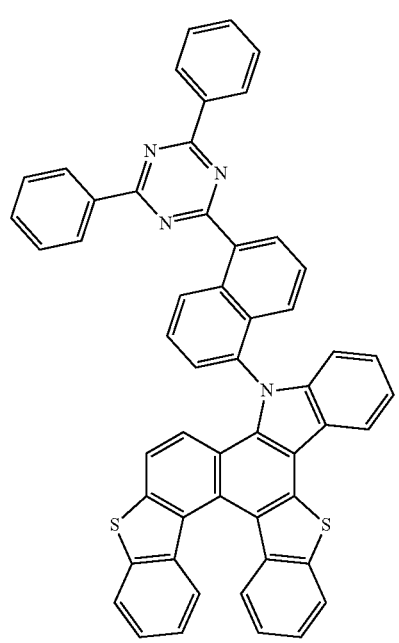
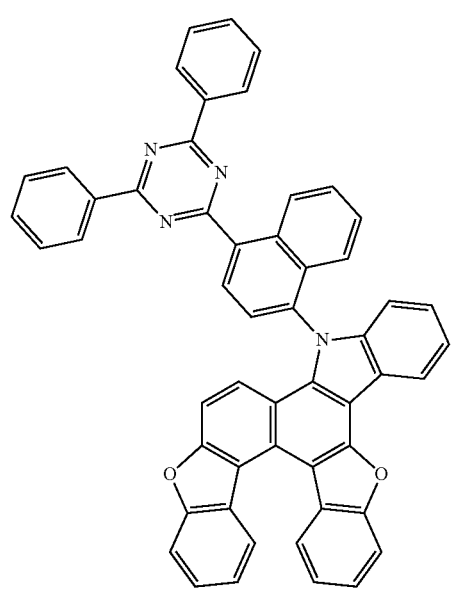
64
-continued
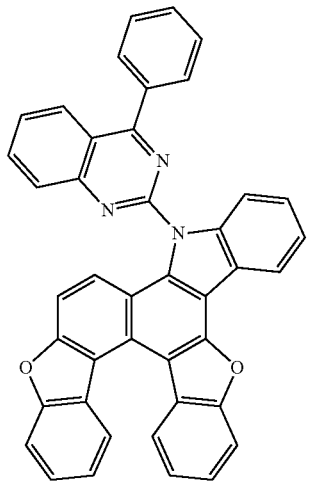
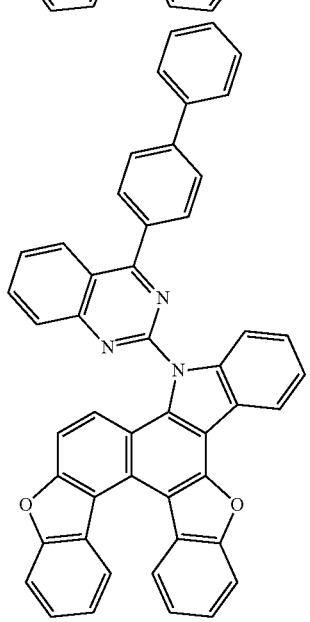
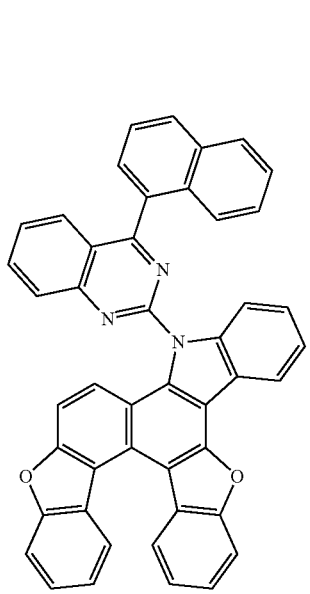

-continued
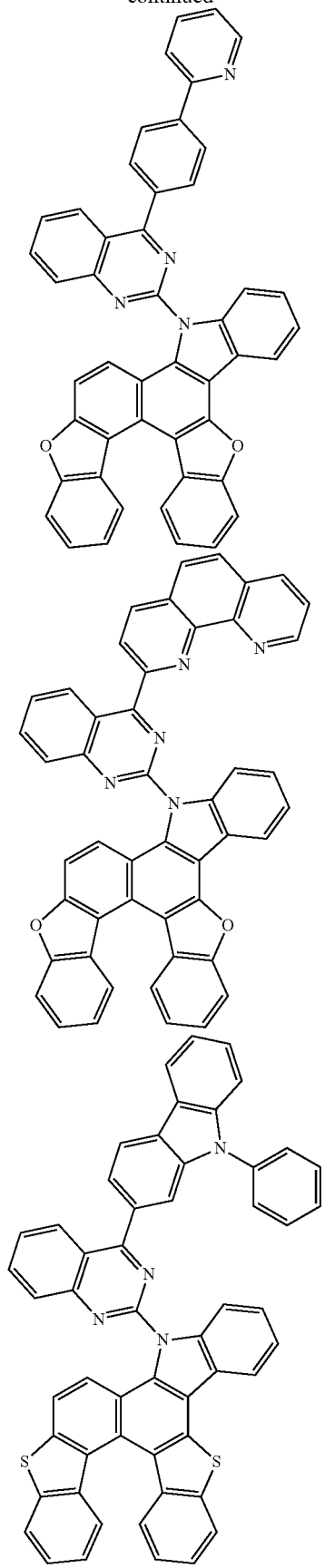
-continued
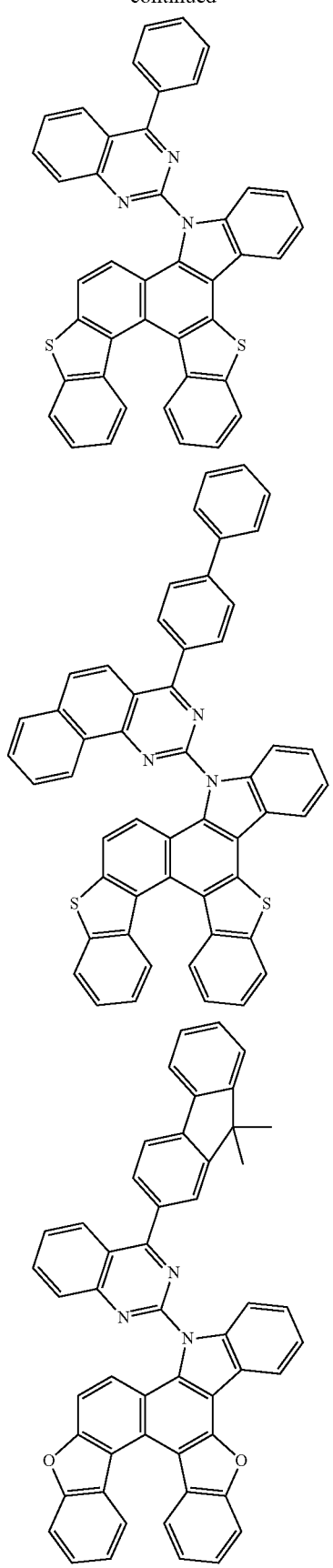

-continued
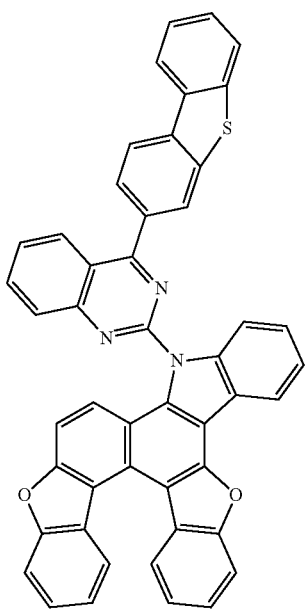
-continued
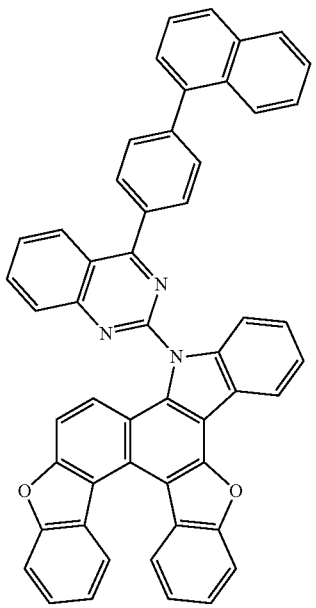
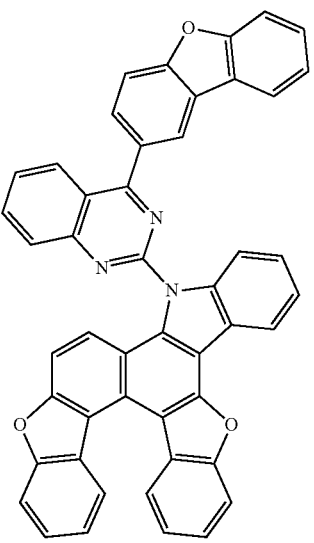
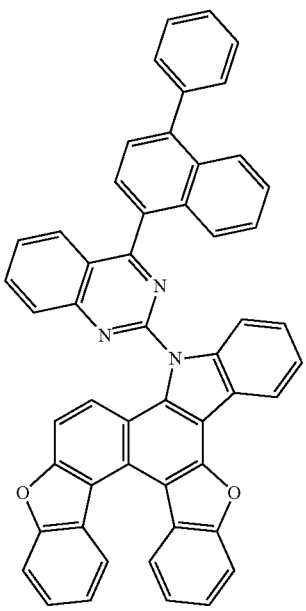

-continued
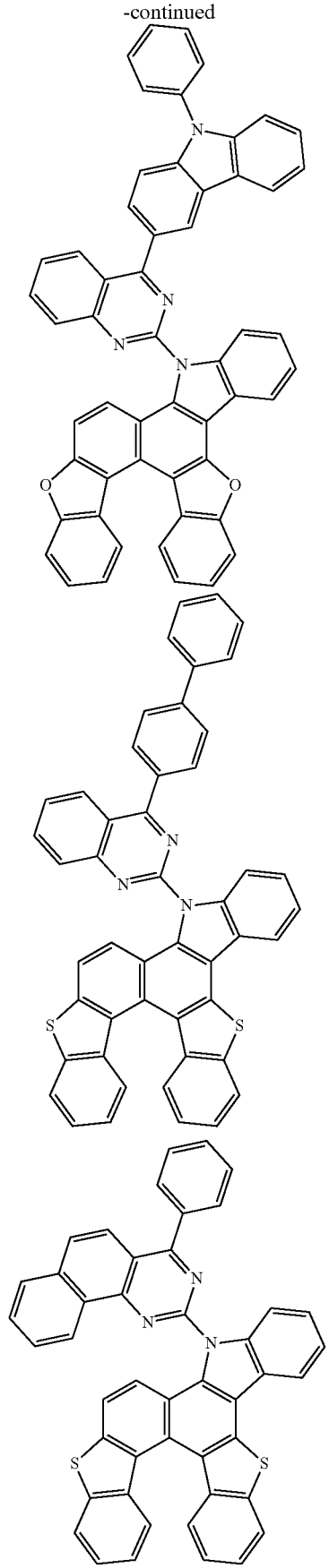
-continued
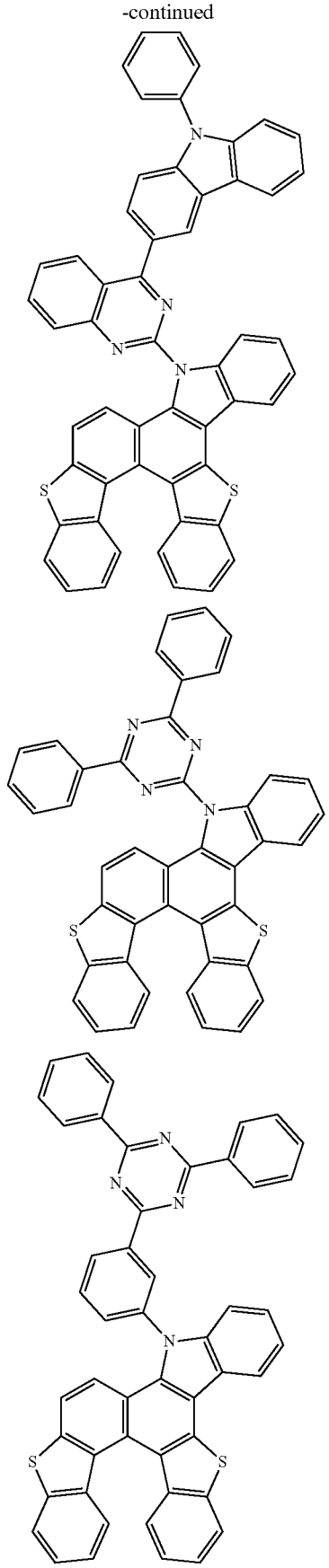

71
-continued
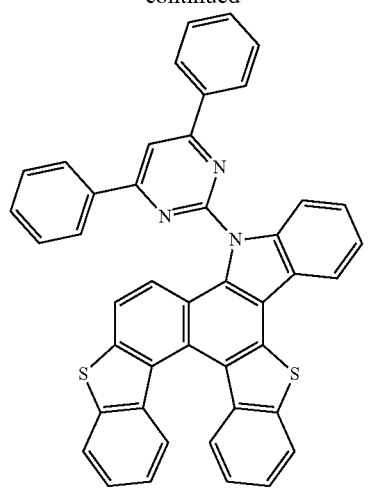
72
-continued
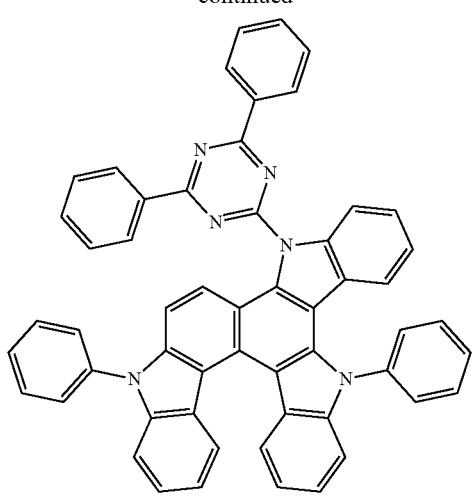
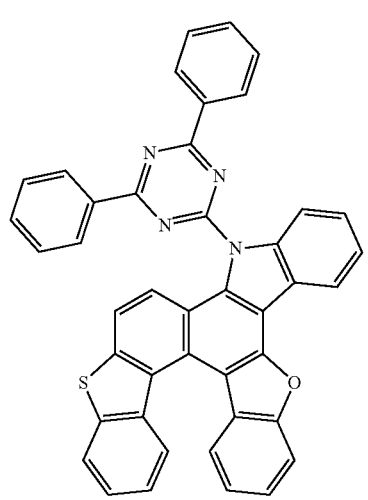
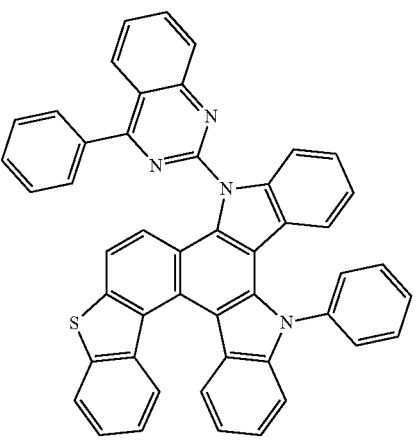
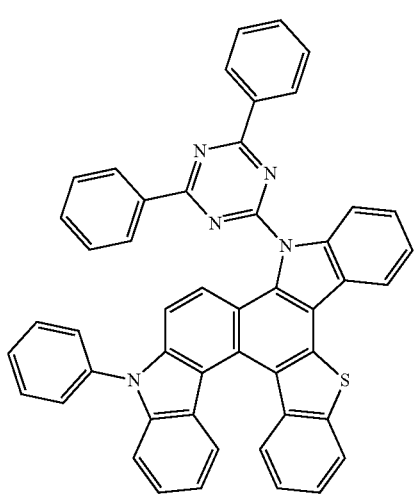
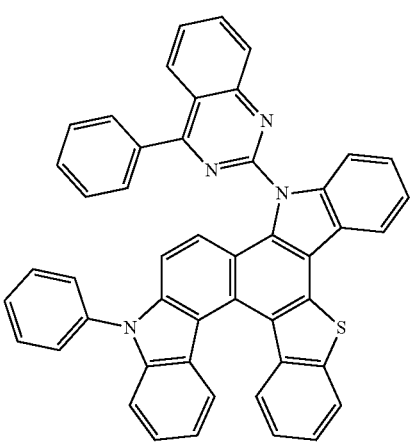

73
-continued
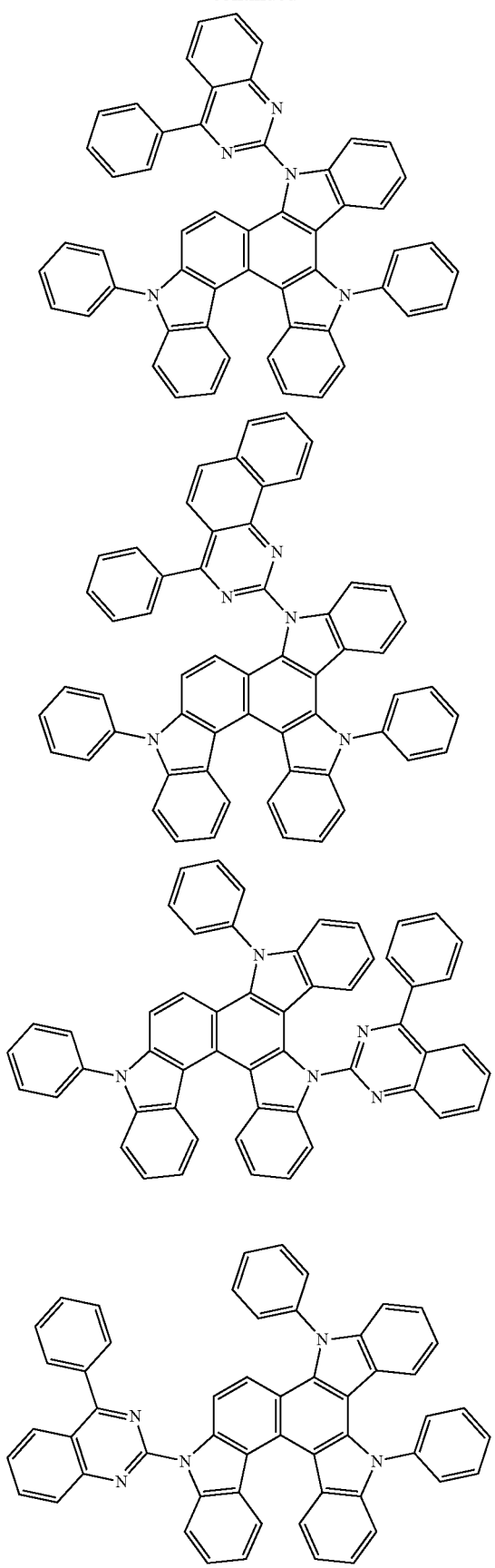
74
-continued
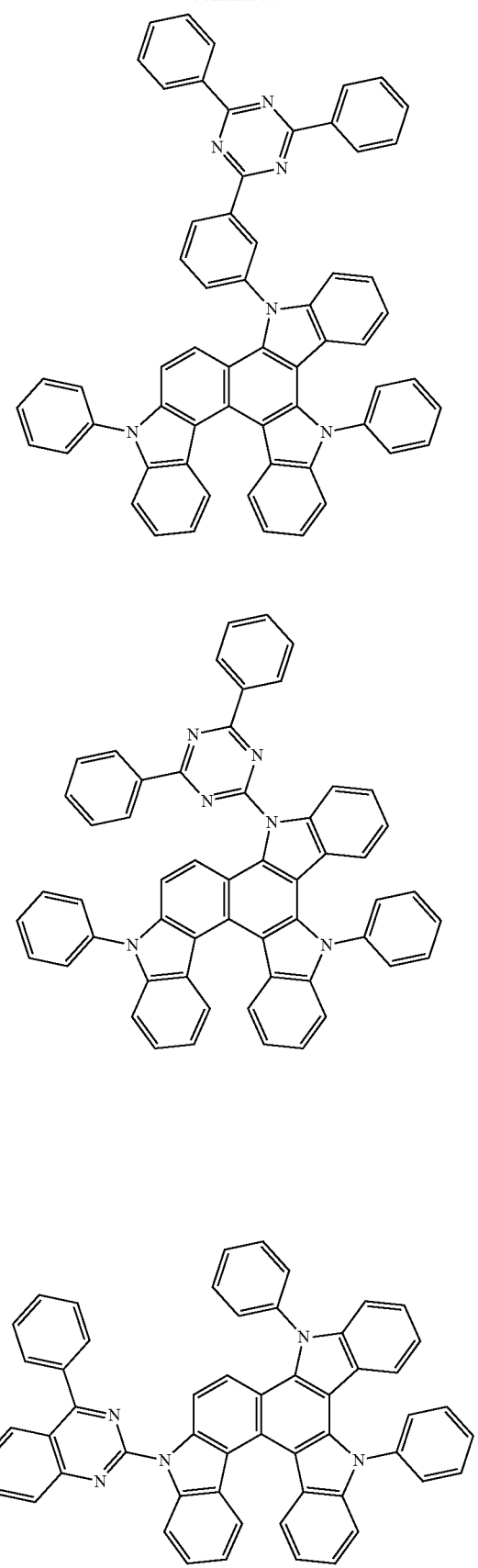

75
-continued
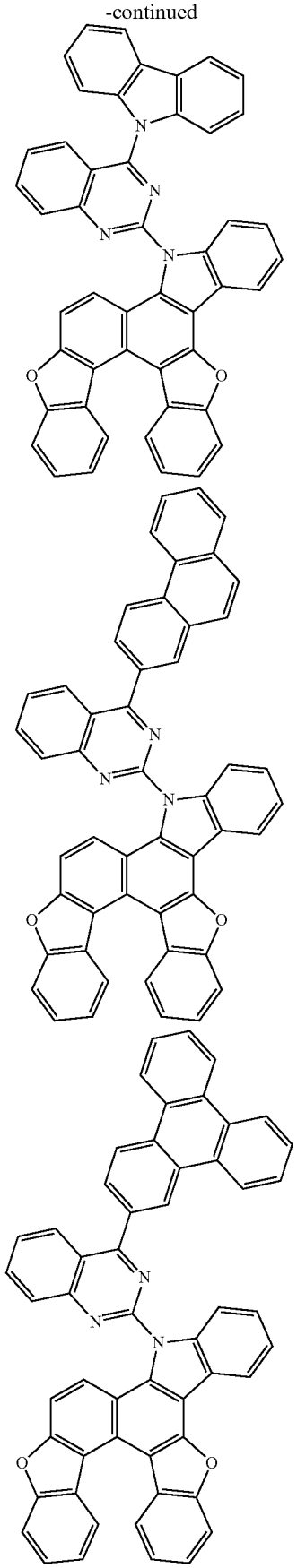
76
-continued
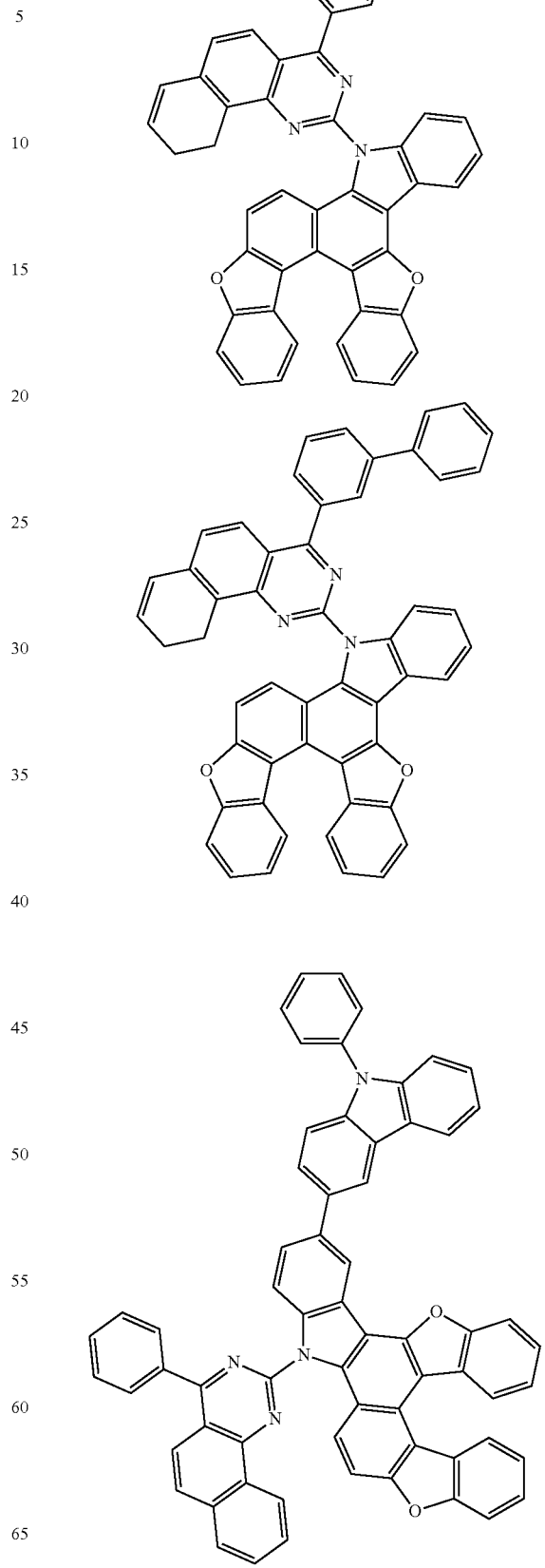

77
-continued
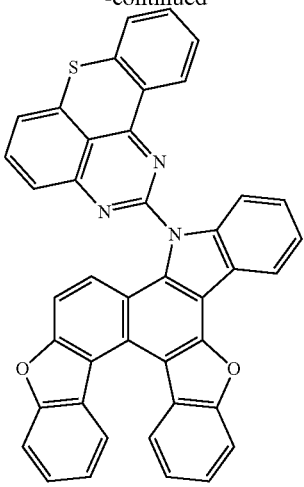
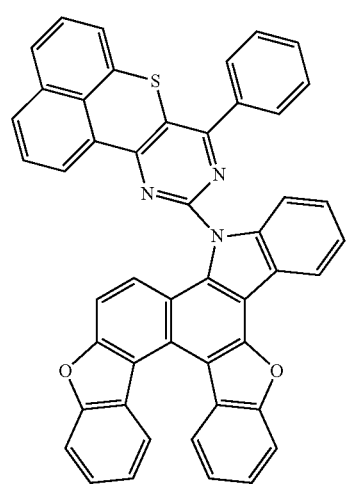
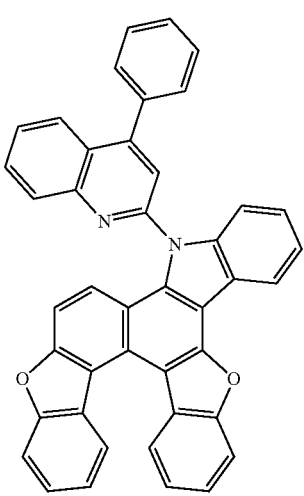
78
-continued
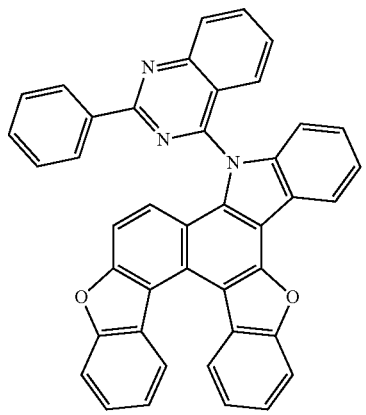
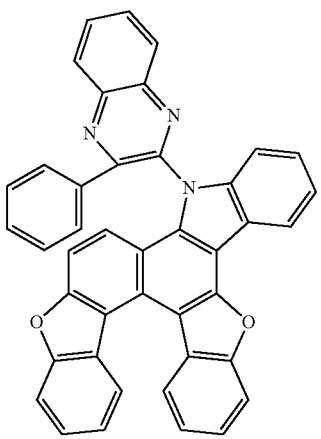
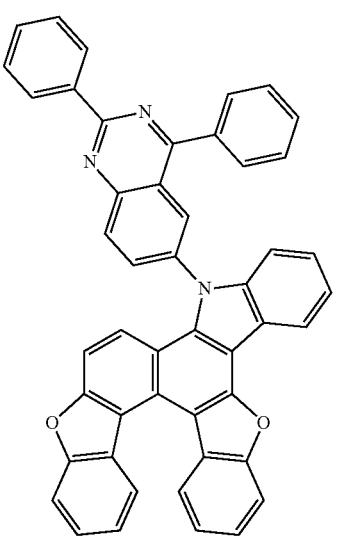

-continued
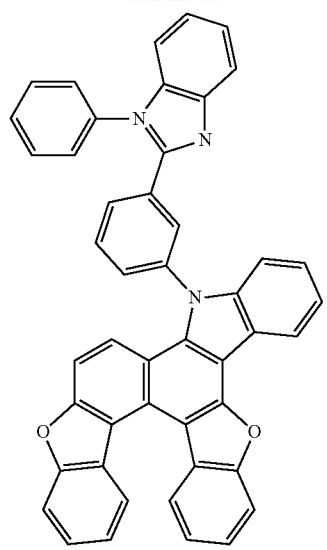
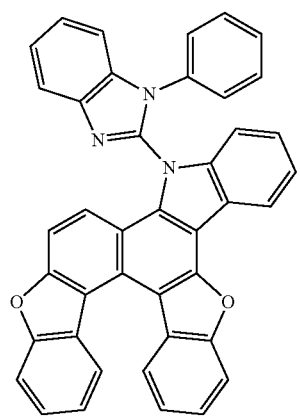
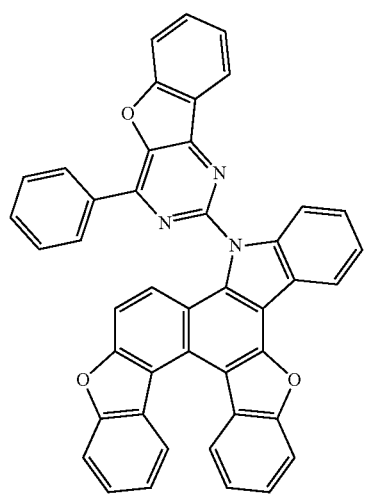
-continued
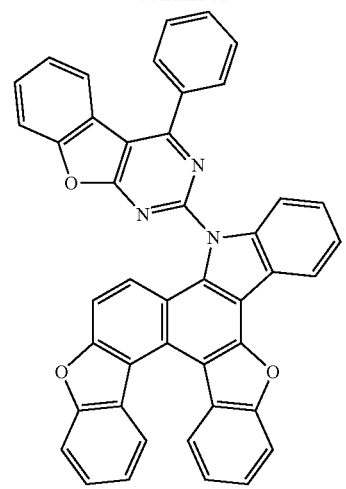
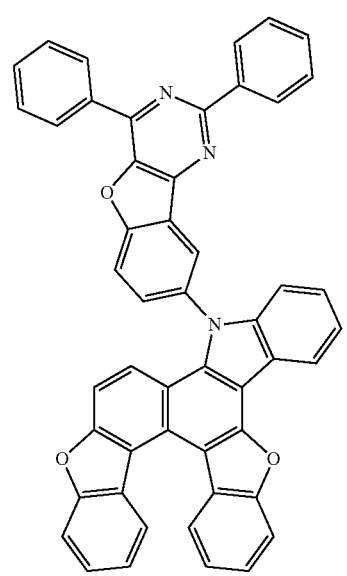
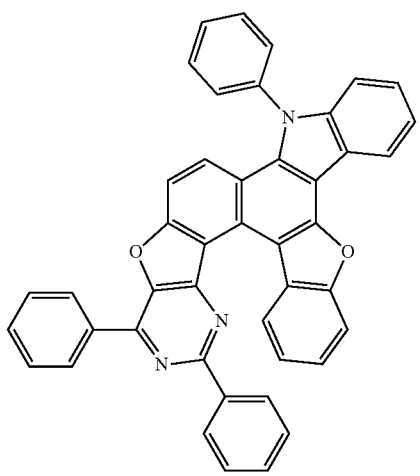

-continued
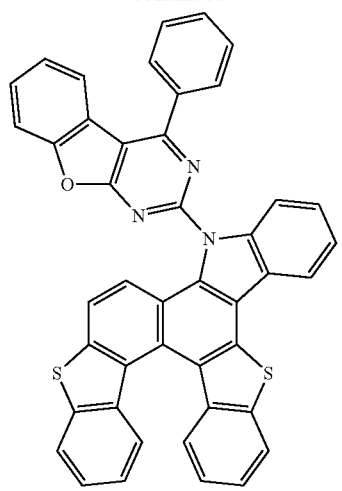
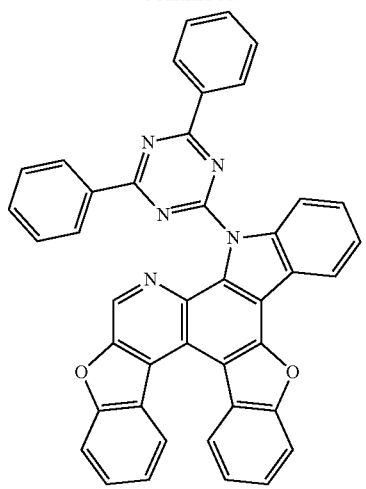
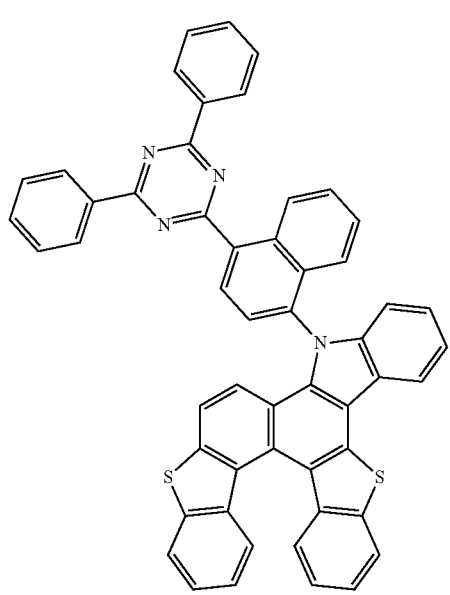
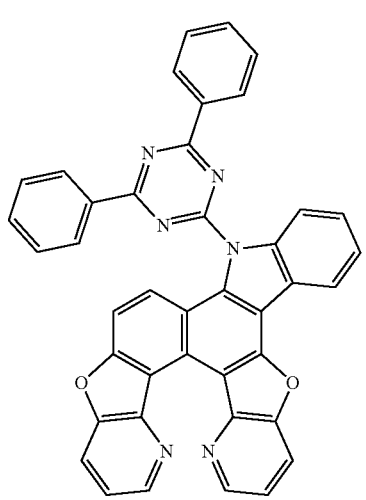
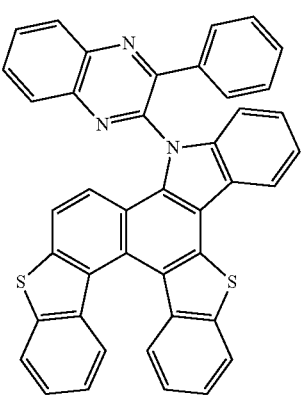
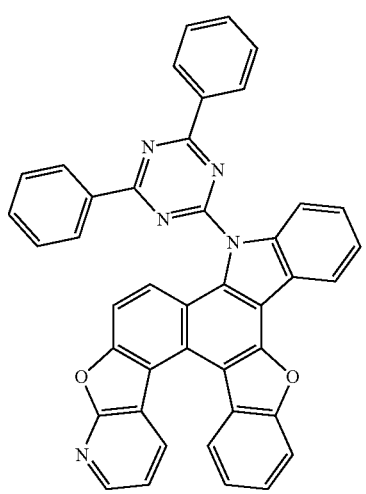

83
-continued
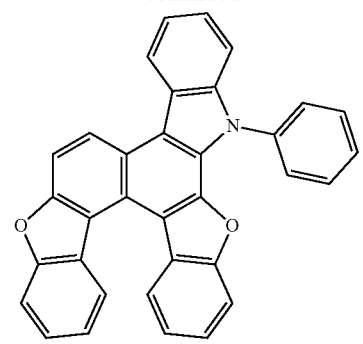
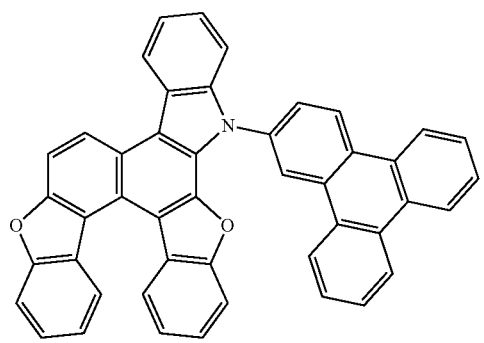
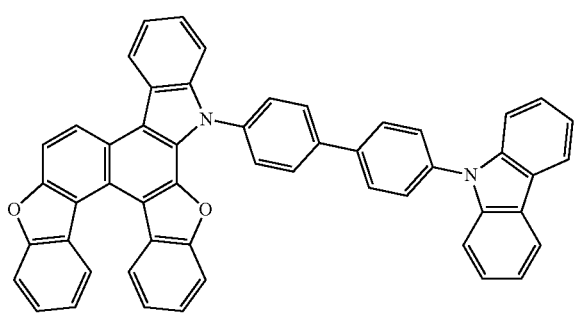
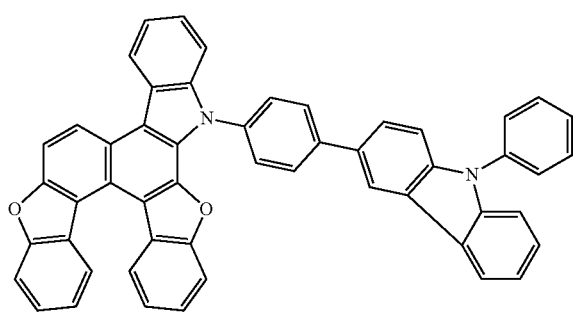
84
-continued
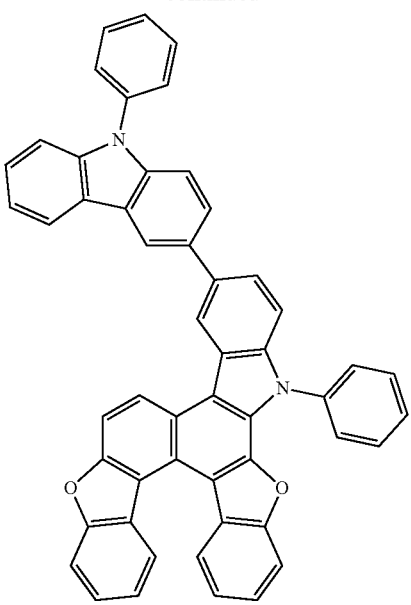
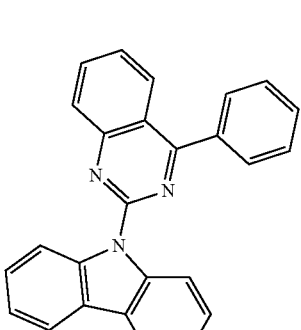
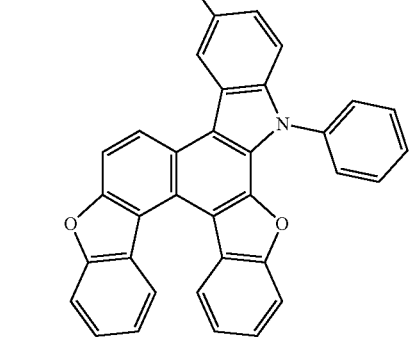

85
-continued
86
-continued
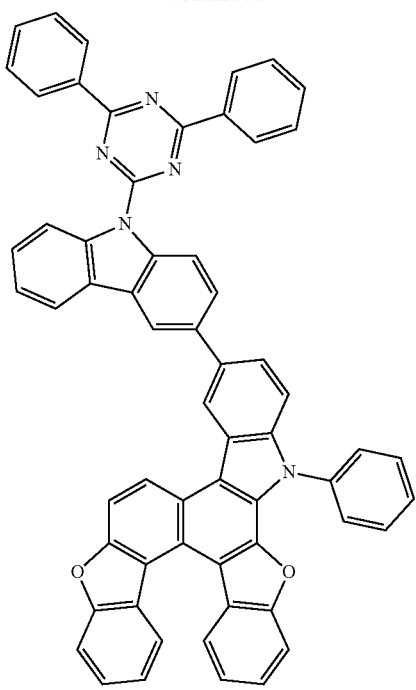
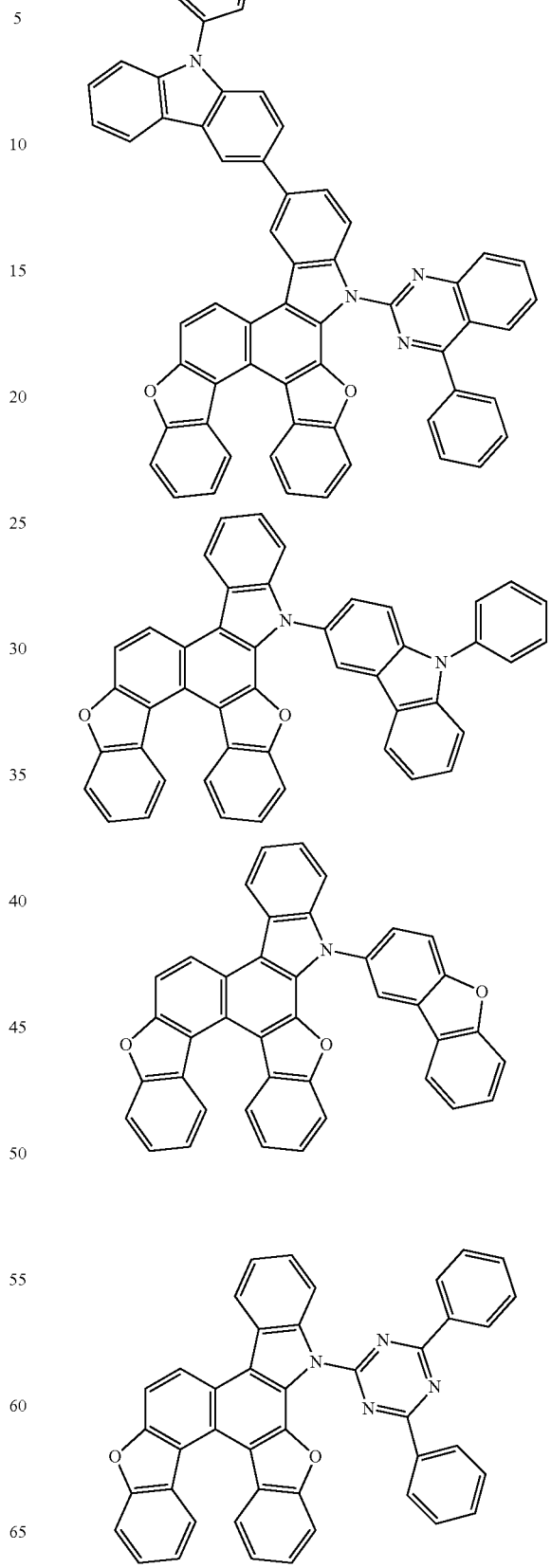

87
-continued
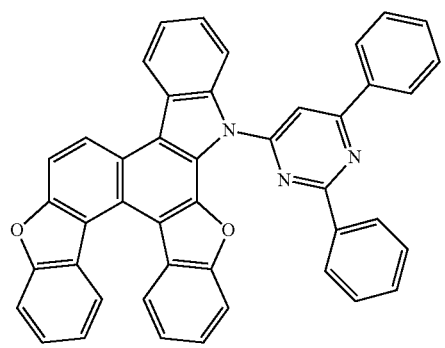
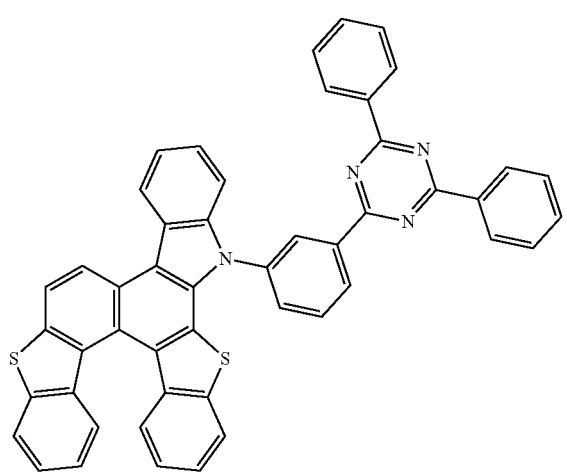
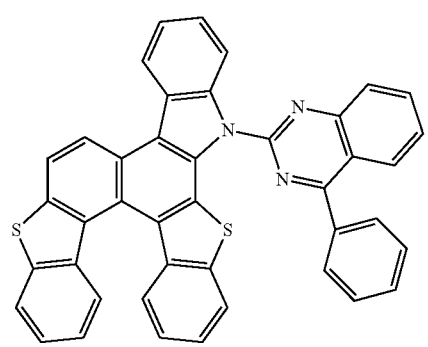
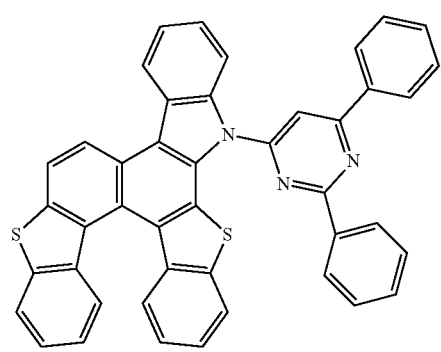
88
-continued
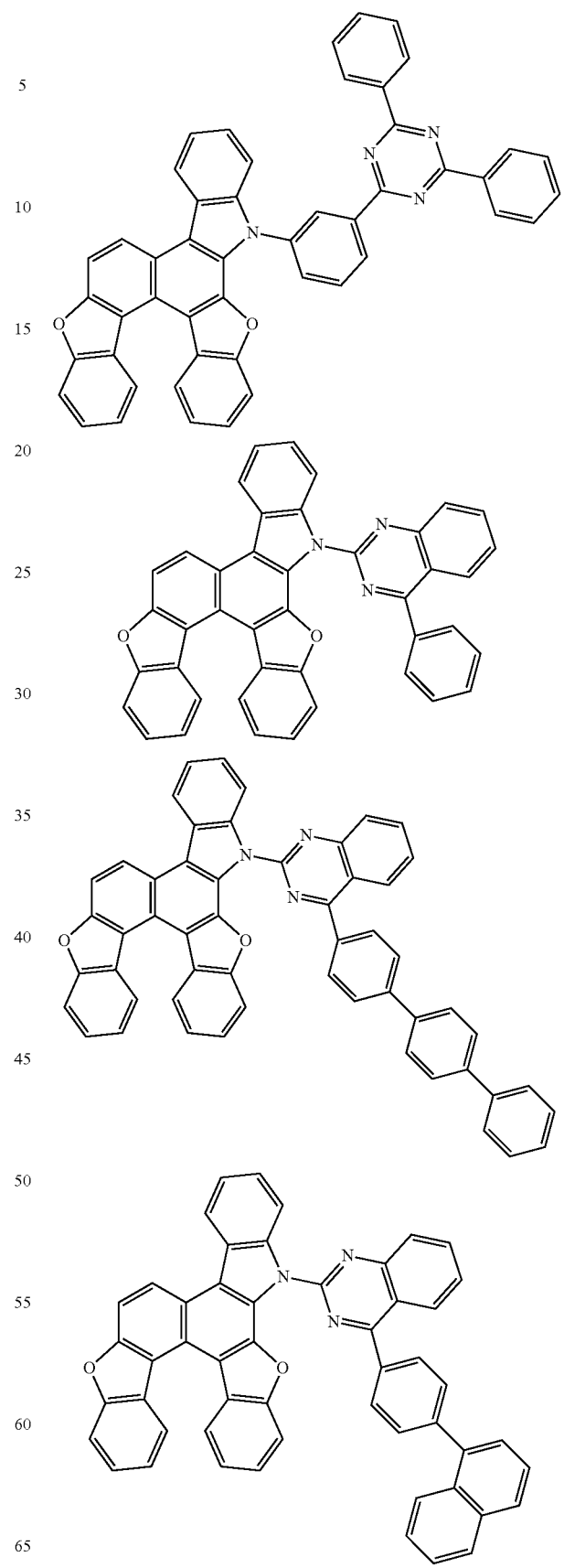

89
-continued
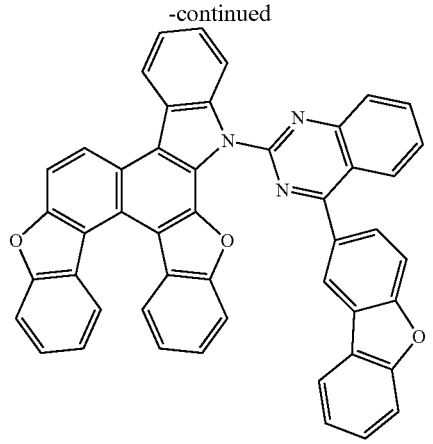
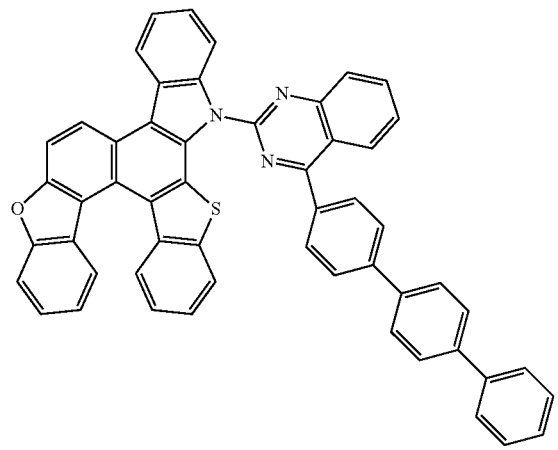
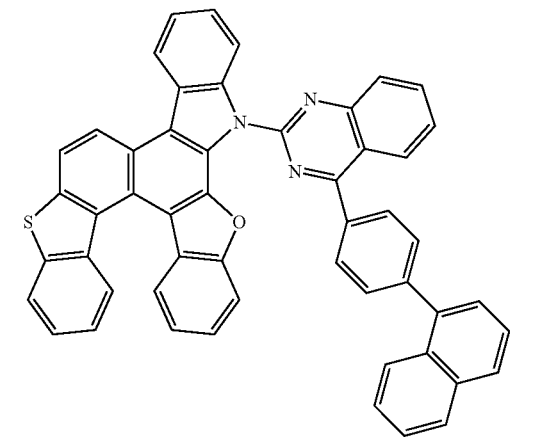
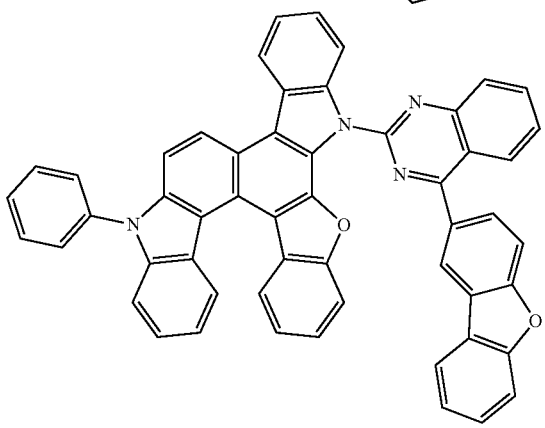
90
-continued
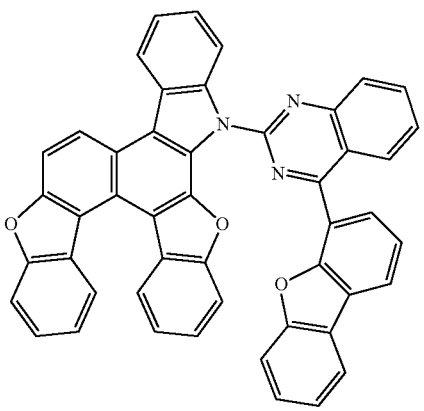
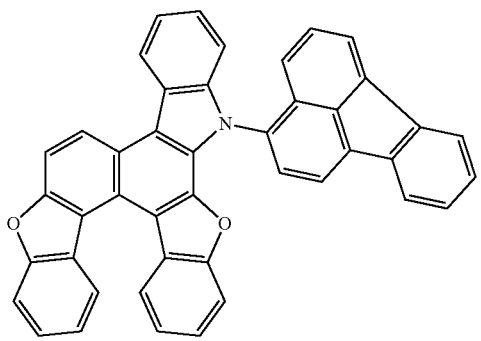
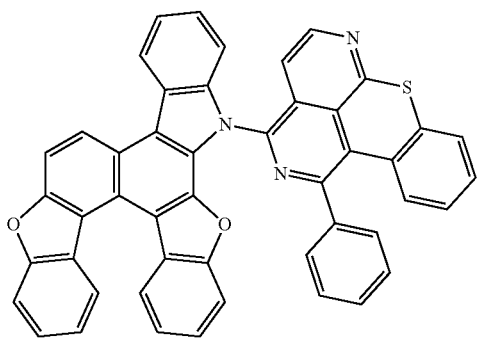

91
-continued
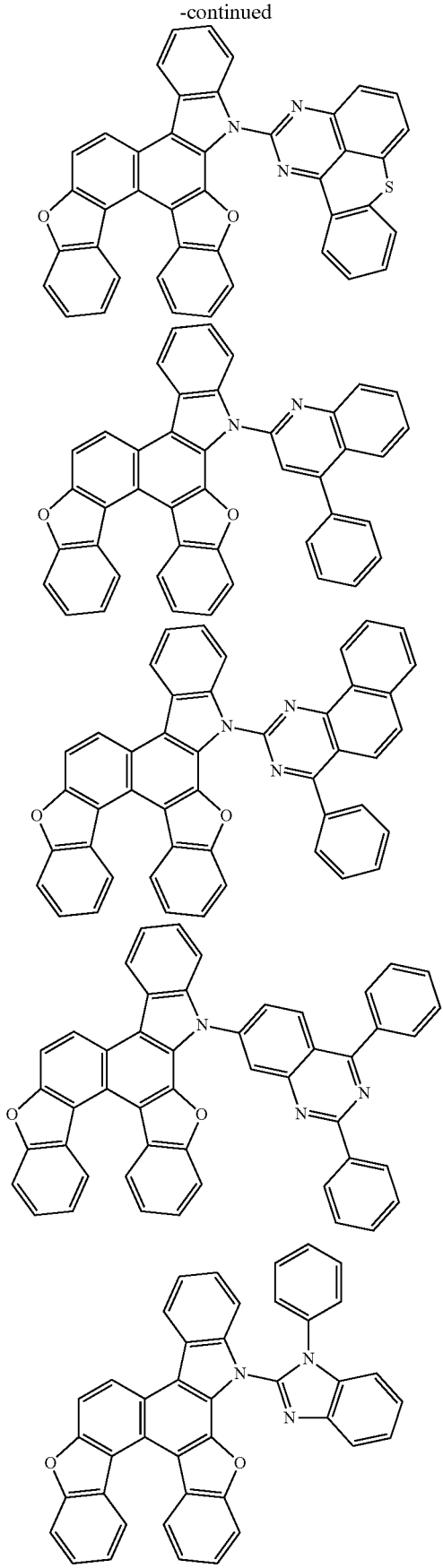
92
-continued
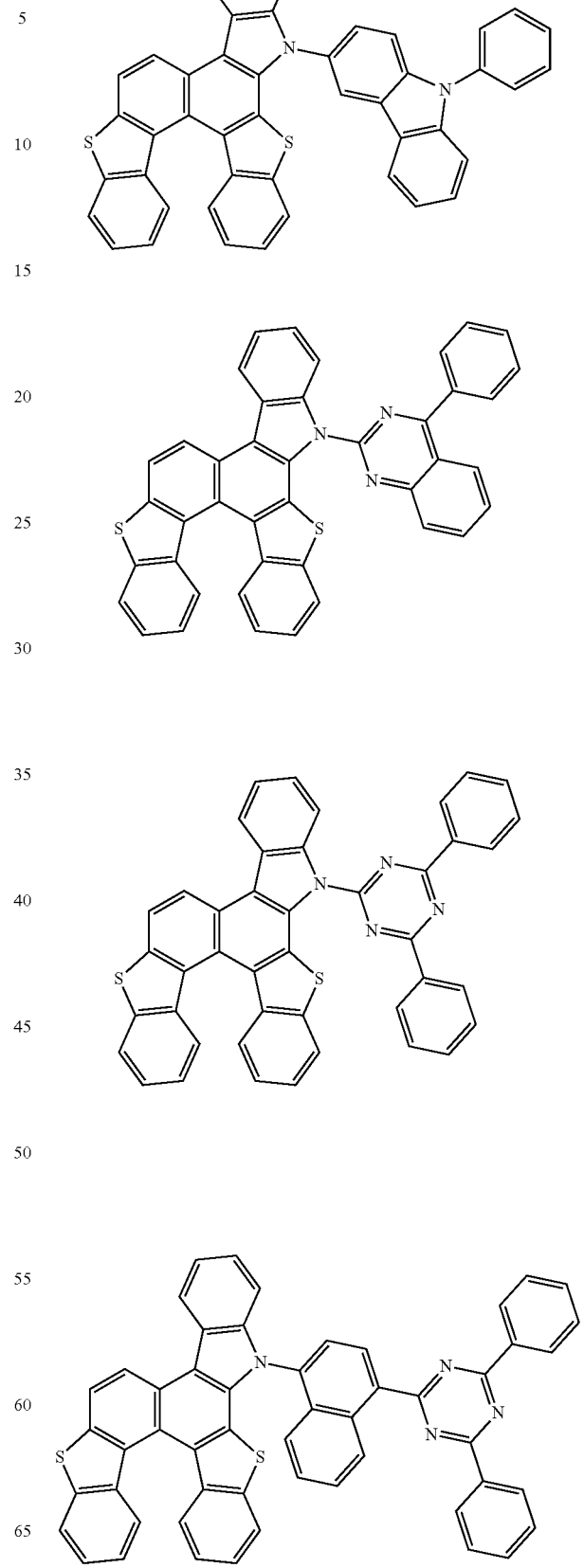

93
-continued
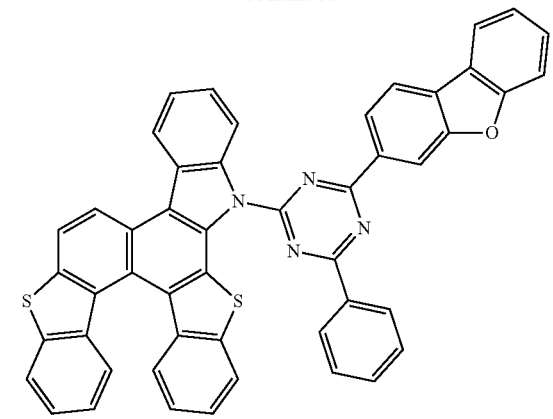
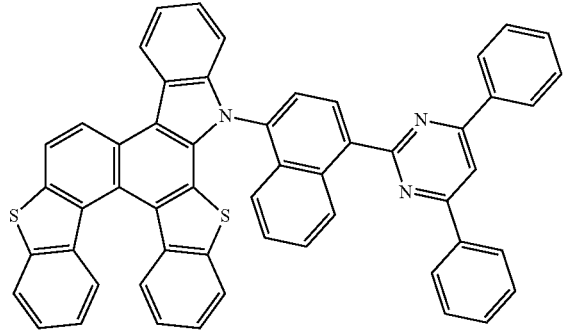
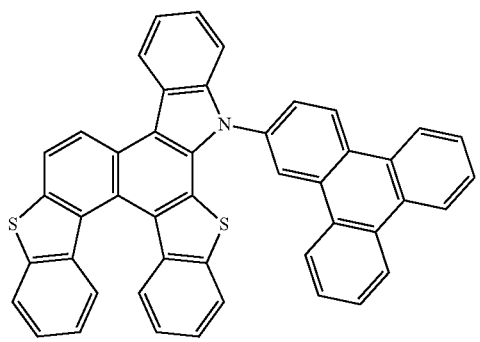
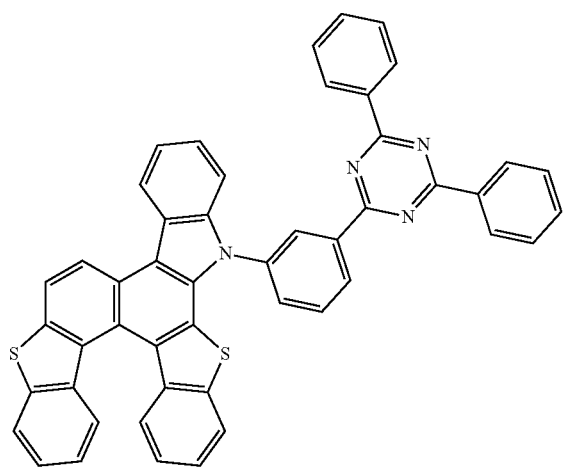
94
-continued
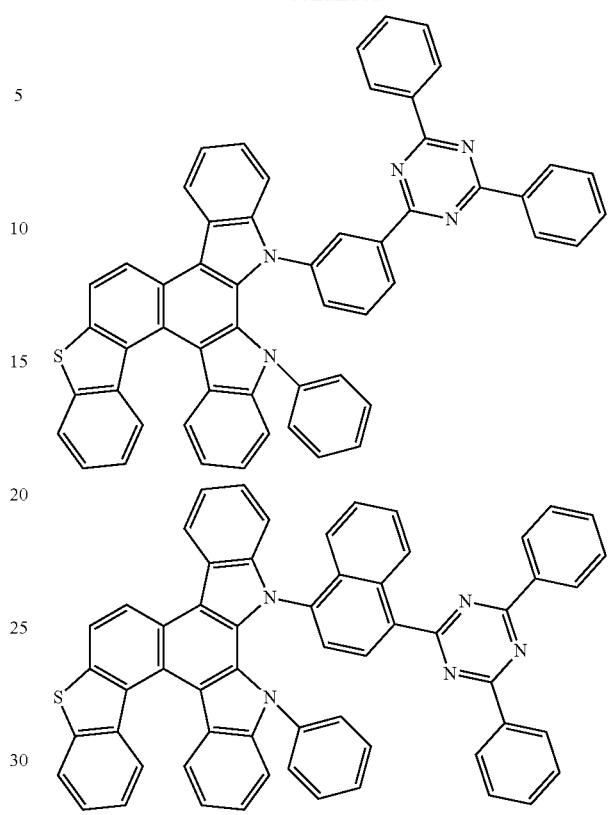
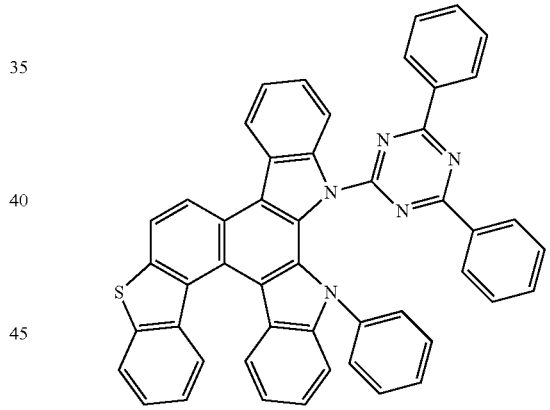
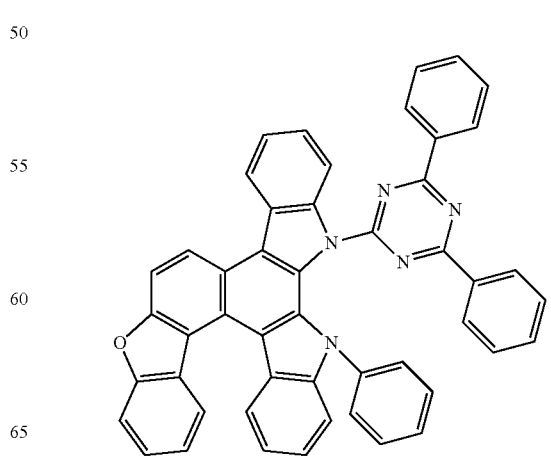

95
-continued
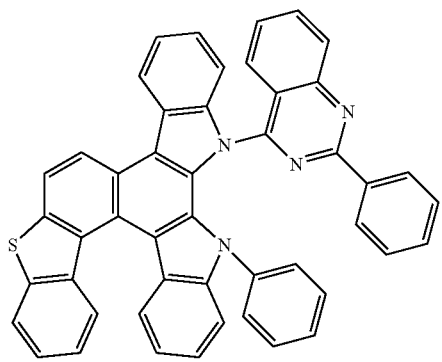
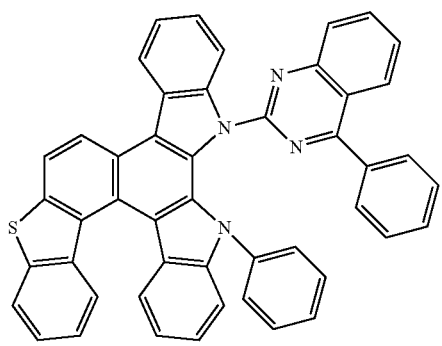
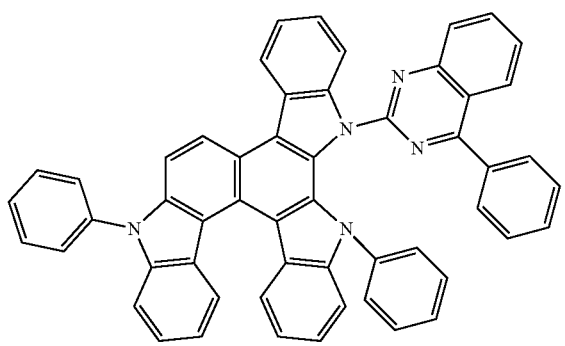
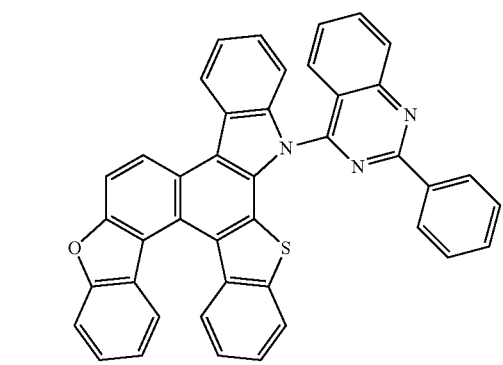
96
-continued
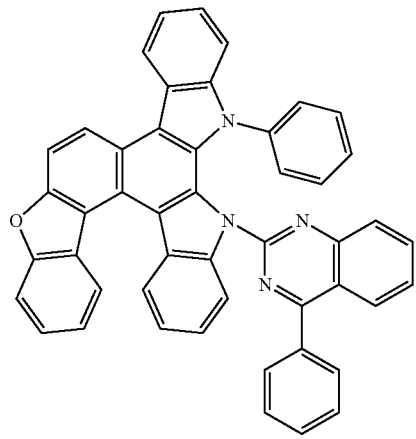
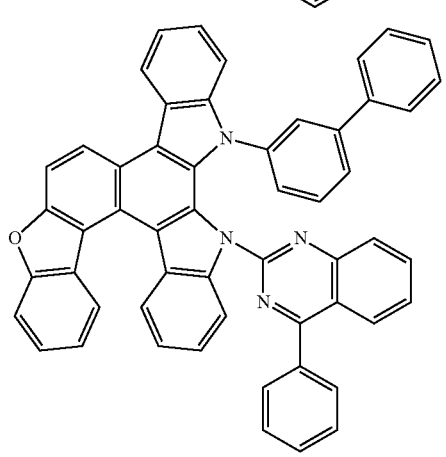
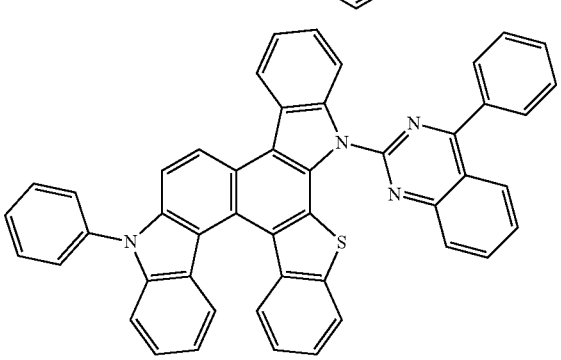
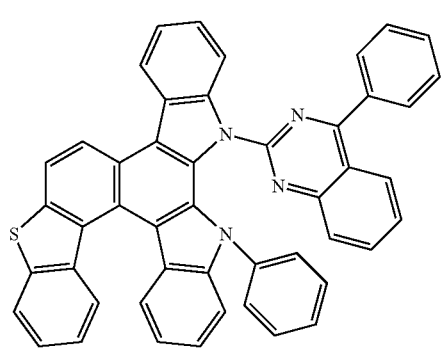

-continued
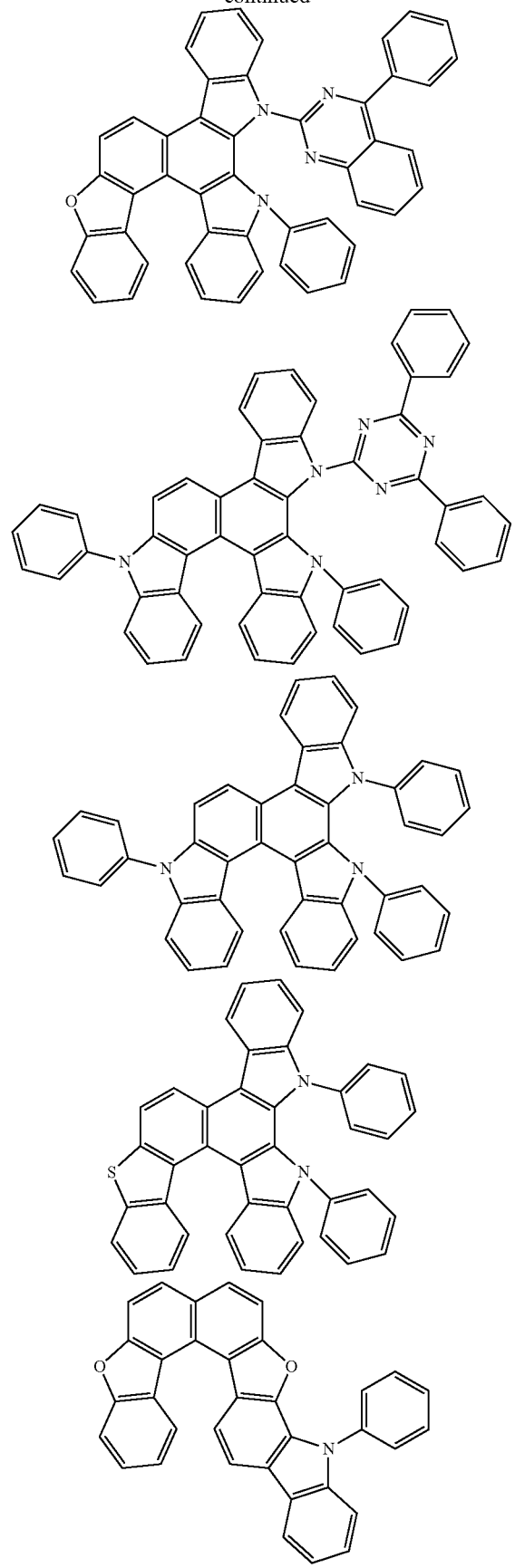
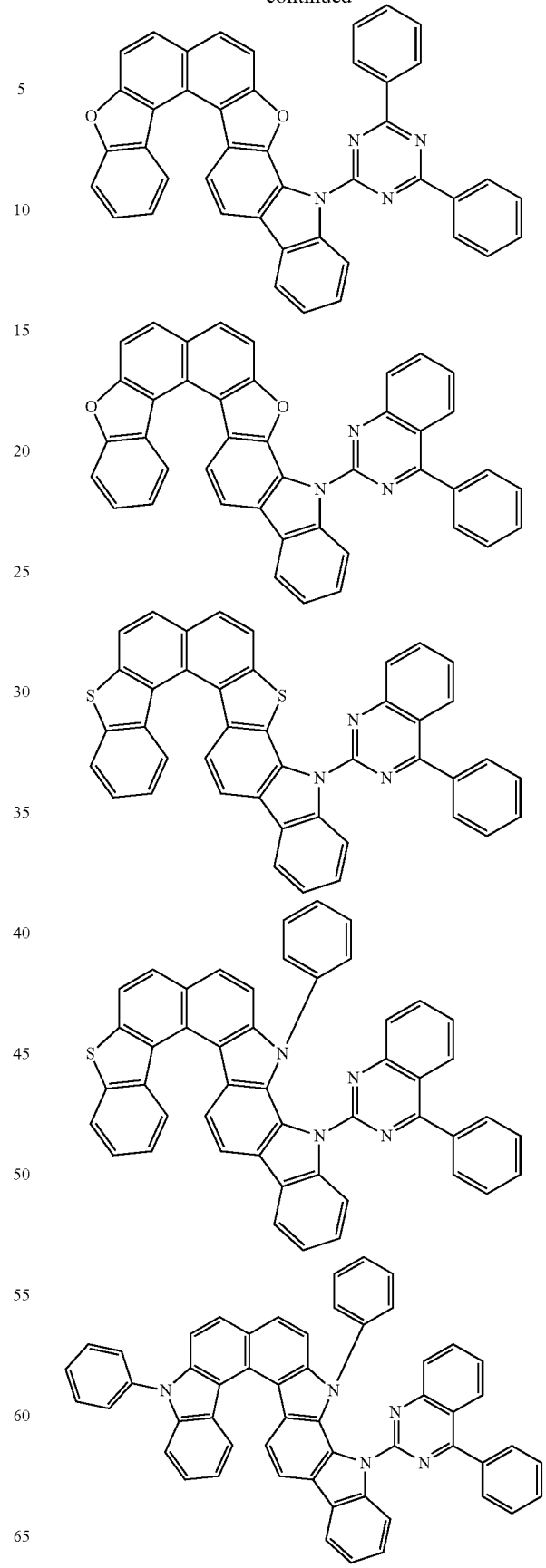

99
-continued
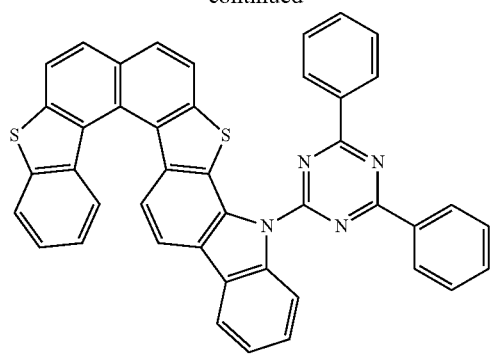
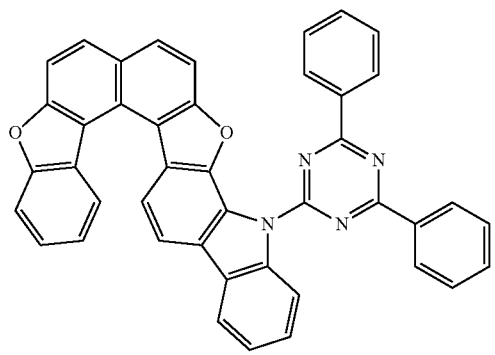
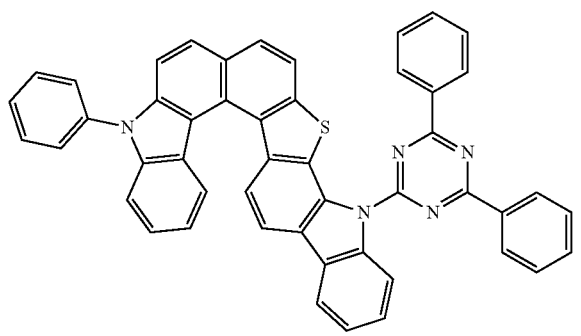
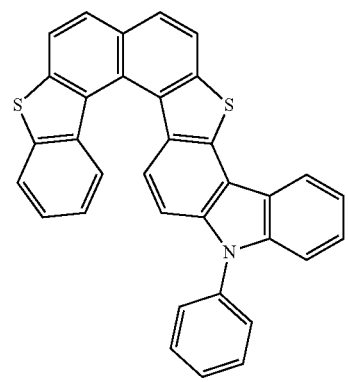
100
-continued
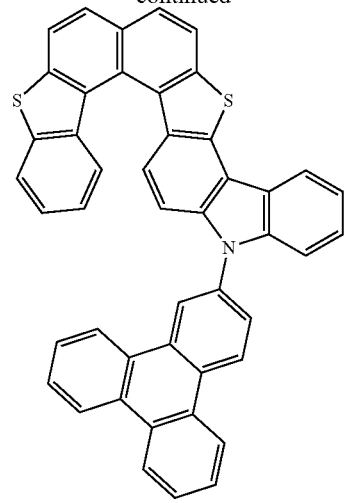
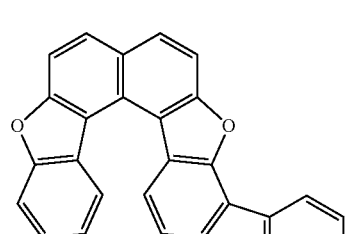
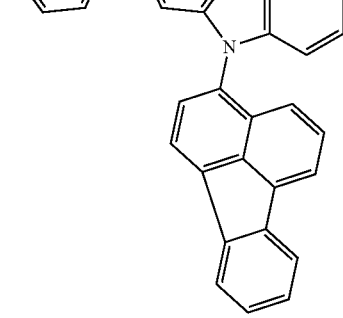
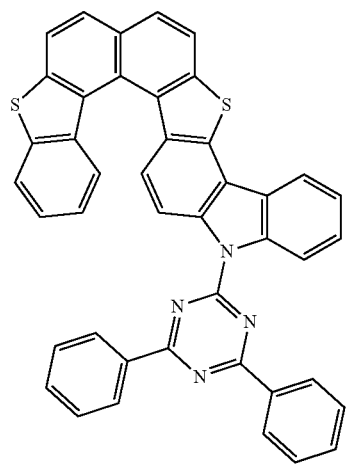

101
-continued
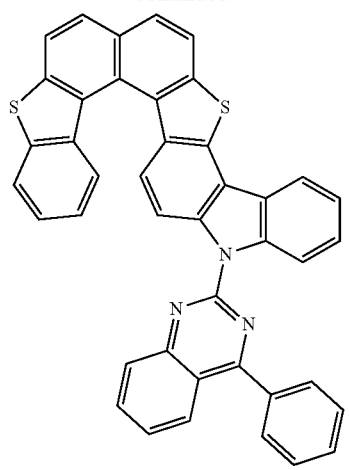
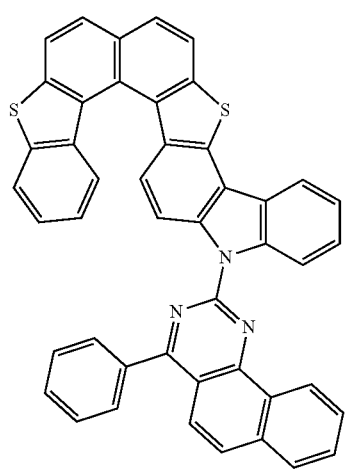
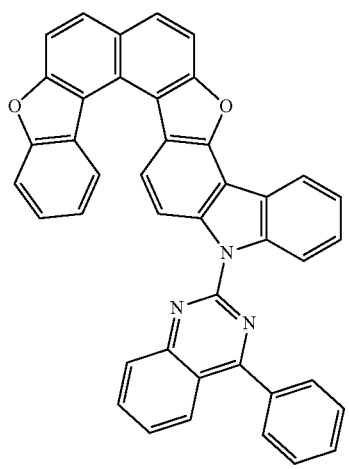
102
-continued
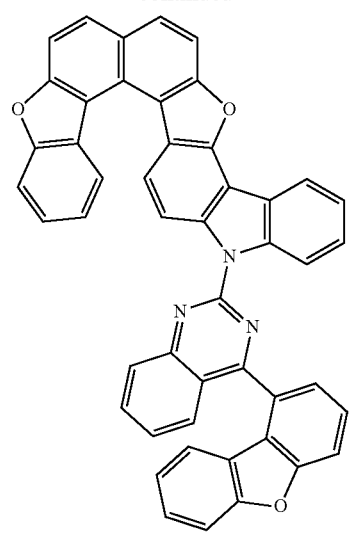
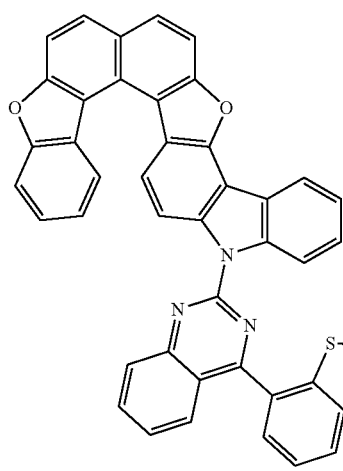
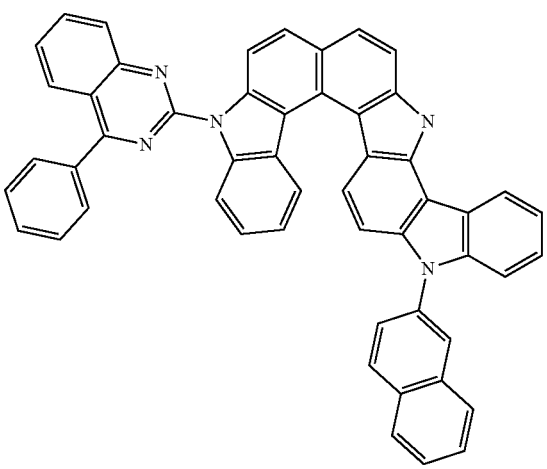

103
-continued
104
-continued
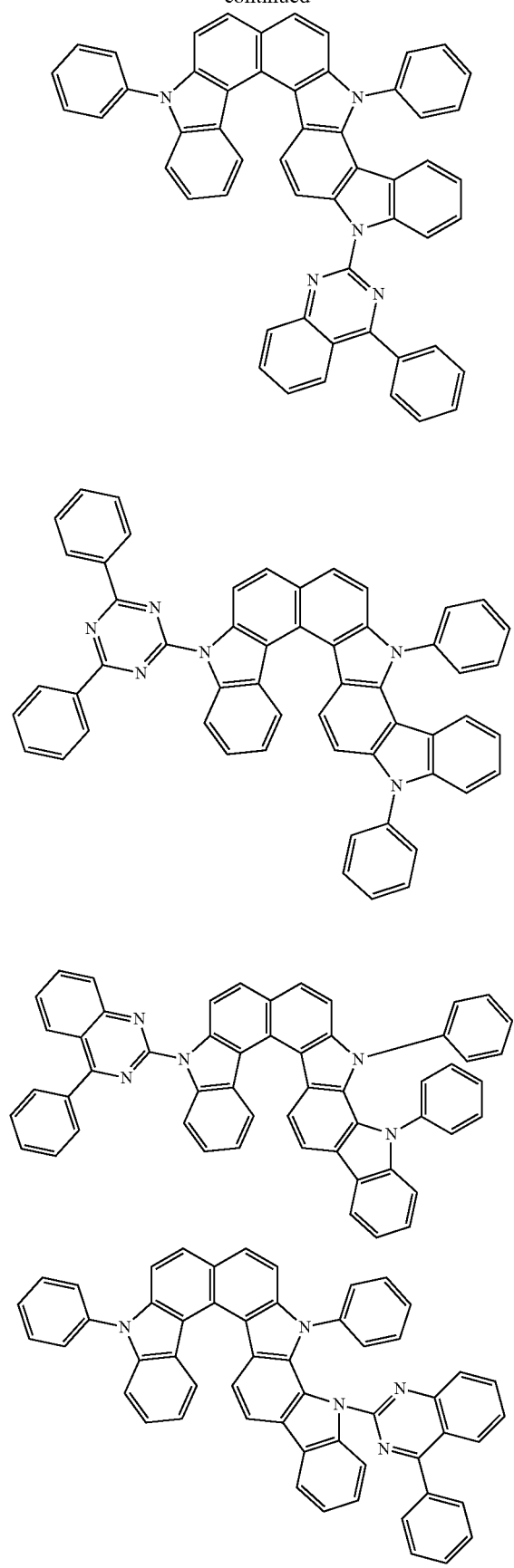

105
-continued
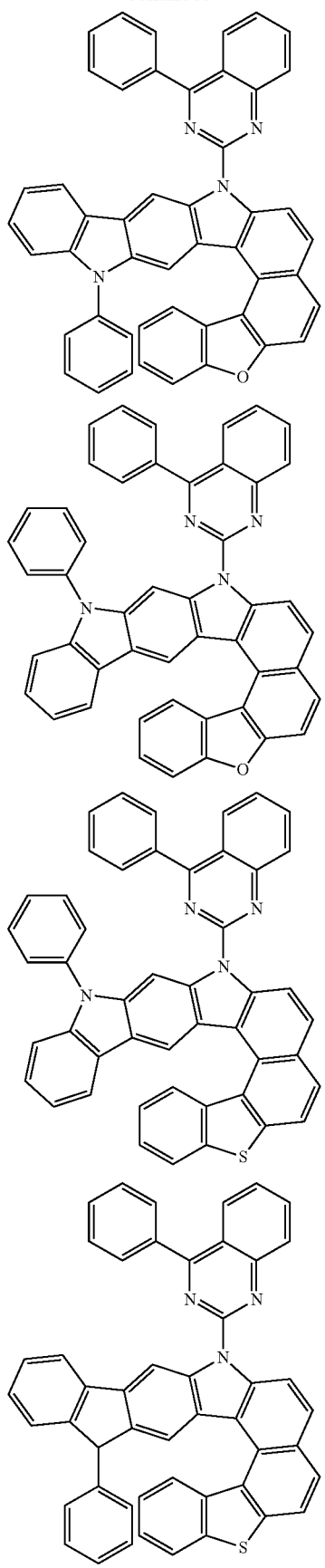
106
-continued
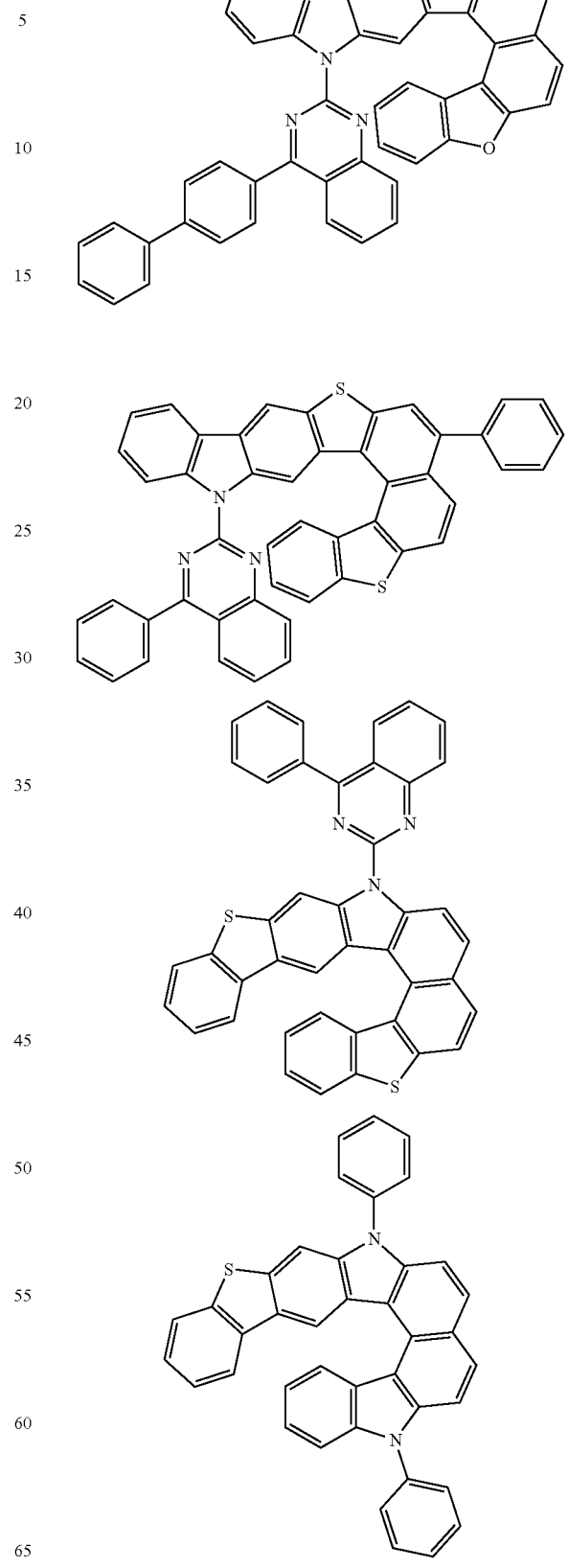

107
-continued
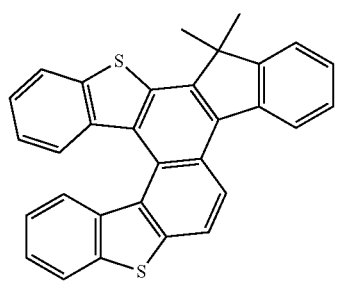
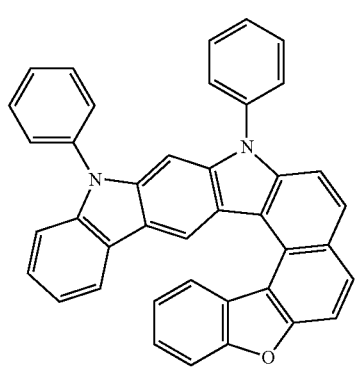
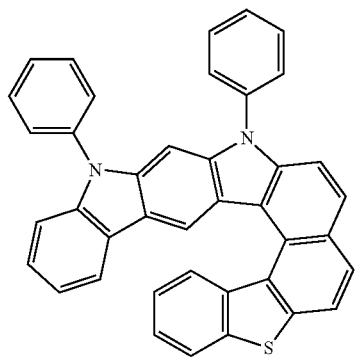
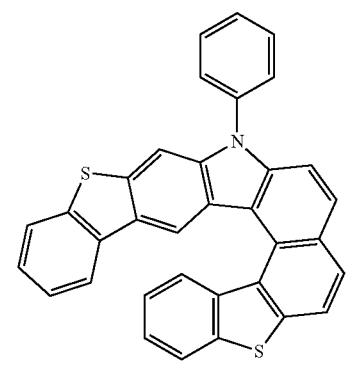
108
-continued
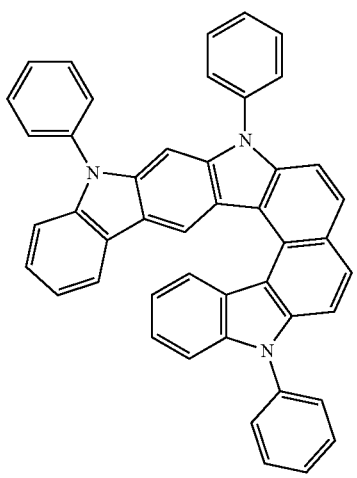
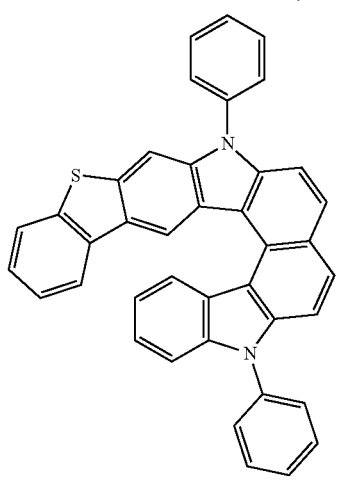
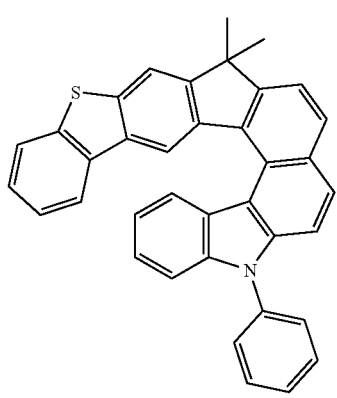
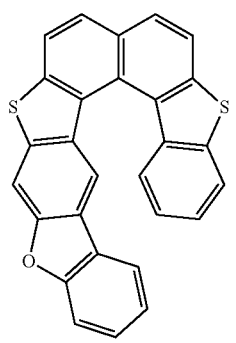

-continued
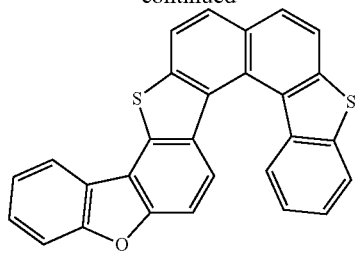
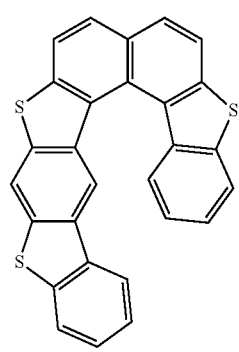
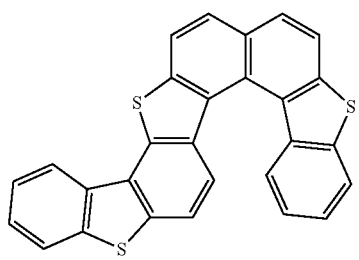
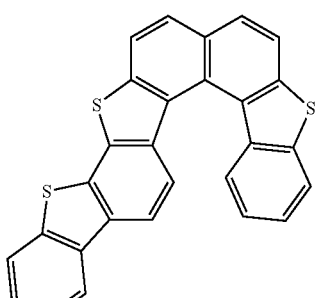
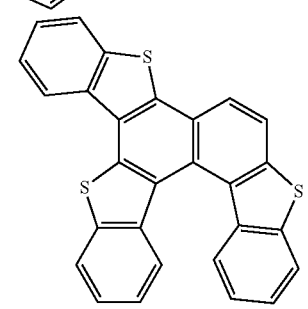
-continued
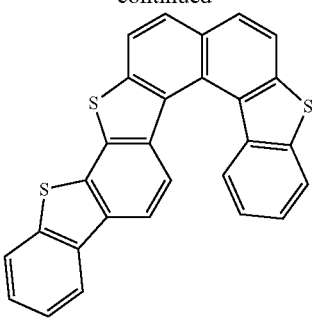
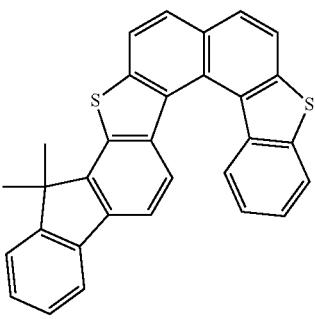
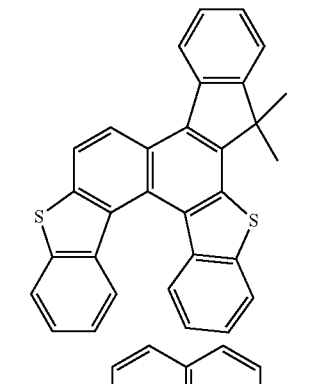
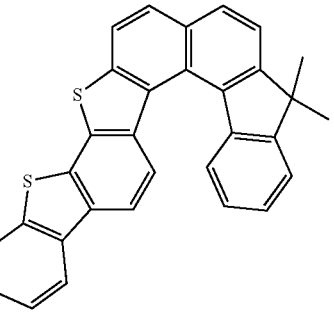
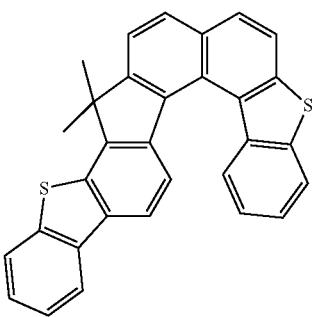

111
-continued
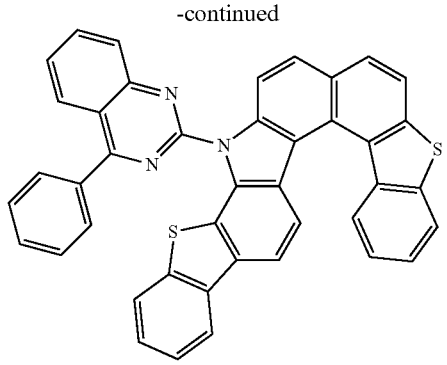
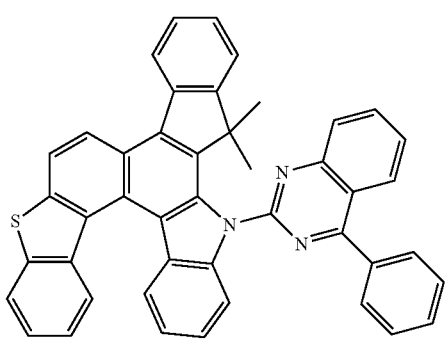
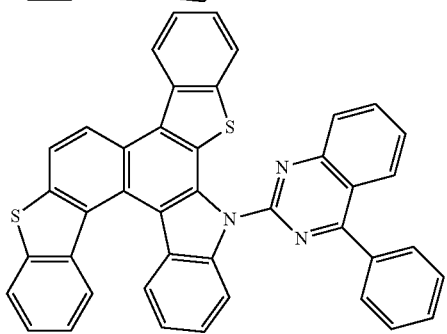
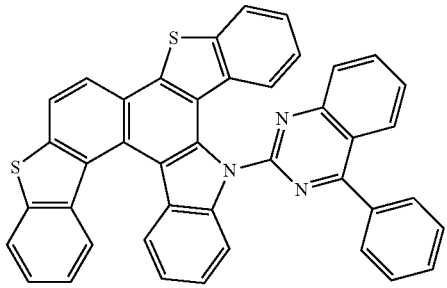
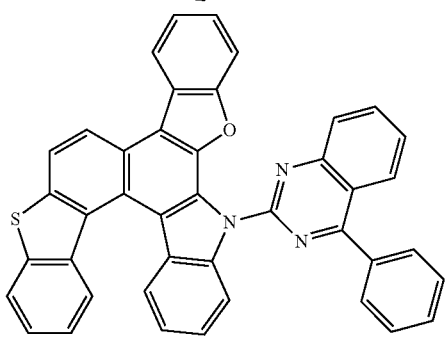
112
-continued
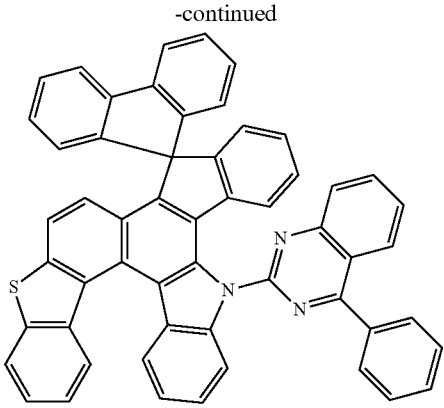
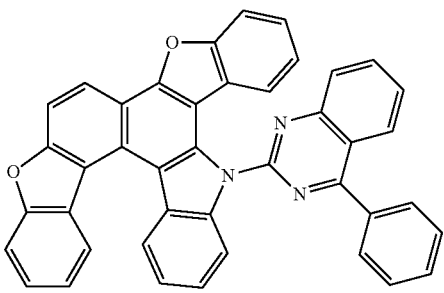
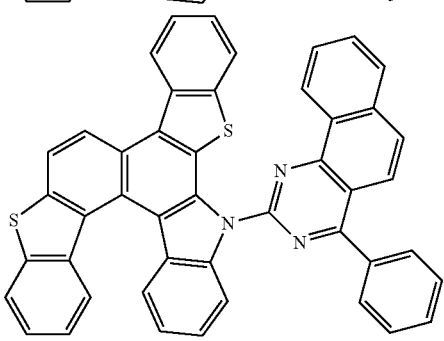
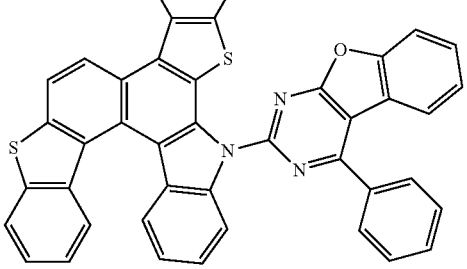
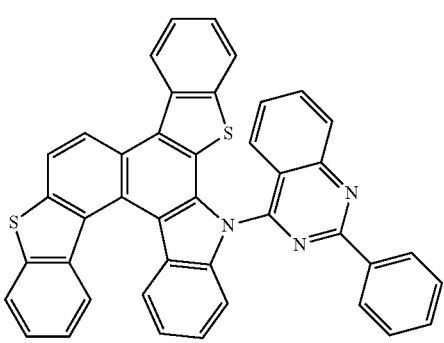

-continued
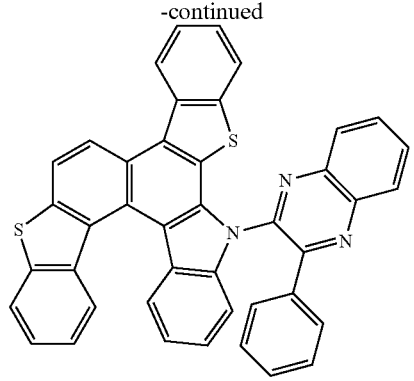
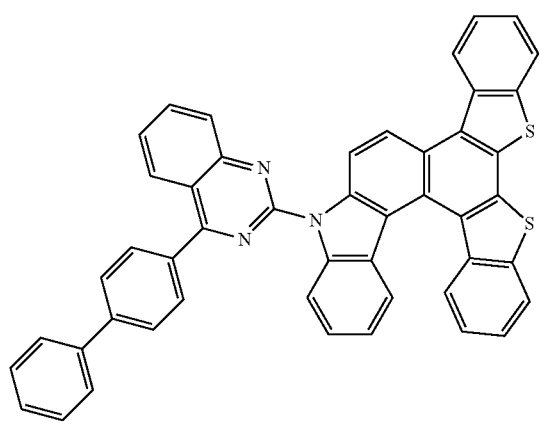
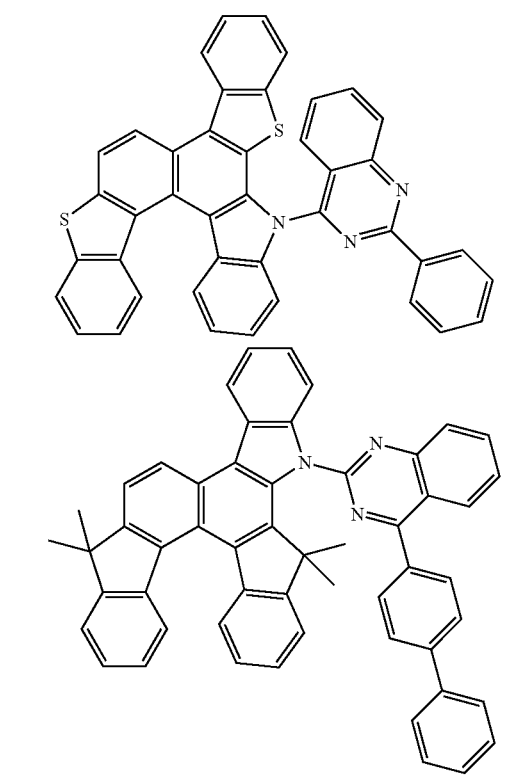
-continued
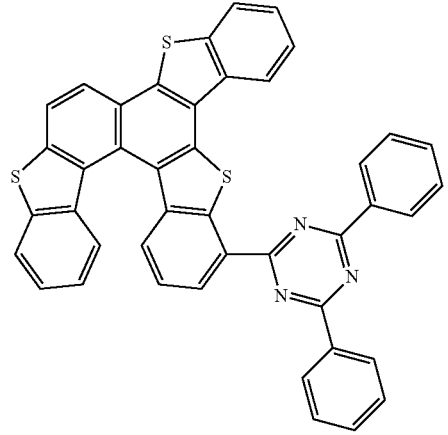
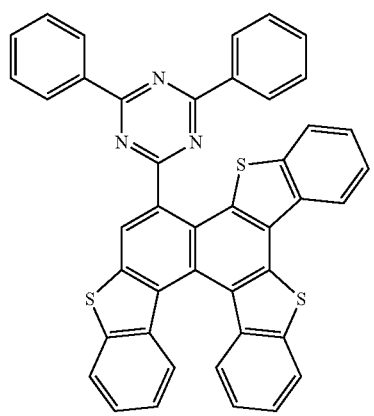
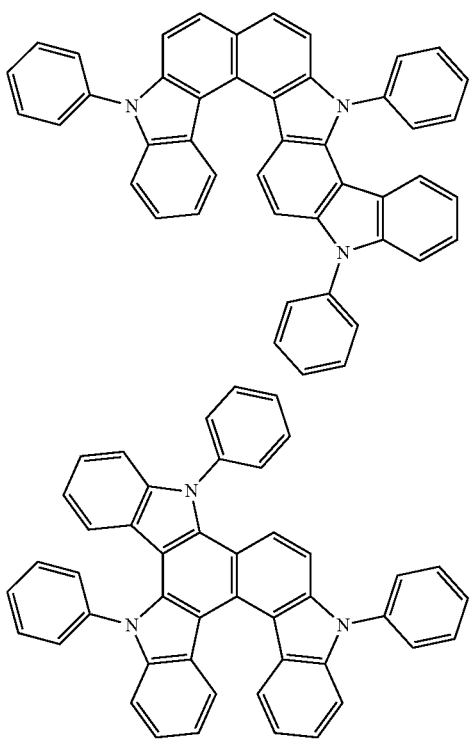

115
-continued
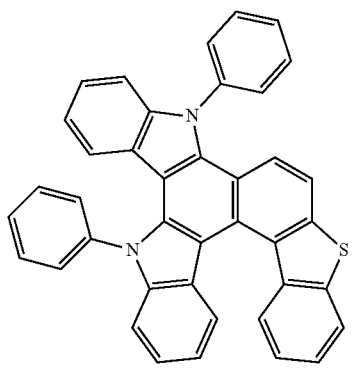
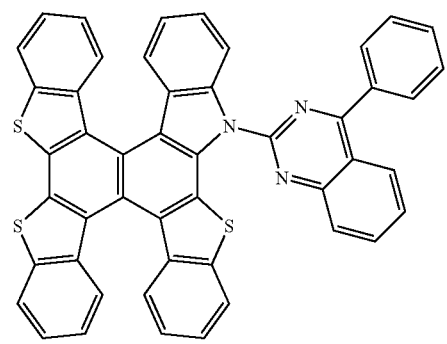
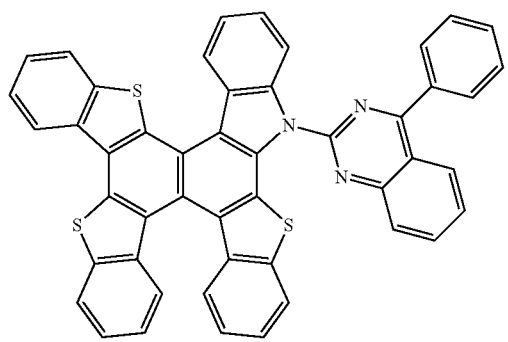
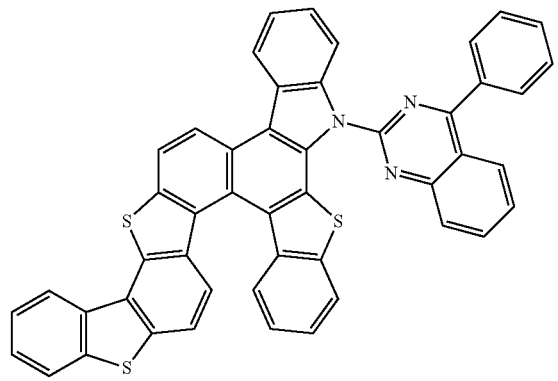
116
-continued
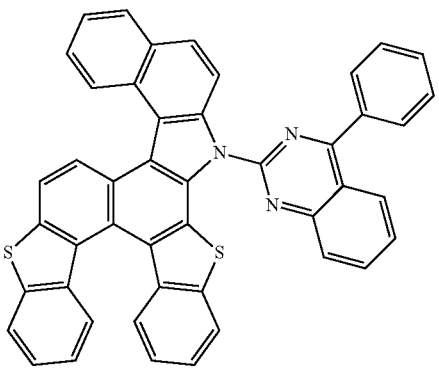
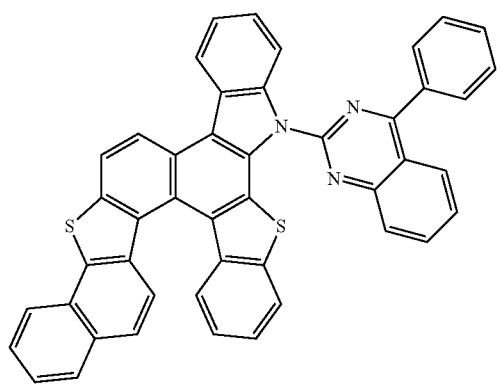
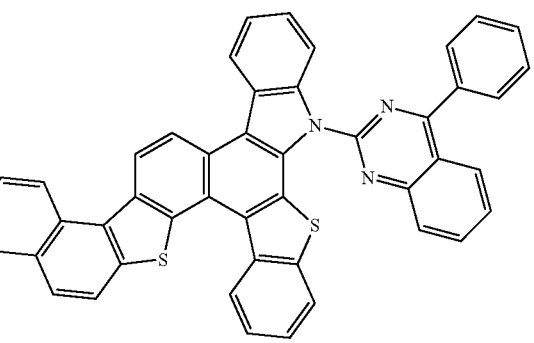
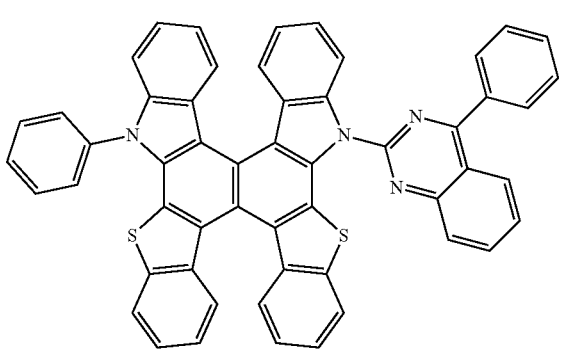

117
-continued
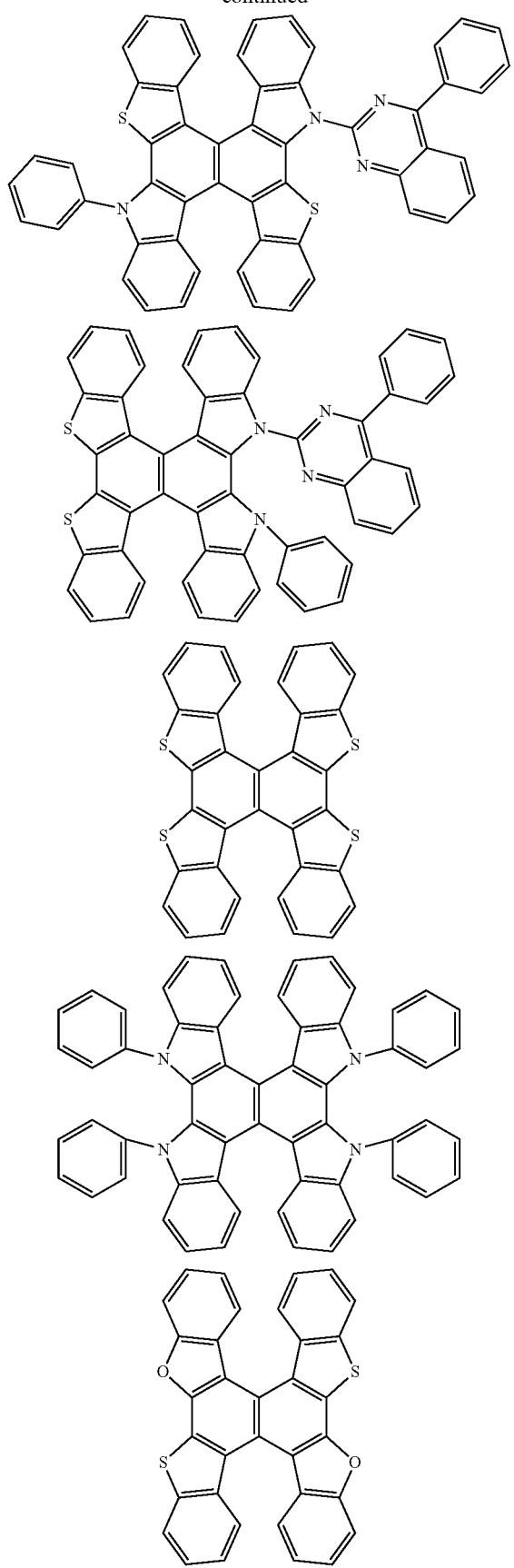
118
-continued
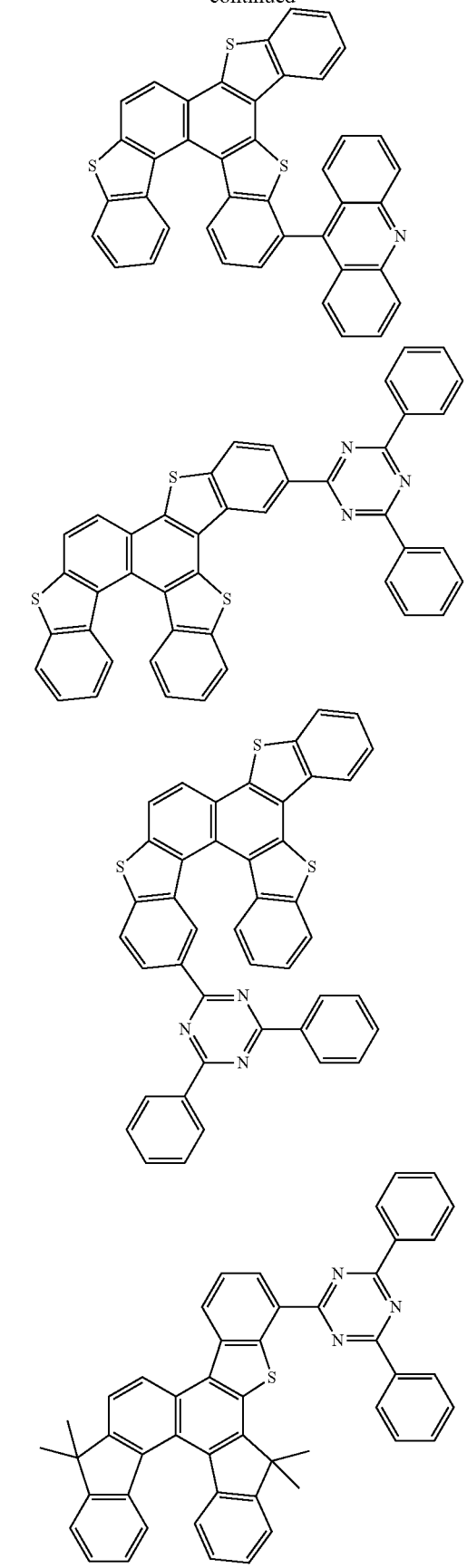

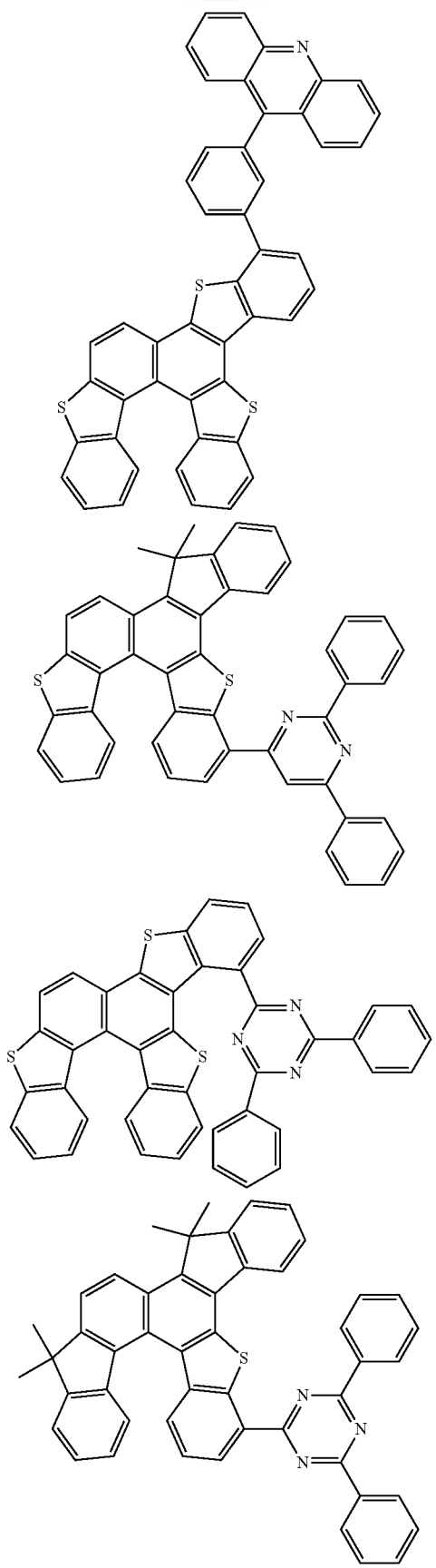
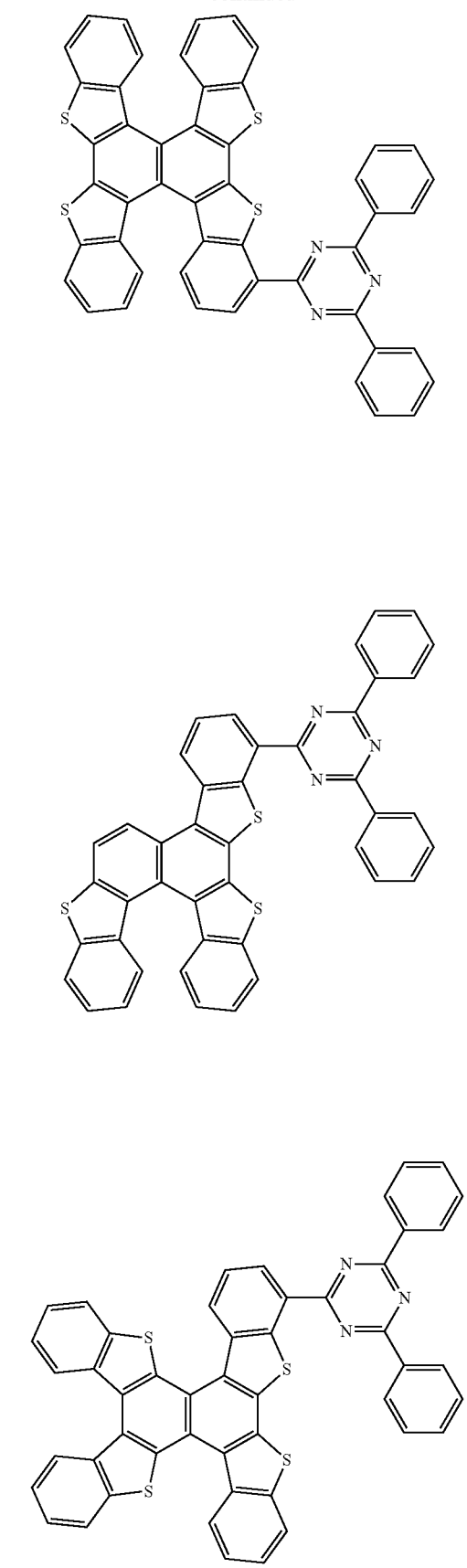

121
-continued
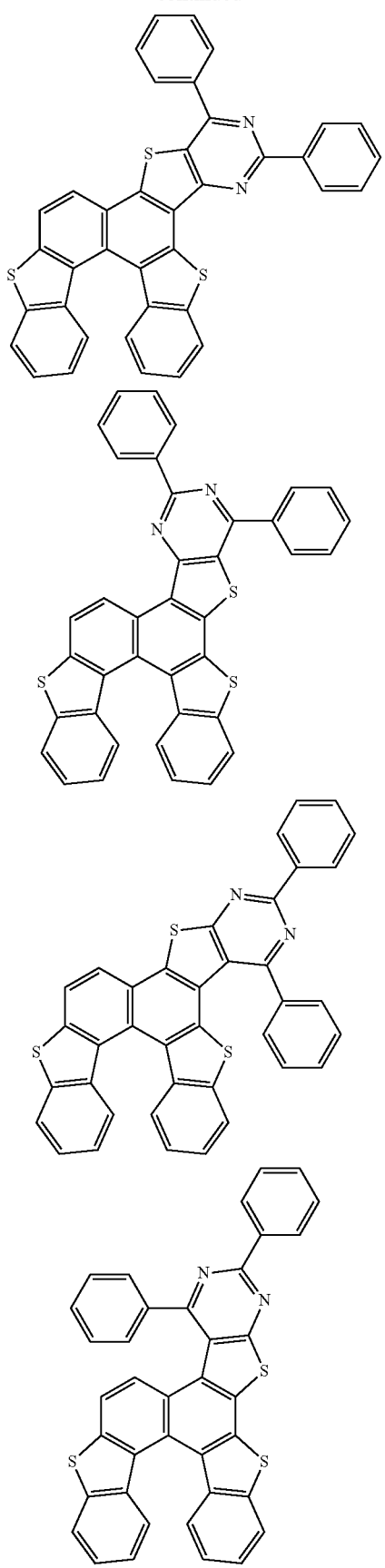
122
-continued
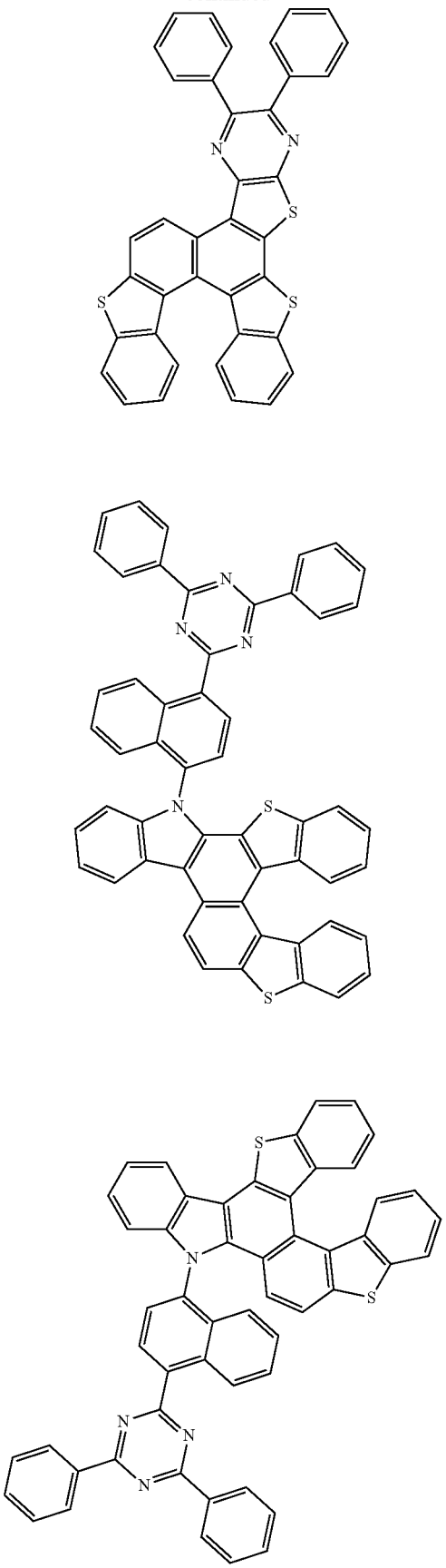 [SMILES: c1ccc(-c2nc3sc4c5sc6ccccc6c5c5c(ccc6sc7ccccc7c65)c4c3nc2-c2ccccc2)cc1 ; c1ccc(-c2nc(-c3ccccc3)nc(-c3ccc(-n4c5ccccc5c5c6ccc7sc8ccccc8c7c6c6c7ccccc7sc6c54)c4ccccc34)n2)cc1 ; c1ccc(-c2nc(-c3ccccc3)nc(-c3ccc(-n4c5ccccc5c5c6sc7ccccc7c6c6c(ccc7sc8ccccc8c76)c54)c4ccccc34)n2)cc1]

123
-continued

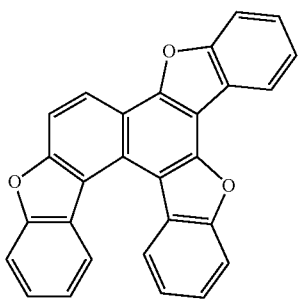

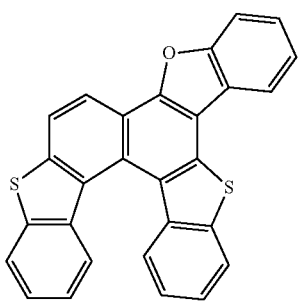

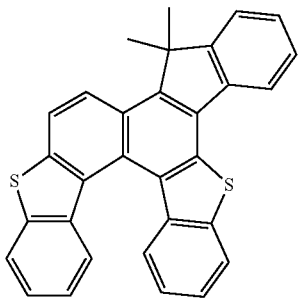

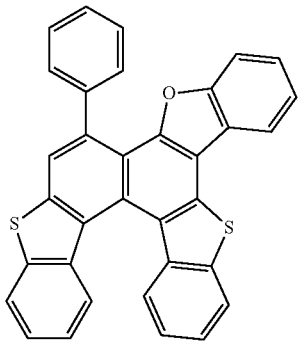

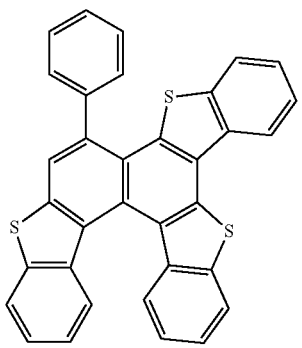

124
-continued

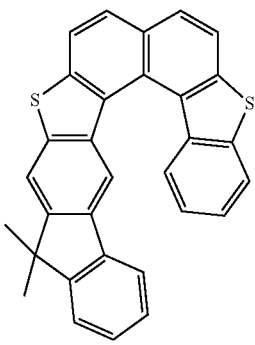

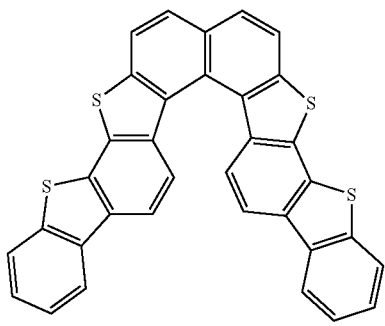

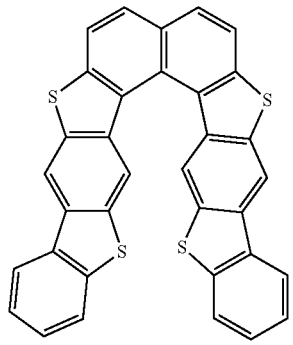

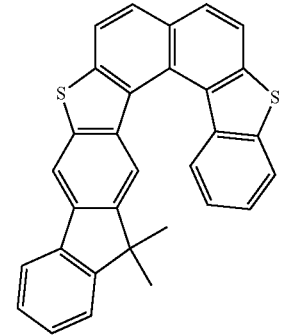

The basic structure of the compounds according to the invention can be prepared by the routes outlined in Scheme 1 to 4. Scheme 1 shows the synthesis of the basic structure, onto which no group of the formula (2) has yet been condensed. The group of the formula (2) can be condensed onto this basic structure by coupling and ring-formation reaction (Scheme 35N 2 to 4), where, for $Z^1$, $Z^2$ and/or $Z^3$ equal to N—Ar, the group Ar can then be introduced in a nucleophilic aromatic substitution or a coupling reaction.

Scheme 1 Synthesis of the precursors
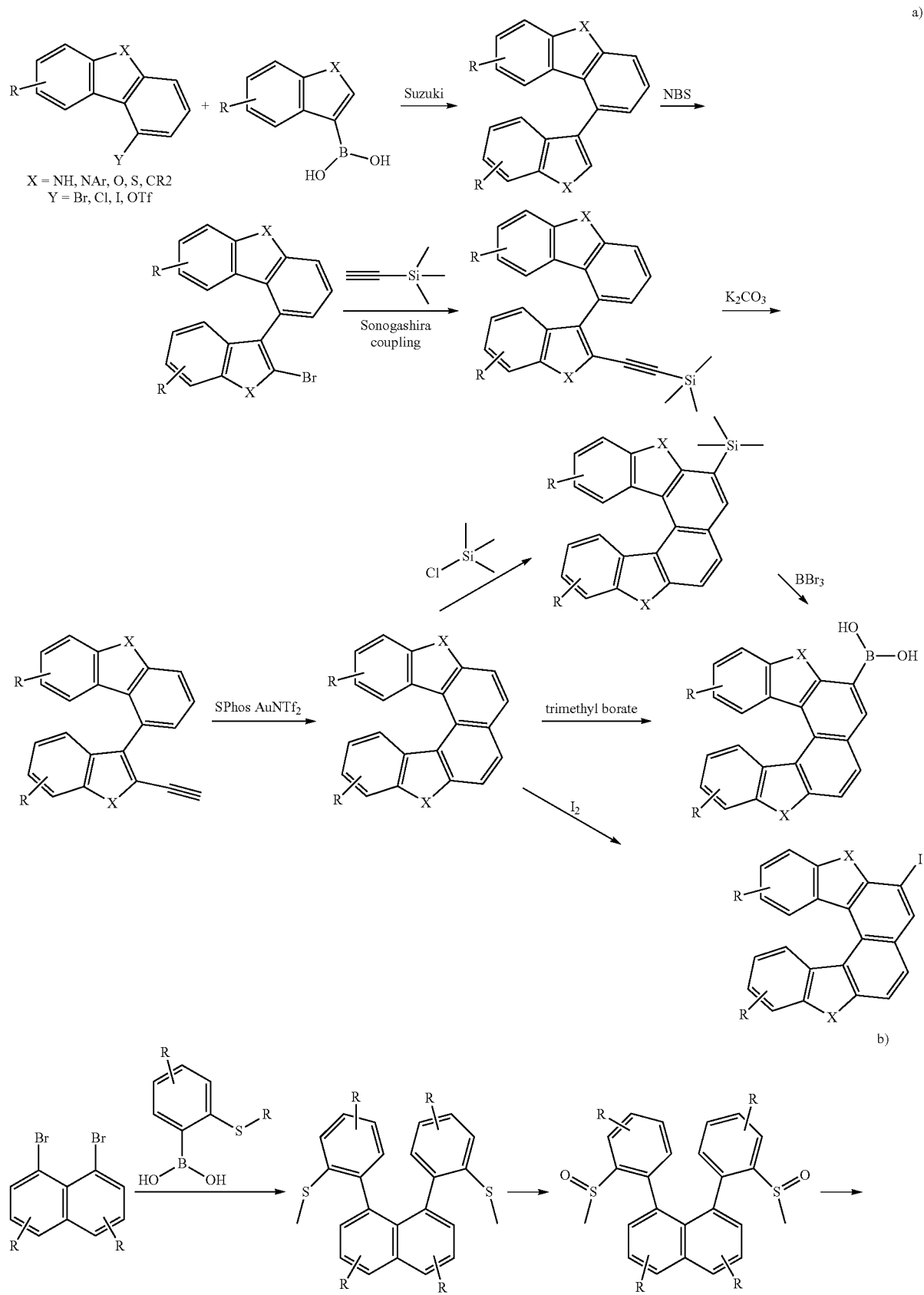

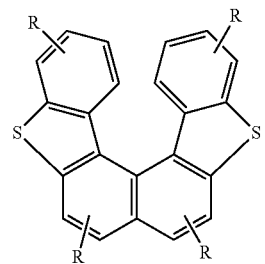
-continued
Scheme 2 Cyclisation and N-arylation
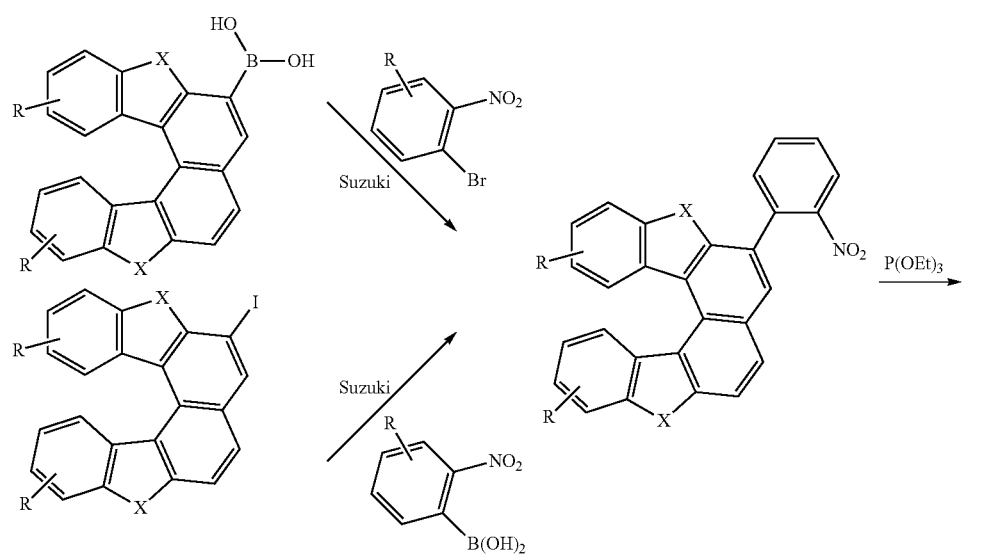
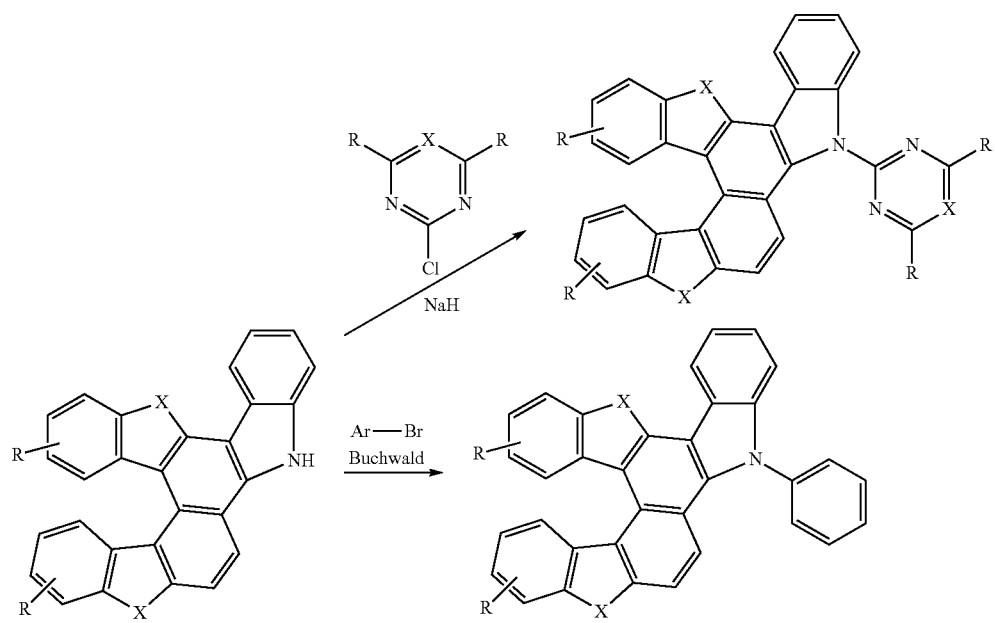

Scheme 3 Cyclisation and N-arylation
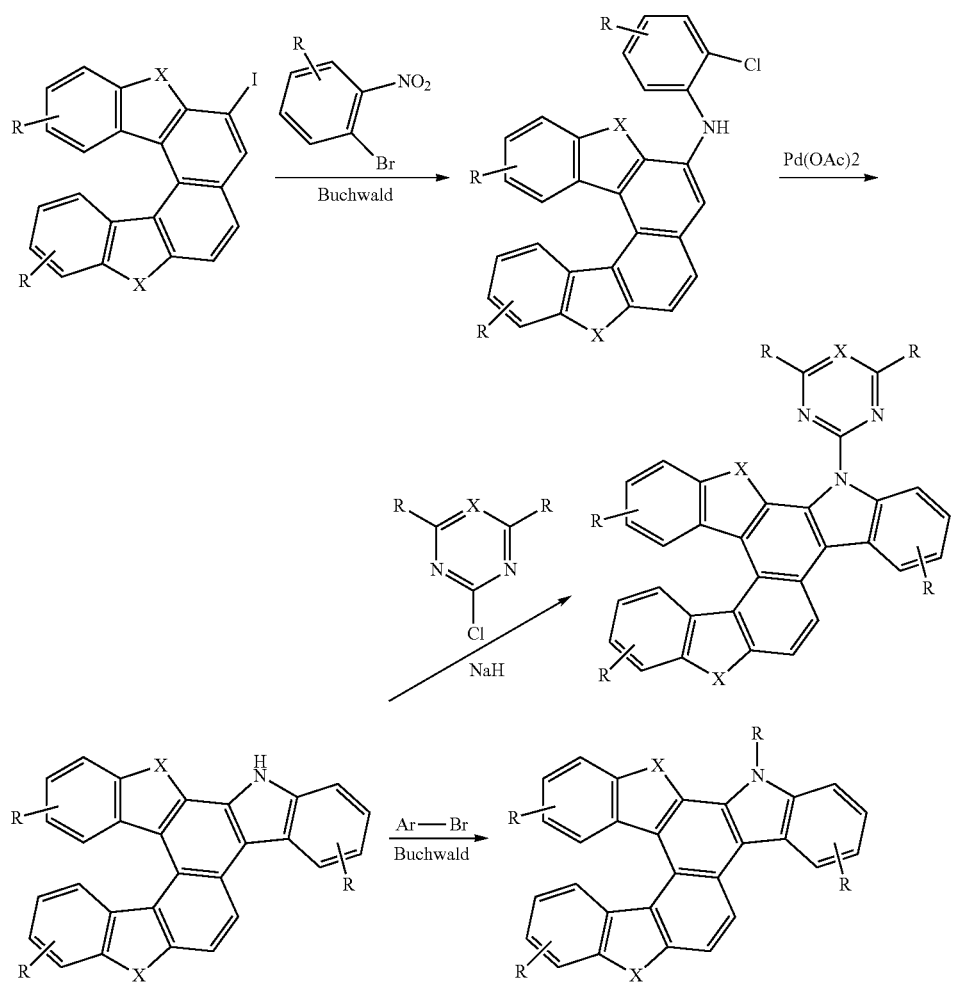
Scheme 4 Cyclisation
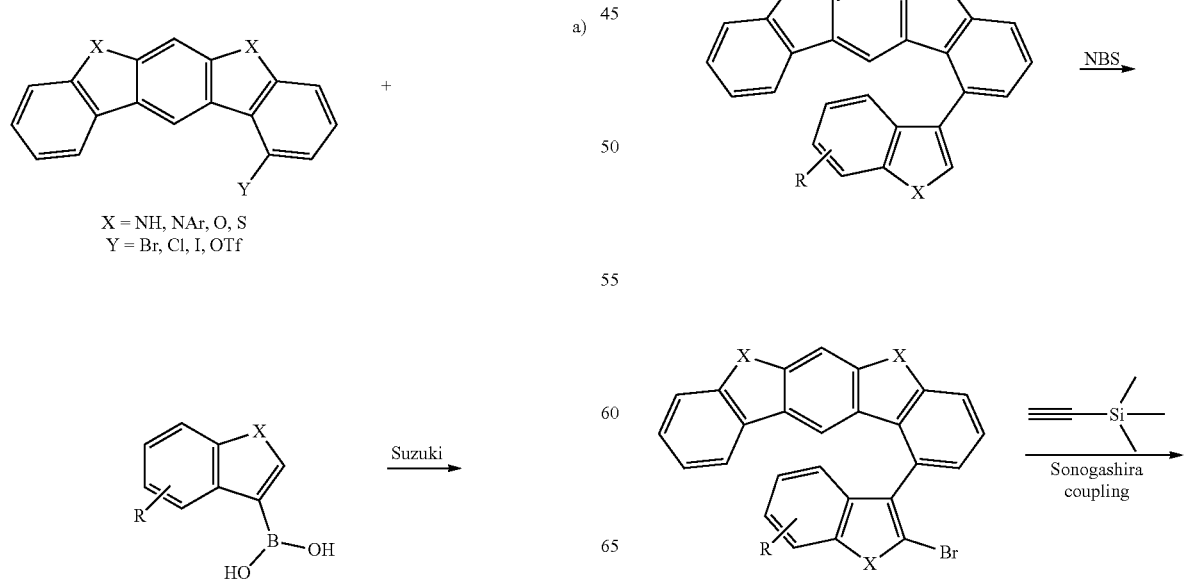
X = NH, NAr, O, S
Y = Br, Cl, I, OTf

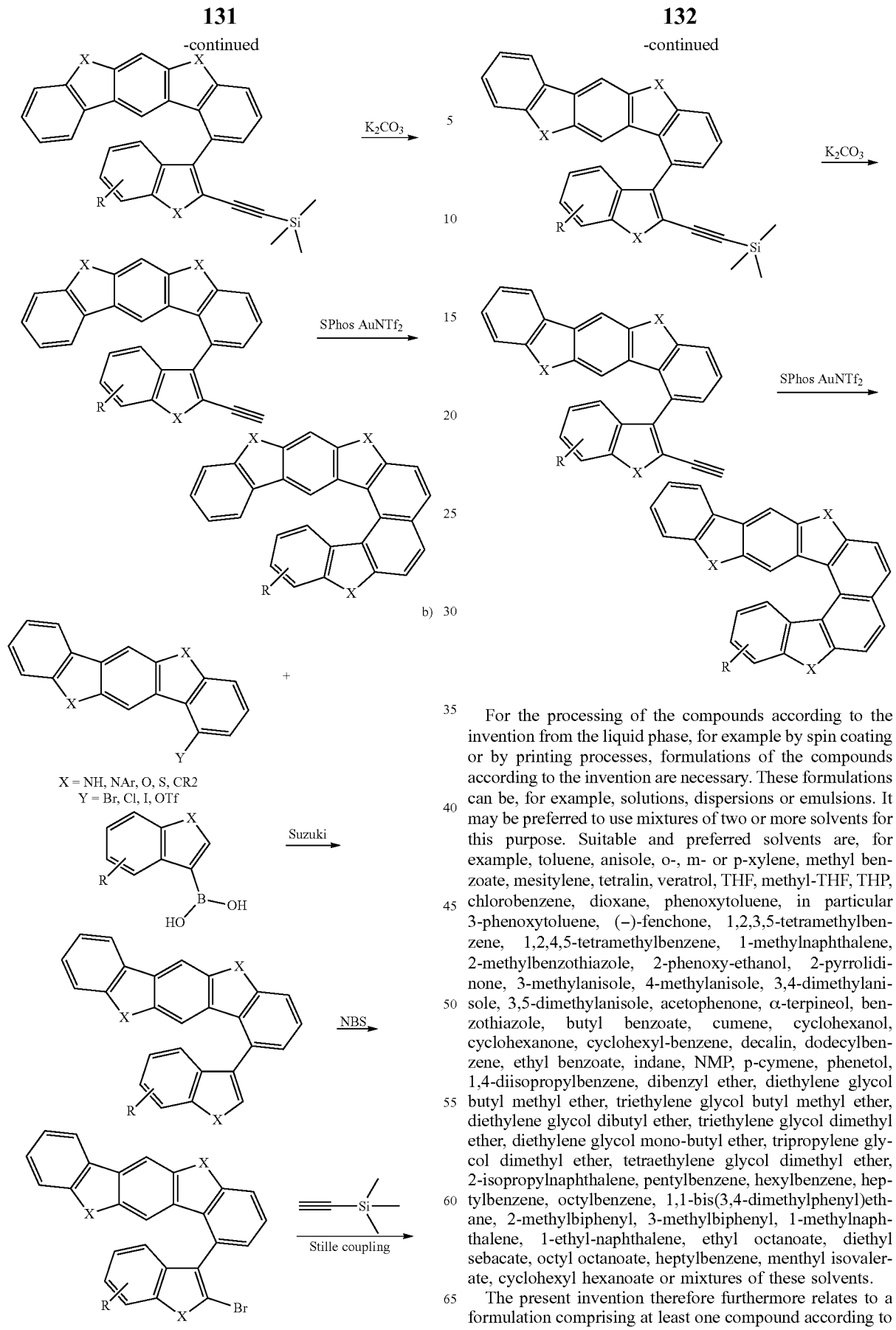

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxy-ethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexyl-benzene, decalin, dodecylbenzene, ethyl benzoate, indane, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol mono-butyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, 2-methylbiphenyl, 3-methylbiphenyl, 1-methylnaphthalene, 1-ethyl-naphthalene, ethyl octanoate, diethyl sebacate, octyl octanoate, heptylbenzene, menthyl isovalerate, cyclohexyl hexanoate or mixtures of these solvents.

The present invention therefore furthermore relates to a formulation comprising at least one compound according to the invention and at least one further compound. The further compound can be, for example, a solvent, in particular one of the above-mentioned solvents or a mixture of these solvents. However, the further compound can also be at least one further organic or inorganic compound which is likewise employed in the electronic device, for example an emitting compound and/or a further matrix material. Suitable emitting compounds and further matrix materials are mentioned below in connection with the organic electroluminescent device. This further compound may also be polymeric.

The compounds according to the invention are suitable for use in an electronic device, in particular in an organic electroluminescent device.

The present invention therefore furthermore relates to the use of a compound according to the invention in an electronic device, in particular in an organic electroluminescent device. An electronic device in the sense of the present invention is a device which contains at least one layer which comprises at least one organic compound. The component may also comprise inorganic materials or also layers built are entirely from inorganic materials.

The present invention still furthermore relates to an electronic device containing at least one compound according to the invention. The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), dye-sensitised organic solar cells (DSSCs), organic optical detectors, organic photoreceptors, organic field-quench devices (O-FQDs), light-emitting electrochemical cells (LECs), organic laser diodes (O-lasers) and organic plasmon emitting devices, but preferably organic electroluminescent devices (OLEDs), in particular phosphorescent OLEDs.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers which have, for example, an exciton-blocking function to be located between two emitting layers. However, it should be pointed out that each of these layers does not necessarily have to be present. The organic electroluminescent device may comprise one emitting layer or a plurality of emitting layers. If a plurality of emission layers are present, these preferably have in total a plurality of emission maxima between 380 nm and 750 nm auf, resulting overall in white emission, i.e. various emitting compounds, which may fluoresce or phosphoresce, are used in the emitting layers. Particular preference is given to systems having three emitting layers, where the three layers exhibit blue, green and orange or red emission. The organic electroluminescent device according to the invention may also be a tandem OLED, in particular for white-emitting OLEDs.

The compound according to the invention in accordance with the above-mentioned embodiments can be employed in various layers here, depending on the precise structure and depending on the choice of $Z^1$, $Z^2$ and $Z^3$. Preference is given to an organic electroluminescent device comprising a compound of the formula (1) or the above-mentioned preferred embodiments in an emitting layer as matrix material for phosphorescent emitters or for emitters which exhibit TADF (thermally activated delayed fluorescence), in particular for phosphorescent emitters. The compound of the formula (1) can furthermore be employed as fluorescent emitter in an emitting layer. The organic electroluminescent device here may comprise one emitting layer or a plurality of emitting layers, where at least one emitting layer comprises at least one compound according to the invention as matrix material. Furthermore, the compound according to the invention can also be employed in an electron-transport layer and/or in a hole-blocking layer and/or in a hole-transport layer and/or in an exciton-blocking layer.

If the compounds according to the invention are employed as matrix material for phosphorescent compounds, it is preferred if at least one of the groups $Z^1$, $Z^2$ and/or $Z^3$, in particular $Z^3$, stands for N—Ar.

If the compounds according to the invention are employed as fluorescent emitters, it is preferred if the groups $Z^1$, $Z^2$ and $Z^3$ stand, identically or differently, preferably identically, for O or S.

If the compounds according to the invention are employed as electron-transport material, it is preferred if at least two of the groups $Z^1$, $Z^2$ and $Z^3$ stand, identically or differently, preferably identically, for O or S and the basic structure is substituted by an optionally substituted triazine or pyrimidine.

If the compounds according to the invention are employed as hole-transport material, it is preferred if at least two of the groups $Z^1$, $Z^2$ and $Z^3$ stand for NAr.

If the compound according to the invention is employed as matrix material for a phosphorescent compound in an emitting layer, it is preferably employed in combination with one or more phosphorescent materials (triplet emitters). Phosphorescence in the sense of this invention is taken to mean luminescence from an excited state having relatively high spin multiplicity, i.e. a spin state>1, in particular from an excited triplet state. In the sense of this application, all luminescent complexes with transition metals or lanthanides, in particular all iridium, platinum and copper complexes, are to be regarded as phosphorescent compounds.

The mixture of the compound according to the invention and the emitting compound comprises between 99 and 1% by vol., preferably between 98 and 10% by vol., particularly preferably between 97 and 60% by vol., in particular between 95 and 80% by vol., of the compound according to the invention, based on the entire mixture of emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture emitter and matrix material.

A further preferred embodiment of the present invention is the use of the compound according to the invention as matrix material for a phosphorescent emitter in combination with a further matrix material. Suitable matrix materials that can be employed in combination with the compounds according to the invention are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or those in WO 2005/039246, US 2005/0069729, JP 2004/288381, EP 1205527, WO 2008/086851 or WO 2013/041176, indolocarbazole derivatives, for example in accordance with WO 2007/063754 or WO 2008/056746, indenocarbazole derivatives, for example in accordance with WO 2010/136109, WO 2011/000455, WO 2013/041176 or WO 2013/056776, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2007/063754, WO 2008/056746, WO 2010/015306, WO 2011/057706, WO 2011/060859 or WO 2011/060877, zinc complexes, for example in accordance with EP 652273 or WO 2009/062578, diazasilole or tetraazasilole derivates, for example in accordance with WO 2010/054729, diazaphosphole derivates, for example in accordance with WO 2010/054730, bridged carbazole derivatives, for example in accordance with WO 2011/042107, WO 2011/060867, WO 2011/088877 and WO 2012/143080, triphenylene derivatives, for example in accordance with WO 2012/048781, or dibenzofuran derivatives, for example in accordance with WO 2015/169412, WO 2016/015810, WO 2016/023608, WO 2017/148564 or WO 2017/148565. A further phosphorescent emitter that emits at shorter wavelength than the actual emitter may likewise be present in the mixture as co-host or a compound which does not participate in charge transport, or only does so to an insignificant extent, as described, for example, in WO 2010/108579.

In particular, compounds which have a large band gap and do not them-selves participate in charge transport of the emitting layer, or at least only do so to an insignificant extent, are suitable as co-matrix material in combination with the compound according to the invention. Such materials are preferably pure hydrocarbons. Examples of such materials can be found, for example, in WO 2006/130598, WO 2009/021126, WO 2009/124627 and WO 2010/006680.

In a preferred embodiment of the invention, the materials are employed in combination with a further matrix material. Preferred co-matrix materials are selected from the group of the biscarbazoles, the bridged carbazoles, the triarylamines, the dibenzofuran-carbazole derivatives or dibenzofuran-amine derivatives and the carbazolamines.

Preferred biscarbazoles are the structures of the following formulae (9) and (10), formula (9)

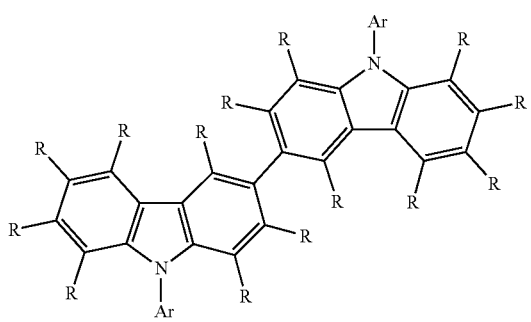

formula (10)

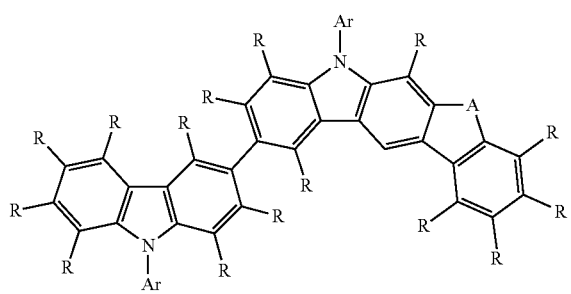

where Ar and A have the meanings given above and R has the meanings given above, but radicals R here may also form an aromatic or heteroaromatic ring system with one another. In a preferred embodiment of the invention, A stands for $CR_2$.

Preferred embodiments of the compounds of the formulae (9) or (10) are the compounds of the following formulae (9a) or (10a), formula (9a)

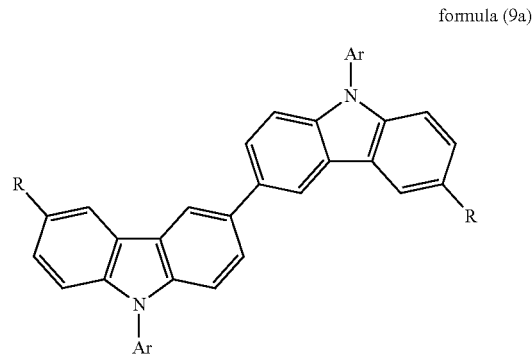

formula (10a)

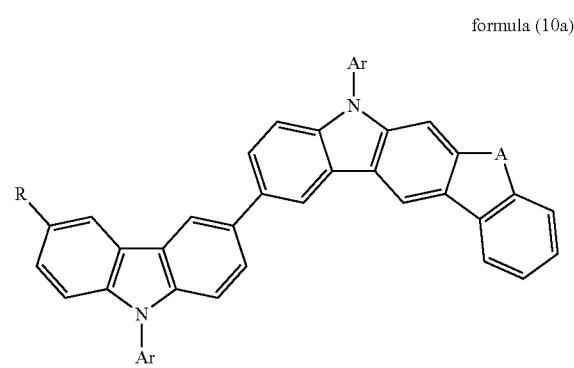

where the symbols used have the meanings given above.

Examples of suitable compounds of the formula (9) or (10) are the compounds depicted below.

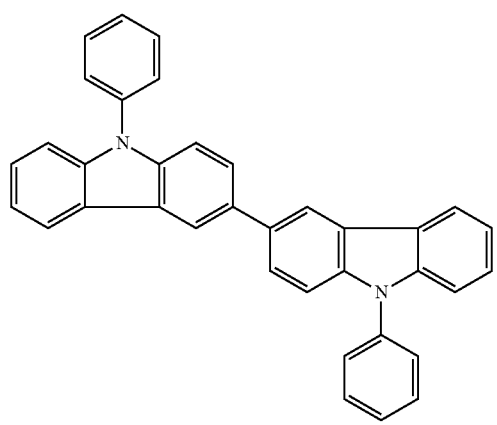

137
-continued
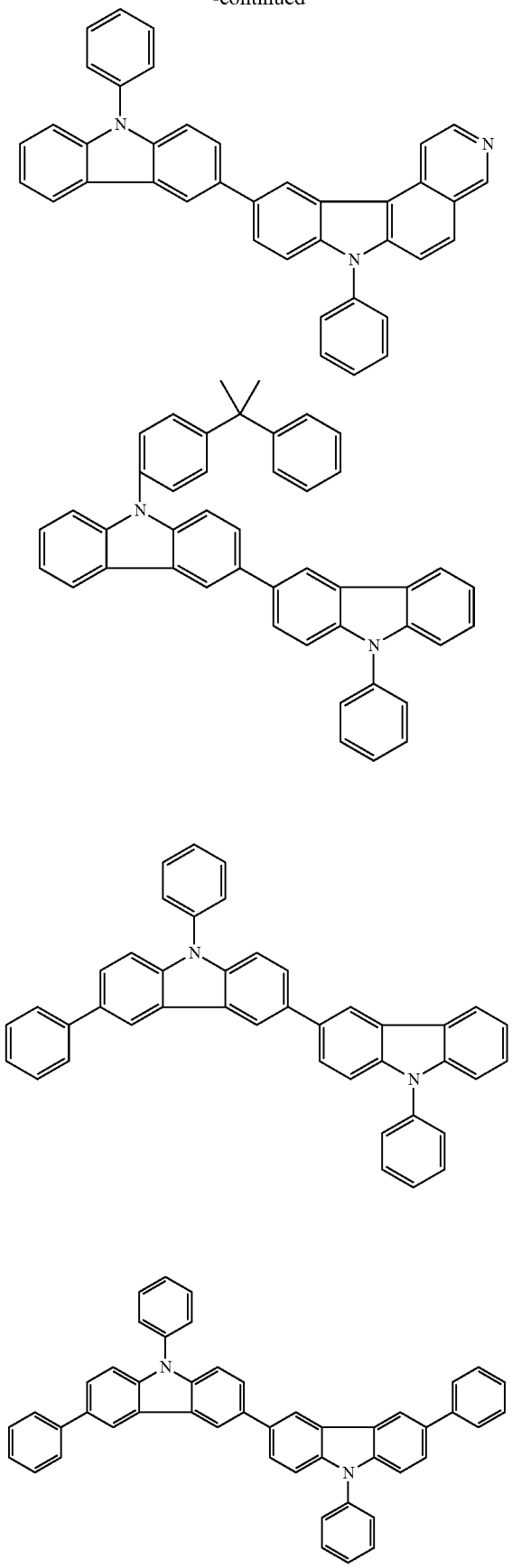
138
-continued
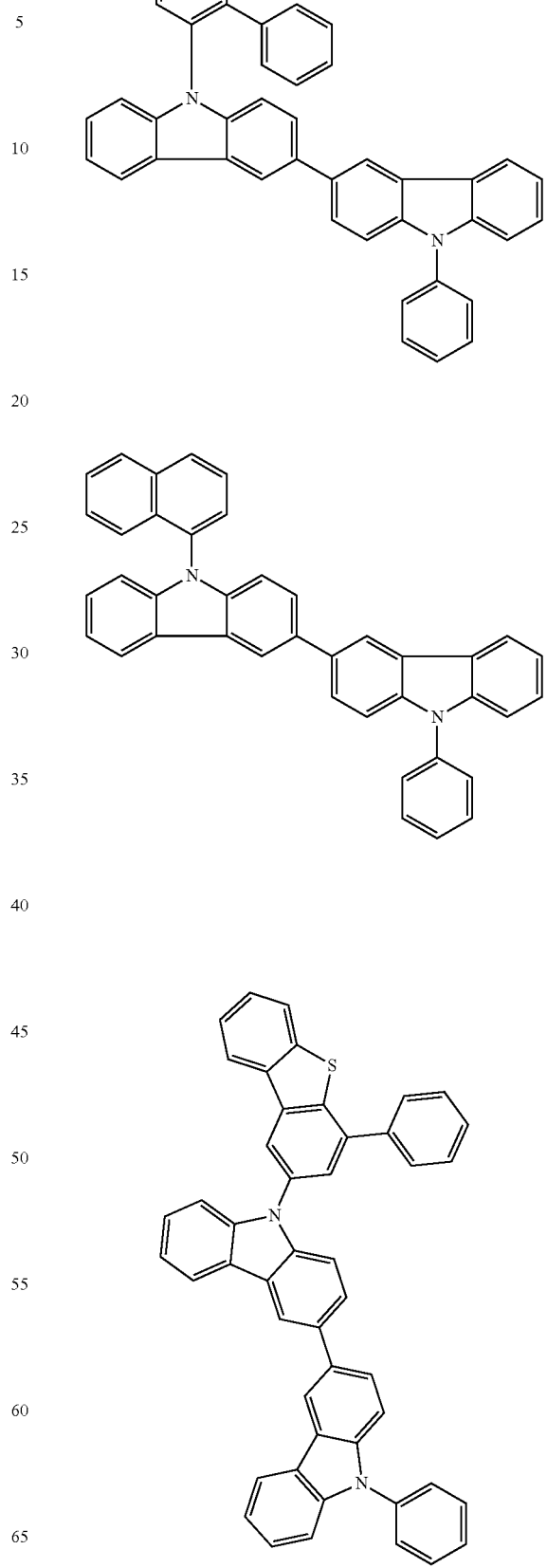

-continued
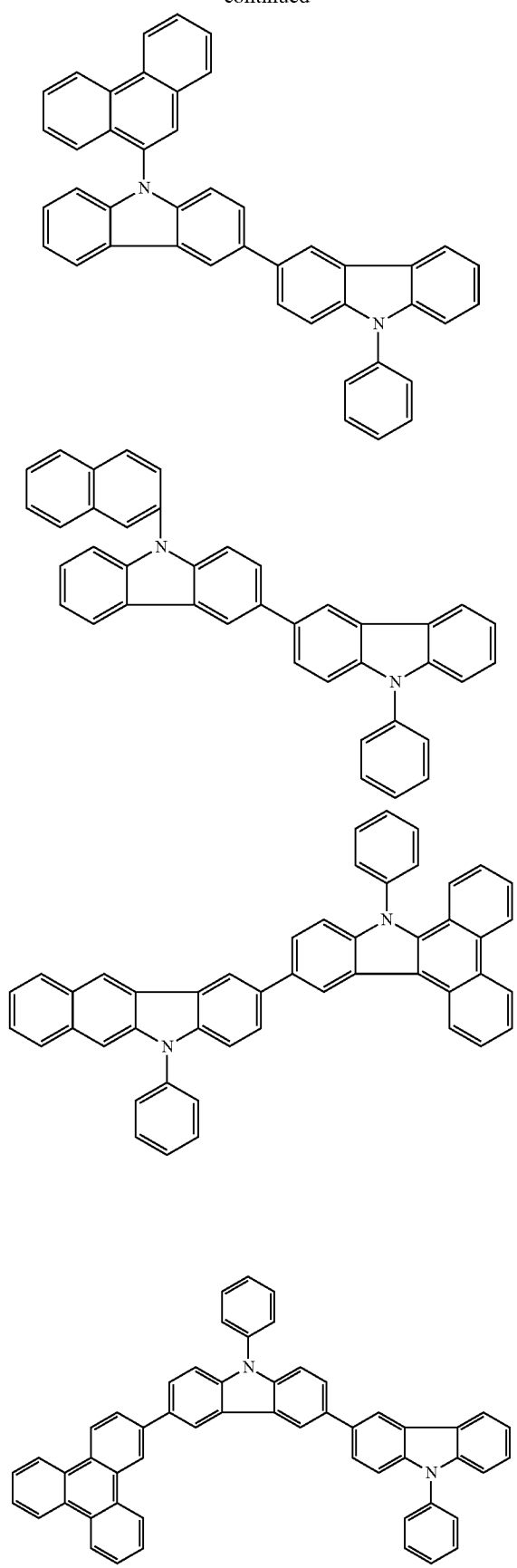
-continued
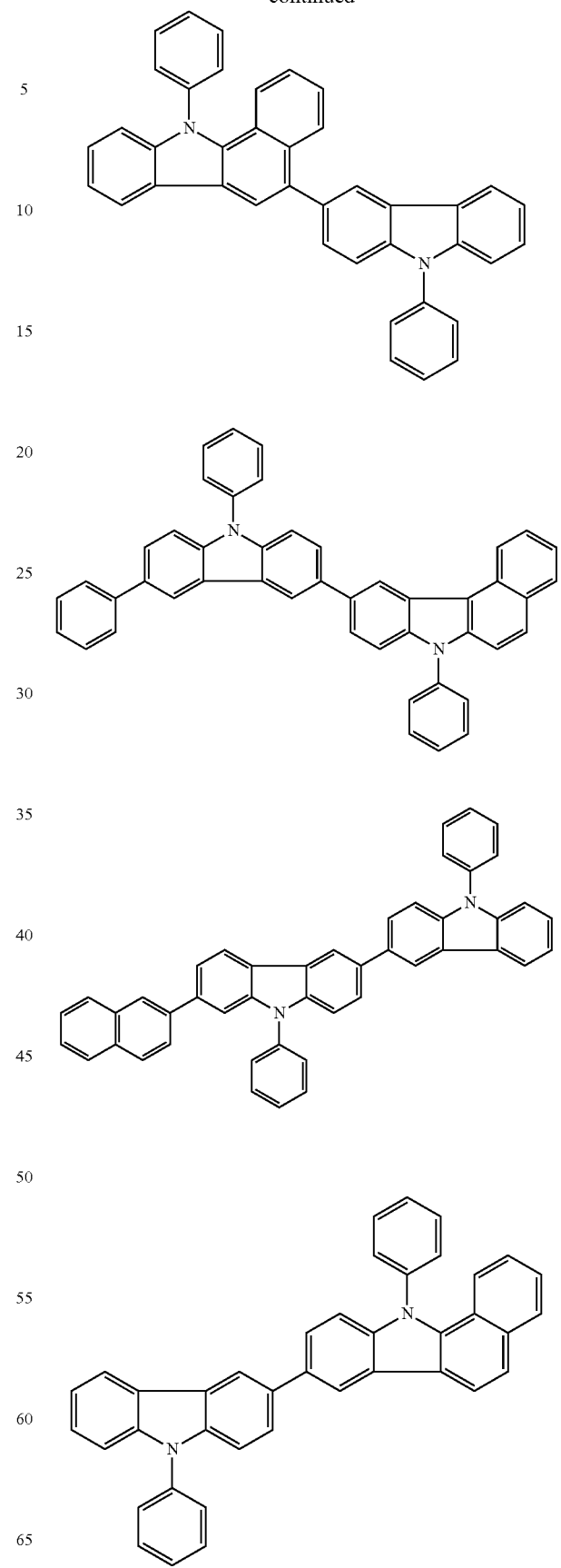

141
-continued
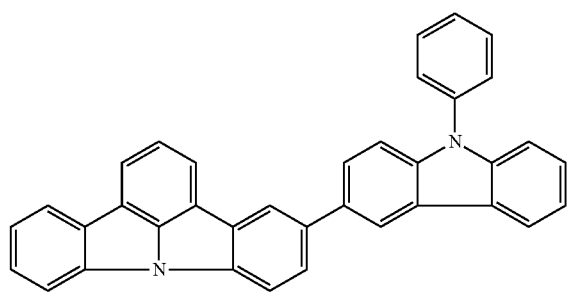
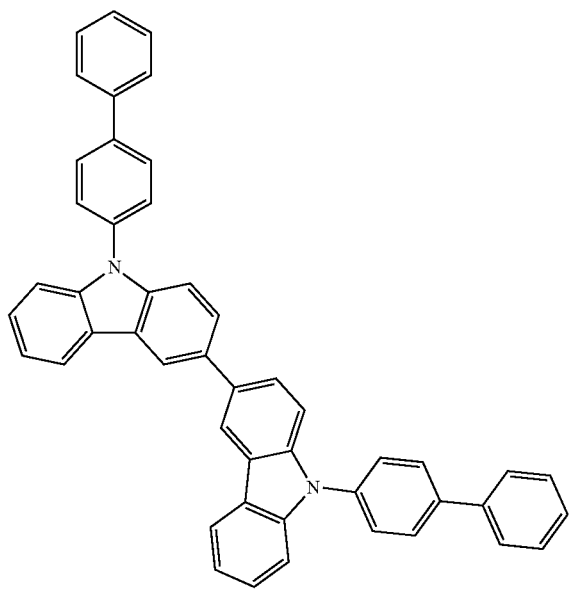
142
-continued
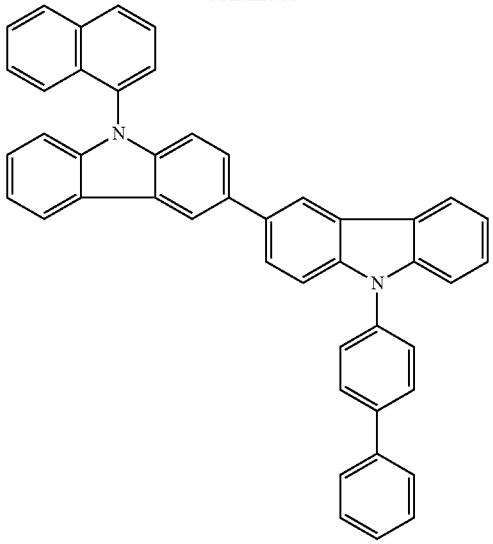
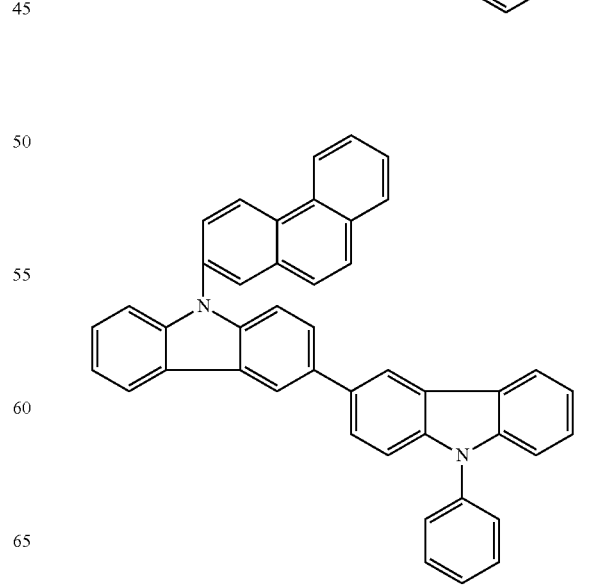

143
-continued
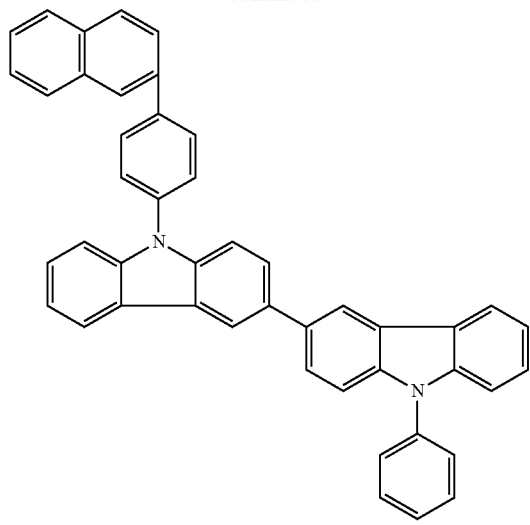
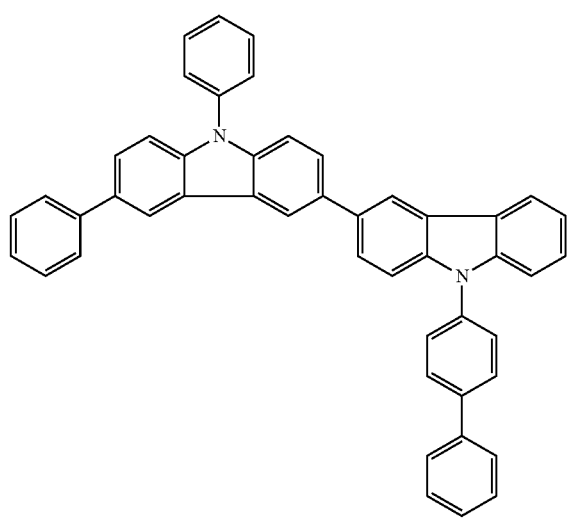
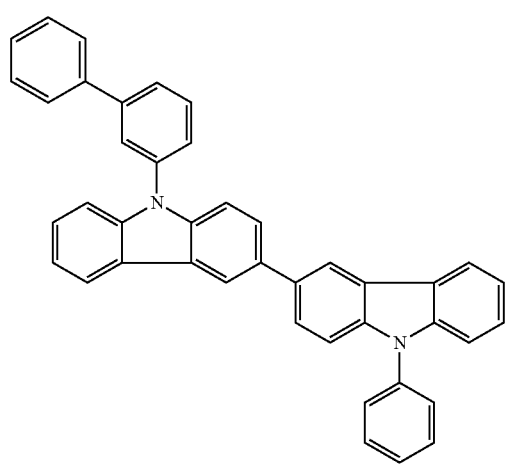
144
-continued
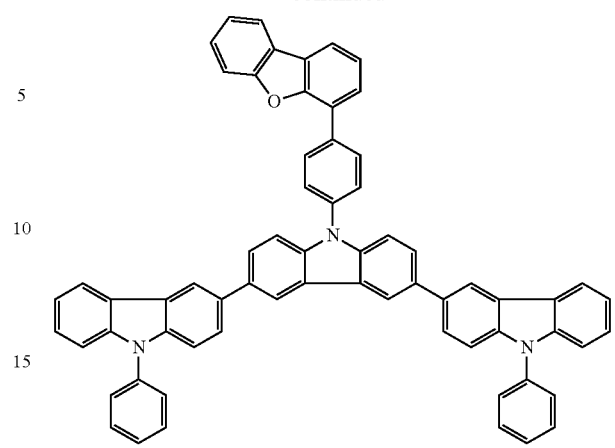
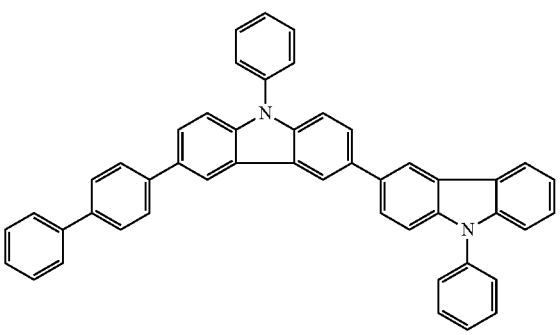
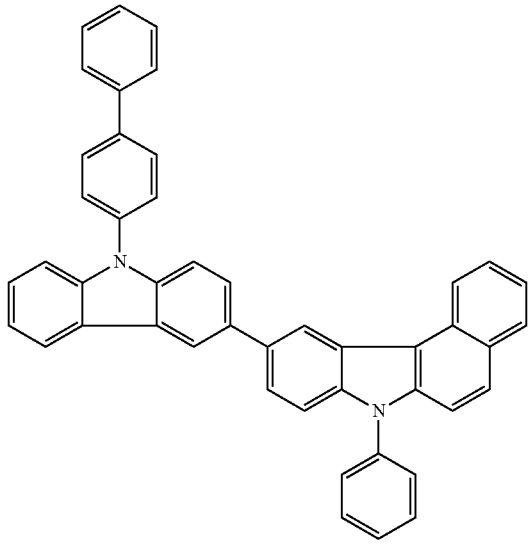

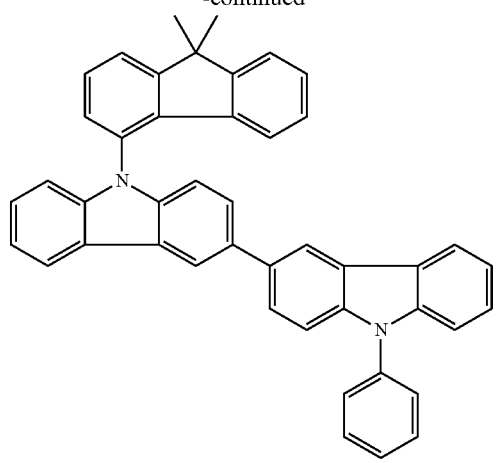
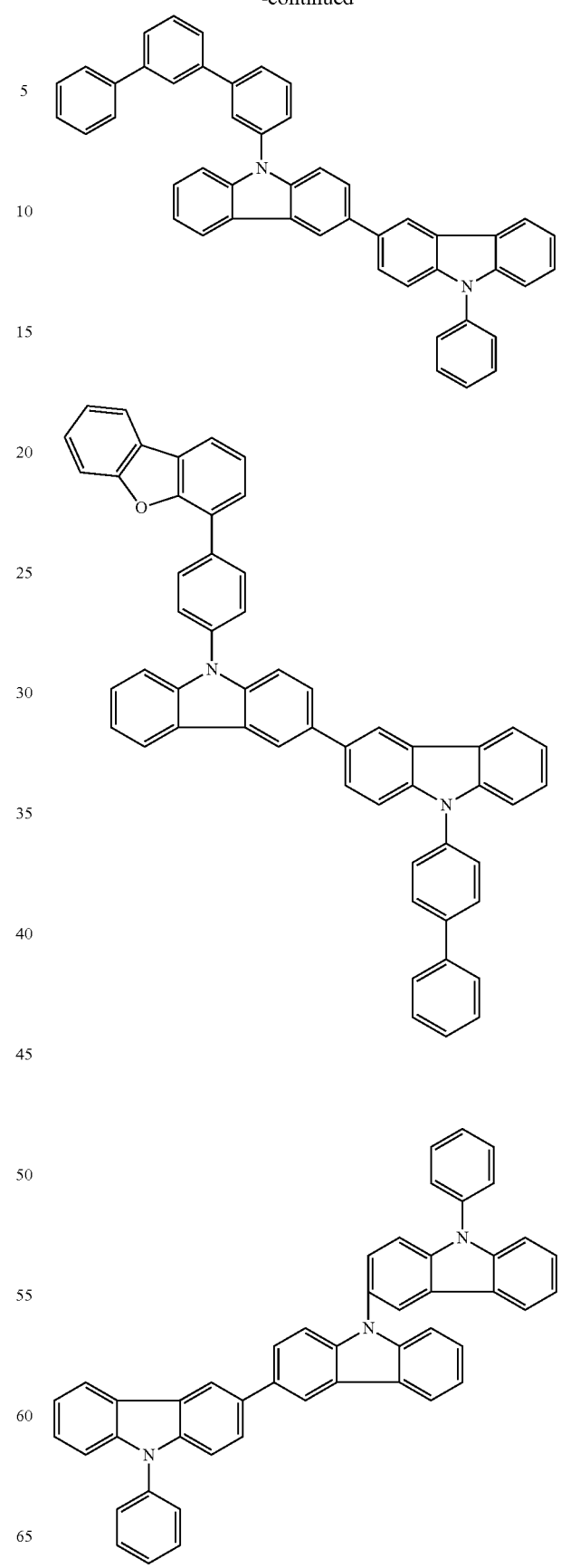

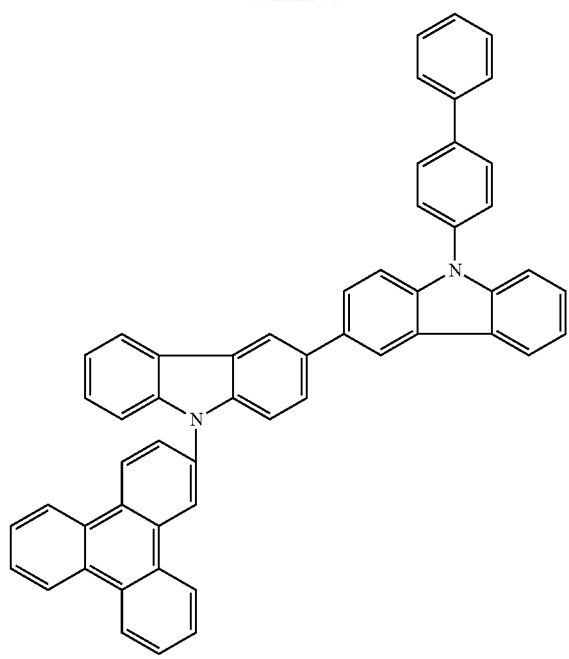
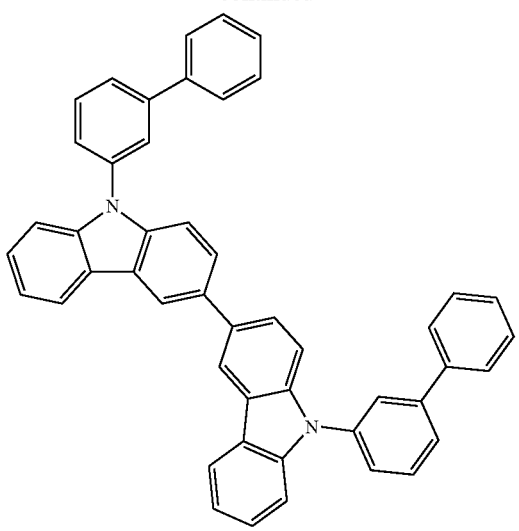
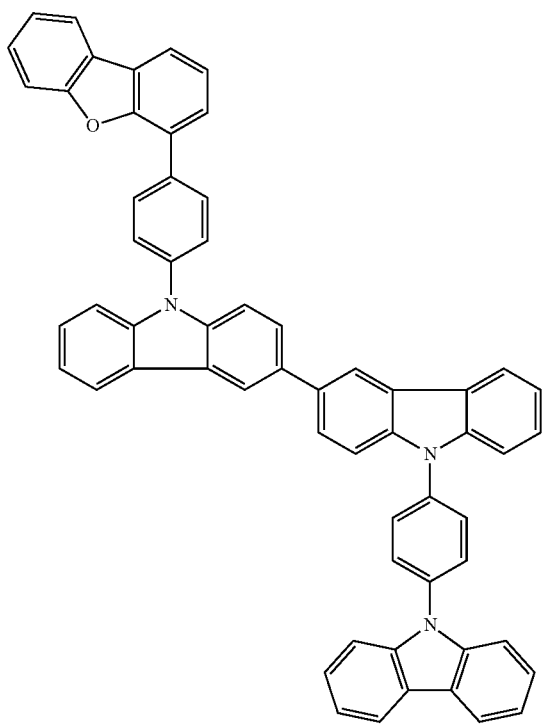
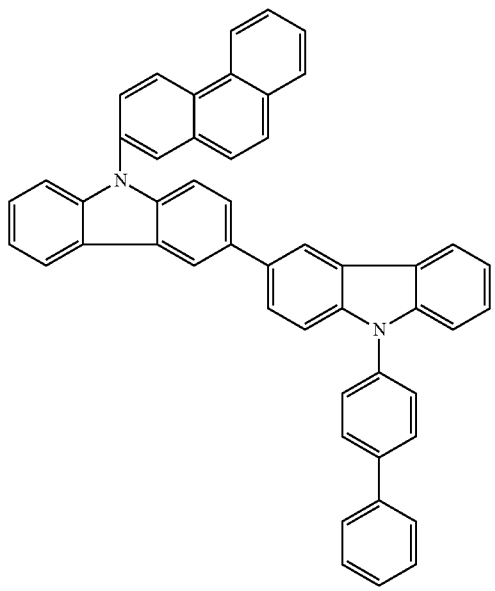

149
-continued
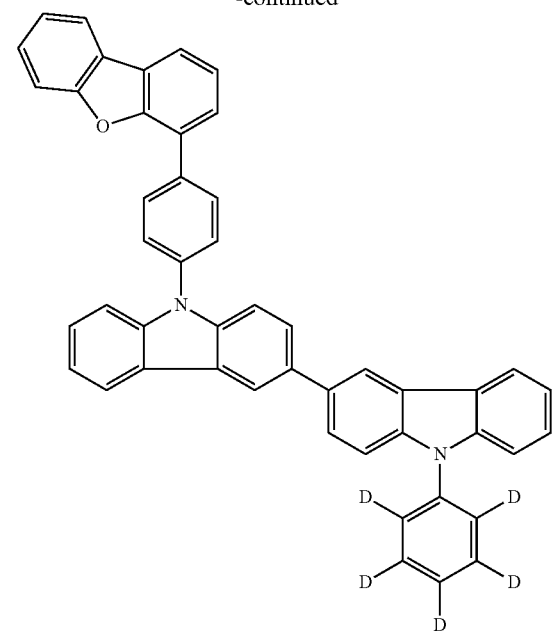
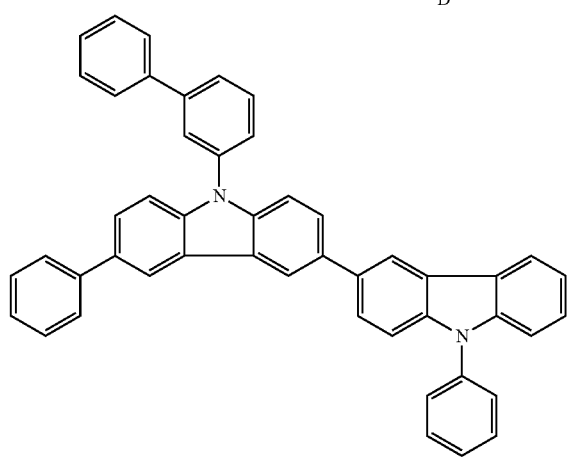
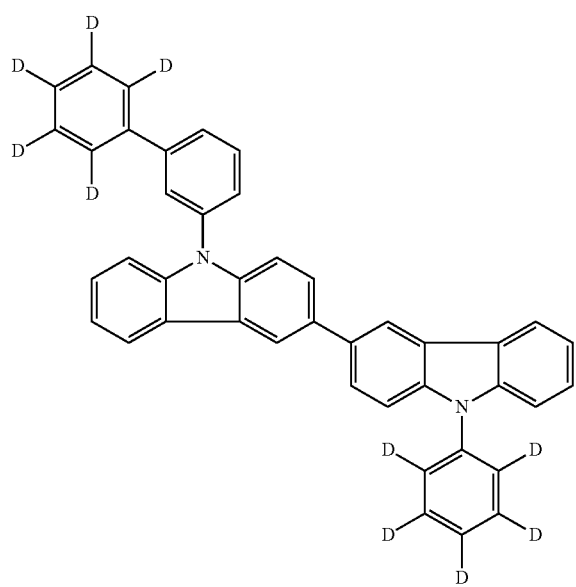
150
-continued
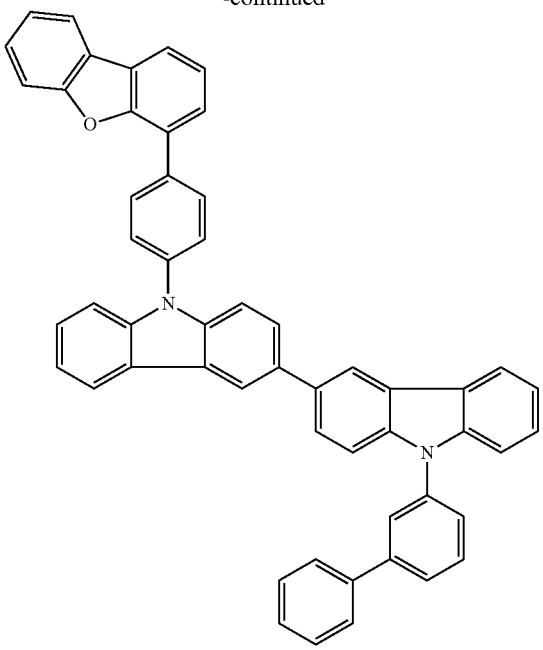
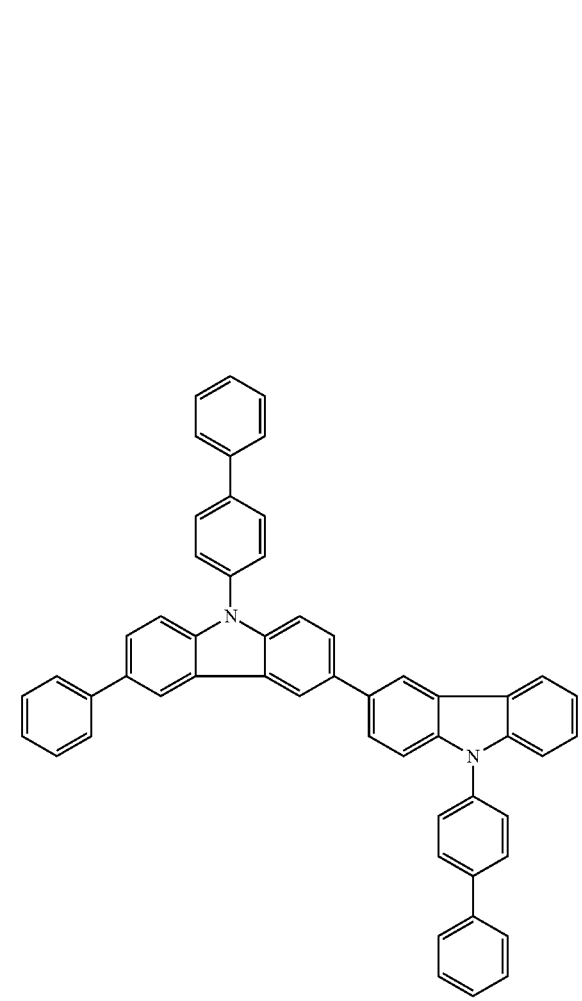

151
-continued
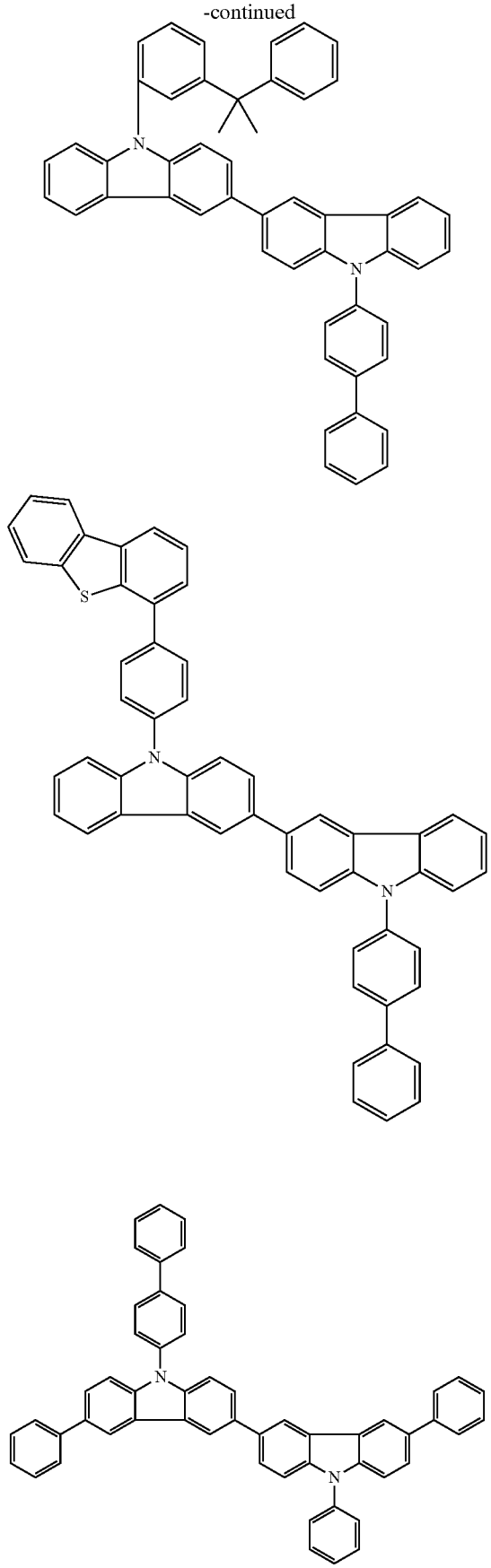
152
-continued
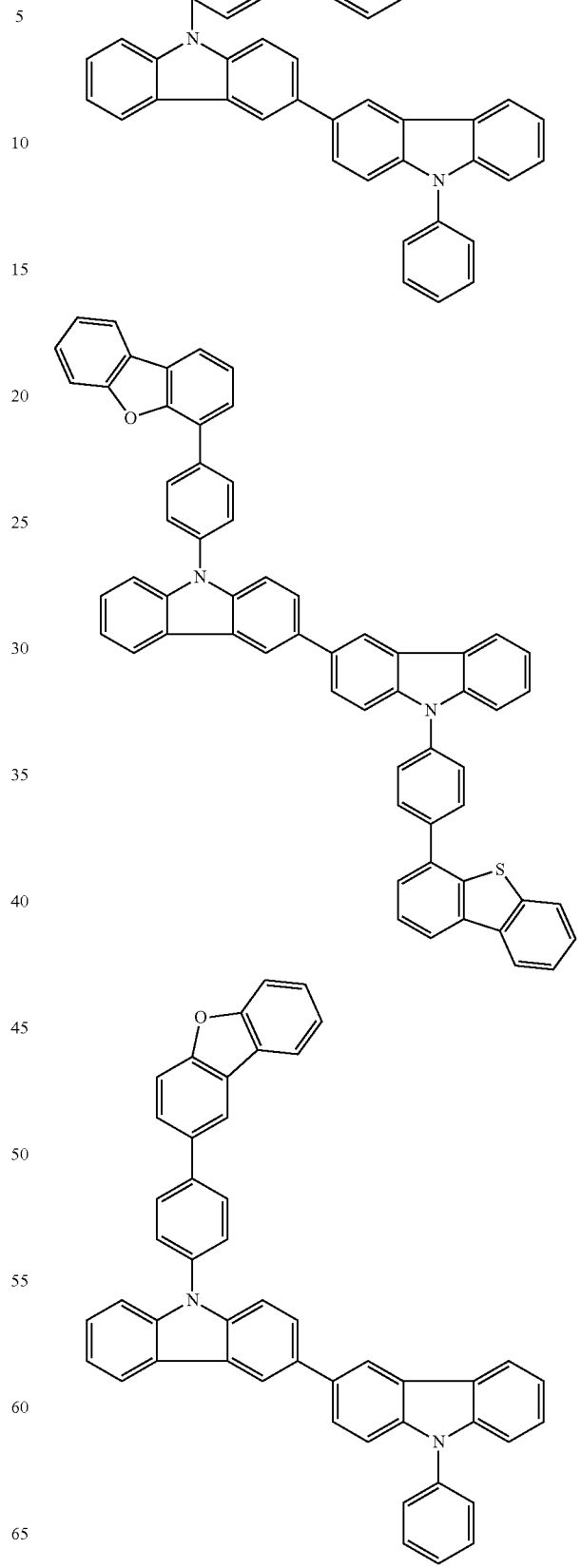

153
-continued
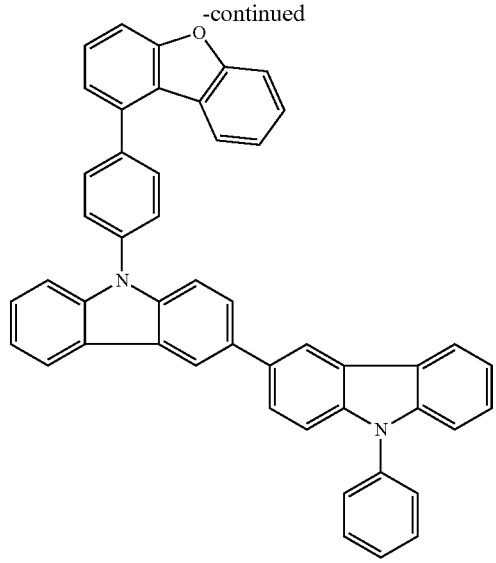
154
-continued
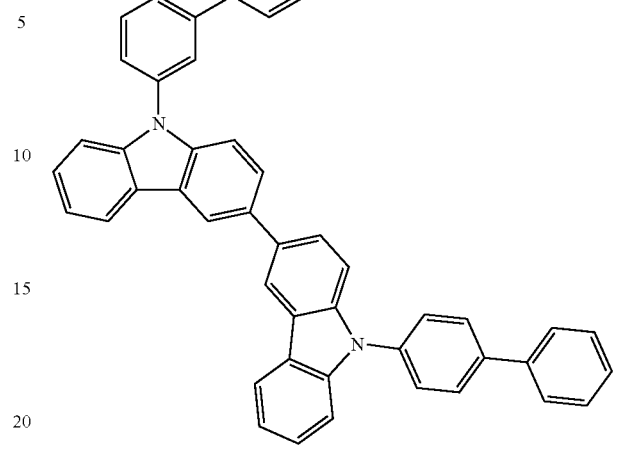
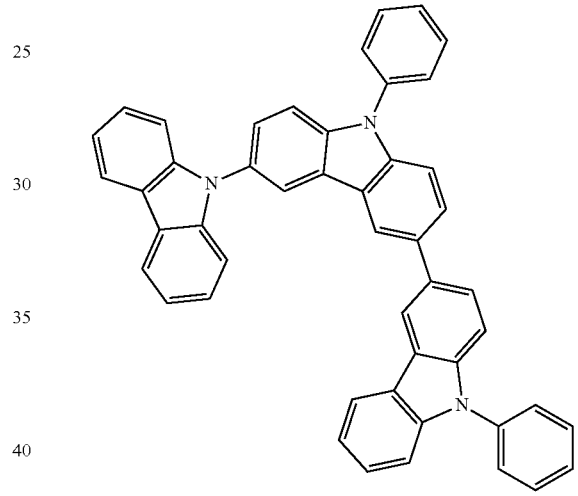
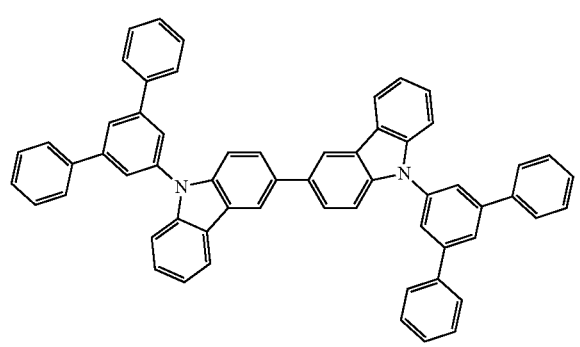
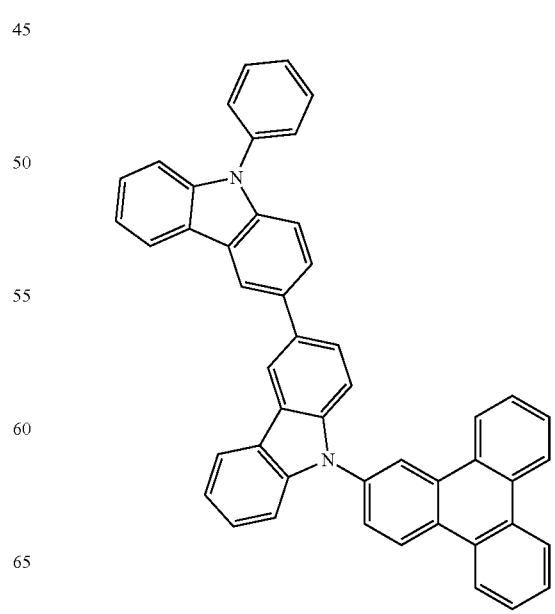

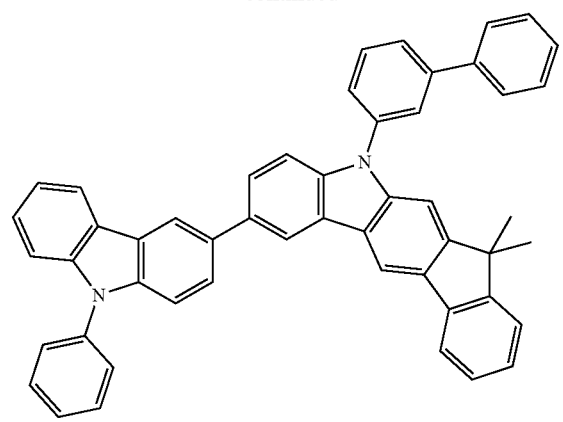

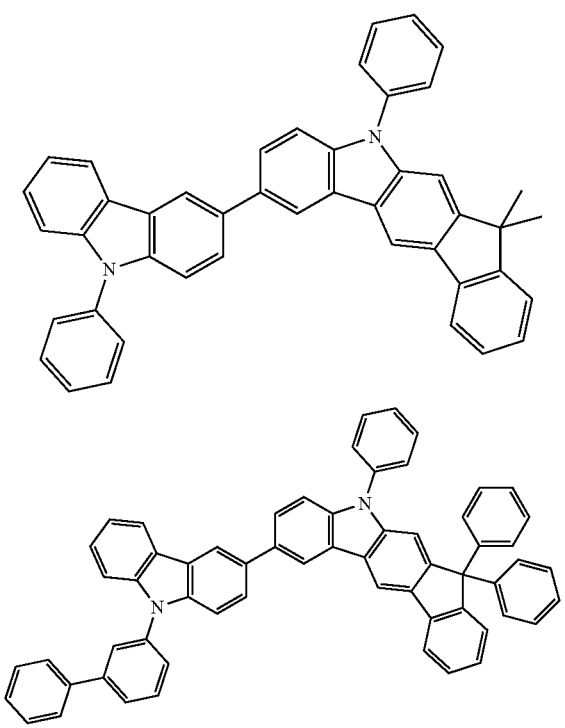

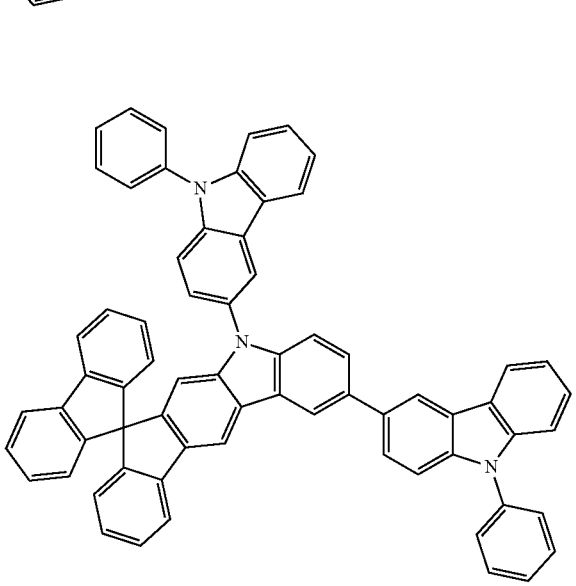

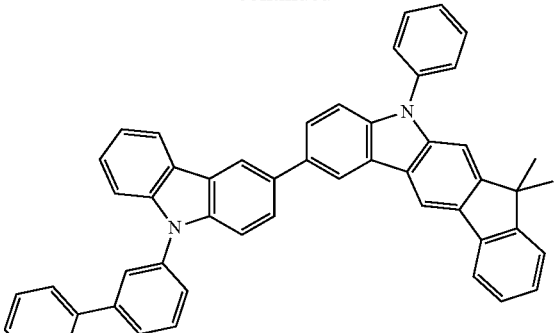

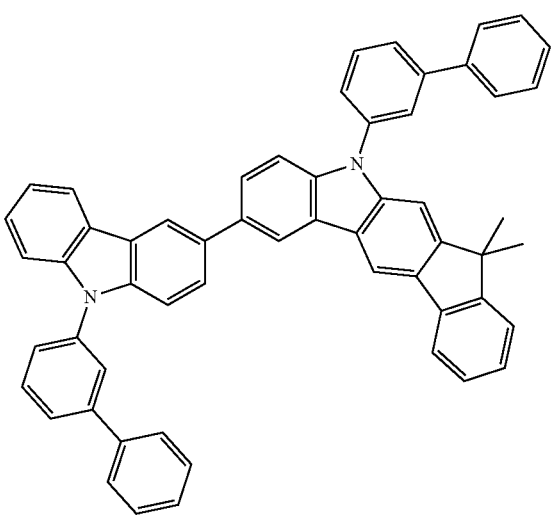 [SMILES: CC1(C)c2ccccc2-c2cc3c4cc(-c5ccc6c(c5)c5ccccc5n6-c5cccc(-c6ccccc6)c5)ccc4n(-c4cccc(-c5ccccc5)c4)c3cc21]

Preferred bridged carbazoles are the structures of the following formula (11),

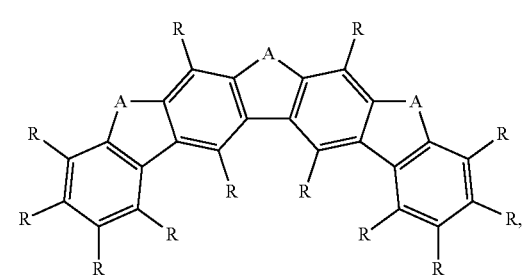

formula (11)

where A and R have the meanings given above and A is preferably selected, identically or differently on each occurrence, from the group consisting of NAr and $CR_2$.

A preferred embodiment of the formula (11) are the compounds of the formula (11a), the compounds of the formula (11 b) are particularly preferred, and the compounds of the formula (11c) are very particularly preferred, formula (11a)

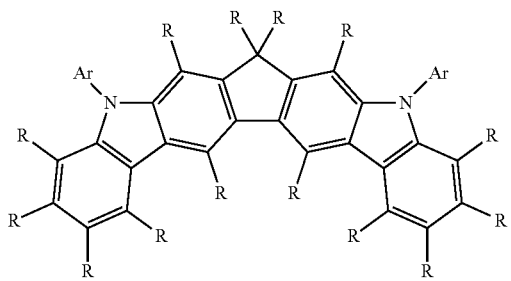

formula (11b)

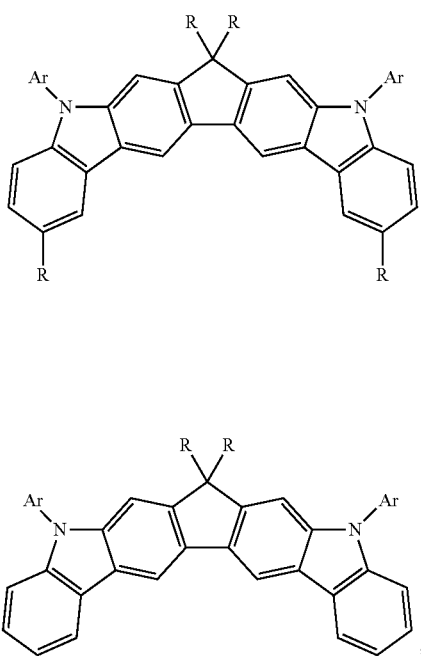

formula (11c)

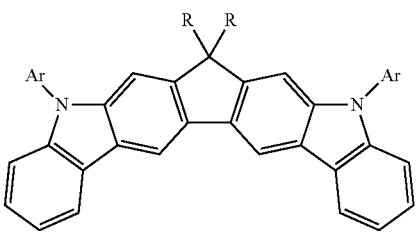

where Ar and R have the meanings given above. Ar here preferably stands, identically or differently on each occurrence, for an aromatic ring system having 6 to 18 aromatic ring atoms, for example for phenyl, ortho-, meta- or para-biphenyl or terphenyl. The radical R on the indene carbon atom preferably stands, identically or differently on each occurrence, for an alkyl group having 1 to 5 C atoms, in particular for methyl, or an aromatic ring system having 6 to 18 aromatic ring atoms, in particular phenyl.

Preferred triarylamines are the structures of the following formula (12),

Formel (12)

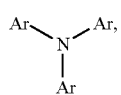

where Ar has the meanings given above.

Preferred dibenzofuran derivatives are the compounds of the following formula (13), formula (12)

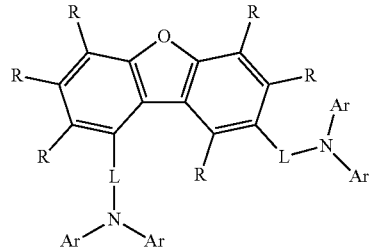

where the oxygen may also be replaced by sulfur, so that a dibenzothiophene forms, L stands for a single bond or an aromatic or heteroaromatic ring system having 5 to 30 aromatic ring atoms, which may also be substituted by one or more radicals R, and R and Ar have the meanings given above. Both groups Ar that are bonded to the same nitrogen atom, or one group Ar and one group L that are bonded to the same nitrogen, may also be connected to one another, for example to form a carbazole.

Preferred embodiments of the compounds of the formula (13) are the compounds of the following formulae (13a) and (13b),

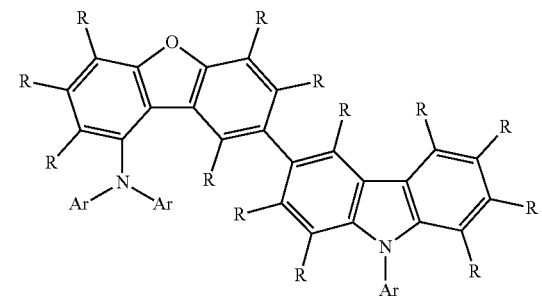

formula (13b)

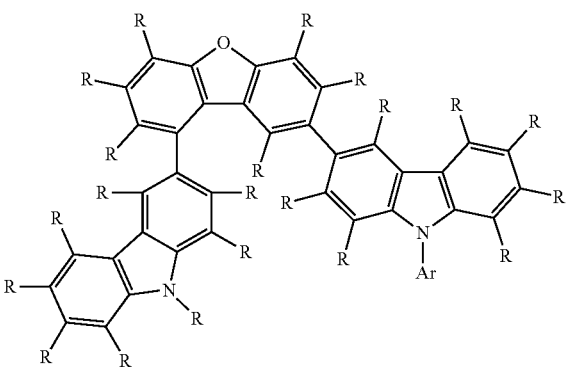

where the oxygen may also be replaced by sulfur, so that a dibenzothiophene forms, and R and Ar have the meanings given above, where two adjacent radicals R, in particular on the carbazole, here may also form an aromatic or heteroaromatic ring system with one another.

Particularly preferred embodiments are the compounds of the following formulae (13c) and (13d),

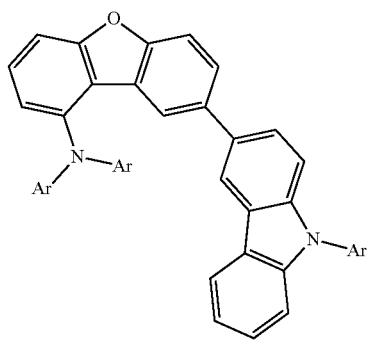

formula (13c)

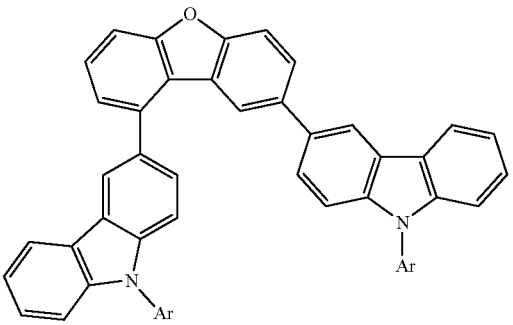

formula (13d)

where the oxygen may also be replaced by sulfur, so that a dibenzothiophene forms, and Ar has the meanings given above, where two adjacent radicals R, in particular on the carbazole, here may also form an aromatic or heteroaromatic ring system with one another.

Examples of suitable dibenzofuran derivatives are the compounds depicted below.

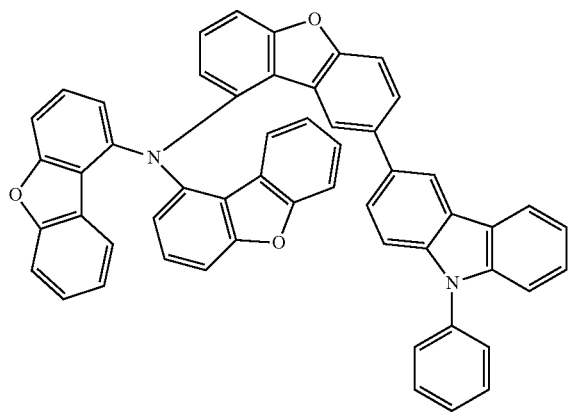

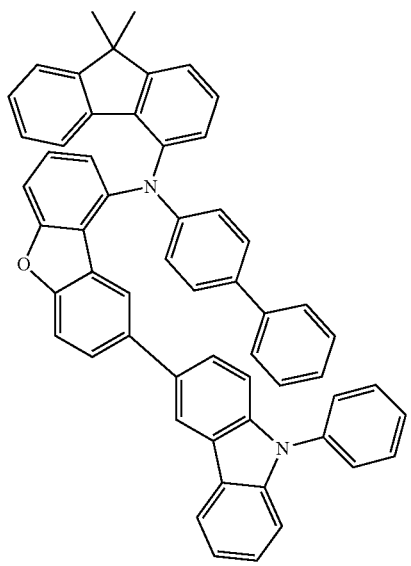

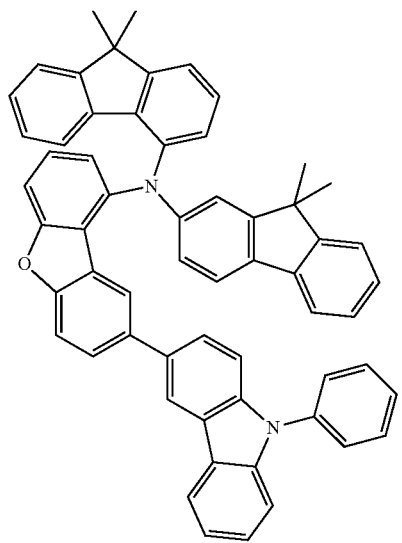

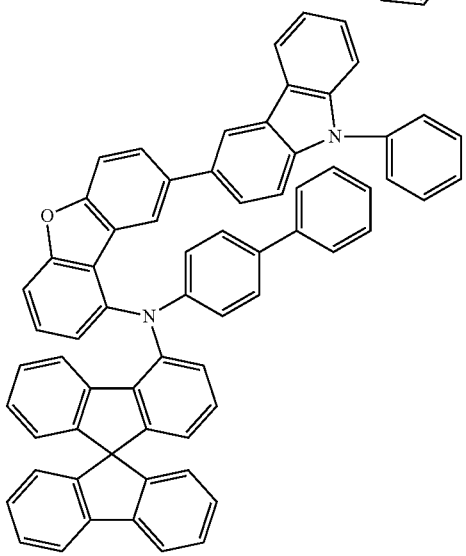

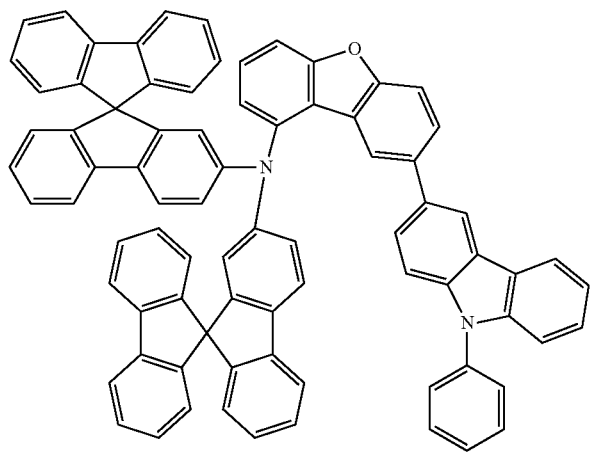
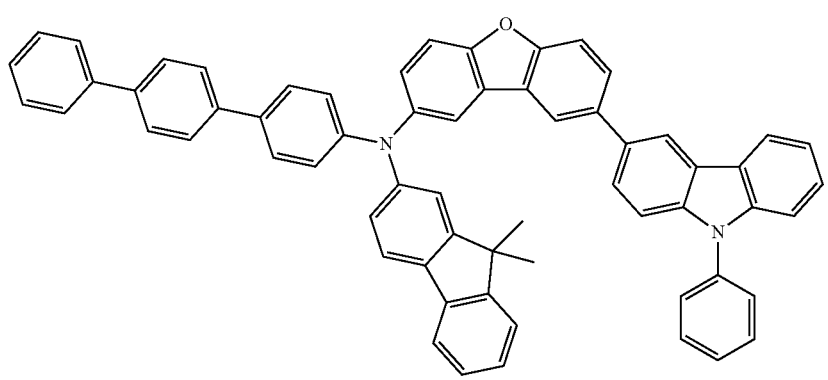
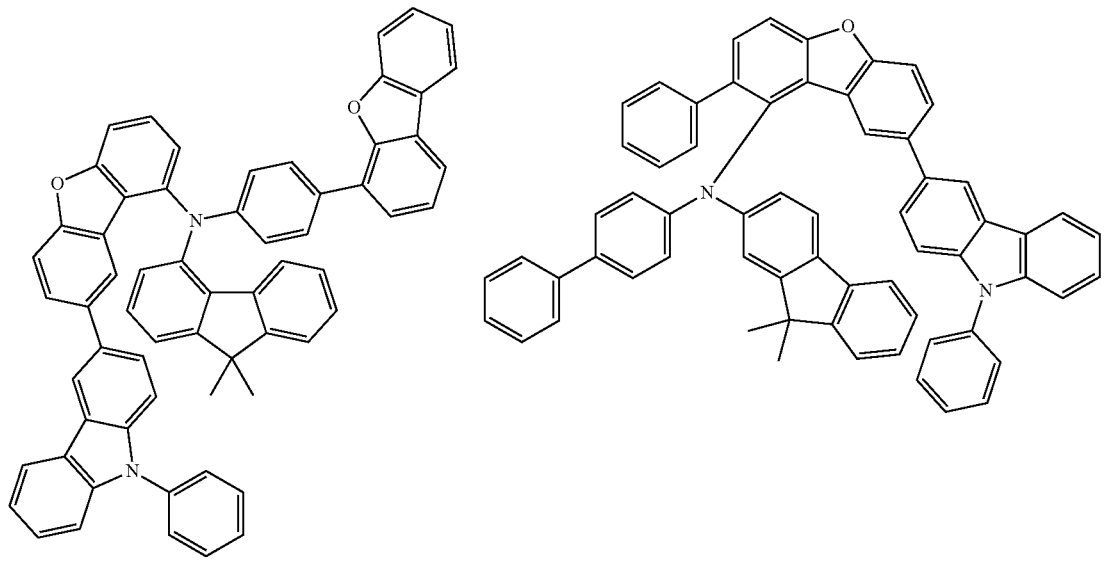

163
164
-continued
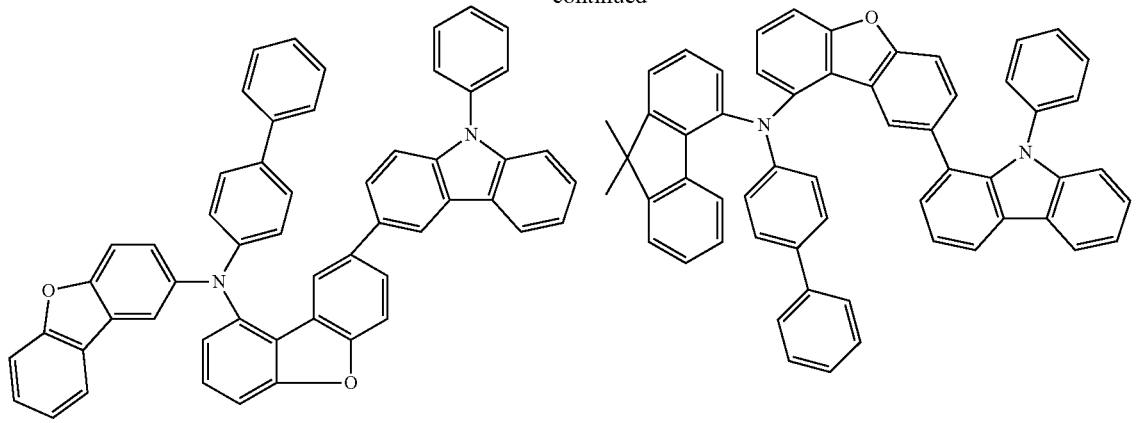
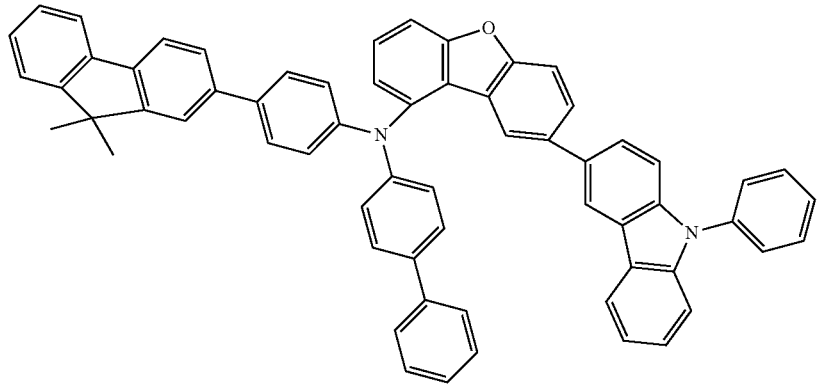
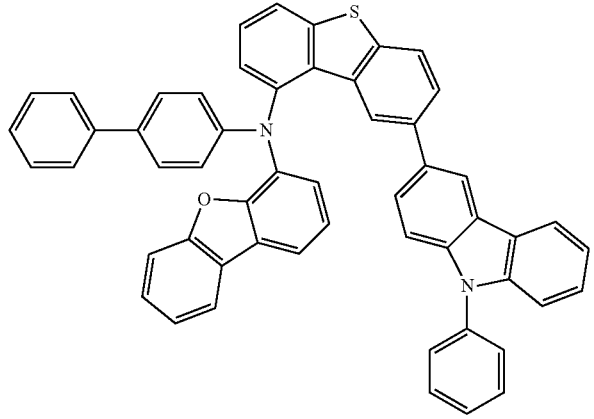
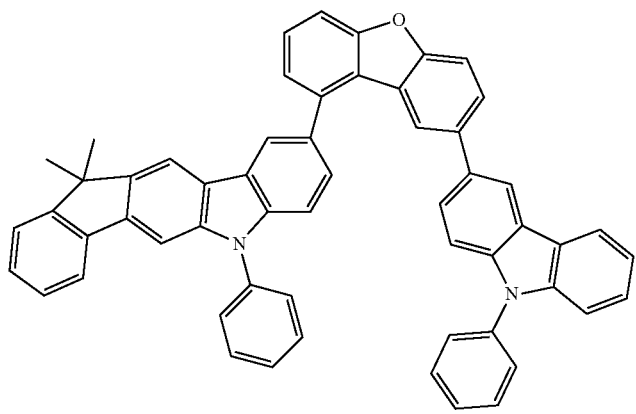

-continued
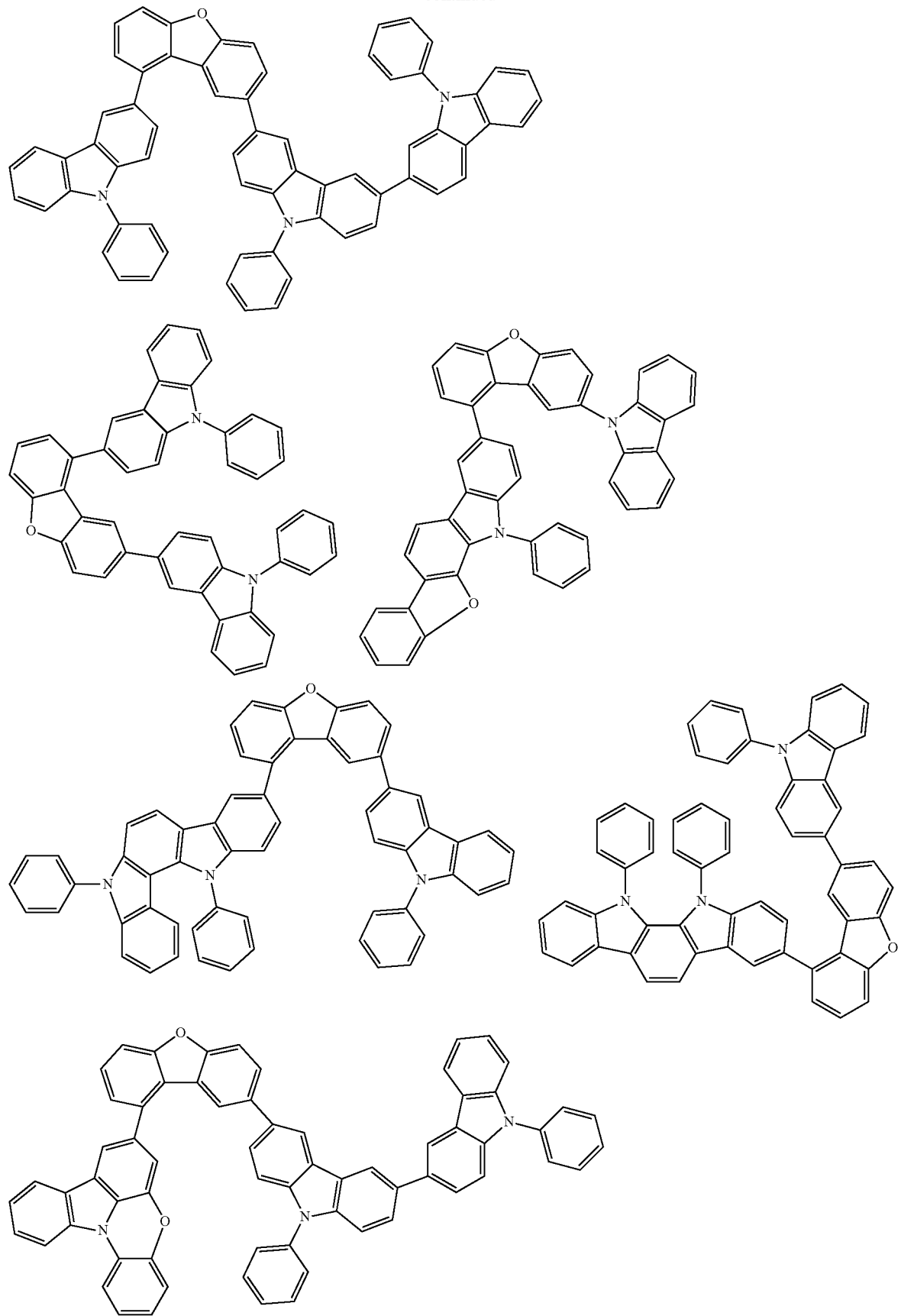

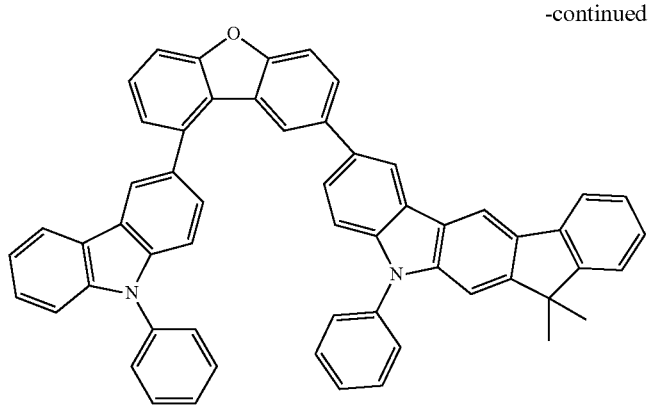

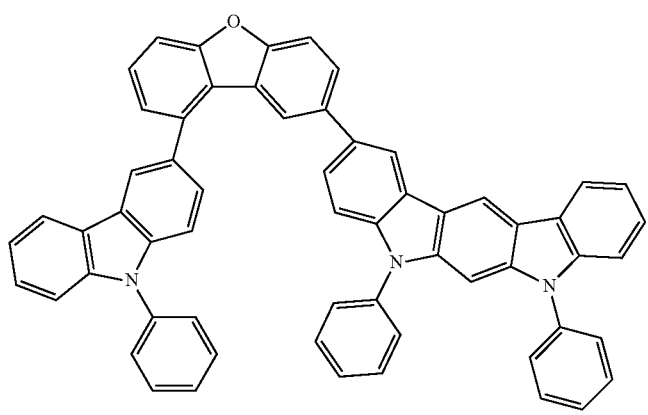

Preferred carbazolamines are the structures of the following formulae (14), (15) and (16), formula (14)

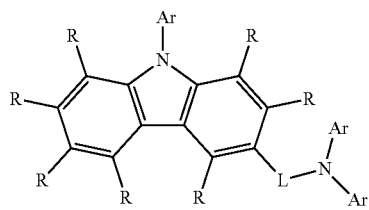

formula (15)

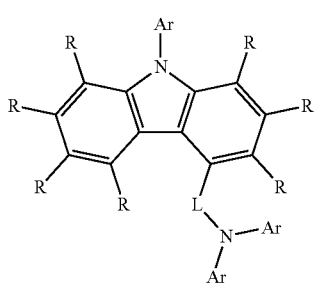

formula (16)

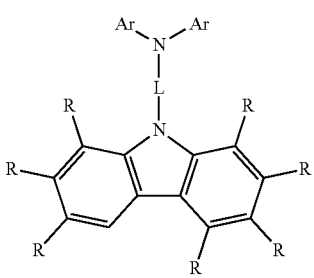

where L stands for an aromatic or heteroaromatic ring system having 5 to 30 aromatic ring atoms, which may be substituted by one or more radicals R, and R and Ar have the meanings given above, where two adjacent radicals R here may also form an aromatic ring system.

Examples of suitable carbazolamine derivatives are the compounds depicted below.

-continued
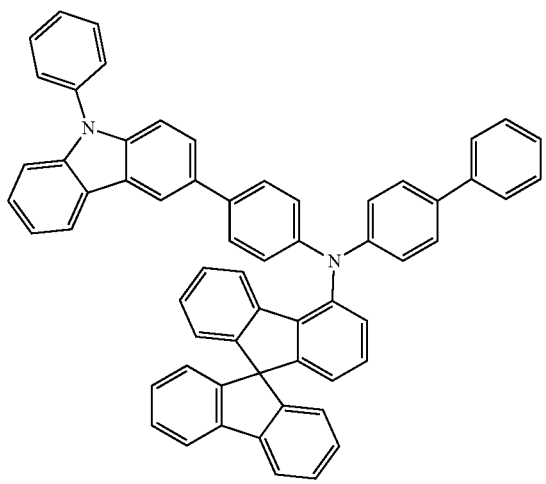
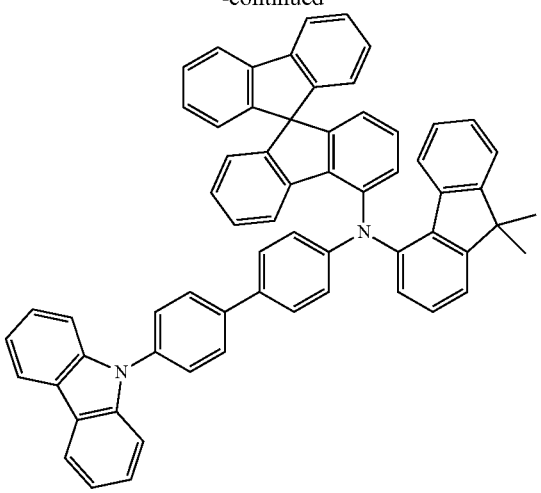
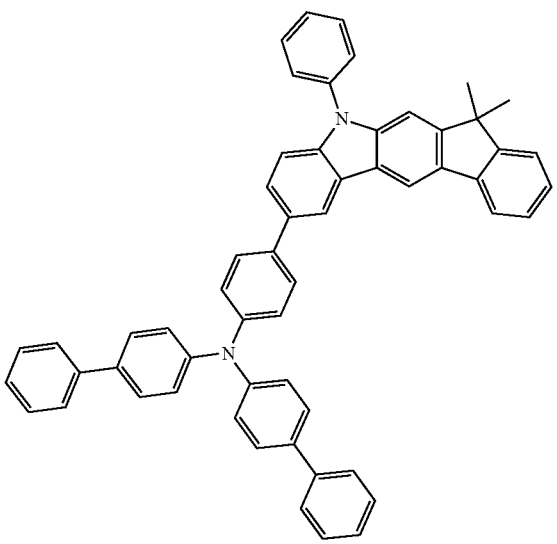
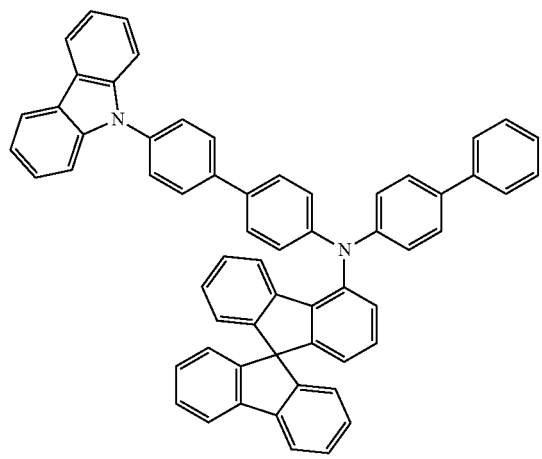
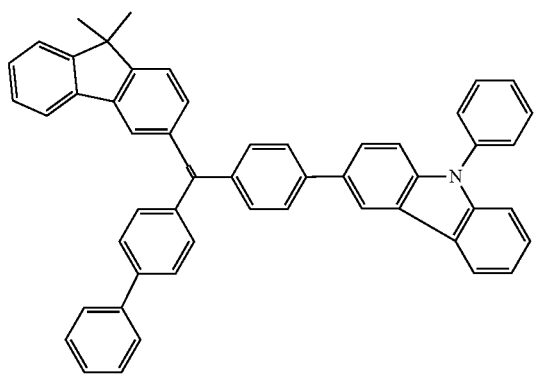

171
-continued
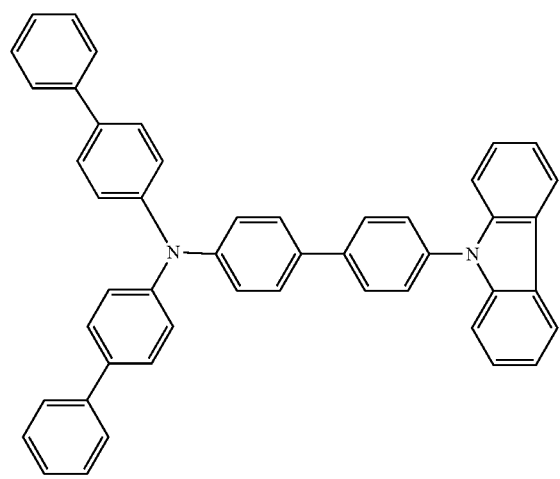
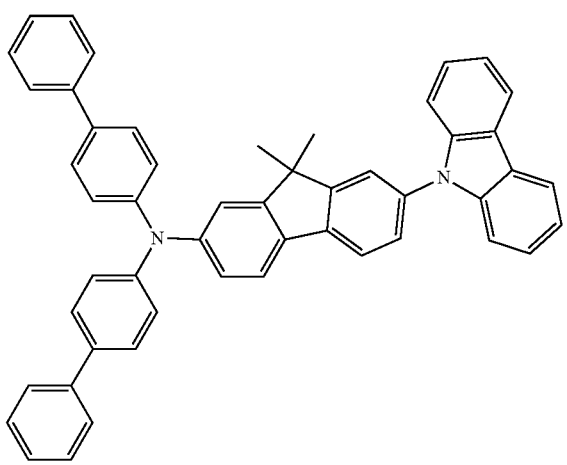
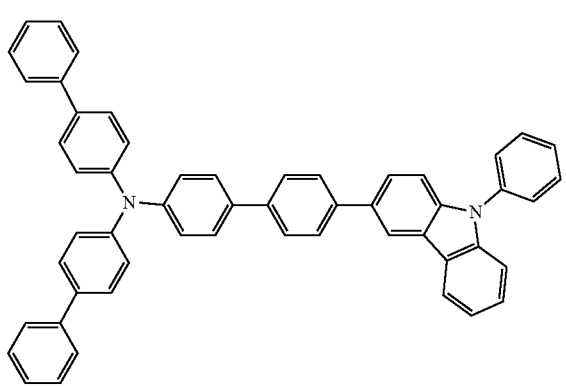
172
-continued
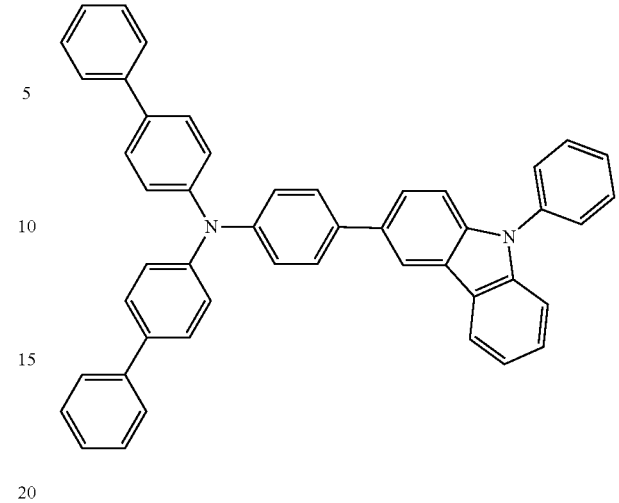
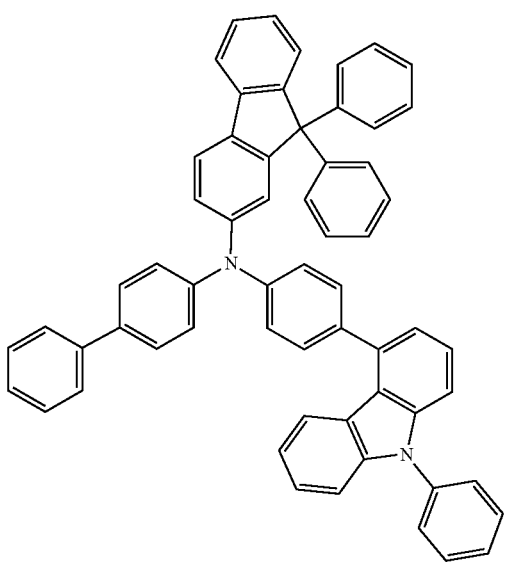

173
-continued
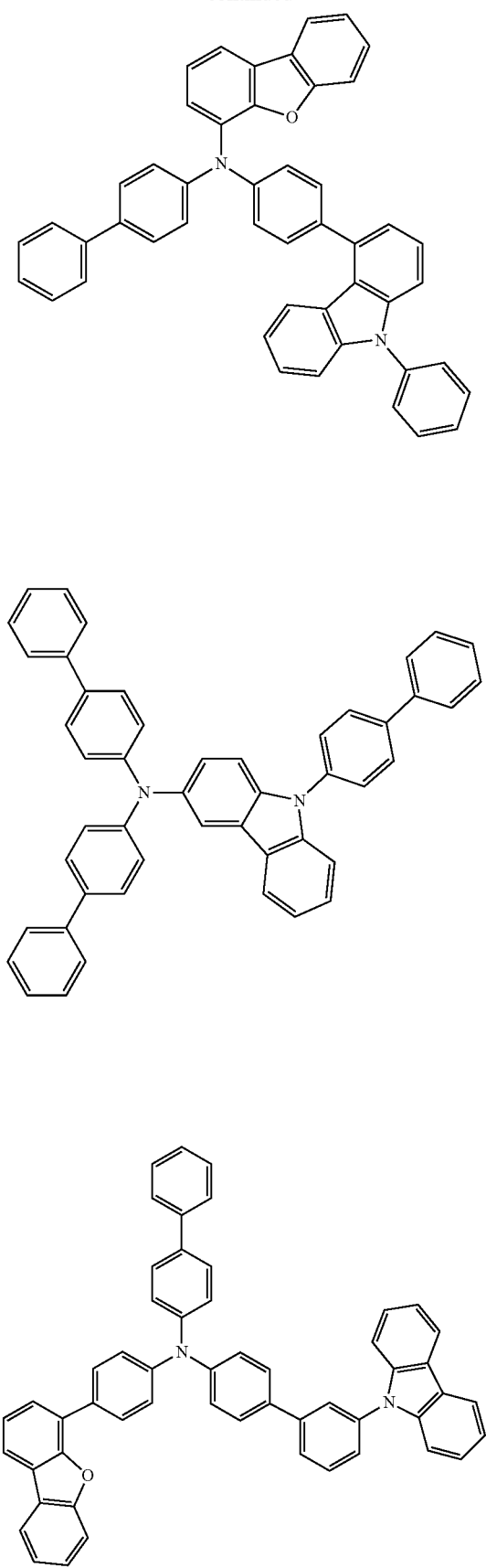
174
-continued
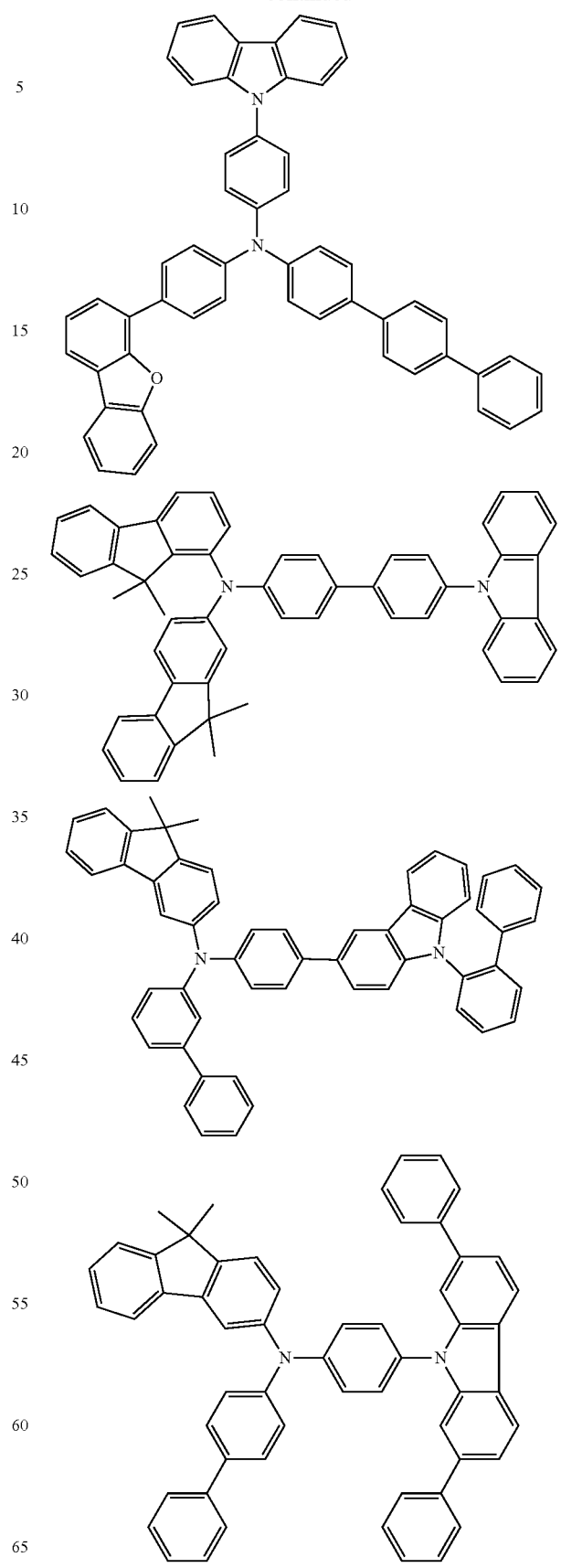

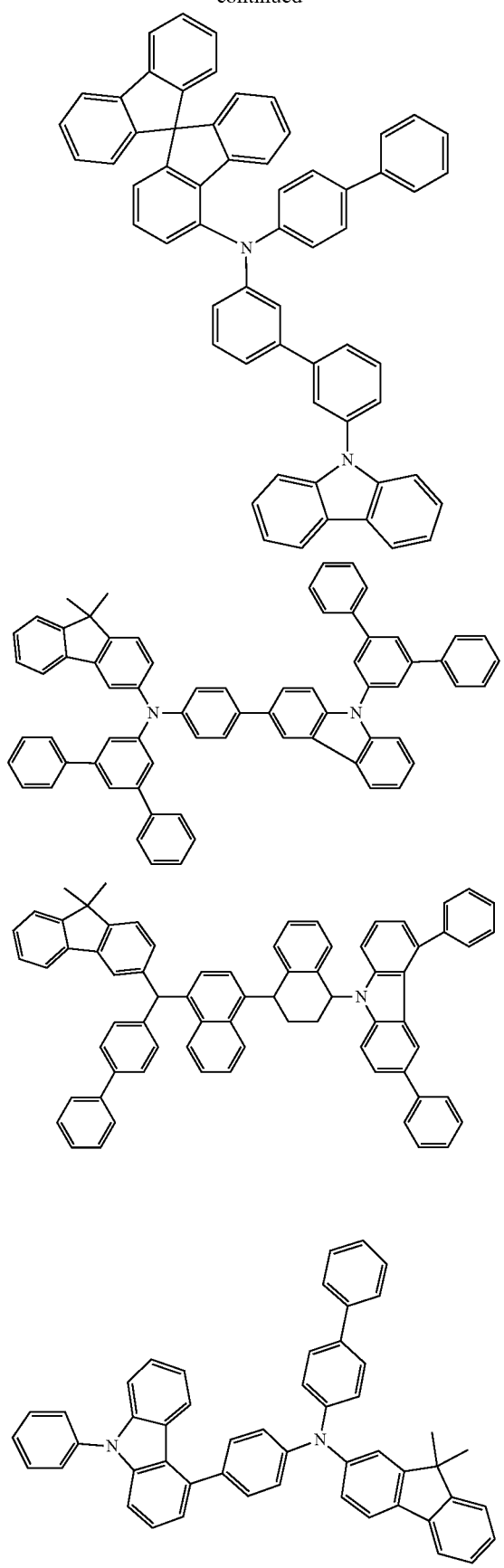
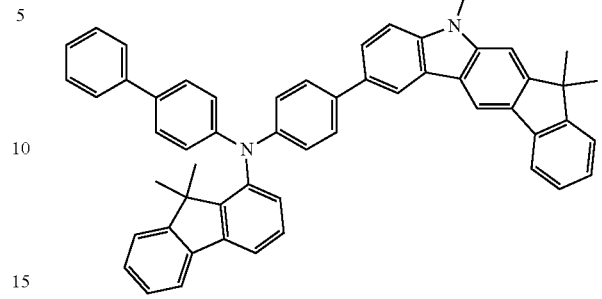
Preferred indeno- and indolocarbazole derivatives are the structures of the following formulae (17), (18), (19) and (20),
formula (17)
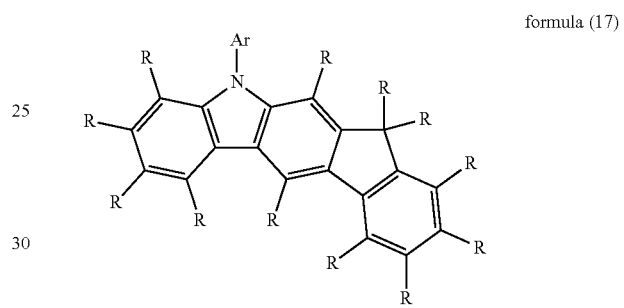
formula (18)
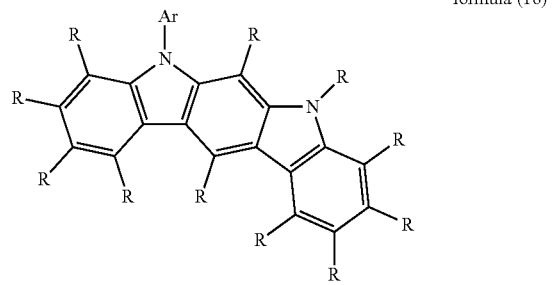
formula (19)
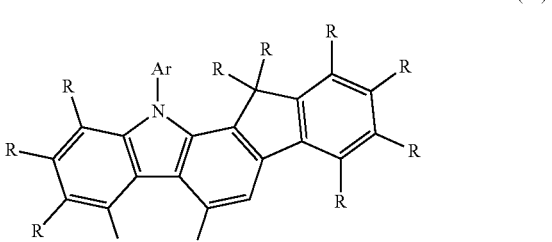
formula (20)
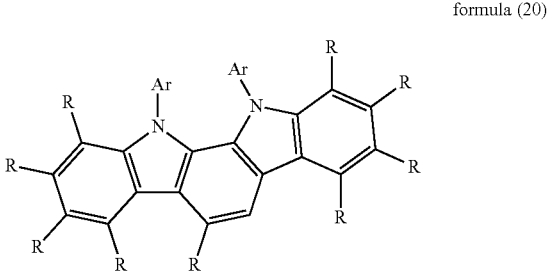
where the symbols used have the meanings given above.

Examples of indolo- and indenocarbazole derivatives that can be employed, depending on the substitution pattern, as hole- or electron-transporting matrix materials are the following structures:
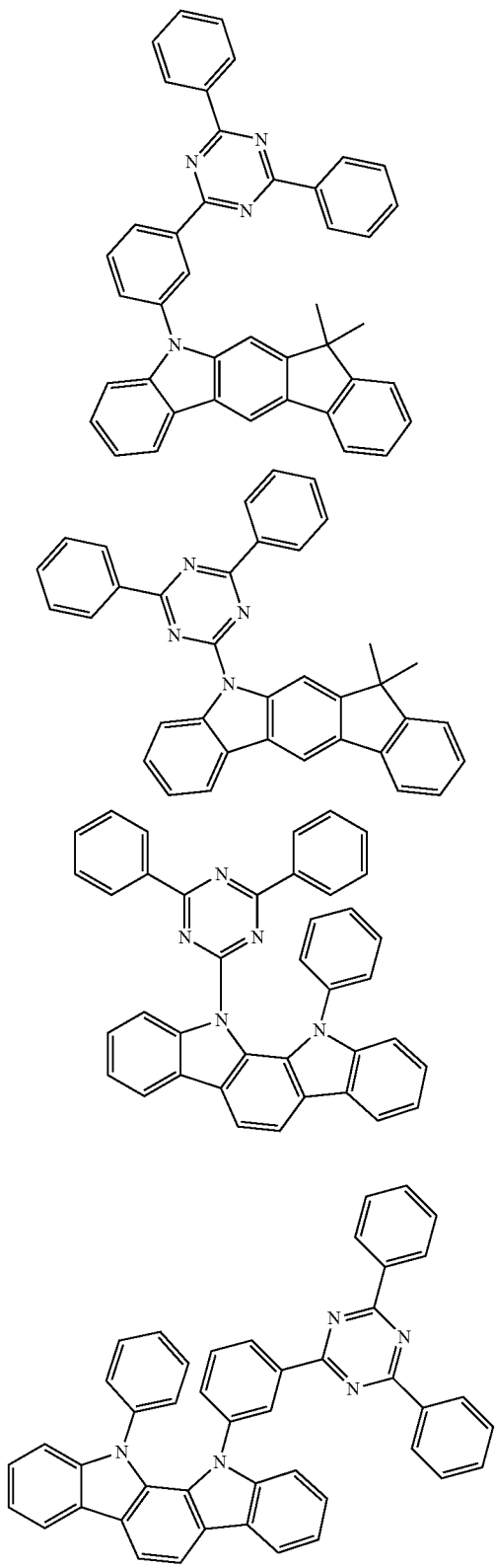
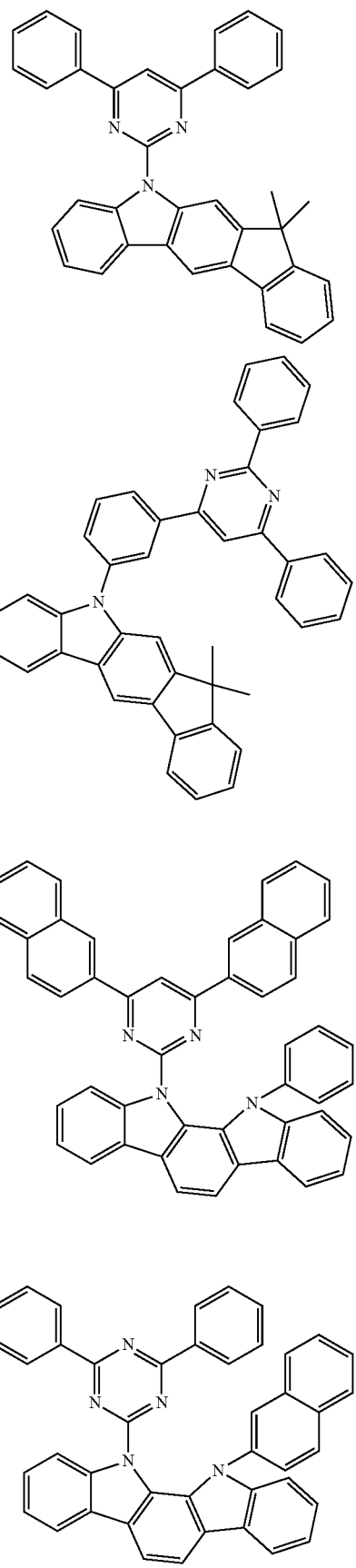

179
-continued
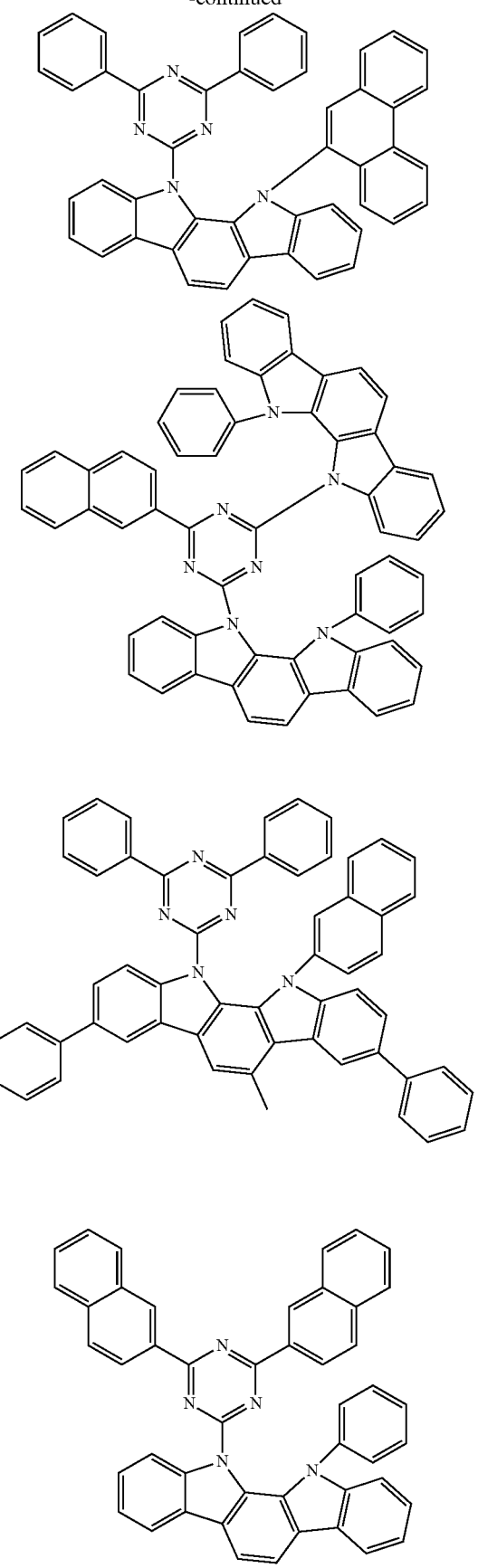
180
-continued
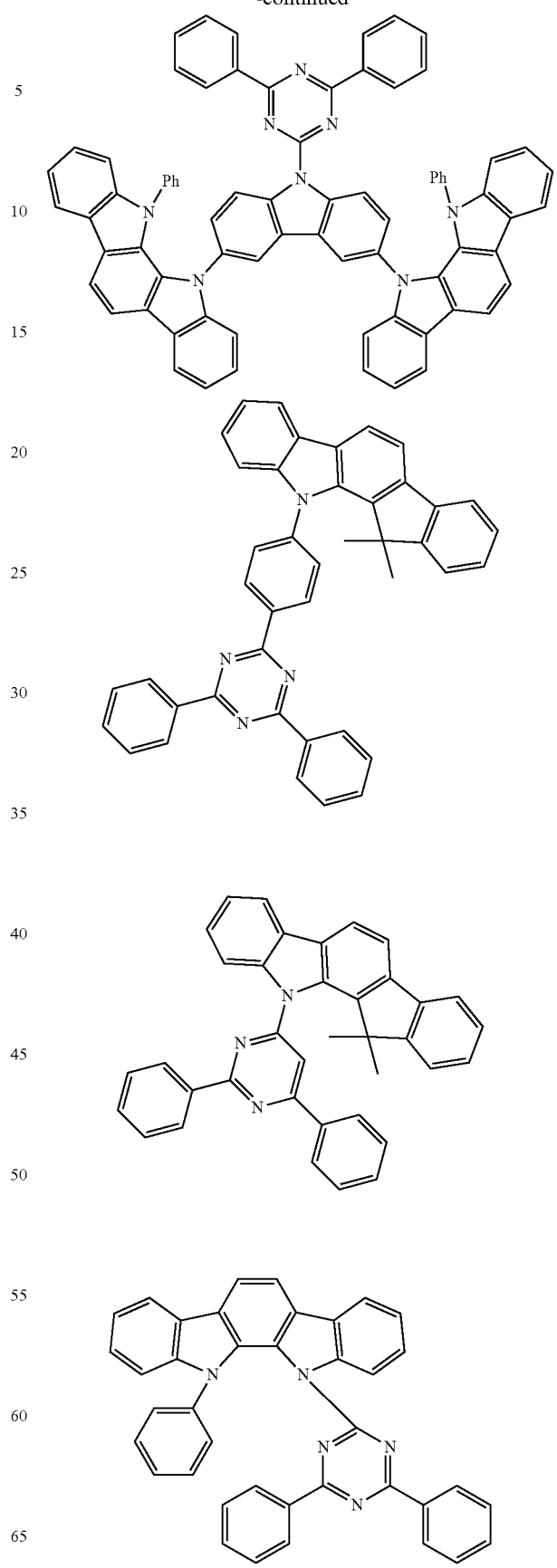

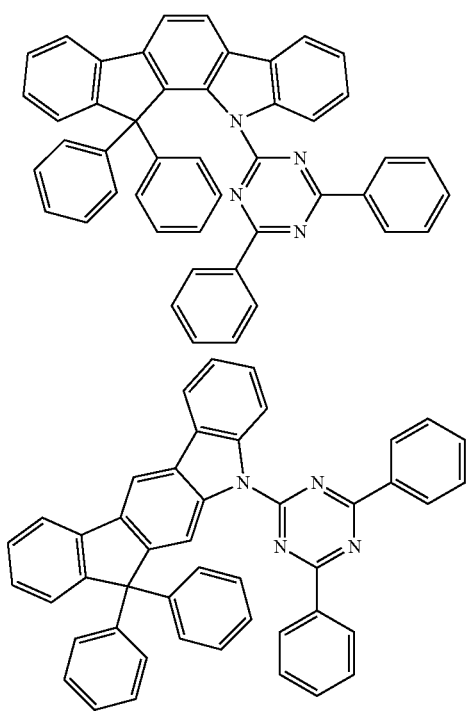
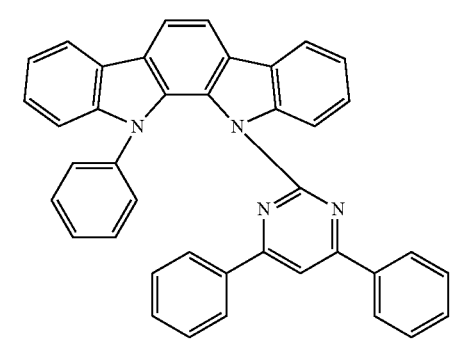
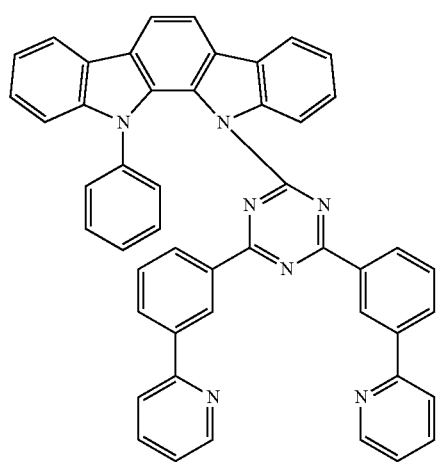
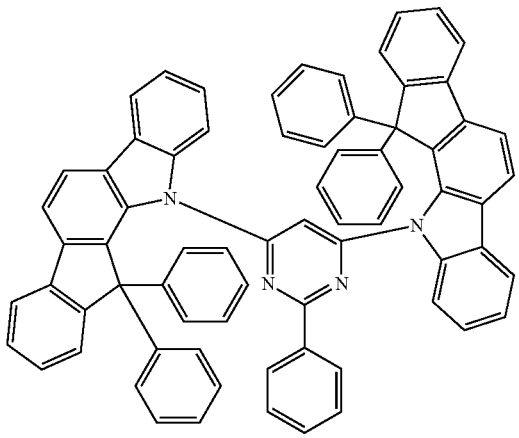
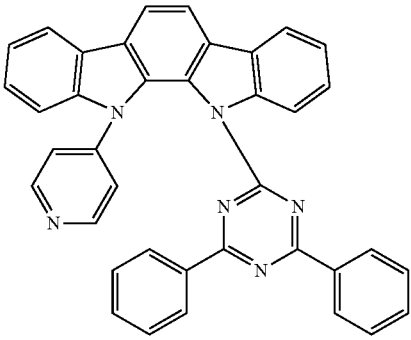
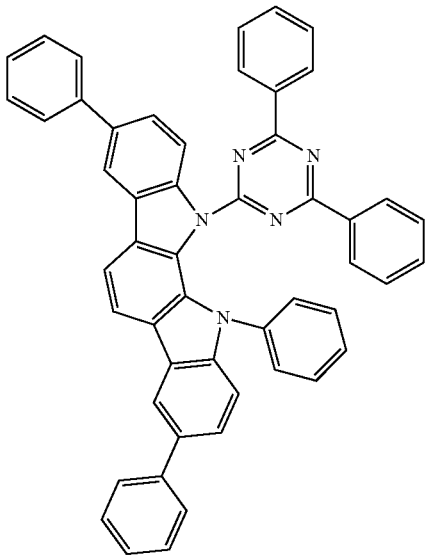

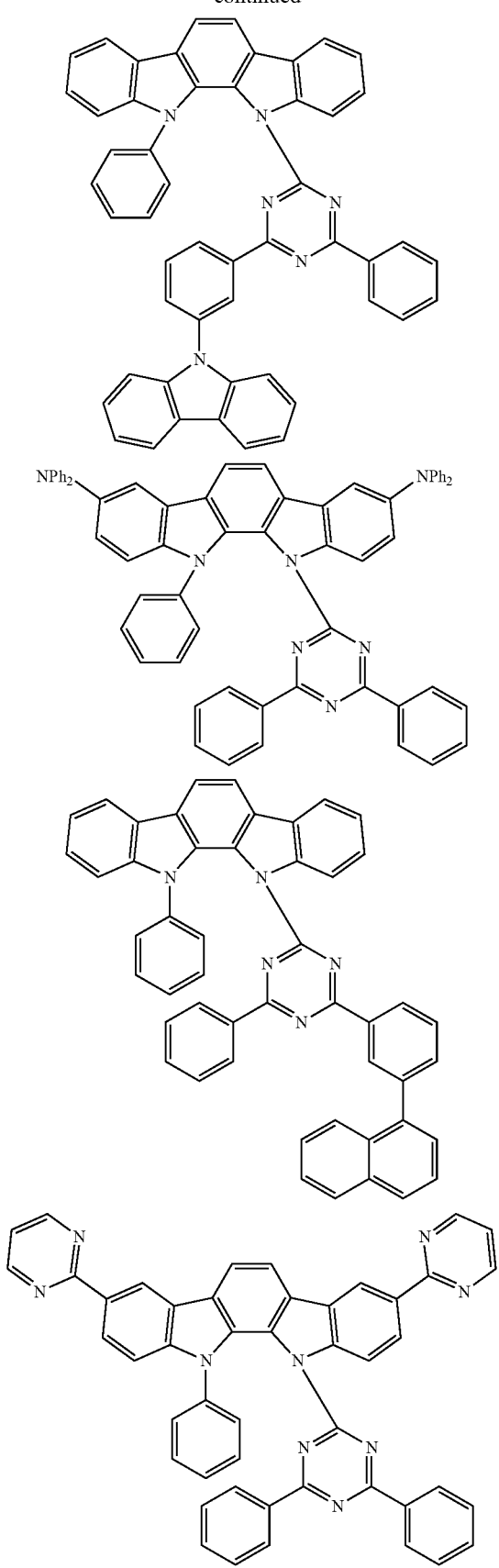
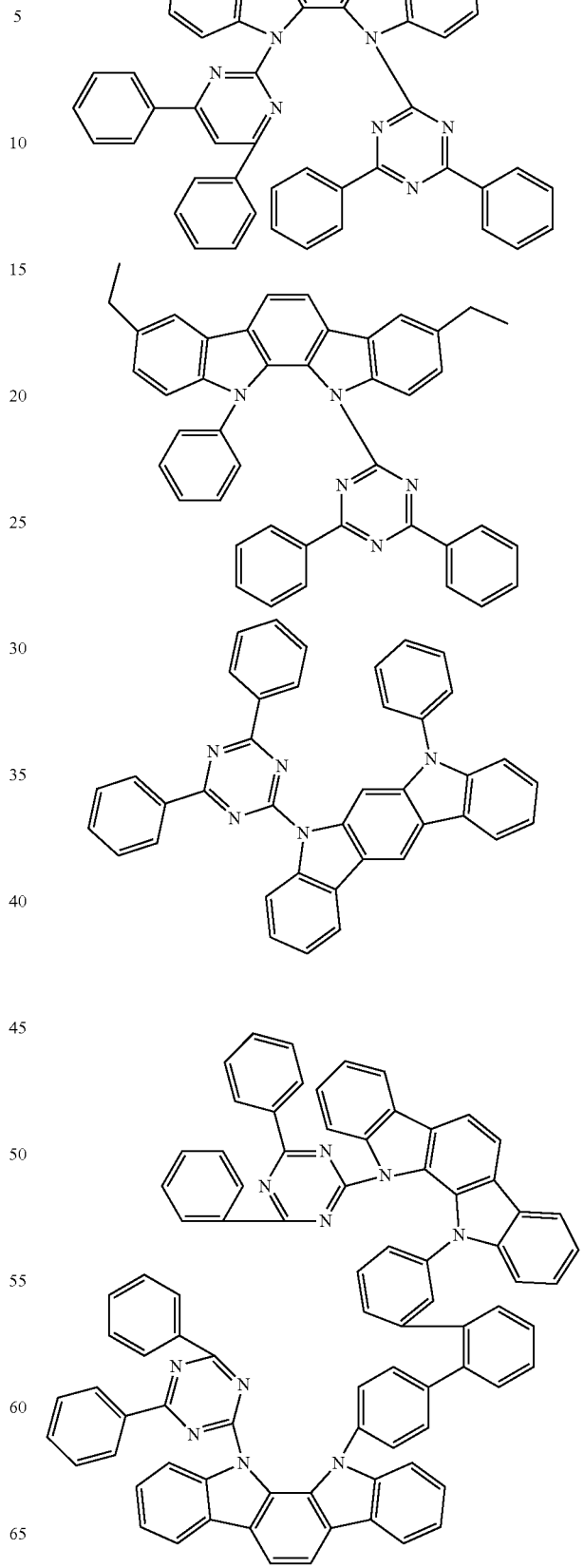

185
-continued
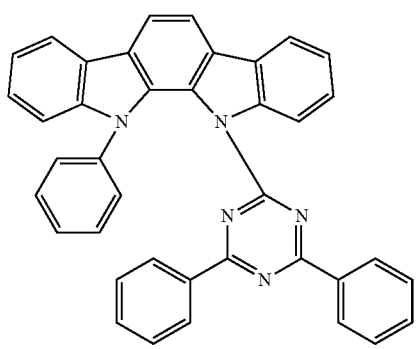
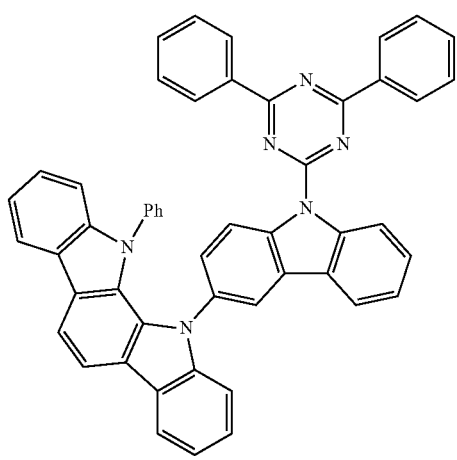
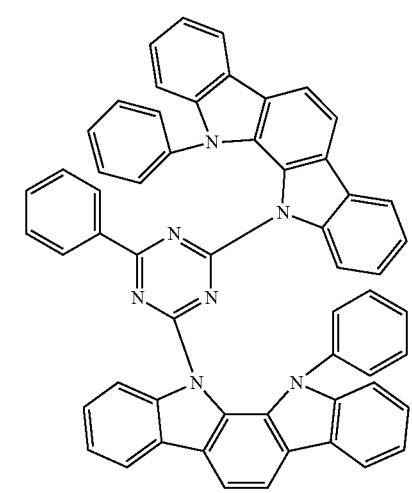
186
-continued
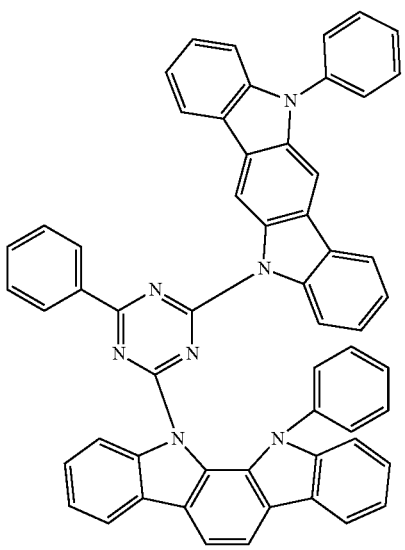
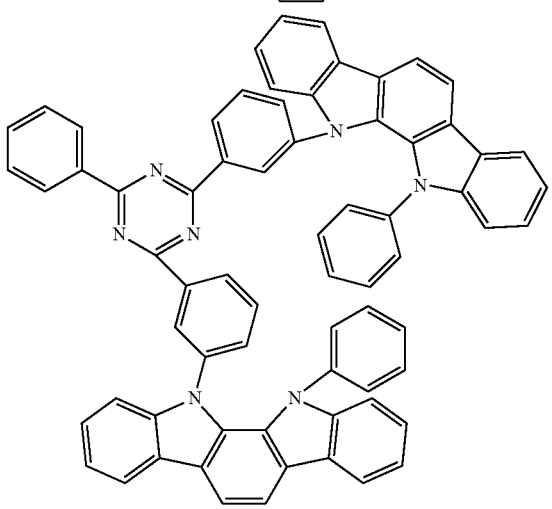
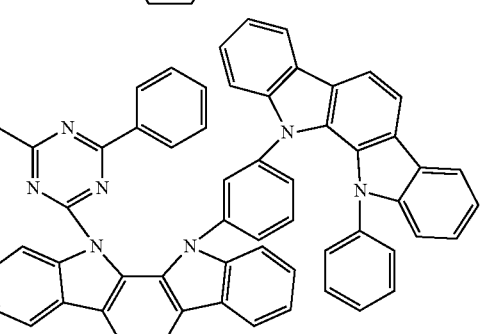
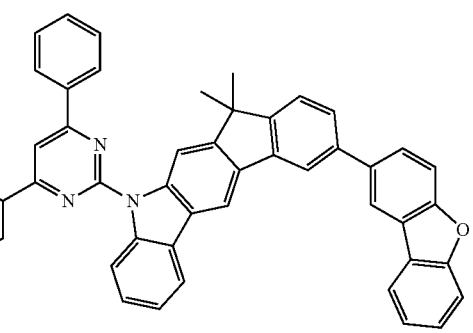

187
-continued
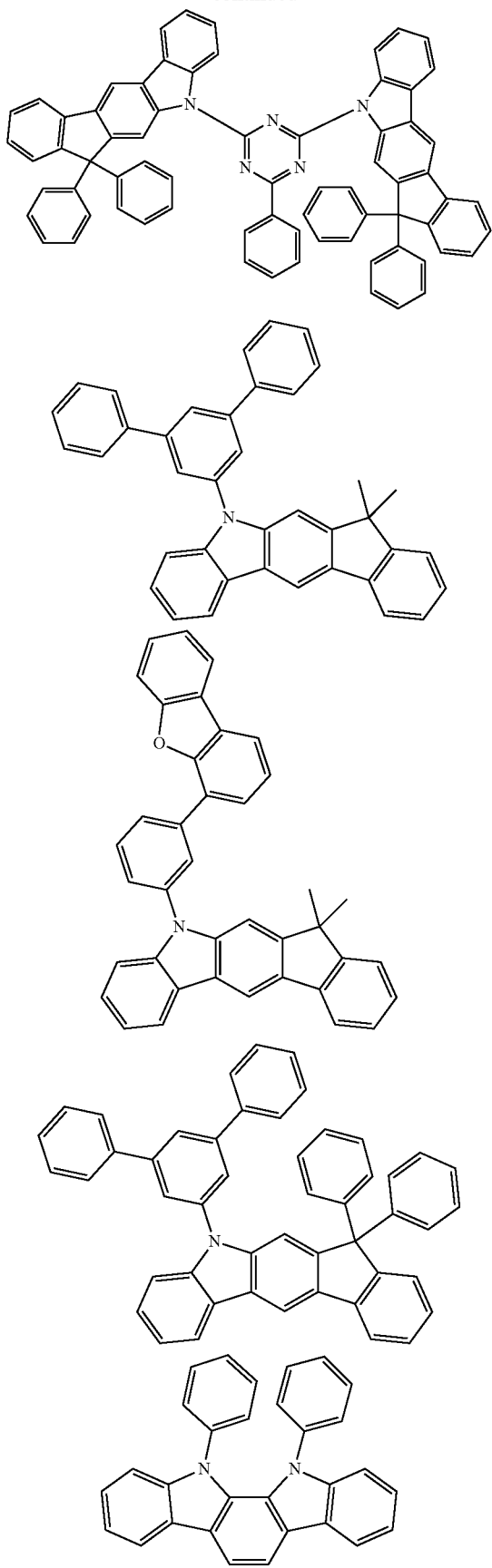
188
-continued
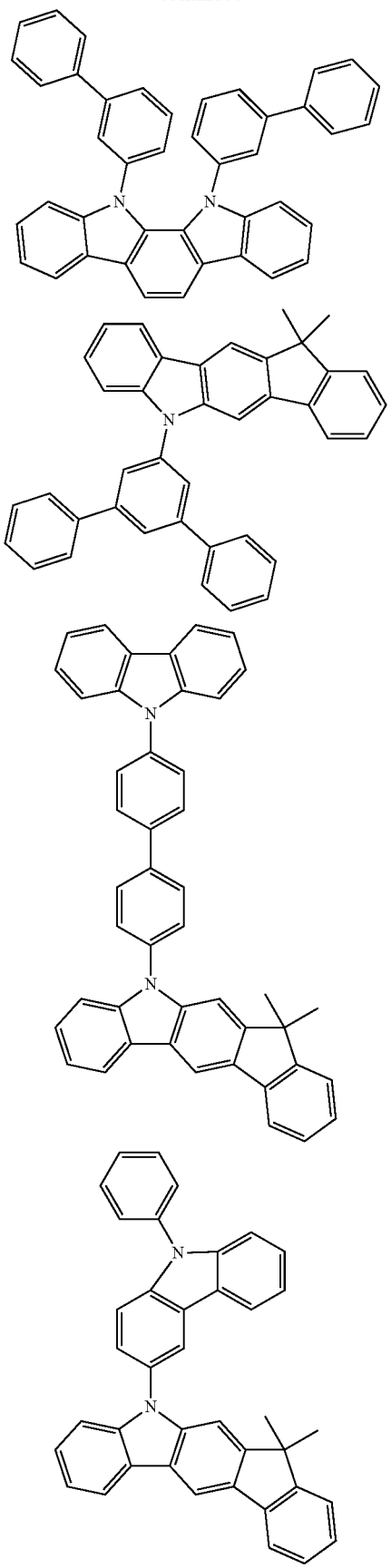

189
-continued
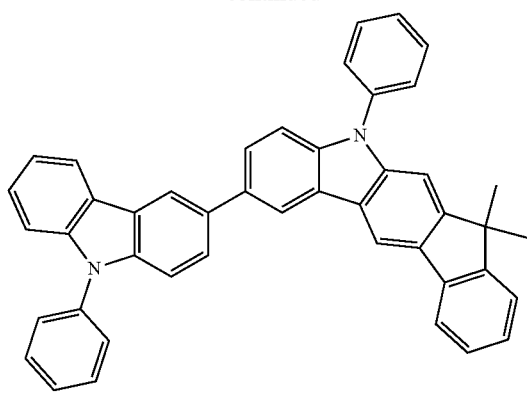
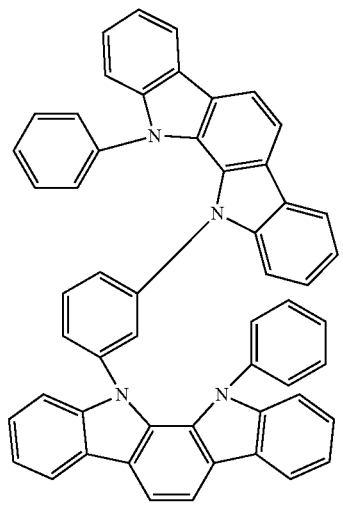
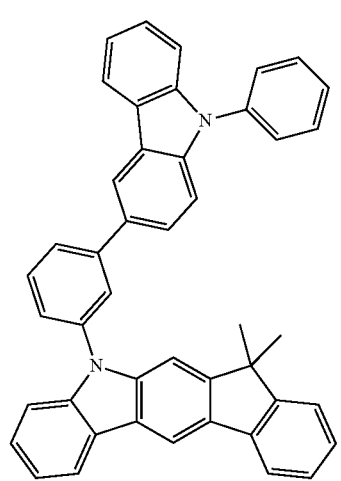
190
-continued
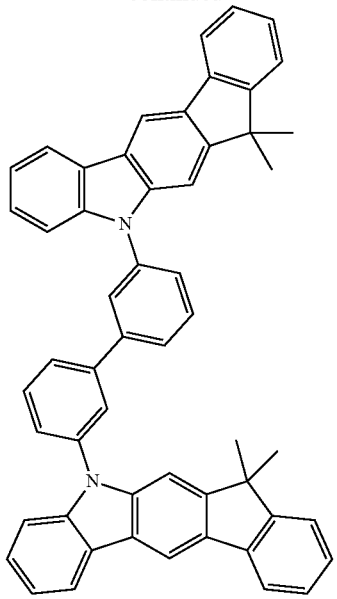
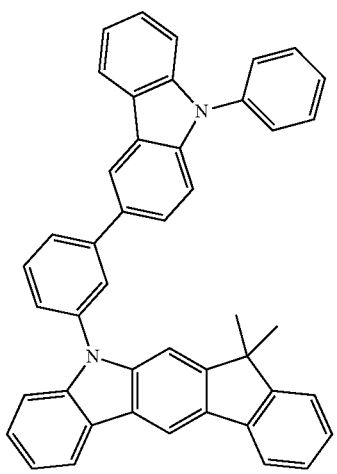
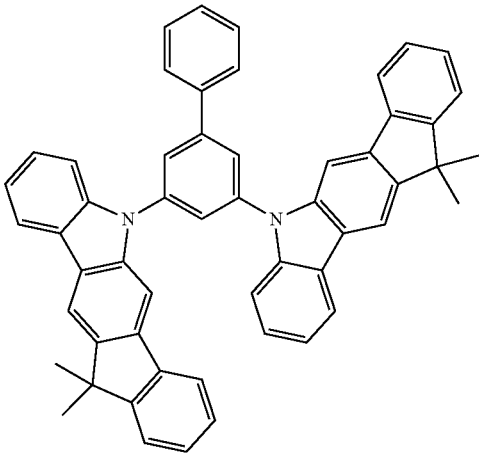

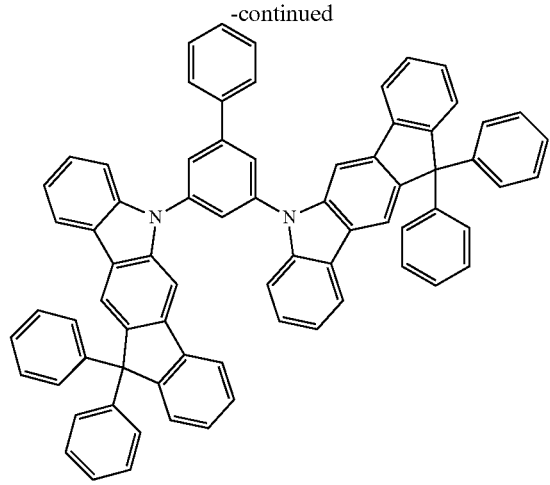

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above can be obtained from the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/007086, WO 2014/008982, WO 2014/023377, WO 2014/094961, WO 2014/094960, WO 2015/036074, WO 2015/104045, WO 2015/117718, WO 2016/015815, WO 2016/124304, WO 2017/032439, WO 2018/011186 and WO 2018/041769, and the as yet unpublished patent applications EP 17182995.5, EP 17205103.9, EP 17206950.2 and EP 18156388.3. In general, all phosphorescent complexes as are used in accordance with the prior art for phosphorescent OLEDs and as are known to the person skilled in the art in the area of organic electroluminescence are suitable, and the person skilled in the art will be able to use other phosphorescent complexes without inventive step.

Examples of phosphorescent dopants are shown below.

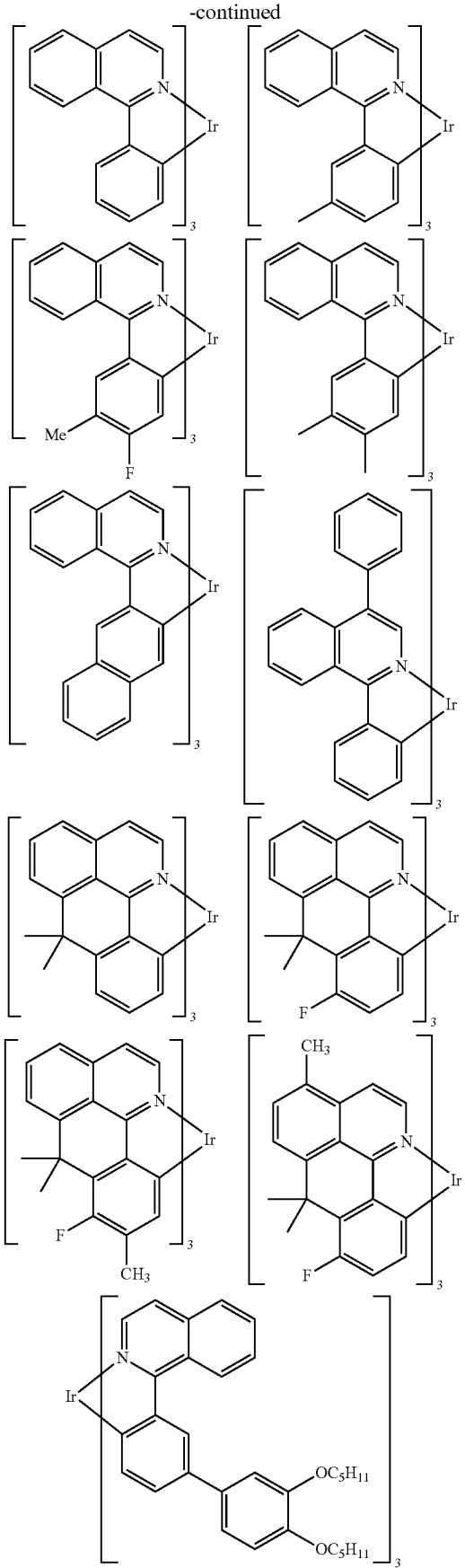

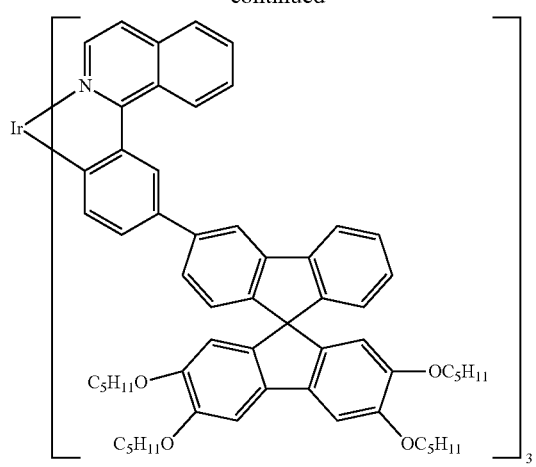
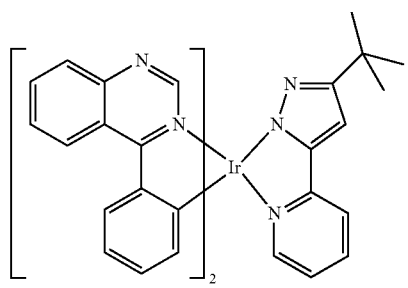
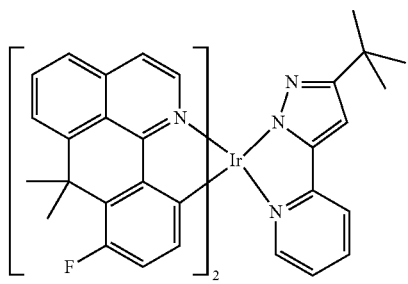
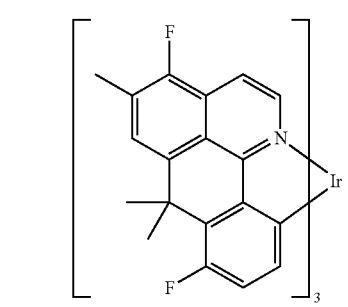
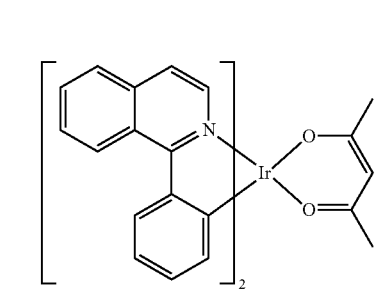
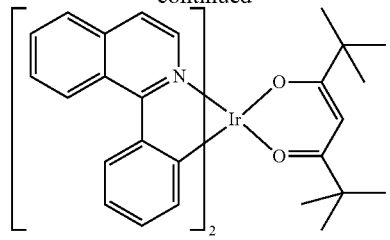
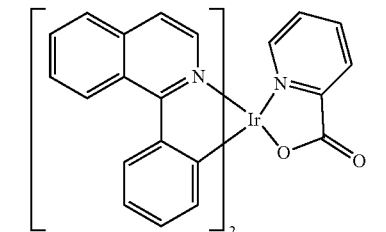
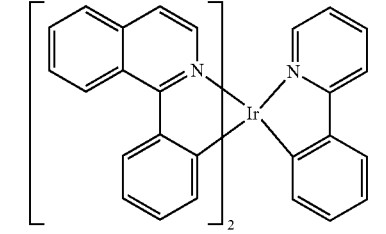
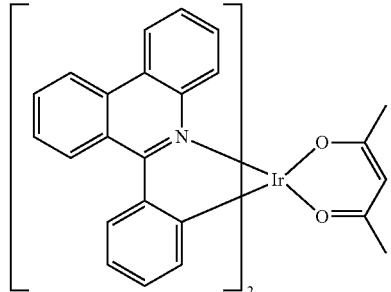
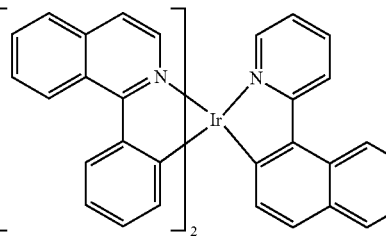
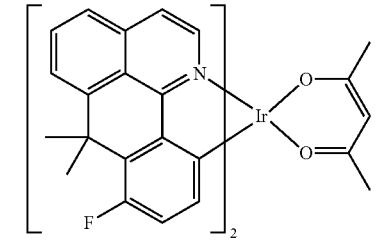
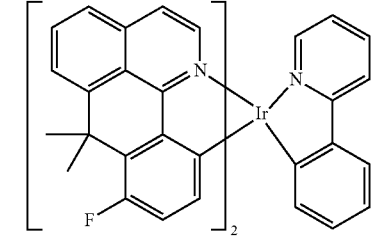

195
-continued
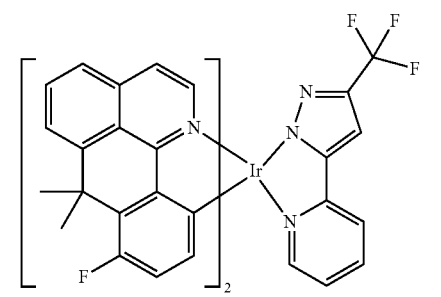
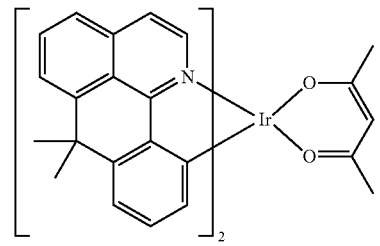
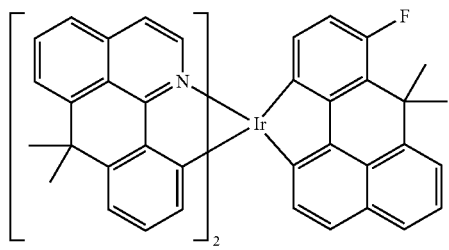
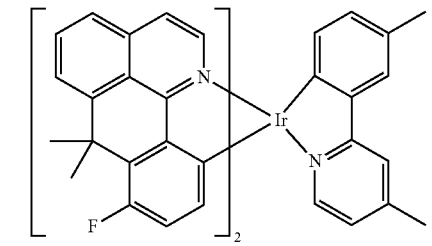
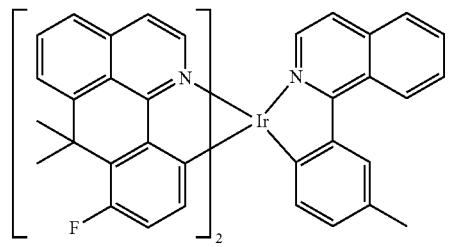
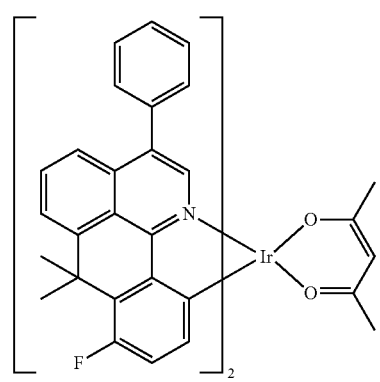
196
-continued
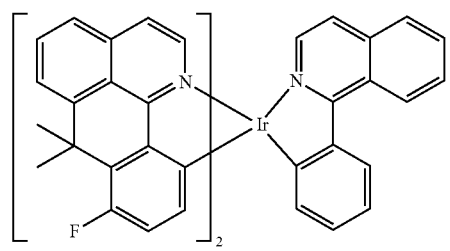
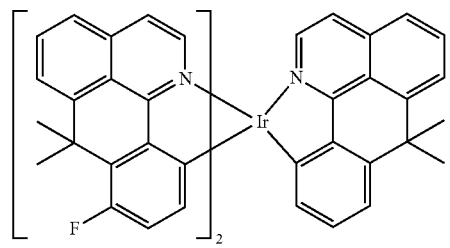
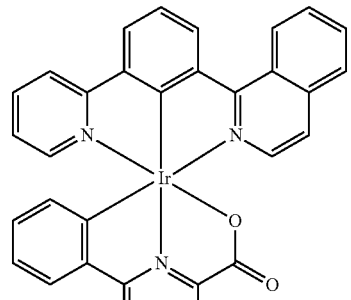
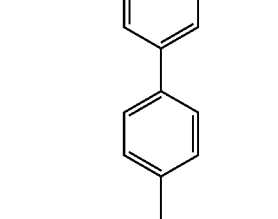
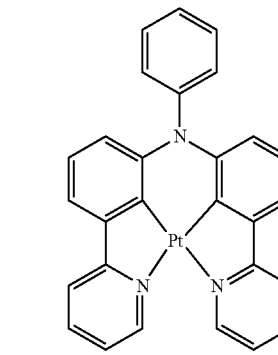
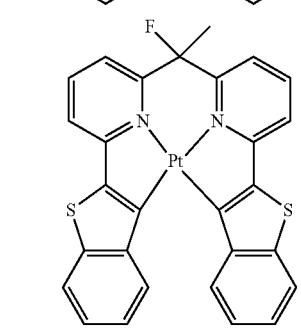

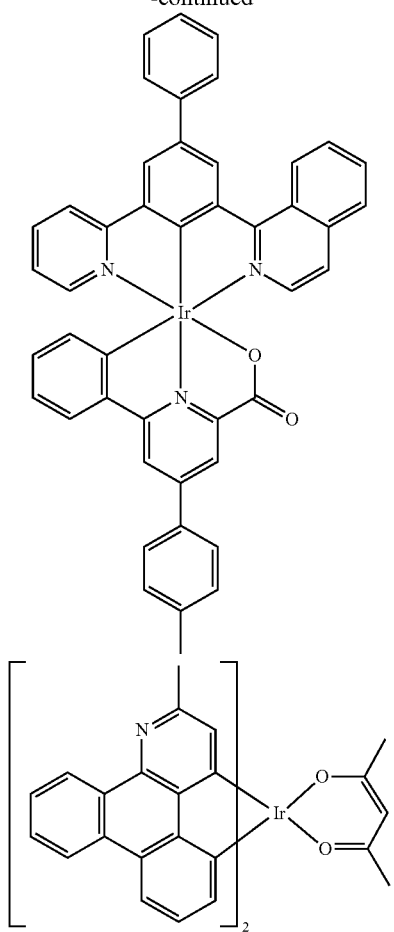
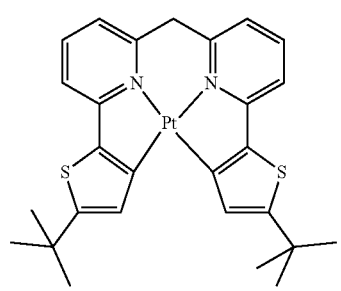
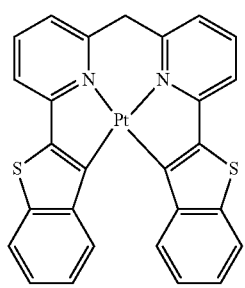
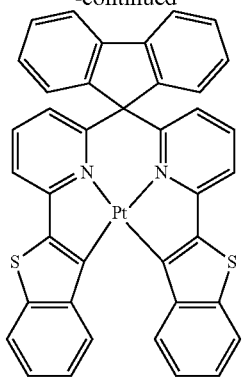
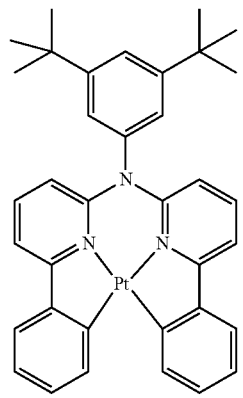
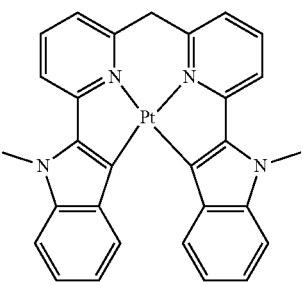
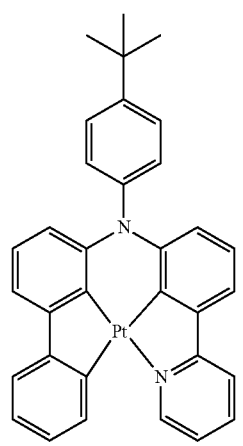

199
-continued
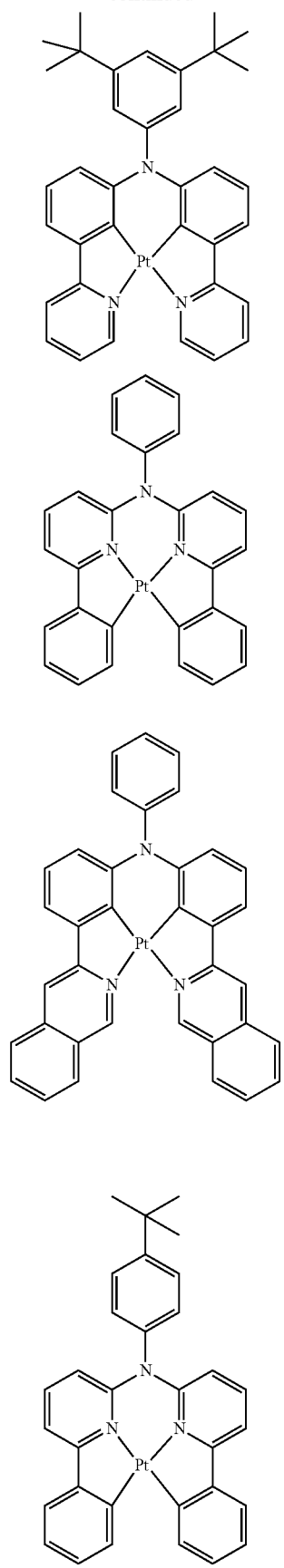
200
-continued
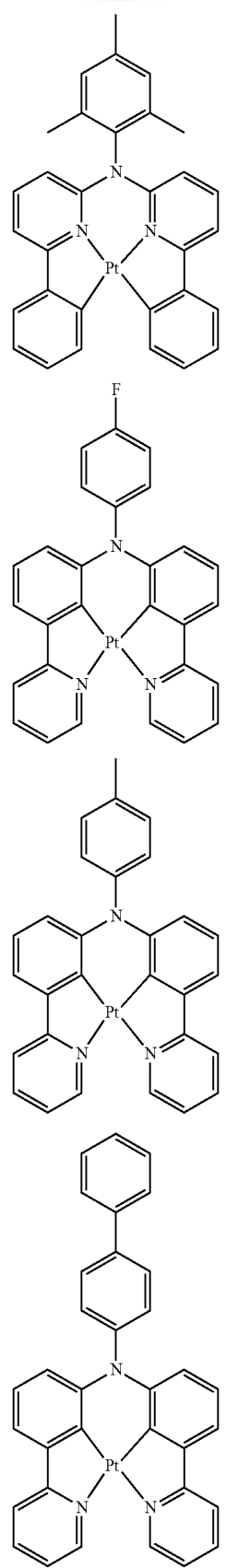

201
-continued
202
-continued
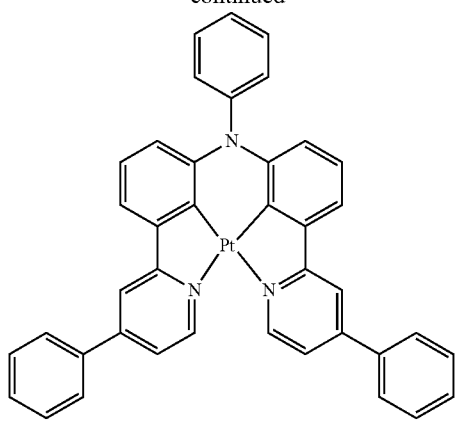
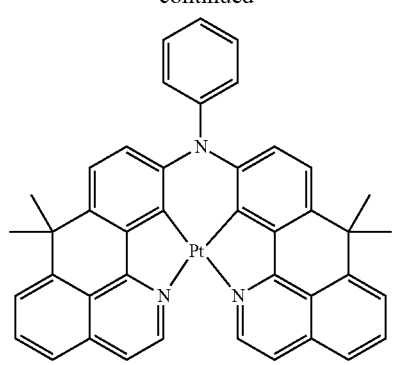
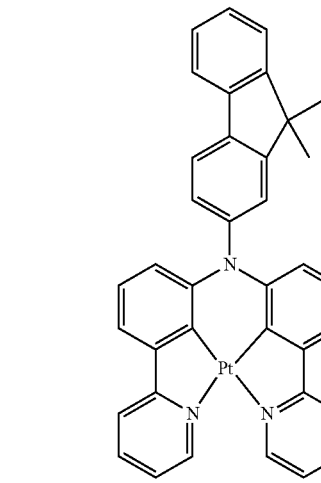
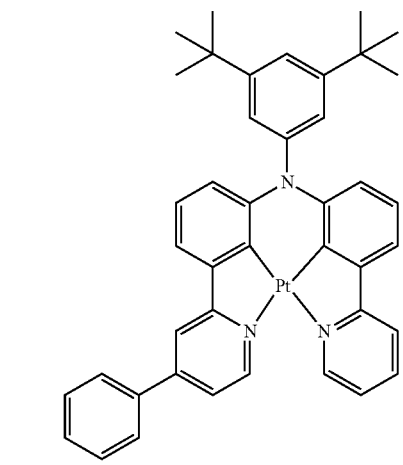
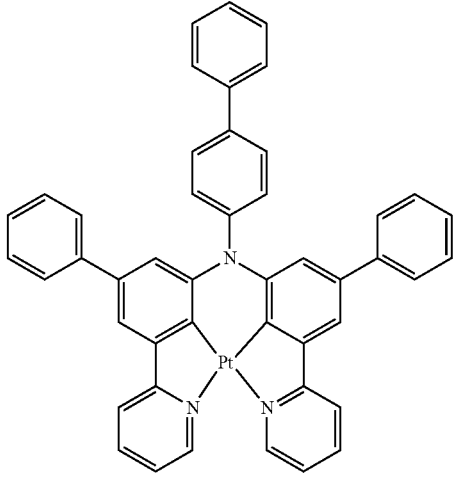
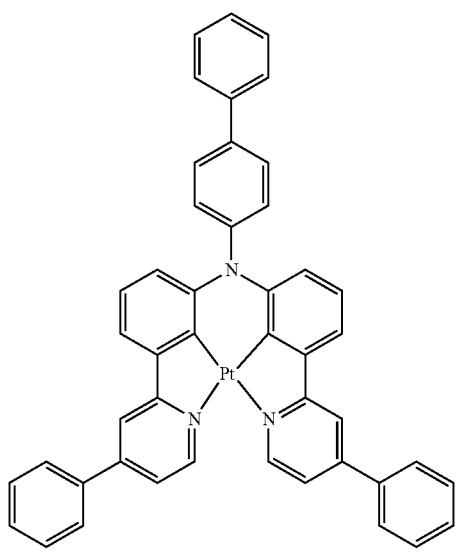
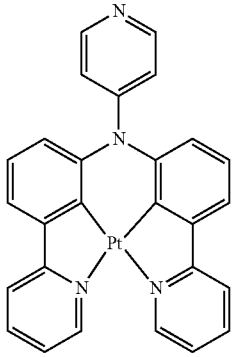

-continued
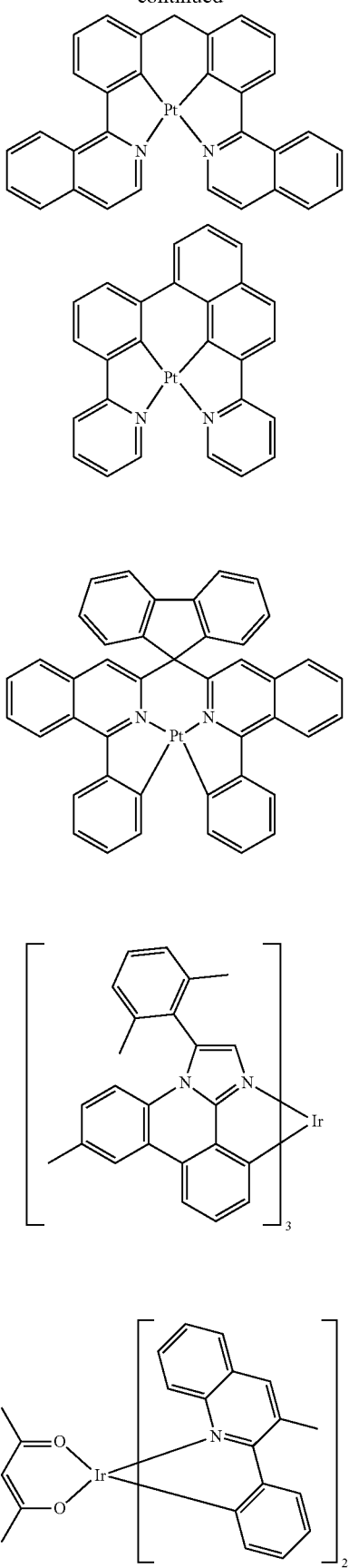
-continued
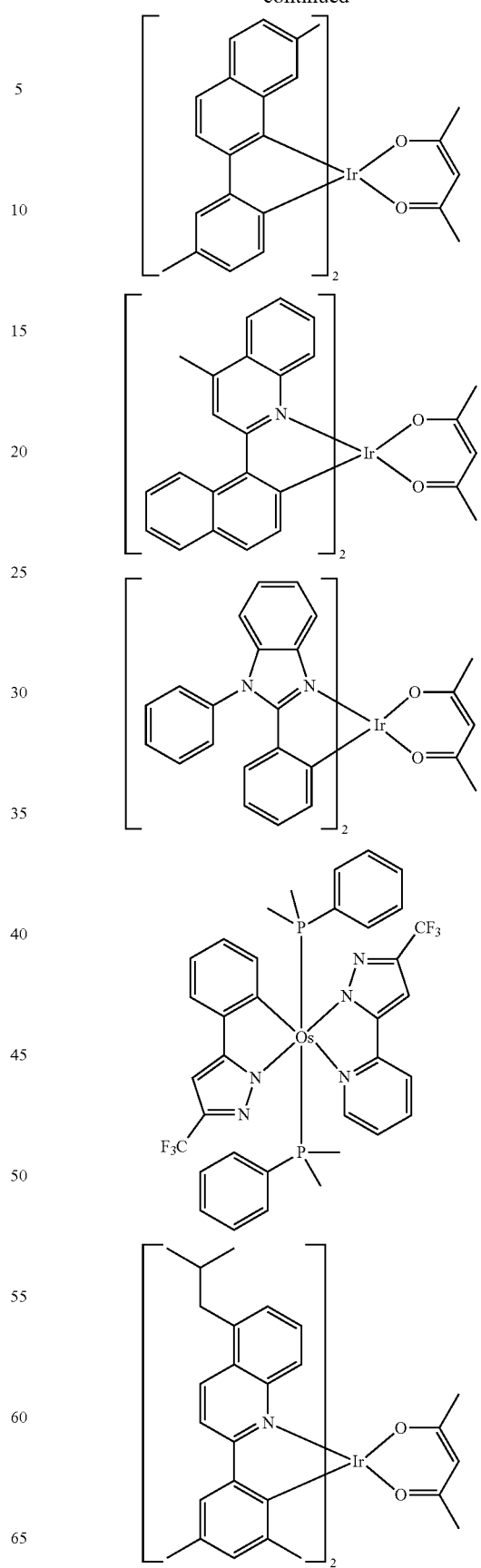

-continued
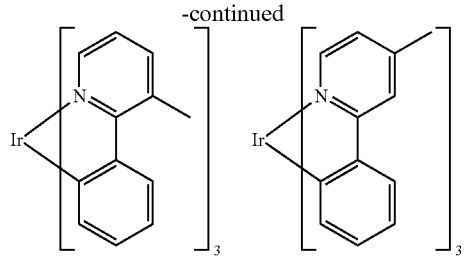
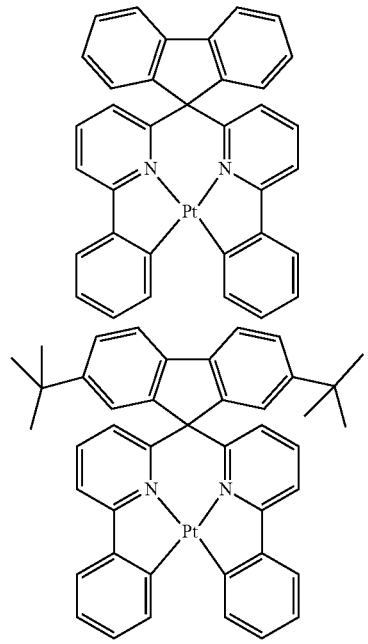
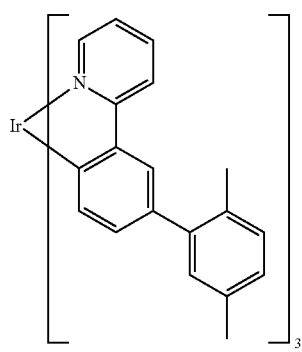
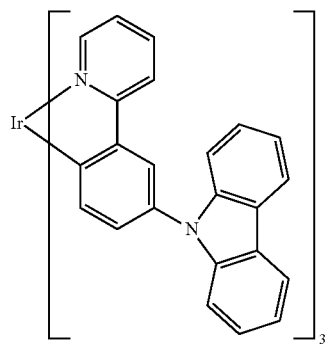
-continued
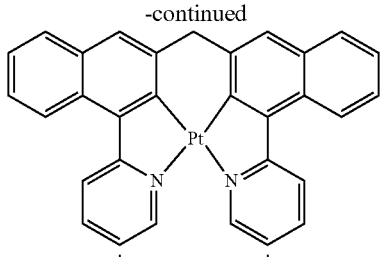
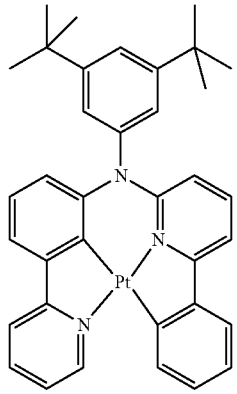
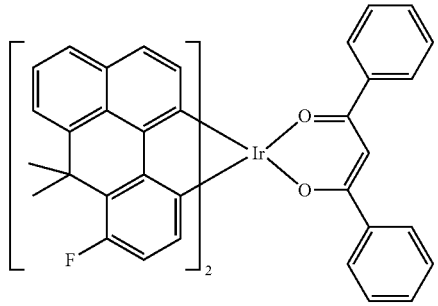
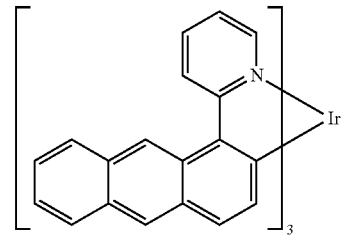
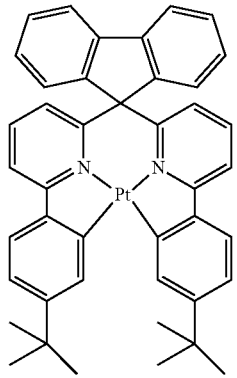

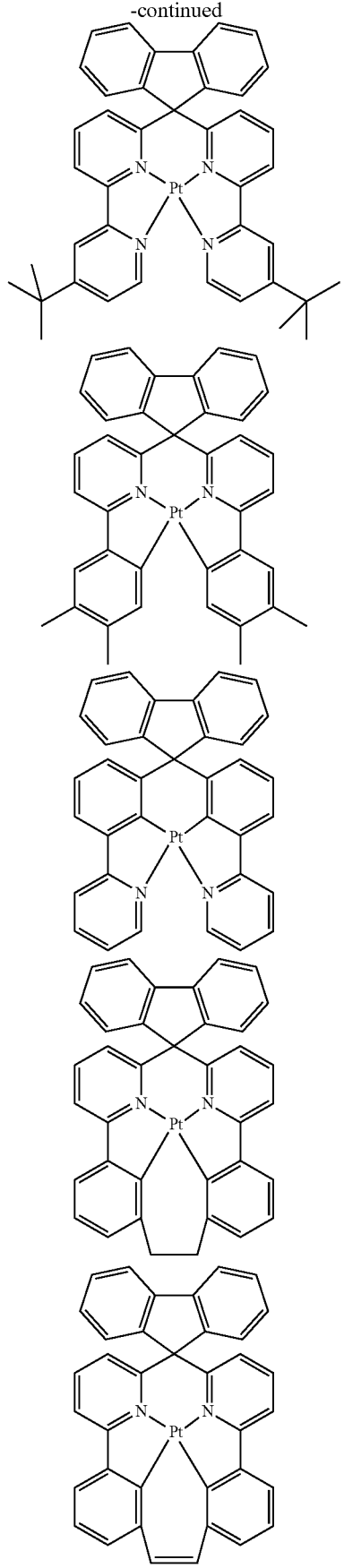
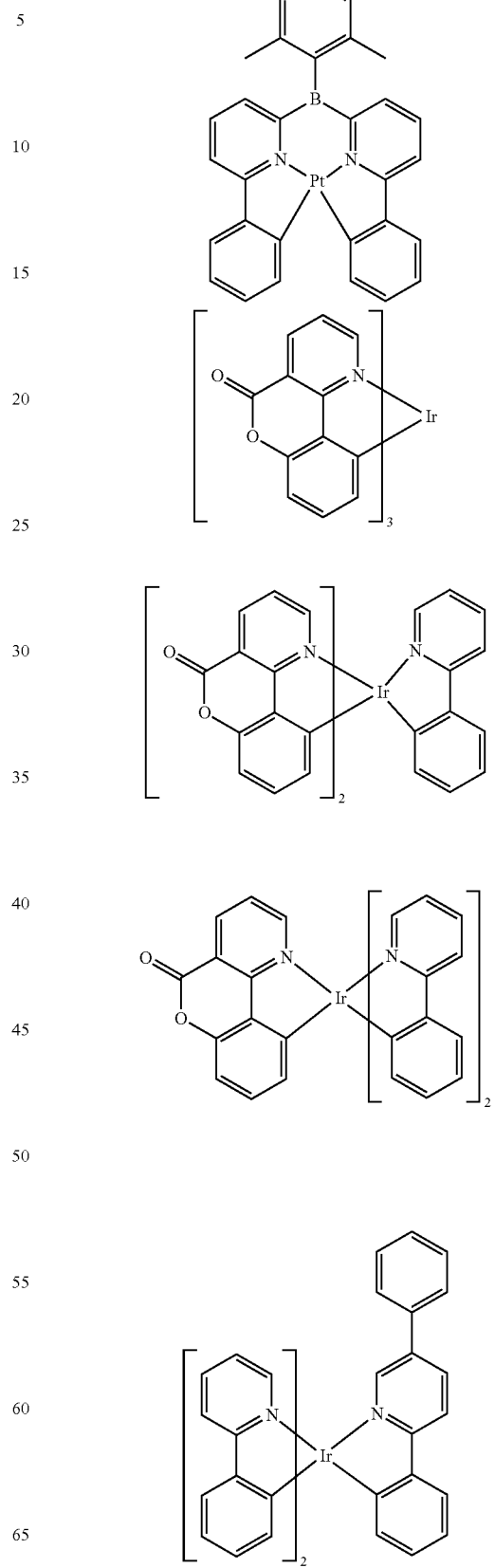

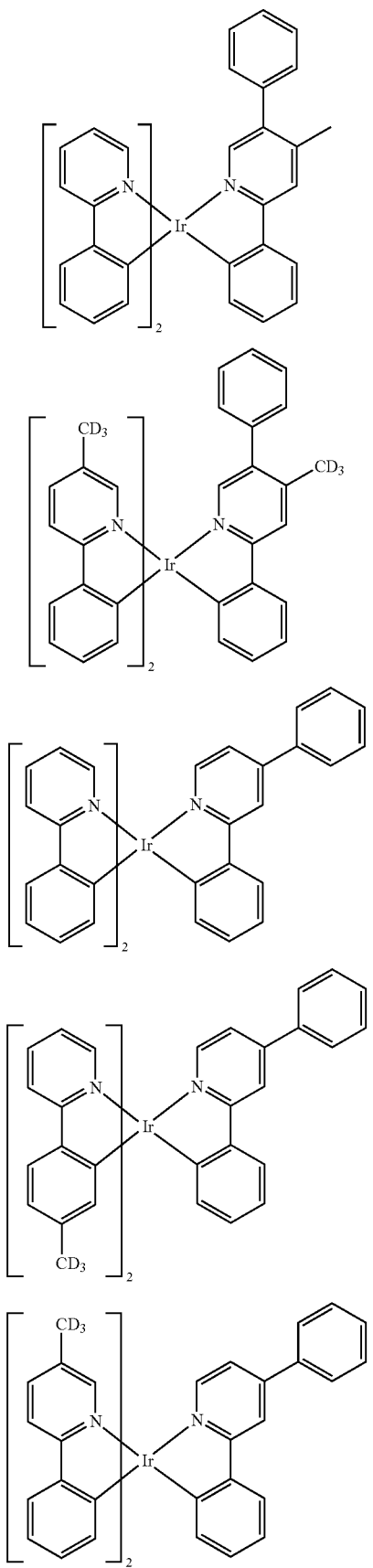
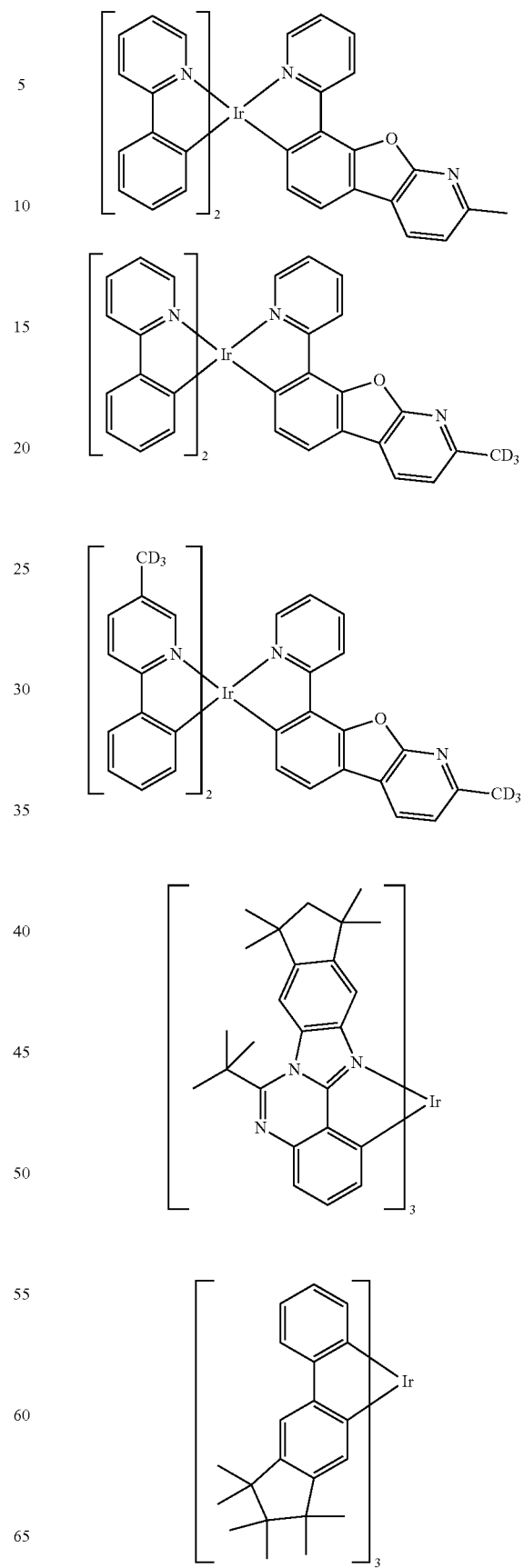

211
-continued
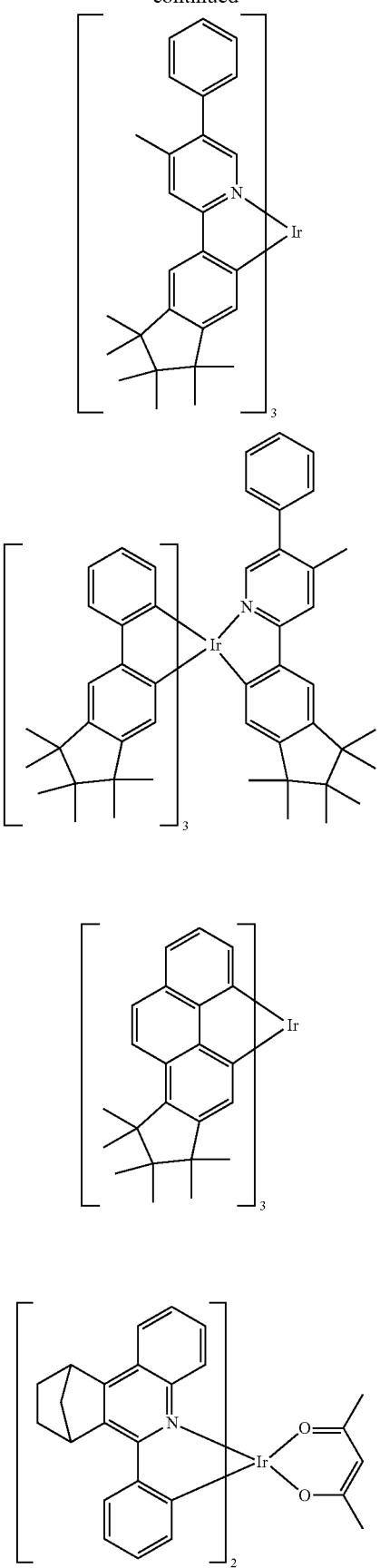
212
-continued
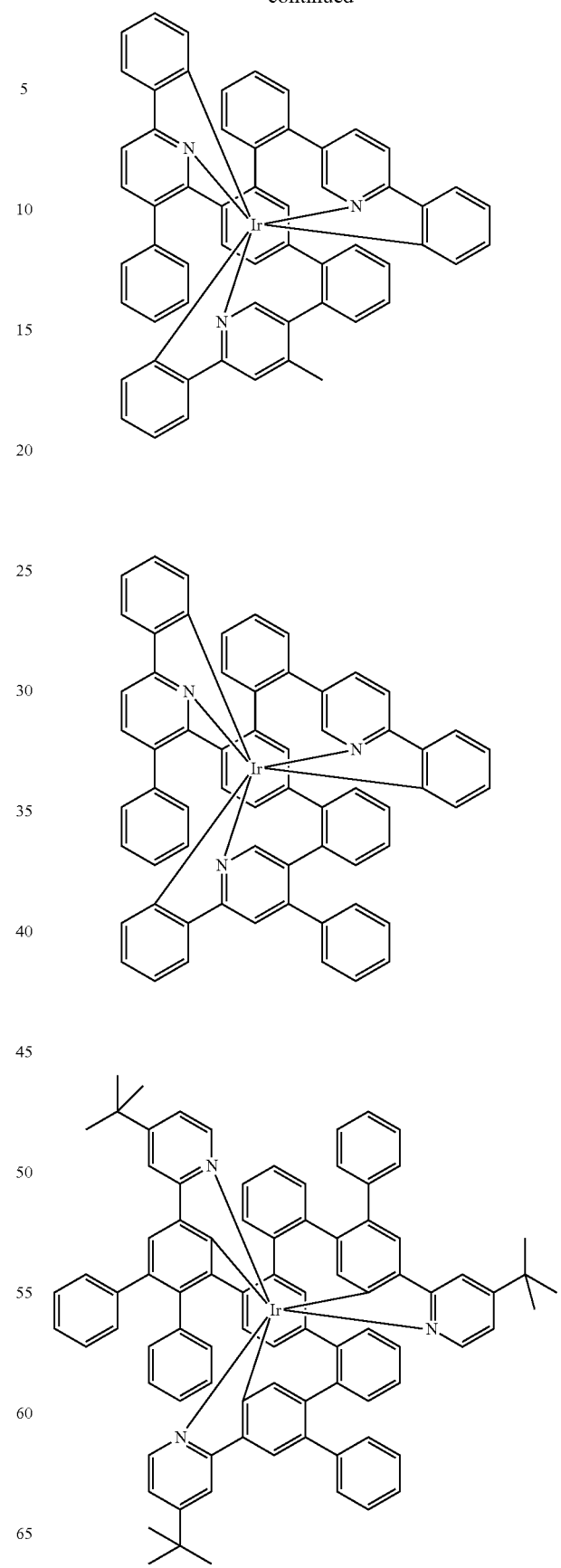

-continued

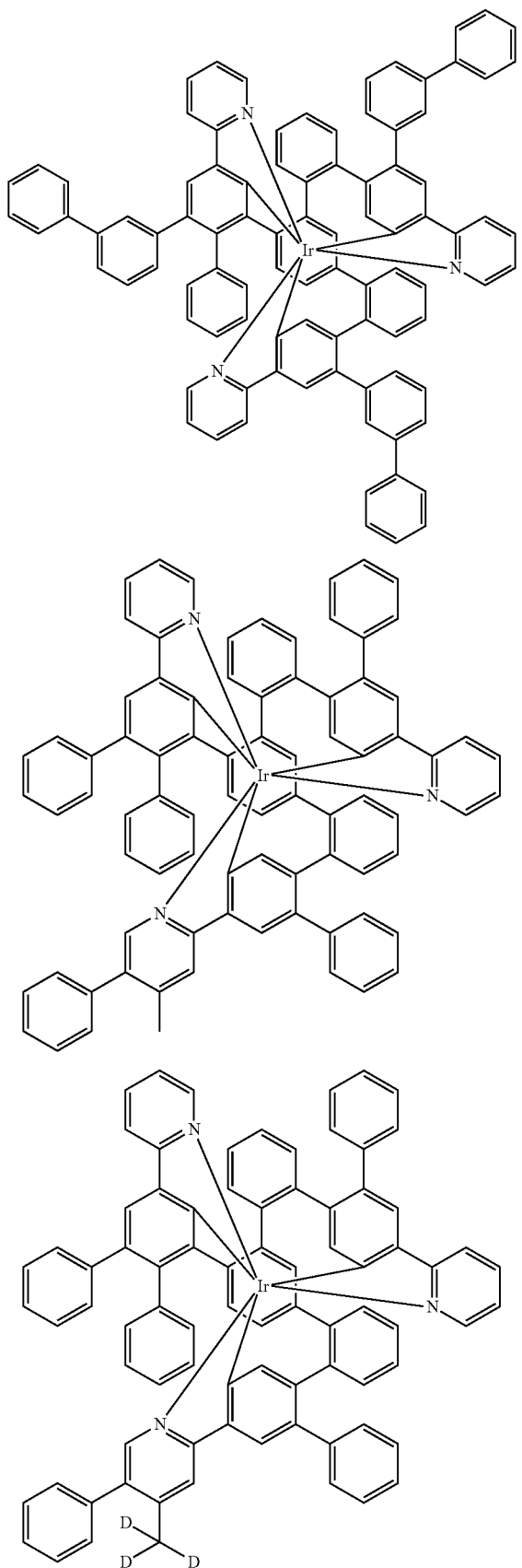

The compounds according to the invention are, in particular, also suitable as matrix materials for phosphorescent emitters in organic electroluminescent devices, as described, for example, in WO 98/24271, US 2011/0248247 and US 2012/0223633. In these multicolour display components, an additional blue emission layer is vapour-deposited over the entire area onto all pixels, including those having a colour other than blue.

In a further embodiment of the invention, the organic electroluminescent device according to the invention does not contain a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. Furthermore, it is possible to use a metal complex which is identical or similar to the metal complex in the emitting layer as hole-transport or hole-injection material directly adjacent to the emitting layer, as described, for example, in WO 2009/030981.

All materials as are usually employed in accordance with the prior art can be used in the further layers of the organic electroluminescent device according to the invention. The person skilled in the art will therefore be able, without inventive step, to employ all materials known for organic electroluminescent devices in combination with the compounds of the formula (1) according to the invention or the preferred embodiments mentioned above.

Preference is furthermore given to an organic electroluminescent device, characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured.

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose.

Also possible are hybrid processes, in which, for example, one or more layers are applied from solution and one or more further layers are applied by vapour deposition.

These processes are generally known to the person skilled in the art and can be applied by him, without inventive step, to organic electroluminescent devices containing the compounds according to the invention.

The compounds according to the invention and the organic electroluminescent devices according to the invention are distinguished over the prior art by one or more of the following surprising advantages:

1. The compounds according to the invention, employed as matrix material for phosphorescent emitters, lead to long lifetimes.
2. The compounds according to the invention lead to low use and operating voltages. This applies, in particular, if the compounds are employed as matrix material for a phosphorescent emitter.
3. The compounds according to the invention lead to high efficiencies. This applies, in particular, if the compounds are employed as matrix material for a phosphorescent emitter.
4. The compounds according to the invention can be employed as blue-fluorescing emitters and in this function lead to high efficiencies and lifetimes.

The invention is explained in greater detail by the following examples, without wishing to restrict it thereby. The person skilled in the art will be able to carry out the invention throughout the range disclosed from the descriptions and prepare further compounds according to the invention without inventive step and use them in electronic devices or use the process according to the invention.

EXAMPLES

Synthesis Examples

The following syntheses are, unless indicated otherwise, carried out under a protective-gas atmosphere in dried solvents. The solvents and reagents can be obtained from ALDRICH or ABCR. The numbers indicated for the starting materials which are not commercially available are the corresponding CAS numbers.

a) 1-(Benzofuran-3-yl)dibenzo[b,d]furan

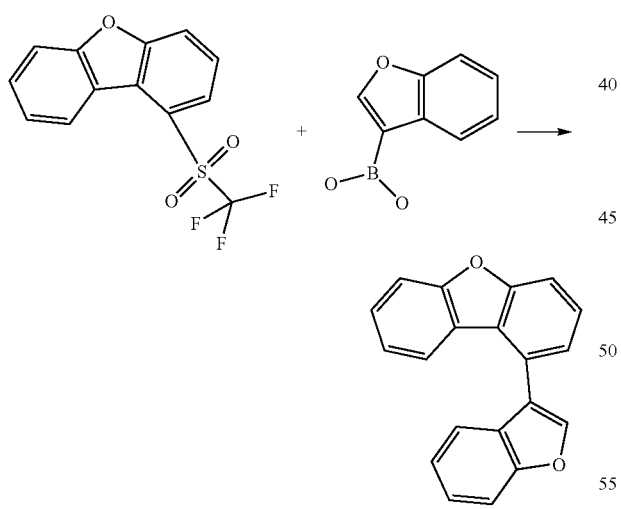

Under a protective atmosphere, 20 g (63.2 mmol) of (trifluoromethyl)-sulfonyl)dibenzo[b,d]furan, 11.3 g (69.6 mmol) of benzofuran-3-ylboronic acid, 33.6 g (158.1 mmol) of potassium phosphate, 0.3 g (1.3 mmol) of palladium acetate and 1.2 g (2.5 mmol) of XPhos are heated in a mixture of 100 ml of water and 100 ml of THF under reflux for 17 h. After cooling, the organic phase is separated off, washed three times with 200 ml of water and once with 200 ml of saturated, aqueous sodium chloride solution, dried over magnesium sulfate and evaporated to dryness in a rotary evaporator. The oil is purified by chromatography with heptane. Yield: 15 g (52.8 mmol); 83% of theory.

b) 1-(2-Bromobenzofuran-3-yl)dibenzo[b,d]furan

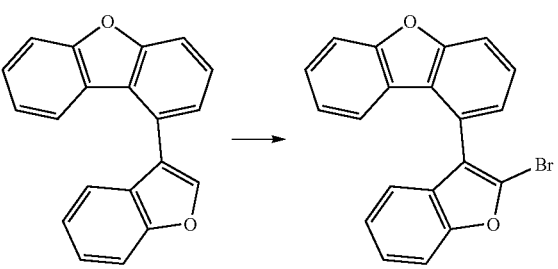 [SMILES: c1ccc2c(-c3cccc4oc5ccccc5c34)coc2c1 ; Brc1oc2ccccc2c1-c1cccc2oc3ccccc3c12]

15 g (57 mmol) of 1-(benzofuran-3-yl)dibenzo[b,d]furan are dissolved in 150 ml of dichloromethane. 9.4 g (52.7 mmol) of NBS are added in portions to this solution and stirred in the dark for 9 h. Water/ice is then added, the solid is separated off and rinsed with ethanol. The residue is filtered through alumina. Yield: 16.2 g (44 mmol); 84% of theory.

c) ((3-(Dibenzo[b,d]furan-1-yl)benzofuran-2-yl)ethynyl)trimethylsilane

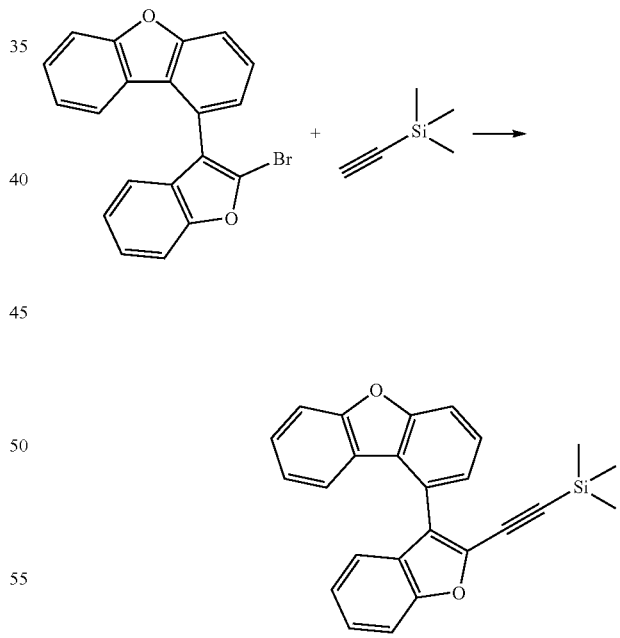

Under a protective atmosphere, 500 ml of triethylamine are added to 16 g (362 mmol) of 1-(2-bromobenzofuran-3-yl)dibenzo[b,d]furan, 0.3 g (1.3 mmol) of copper iodide, 0.6 g (0.9 mmol) of bis(triphenylphosphine)-palladium(II) chloride and 18.9 ml (133.8 mmol) of trimethylsilylacetylene, and the mixture is boiled under reflux over night. The product is purified by chromatography with heptane. Yield: 13.6 g (35.7 mmol); 80% of theory.

d) 1-(2-Ethynylbenzofuran-3-yl)dibenzo[b,d]furan

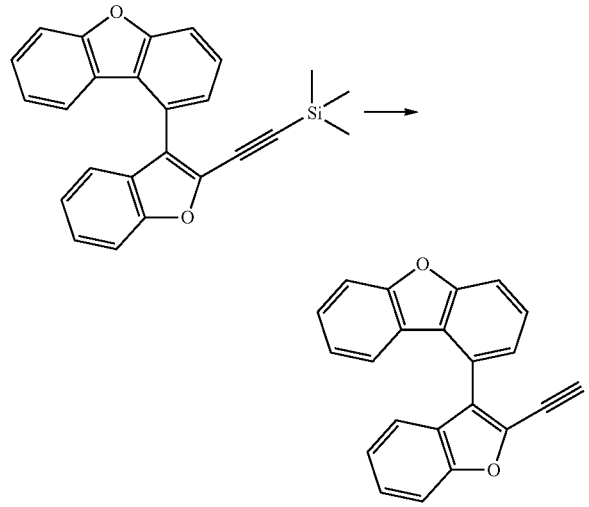

10 g (26.3 mmol) of ((3-(dibenzo[b,d]furan-1-yl)benzo-furan-2-yl)ethynyl)-trimethylsilane, 0.7 g (5.3 mmol) of potassium carbonate are stirred in 100 ml methanol under reflux for 1 h. The solvent is removed in vacuo. 100 ml of dichloromethane and 100 ml of water are added to the mixture. The organic phase is then separated off and subsequently evaporated. Yield: 8.1 g (26.3 mmol); 100% of theory.

e) Naphthobisbenzofuran

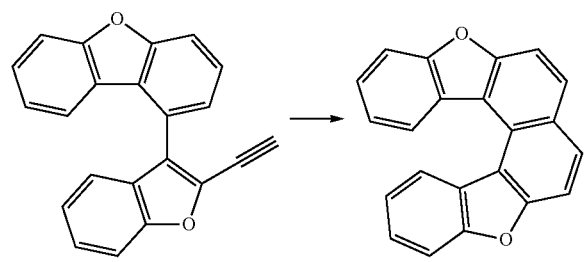 [SMILES: C#Cc1oc2ccccc2c1-c1cccc2oc3ccccc3c12 ; c1ccc2c(c1)oc1ccc3ccc4oc5ccccc5c4c3c12]

Under a protective atmosphere, 8.1 g (26 mmol) of 1-(2-ethynylbenzo-furan-3-yl)dibenzo[b,d]furan and 690 mg (2.6 mmol) of platinum dichloride are boiled in 500 ml of toluene under reflux overnight. The product is purified by chromatography with toluene. Yield: 3.1 g (10 mmol); 38.7% of theory.

f) 1,8-Bis(2-methylsulfanylphenyl)naphthalene

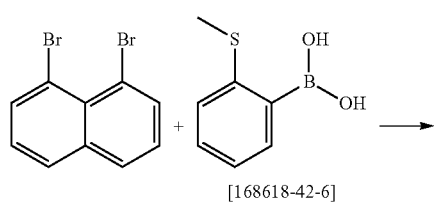
[168618-42-6]

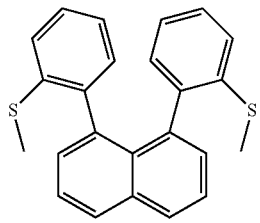

0.71 g (1.7 mmol) of SPhos and 1.68 g (1.7 mmol) of Pd$_2$(dba)$_3$ are added to a vigorously stirred, degassed suspension of 5 g (17.4 mmol) of 1,8-dibromonaphthalene, 7 g (43.7 mmol) of [2-(methylsulfanylphenyl)]boronic acid and 28 g (87 mmol) of caesium carbonate in a mixture of 200 ml of water and 200 ml N,N-dimethylformamide, and the mixture is heated under reflux for 17 h. After cooling, the organic phase is separated off, washed three times with 200 ml of water and once with 200 ml of saturated, aqueous sodium chloride solution, dried over magnesium sulfate and evaporated to dryness in a rotary evaporator. The grey residue is recrystallised from hexane. The deposited crystals are filtered off with suction, washed with a little MeOH and dried in vacuo. Yield: 5.9 g (15.9 mmol); 91% of theory.

g) 1,8-Bis(2-methylsulfinylphenyl)naphthalene

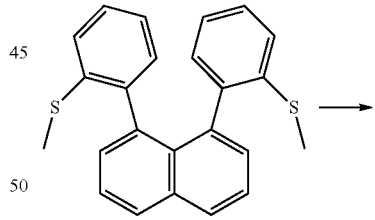

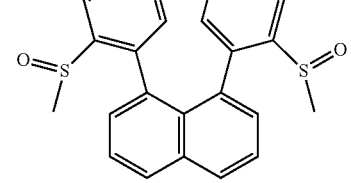

30 g (80 mmol) of 1,8-bis[2-methylsulfanylphenyl)naphthalene is initially introduced in 60 ml of glacial acetic acid and cooled to 0° C. 18.2 ml (160 mmol) of a 30% $H_2O_2$ solution are added dropwise to this solution and stirred overnight. $Na_2SO_3$ solution is added to the mixture, the phases are separated, and the solvent is removed in vacuo. Yield: 26 g (65 mmol); 80% of theory; purity: 92% according to HPLC.

h) Naphtho[2,1-b:7,8-b']bis[1]benzothiophene

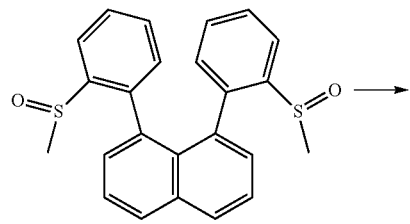

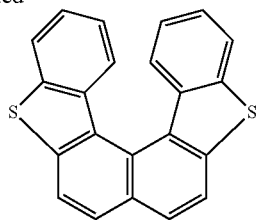

A mixture of 54 g (134 mmol) of 1,8-bis(2-methylsulfinylphenyl)naphthalene and 737 ml of trifluoromethanesulfonic acid is stirred at 5° C. for 48 h. 2.4 l of water/pyridine 5:1 are subsequently added to the mixture, which is then heated under reflux for 20 min. After cooling to room temperature, 500 ml of water and 1000 ml of dichloromethane are carefully added. The organic phase is washed with 4×50 ml of $H_2O$, dried over $MgSO_4$ and the solvent is removed in vacuo. The pure product is obtained by recrystallisation. Yield: 40 g (117 mmol); 80% of theory; purity: 96% according to HPLC.

The following compounds can be obtained analogously:

| | Starting material 1 | Product | Yield |
|---|---|---|---|
| h1 | 4j | | 73% |
| h2 | 11n | | 77% |

| Starting material 1 | Product | Yield |
|---|---|---|
| h3 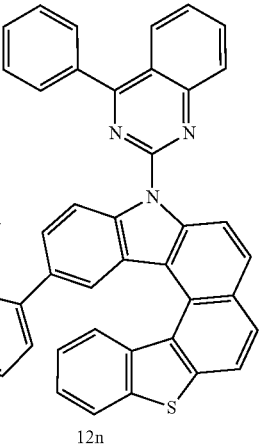 12n | 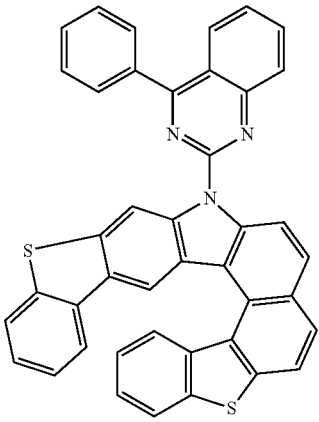 [SMILES: c1ccc(-c2nc(-n3c4cc5sc6ccccc6c5cc4c4c5c(ccc6sc7ccccc7c65)ccc43)nc3ccccc23)cc1] | 73% |
| h4 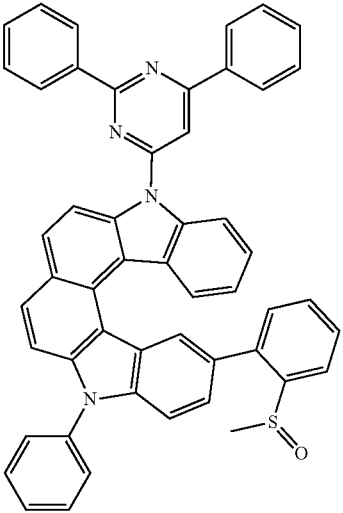 13n | 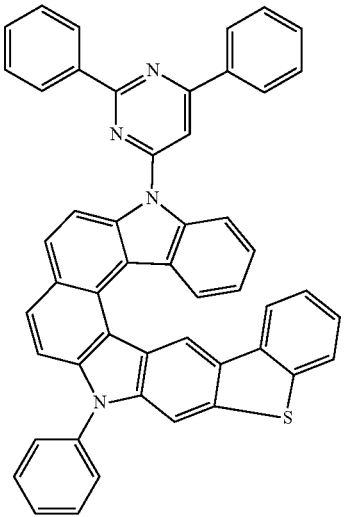 [SMILES: c1ccc(-c2cc(-n3c4ccccc4c4c5c(ccc6c5c5cc7c(cc5n6-c5ccccc5)sc5ccccc57)ccc43)nc(-c3ccccc3)n2)cc1] | 68% |
| h5 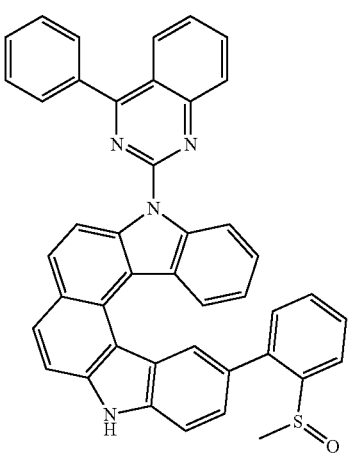 14n | 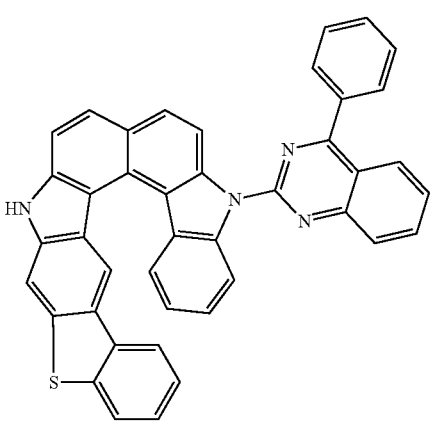 [SMILES: c1ccc(-c2nc(-n3c4ccccc4c4c5c(ccc6[nH]c7cc8sc9ccccc9c8cc7c65)ccc43)nc3ccccc23)cc1] | 80% |

-continued
| Starting material 1 | Product | Yield |
|---|---|---|
| h6 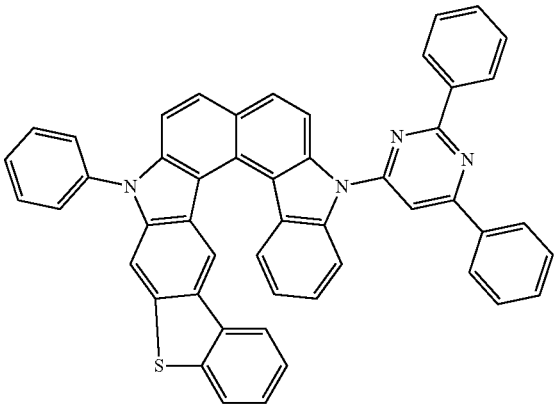 [SMILES: c1ccc(-c2cc(-n3c4ccccc4c4c5c(ccc6c5c5cc7c(cc5n6-c5ccccc5)sc5ccccc57)ccc43)nc(-c3ccccc3)n2)cc1] 13n | 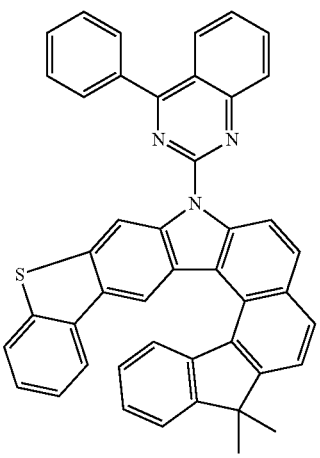 [SMILES: CC1(C)c2ccccc2-c2c1ccc1ccc3c(c4cc5c(cc4n3-c3nc(-c4ccccc4)c4ccccc4n3)sc3ccccc35)c21] | 71% |
| h7 15n | | 69% | h1-h4 and h6-h7 are extracted with hot toluene, recrystallised from toluene/n-heptane and finally sublimed in a high vacuum. The purity is 99.9%.

i) Silylation

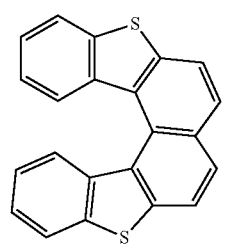 [SMILES: c1ccc2c(c1)oc1ccc3ccc4oc5ccccc5c4c3c12]
[91538-68-0]

→

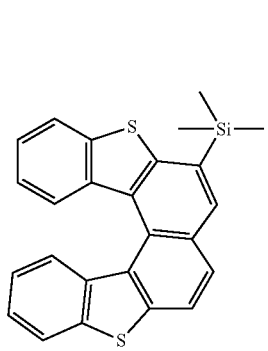

138 ml (245 mmol) of n-buthyllithium (2.5 M in hexane) are added dropwise to a solution, cooled to 15° C., of 82 g (240 mmol) of naphtho-[2,1-b:7,8-b']bis[1]benzothiophene and 28.3 g (245 mmol) of TMEDA in 1000 ml of THF. The reaction mixture is stirred at room temperature for 3 h, then cooled to 0° C., 27 g (251 mmol) of chlorotrimethylsilane are added dropwise over the course of 30 min. and the mixture is stirred at room temperature for 16 h. The solvent is subsequently removed in vacuo, and the residue is purified by chromatography over silica gel with toluene:dichloromethane 2:2. Yield: 64 g (154 mmol); 65% of theory.

The following compound can be obtained analogously:

| Starting material | Product | Yield |
|---|---|---|
| 1i 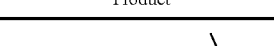 | 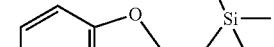 | 71% | j) Borylation

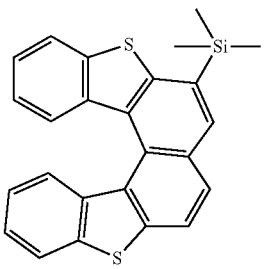

→

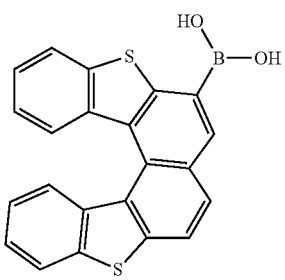

Under a protective gas, 7.8 g (31 mmol) of boron tribromide are added dropwise to a solution of 10.3 g (26 mmol) of compound i in 100 ml of dichloromethane, and the mixture is stirred at room temperature for 10 h. A little water is then slowly added to the mixture, and the precipitated residue is filtered off and washed with heptane. The yield is 9.1 g (24 mmol), corresponding to 95% of theory.

The following compound can be obtained analogously:

| Starting material 1 | Product | Yield |
|---|---|---|
| 1j | | 92% |

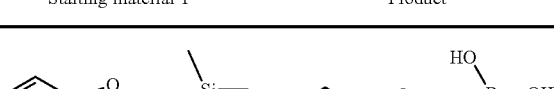

k) Iodination

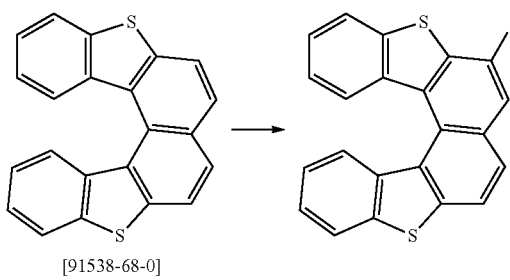

[91538-68-0]

138 ml (245 mmol) of n-butyllithium (2.5 M in hexane) are added dropwise at −78° C. to a solution, cooled to 15° C., of 82 g (240 mmol) of naphtho-[2,1-b:7,8-b']bis[1]benzothiophene in 1000 ml of THF. The reaction mixture is stirred at −78° C. for 3 h. 95 g (377 mmol) of iodine dissolved in 400 ml of THF is subsequently slowly added dropwise. The mixture is allowed to come to room temperature, stirred for a further 2 h, 100 ml of saturated Na₂SO₃ solution and 500 ml of ethyl acetate are added to the mixture, the phases are separated, the solvent is removed in vacuo the residue is purified by chromatography over silica gel with toluene:dichloromethane 2:2. Yield: 76 g (164 mmol); 68% of theory.

The following compounds can be obtained analogously:

| Starting material | Product | Yield |
|---|---|---|
| 1k | | 64% |
| 2k [1206462-91-0] | | 60% |
| 3k | | 65% |
| [91538-70-4] | | |
| 4k | | 82% | l) Amination 55.2 g (140 mmol) of compound k, 18.2 g (142 mmol) of 2-chloroaniline, 68.2 g (710 mmol) of sodium tert-butoxide, 613 mg (3 mmol) of palladium (II) acetate and 3.03 g (5 mmol) of dppf are dissolved in 1.3 l of toluene and stirred under reflux for 5 h. The reaction mixture is cooled to room temperature, extended with toluene and filtered through Celite. The filtrate is evaporated in vacuo, and the residue is crystallised from toluene/heptane. The product is isolated as a colourless solid. Yield: 44 g (96 mmol); 81% of theory.

The following compounds can be prepared analogously:
| | Starting material 1 | Starting material 2 | Product | Yield |
|---|---|---|---|---|
| 1l | 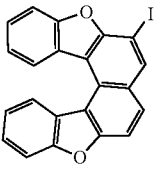 [SMILES: Ic1cc2ccc3oc4ccccc4c3c2c2c1oc1ccccc12] | 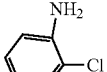 | 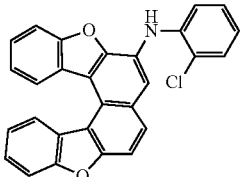 | 79% |
| 2l | 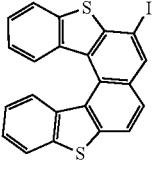 [SMILES: Ic1cc2ccc3sc4ccccc4c3c2c2c1sc1ccccc12] | 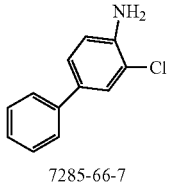 [SMILES: Nc1ccc(-c2ccccc2)cc1Cl] 7285-66-7 | 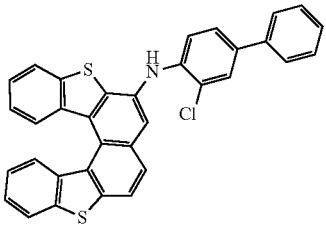 [SMILES: Clc1cc(-c2ccccc2)ccc1Nc1cc2ccc3sc4ccccc4c3c2c2c1sc1ccccc12] | 74% |
| 3l | 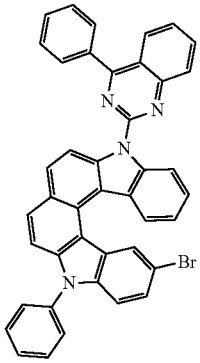 [SMILES: Brc1ccc2c(c1)c1c3c(ccc1n2-c1ccccc1)ccc1c3c2ccccc2n1-c1nc(-c2ccccc2)c2ccccc2n1] | 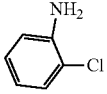 | 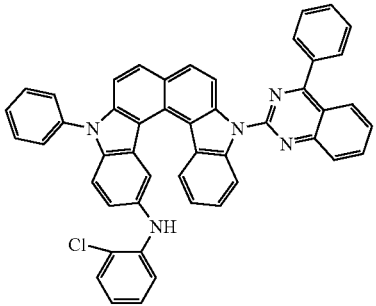 [SMILES: Clc1ccccc1Nc1ccc2c(c1)c1c3c(ccc1n2-c1ccccc1)ccc1c3c2ccccc2n1-c1nc(-c2ccccc2)c2ccccc2n1] | 76% |
| 4l | 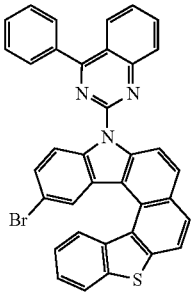 [SMILES: Brc1ccc2c(c1)c1c3c(ccc4sc5ccccc5c43)ccc1n2-c1nc(-c2ccccc2)c2ccccc2n1] | 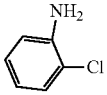 | 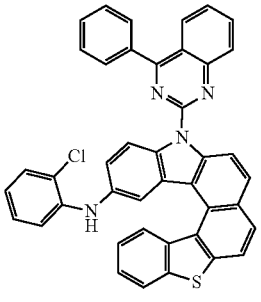 [SMILES: Clc1ccccc1Nc1ccc2c(c1)c1c3c(ccc4sc5ccccc5c43)ccc1n2-c1nc(-c2ccccc2)c2ccccc2n1] | 81% |
| 5l | 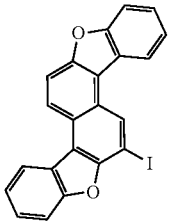 [SMILES: Ic1cc2c(ccc3oc4ccccc4c32)c2c1oc1ccccc12] | 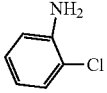 | 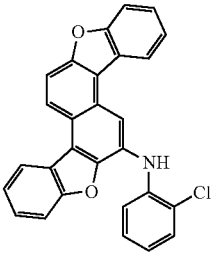 [SMILES: Clc1ccccc1Nc1cc2c(ccc3oc4ccccc4c32)c2c1oc1ccccc12] | 82% | m) Cyclisation

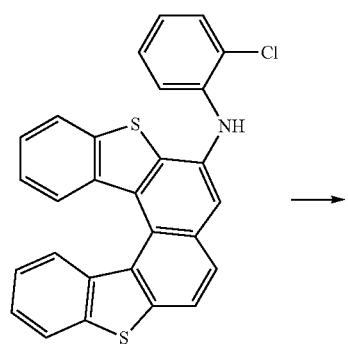

→

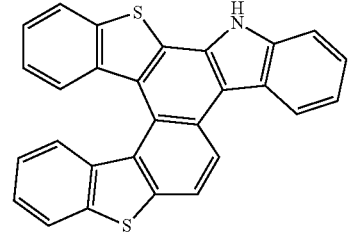

41.5 g (102 mmol) of compound c, 56 g (409 mmol) of potassium carbonate, 4.5 g (12 mmol) of tricyclohexylphosphine tetrafluoroborate and 1.38 g (6 mmol) of palladium(II) acetate are suspended in 500 ml of dimethylacetamide and stirred under reflux for 6 h. After cooling, 300 ml of water and 400 ml of dichloromethane are added to the reaction mixture. The mixture is stirred for a further 30 min., the organic phase is separated off and filtered through a short Celite bed, and the solvent is then removed in vacuo. The crude product is extracted with hot toluene and recrystallised from toluene. The product is isolated as a beige solid. Yield: 27.5 g (64 mmol); 74% of theory.

The following compounds can be prepared analogously:

| | Starting material | Product | Yield |
|---|---|---|---|
| 1m | | | 68% |
| 2m | | | 61% |
| 3m | | | 60% |
| 4m | | | 60% |

-continued
| Starting material | Product | Yield |
|---|---|---|
| 5m | | 62% |
| 6m | | 71% |
| 7m | | 55% |
n) Suzuki Coupling
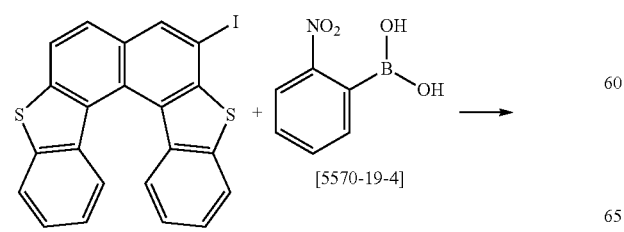
[5570-19-4]

-continued

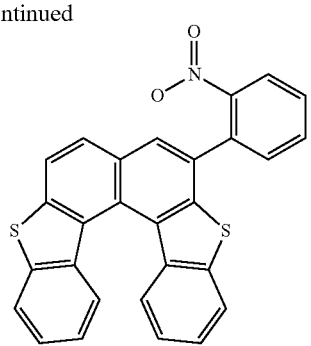

0.85 g (0.74 mmol) of Pd(PPh$_3$)$_4$ is added to a vigorously stirred, degassed suspension of 43 g (92 mmol) of compound d, 153 g (92 mmol) of 2-nitrophenylboronic acid and 33.2 g (106 mmol) of potassium carbonate in a mixture of 200 ml of water and 200 ml of THE, and the mixture is heated under reflux for 17 h. After cooling, the organic phase is separated off, washed three times with 200 ml of water and once with 200 ml of saturated, aqueous sodium chloride solution, dried over magnesium sulfate and evaporated to dryness in a rotary evaporator. The grey residue is recrystallised from hexane. The deposited crystals are filtered off with suction, washed with a little MeOH and dried in vacuo. Yield: 35.5 g (76.5 mmol); 91% of theory.

The following compounds can be prepared analogously:

| | Starting material 1 | Starting material 2 | Product | Yield |
|---|---|---|---|---|
| 1n | | [1820664-27-4] | | 83% |
| 2n | | [1199798-20-3] | | 87% |

-continued

| | Starting material 1 | Starting material 2 | Product | Yield |
|---|---|---|---|---|
| 3n | | [1642127-06-7] | | 81% |
| 4n | | [5570-19-4] | | 73% |
| 5n | | [5570-19-4] | | 75% |

-continued

| | Starting material 1 | Starting material 2 | Product | Yield |
|---|---|---|---|---|
| 6n | | [5570-19-4] | | 79% |
| 7n | | [5570-19-4] | | 70% |
| 8n | | [5570-19-4] | | 65% |
| 9n | | [5570-19-4] | | 70% |

-continued
| | Starting material 1 | Starting material 2 | Product | Yield |
|---|---|---|---|---|
| 10n | 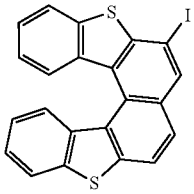 | 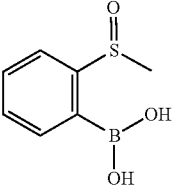\n[850567-97-4] | 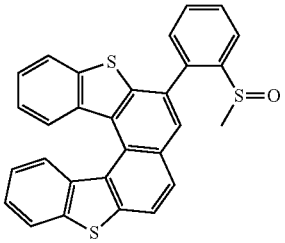 [SMILES: CS(=O)c1ccccc1-c1cc2ccc3sc4ccccc4c3c2c2c1sc1ccccc12] | 87% |
| 11n | 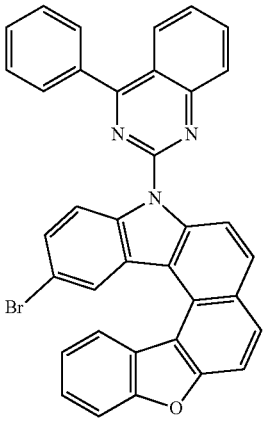 [SMILES: Brc1ccc2c(c1)c1c3c(ccc4oc5ccccc5c43)ccc1n2-c1nc(-c2ccccc2)c2ccccc2n1]\n6r | 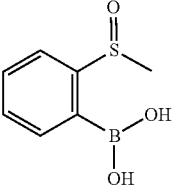\n[850567-97-4] | 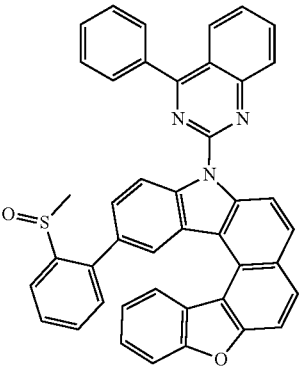 [SMILES: CS(=O)c1ccccc1-c1ccc2c(c1)c1c3c(ccc4oc5ccccc5c43)ccc1n2-c1nc(-c2ccccc2)c2ccccc2n1] | 79% |
| 12n | 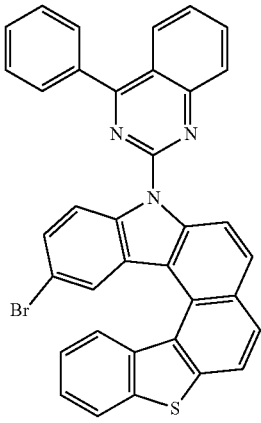 [SMILES: Brc1ccc2c(c1)c1c3c(ccc4sc5ccccc5c43)ccc1n2-c1nc(-c2ccccc2)c2ccccc2n1]\n5r | 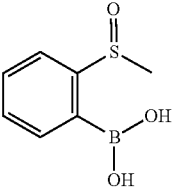\n[850567-97-4] | 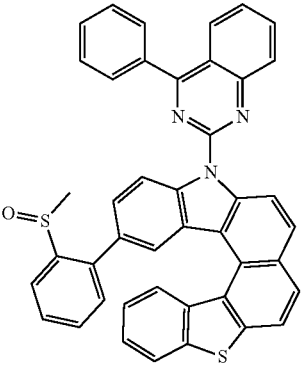 [SMILES: CS(=O)c1ccccc1-c1ccc2c(c1)c1c3c(ccc4sc5ccccc5c43)ccc1n2-c1nc(-c2ccccc2)c2ccccc2n1] | 71% |

-continued

| | Starting material 1 | Starting material 2 | Product | Yield |
|---|---|---|---|---|
| 13n | (structure) 1r | (structure) [850567-97-4] | (structure) | 65% |
| 14n | (structure) 2r | (structure) [850567-97-4] | (structure) | 72% |
| 15n | (structure) 7r | (structure) [850567-97-4] | (structure) | 76% | o) Carbazole Synthesis

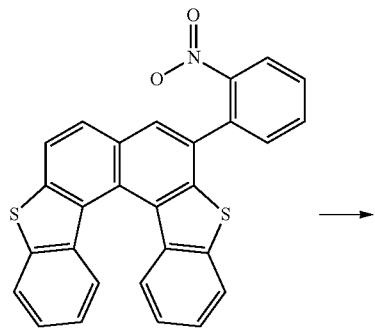

→

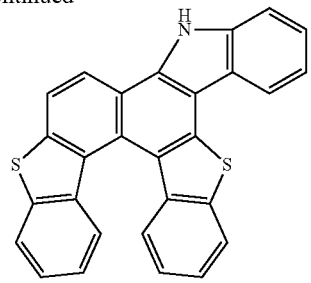

A mixture of 111 g (240 mmol) of compound n and 290.3 ml (1.7 mol) of triethyl phosphite is heated under reflux for 12 h. The triethyl phosphite remaining is subsequently distilled off (72-76° C./9 mm Hg). Water/MeOH (1:1) is added to the residue, the solid is filtered off and recrystallised. Yield: 75 g (175 mmol); 73% of theory.

The following compounds can be prepared analogously:

| | Starting material | Product | Yield |
|---|---|---|---|
| 1o | | | 74% |
| 2o | | | 72% |

| Starting material | Product | Yield |
|---|---|---|
| 3o | | 81% |
| 4o | | 74% |
| 5o | | 70% |
| 6o | | 71% |

-continued
| | Starting material | Product | Yield |
|---|---|---|---|
| 7o | 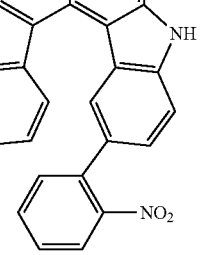 | 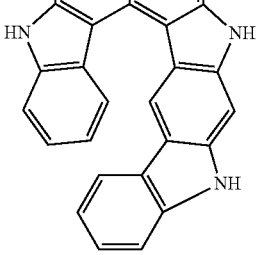 | 65% |
| 8o | 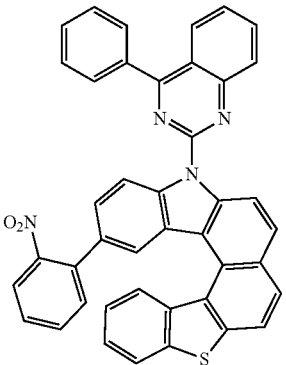 [SMILES: O=[N+]([O-])c1ccccc1-c1ccc2c(c1)c1c3c(ccc4sc5ccccc5c43)ccc1n2-c1nc(-c2ccccc2)c2ccccc2n1] | 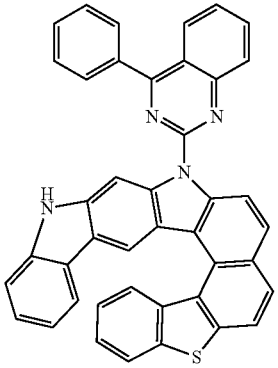 [SMILES: c1ccc(-c2nc(-n3c4cc5[nH]c6ccccc6c5cc4c4c5c(ccc6sc7ccccc7c65)ccc43)nc3ccccc23)cc1] | 76% |
| 9o | 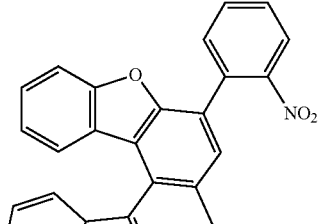 | 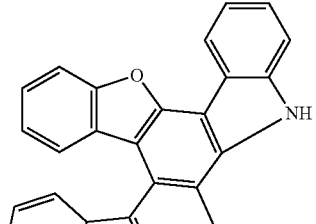 | 77% |
p) Nucleophilic Substitution
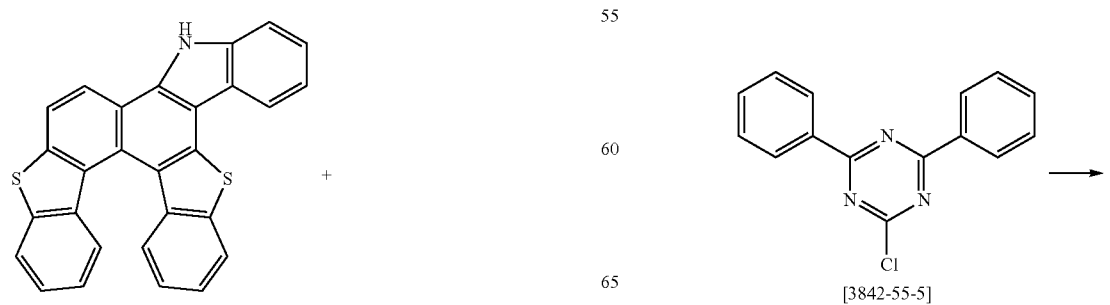
[3842-55-5]

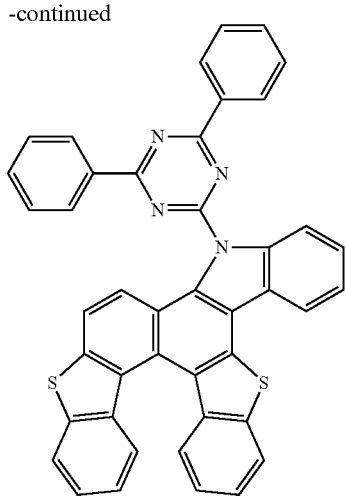

4.2 g of NaH, 60% in mineral oil (106 mmol), are dissolved in 300 ml of dimethylformamide under a protective atmosphere. 54.4 g (106 mmol) of compound f are dissolved in 250 ml of DMF and added dropwise to the reaction mixture. After 1 h at room temperature, a solution of 2-chloro-4,6-diphenyl-1,3,5-triazine (34.5 g, 0.122 mol) in 200 ml THF is added dropwise. The reaction mixture is stirred at room temperature for 12 h and then poured onto ice. After warming to room temperature, the solid which precipitates out is filtered and washed with ethanol and heptane. The residue is extracted with hot toluene, recrystallised from toluene/n-heptane and finally sublimed in a high vacuum. The purity is 99.9%. Yield: 44 g (66 mmol); 63% of theory.

The following compounds can be prepared analogously:

| | Starting Material 1 | Starting Material 2 | Product | Yield |
|---|---|---|---|---|
| 1p | | [3842-55-5] | | 63% |
| 2p | | [1384480-21-0] | | 62% |

-continued
| | Starting Material 1 | Starting Material 2 | Product | Yield |
|---|---|---|---|---|
| 3p | 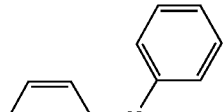 | 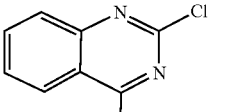<br>[1373265-66-7] | 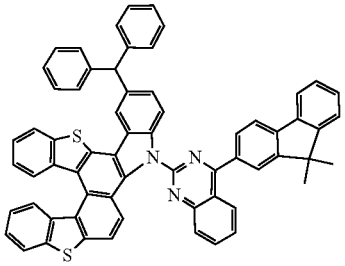 | 59% |
| 4p | 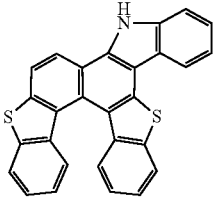 [SMILES: c1ccc2c(c1)[nH]c1c3ccc4sc5ccccc5c4c3c3c4ccccc4sc3c21] | 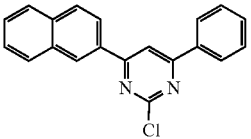 [SMILES: Clc1nc(-c2ccccc2)cc(-c2ccc3ccccc3c2)n1]<br>[1260393-65-4] | 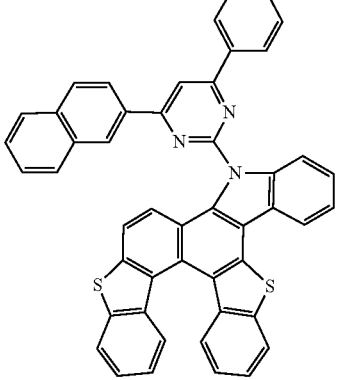 | 53% |
| 5p | 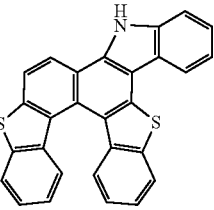 | 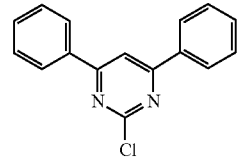 [SMILES: Clc1nc(-c2ccccc2)cc(-c2ccccc2)n1]<br>2915-16-4 | 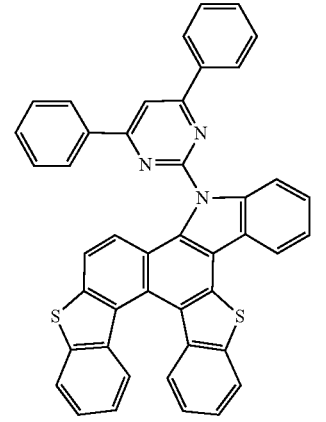 [SMILES: c1ccc(-c2cc(-c3ccccc3)nc(-n3c4ccccc4c4c5sc6ccccc6c5c5c(ccc6sc7ccccc7c65)c43)n2)cc1] | 60% |

-continued
| | Starting Material 1 | Starting Material 2 | Product | Yield |
|---|---|---|---|---|
| 6p | 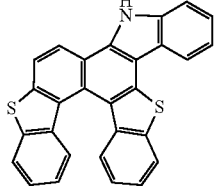 | 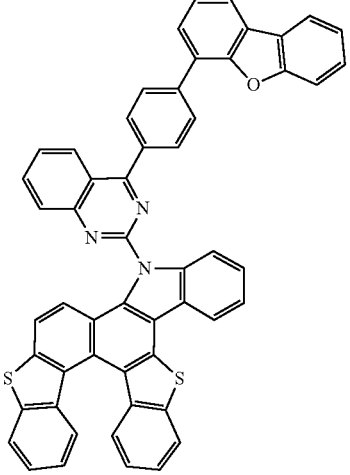 [SMILES: c1ccc2c(-c3ccc(-c4cccc5c4oc4ccccc45)cc3)nc(-n3c4ccccc4c4c5sc6ccccc6c5c5c(ccc6sc7ccccc7c65)c43)nc2c1] [1403252-58-3] | 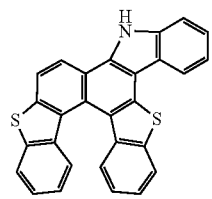 [SMILES: c1ccc2c(c1)[nH]c1c3ccc4sc5ccccc5c4c3c3c4ccccc4sc3c21] | 57% |
| 7p | 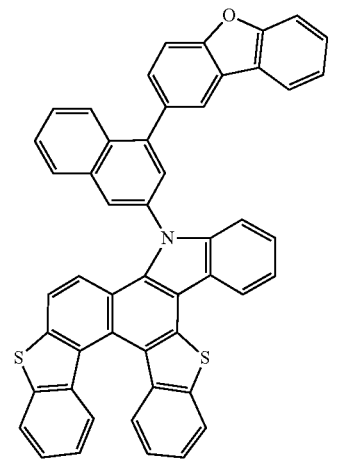 [SMILES: c1ccc2c(-c3ccc4oc5ccccc5c4c3)cc(-n3c4ccccc4c4c5sc6ccccc6c5c5c(ccc6sc7ccccc7c65)c43)cc2c1] | 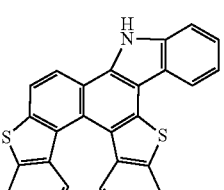 [1616499-38-7] | 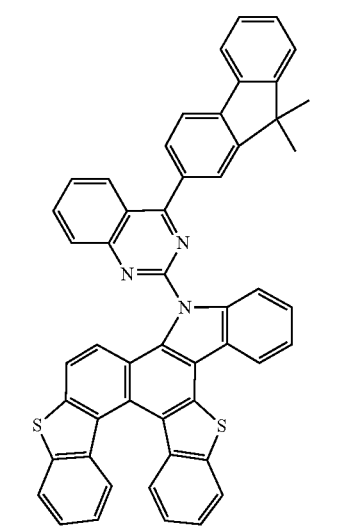 [SMILES: CC1(C)c2ccccc2-c2ccc(-c3nc(-n4c5ccccc5c5c6sc7ccccc7c6c6c(ccc7sc8ccccc8c76)c54)nc4ccccc34)cc21] | 62% |
| 8p | | [1373265-66-7] | | 64% |

-continued
| | Starting Material 1 | Starting Material 2 | Product | Yield |
|---|---|---|---|---|
| 9p | 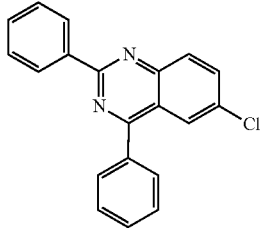 [SMILES: Clc1ccc2nc(-c3ccccc3)nc(-c3ccccc3)c2c1] | 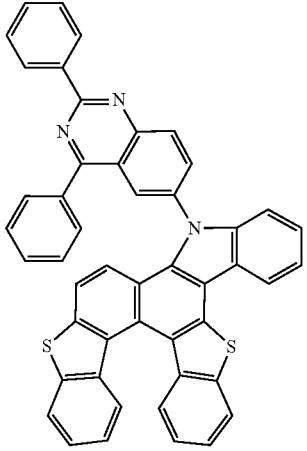 [SMILES: c1ccc(-c2nc(-c3ccccc3)c3cc(-n4c5ccccc5c5c6sc7ccccc7c6c6c(ccc7sc8ccccc8c76)c54)ccc3n2)cc1]  [30169-34-7] | 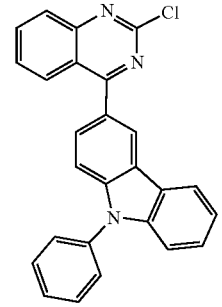 [SMILES: Clc1nc(-c2ccc3c(c2)c2ccccc2n3-c2ccccc2)c2ccccc2n1] | 65% |
| 10p | 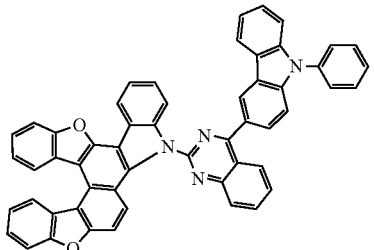 | 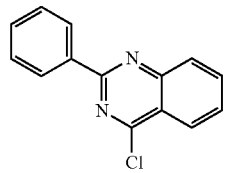 [SMILES: Clc1nc(-c2ccccc2)nc2ccccc12]  [1373317-91-9] | 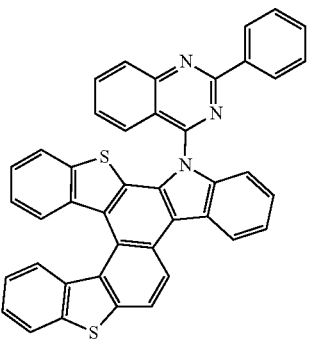 [SMILES: c1ccc(-c2nc(-n3c4ccccc4c4c5ccc6sc7ccccc7c6c5c5c6ccccc6sc5c43)c3ccccc3n2)cc1] | 67% |
| 11p | 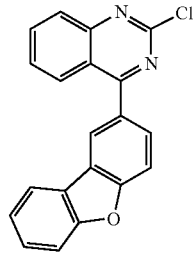 [SMILES: Clc1nc(-c2ccc3oc4ccccc4c3c2)c2ccccc2n1] | 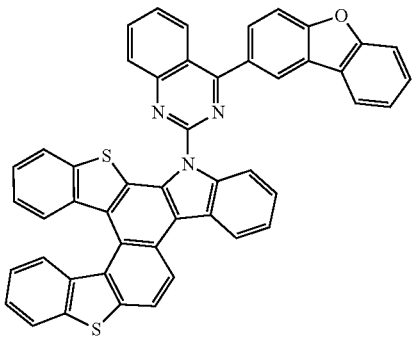 [SMILES: c1ccc2c(-c3ccc4oc5ccccc5c4c3)nc(-n3c4ccccc4c4c5ccc6sc7ccccc7c6c5c5c6ccccc6sc5c43)nc2c1]  [6484-25-9] |  | 65% |
| 12p |  |   [1616499-38-7] |  | |

-continued

| | Starting Material 1 | Starting Material 2 | Product | Yield |
|---|---|---|---|---|
| 13p | | [29874-83-7] | | 63% |
| 14p | | [14003252-55-0] | | 67% |
| 15g | | [1801233-18-0] | | 66% |
| 16p | | [1292317-90-8] | | 61% |

-continued

| | Starting Material 1 | Starting Material 2 | Product | Yield |
|---|---|---|---|---|
| 17p | | [4787-80-5] | | 62% |
| 18p | | 864377-31-1 | | 60% |
| 19p | | [6484-25-9] | | 64% |

-continued

| | Starting Material 1 | Starting Material 2 | Product | Yield |
|---|---|---|---|---|
| 20p | | [29874-83-7] | | 67% |
| 21p | | [760212-40-6] | | 70% |
| 22p | | [29874-83-7] | | 68% |

-continued

| | Starting Material 1 | Starting Material 2 | Product | Yield |
|---|---|---|---|---|
| 23p | | 864377-31-1 | | 66% |
| 24p | | [29874-83-7] | | 64% |
| 25p | | [29874-83-7] | | 74% |
| 26p | | [29874-83-7] | | 61% |

-continued
| Starting Material 1 | Starting Material 2 | Product | Yield |
|---|---|---|---|
| 27p | [29874-83-7] | | 60% |
| 28p | [3842-55-5] | | 72% |
q) Buchwald Coupling
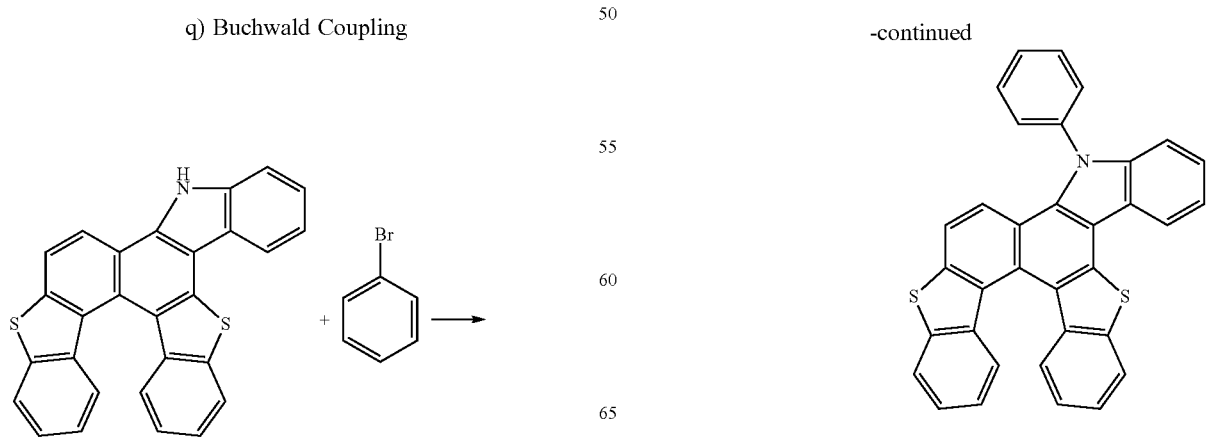

21.4 g (50 mmol) of compound f and 8.4 g (54 mmol) of bromobenzene are dissolved in 400 ml of toluene under an argon atmosphere. 1.0 g (5 mmol) of tri-tert-butylphosphine are added and stirred under an argon atmosphere. 0.6 g (2 mmol) of Pd(OAc)$_2$ are added and stirred under an argon atmosphere, after which 9.5 g (99 mmol) of sodium tert-butoxide are added. The reaction mixture is stirred under reflux for 24 h. After cooling, the organic phase is separated, washed three times with 200 ml of water, dried over MgSO$_4$, filtered, and the solvent is removed in vacuo. The residue is purified by column chromatography over silica gel (eluent: DCM/heptane (1:3)), extracted with hot toluene, recrystallised from toluene/n-heptane and finally sublimed in a high vacuum. Yield: 22.7 g (45 mmol); 90% of theory.

The following compounds are obtained analogously:

| | Starting material 1 | Starting material 2 | Product | Yield |
|---|---|---|---|---|
| 1q | | [19111-87-6] | | 70% |
| 2q | | [1153-85-1] | | 73% |

-continued

| | Starting material 1 | Starting material 2 | Product | Yield |
|---|---|---|---|---|
| 3q | | [212385-73-4] | | 75% |
| 4q | | | | 76% |
| 5q | | | | 78% |
| 6q | | | | 70% |

| | Starting material 1 | Starting material 2 | Product | Yield |
|---|---|---|---|---|
| 7q | | | | 73% |
| 8q | | | | 75% |
| 9q | | | | 70% |

| Starting material 1 | Starting material 2 | Product | Yield |
|---|---|---|---|
| 10q | | | 77% |
| 11q | | | 51% | r) Bromination

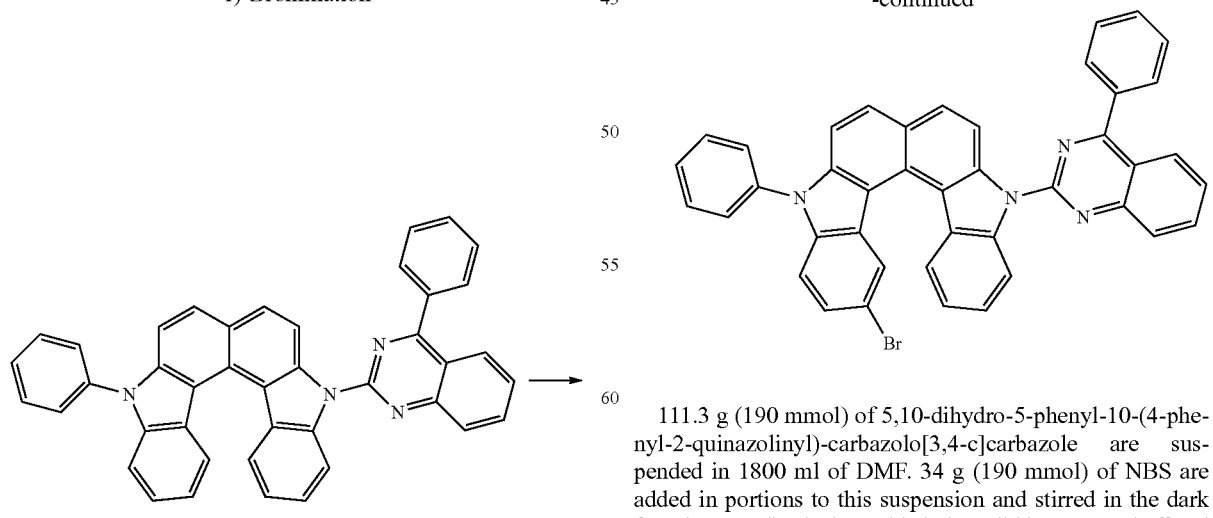

[1980828-73-6]

111.3 g (190 mmol) of 5,10-dihydro-5-phenyl-10-(4-phenyl-2-quinazolinyl)-carbazolo[3,4-c]carbazole are suspended in 1800 ml of DMF. 34 g (190 mmol) of NBS are added in portions to this suspension and stirred in the dark for 2 h. Water/ice is then added, the solid is separated off and rinsed with ethanol. The isomers are separated by recrystallisation. The yield is 82 g (123 mmol); 65% of theory.

The following compounds are prepared analogously:

| | Starting material | Product | Yield |
|---|---|---|---|
| 1r | [1980827-30-2] | | 54% |
| 2r | [1980830-96-3] | | 52% |
| 3r | [7259-13-4] | | 77% |
| 4r | [1613254-46-8] | | 41% |

| Starting material | Product | Yield |
|---|---|---|
| 5r [1980833-19-9] | | 55% |
| 6r [1980830-96-3] | | 67% |
| 7r [81979232-23-9] | | 56% |

Production of OLEDs

The use of the materials according to the invention in OLEDs is presented in the following examples E1 to E11 (see Table 1).

Pretreatment for Examples E1-E11: glass plates coated with structured ITO (indium tin oxide) in a thickness of 50 nm are treated, before coating, with an oxygen plasma, followed by an argon plasma. These plasma-treated glass plates form the substrates to which the OLEDs are applied.

The OLEDs have in principle the following layer structure: substrate/hole-injection layer (HIL)/hole-transport layer (HTL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer having a thickness of 100 nm. The precise structure of the OLEDs is shown in Table 1. The materials required for the production of the OLEDs are shown in Table 2. The data for the OLEDs are listed in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as EG1:IC2:TER5 (55%:35%:10%) here means that material EG1 is present in the layer in a proportion by volume of 55%, IC2 is present in the layer in a proportion by volume of 35% and TER5 is present in the layer in a proportion by volume of 10%. Analogously, the electron-transport layer may also consist of a mixture of two materials.

The OLEDs are characterised by standard methods. For this purpose, the electroluminescence spectra, the current/voltage characteristic lines and the lifetime are determined. The electroluminescence spectra are determined at a luminous density of 1000 cd/m² and the CIE 1931 x and y colour coordinates are calculated therefrom. The term U1000 in Table 3 denotes the voltage required for a luminous density of 1000 cd/m². The lifetime LT is defined as the time after which the luminous density drops from the initial luminous density to a certain proportion L1 on operation at a constant current density jo. An expression L1=95% in Table 3 means that the lifetime indicated in column LT corresponds to the time after which the luminous density drops to 95% of its initial value.

Use of the Materials According to the Invention in OLEDs

Materials EG1 to EG7 according to the invention are employed in Examples E1 to E11 as matrix material in the emission layer of phosphorescent red OLEDs. The particular advantages of these compounds are the comparatively low use voltage, and a long lifetime, which can be significantly extended again in a mixture of a material according to the invention and a co-matrix, in the present case in a mixture of EG1 and IC3.

TABLE 1

Structure of the OLEDs

| Ex | HIL Thickness | HTL Thickness | EBL Thickness | EML Thickness | HBL Thickness | ETL Thickness | EIL Thickness |
|---|---|---|---|---|---|---|---|
| E1 | HATCN 5 nm | SpMA1 125 nm | SpMA3 10 nm | EG1:TER5 (97%:3%) 35 nm | ST2 10 nm | ST2:LiQ (50%:50%) 30 nm | LiQ 1 nm |
| E2 | HATCN 5 nm | SpMA1 125 nm | SpMA3 10 nm | EG1:IC2:TER5 (72%:25%:3%) 35 nm | ST2 10 nm | ST2:LiQ (50%:50%) 30 nm | LiQ 1 nm |
| E3 | HATCN 5 nm | SpMA1 125 nm | SpMA3 10 nm | EG1:IC3:TER5 (72%:25%:3%) 35 nm | ST2 10 nm | ST2:LiQ (50%:50%) 30 nm | LiQ 1 nm |
| E4 | HATCN 5 nm | SpMA1 125 nm | SpMA3 10 nm | EG2:IC3:TER5 (72%:25%:3%) 35 nm | ST2 10 nm | ST2:LiQ (50%:50%) 30 nm | LiQ 1 nm |
| E5 | HATCN 5 nm | SpMA1 125 nm | SpMA3 10 nm | EG3:IC3:TER5 (72%:25%:3%) 35 nm | ST2 10 nm | ST2:LiQ (50%:50%) 30 nm | LiQ 1 nm |
| E6 | HATCN 5 nm | SpMA1 125 nm | SpMA3 10 nm | EG4:IC3:TER5 (72%:25%:3%) 35 nm | ST2 10 nm | ST2:LiQ (50%:50%) 30 nm | LiQ 1 nm |
| E7 | HATCN 5 nm | SpMA1 125 nm | SpMA3 10 nm | EG5:IC3:TER5 (72%:25%:3%) 35 nm | ST2 10 nm | ST2:LiQ (50%:50%) 30 nm | LiQ 1 nm |
| E8 | HATCN 5 nm | SpMA1 125 nm | SpMA3 10 nm | EG6:TER5 (97%:3%) 35 nm | ST2 10 nm | ST2:LiQ (50%:50%) 30 nm | LiQ 1 nm |
| E9 | HATCN 5 nm | SpMA1 125 nm | SpMA3 10 nm | EG6:IC2:TER5 (72%:25%:3%) 35 nm | ST2 10 nm | ST2:LiQ (50%:50%) 30 nm | LiQ 1 nm |
| E20 | HATCN 5 nm | SpMA1 125 nm | SpMA3 10 nm | EG7:TER5 (97%:3%) 35 nm | ST2 10 nm | ST2:LiQ (50%:50%) 30 nm | LiQ 1 nm |
| E11 | HATCN 5 nm | SpMA1 125 nm | SpMA3 10 nm | EG7:IC2:TER5 (72%:25%:3%) 35 nm | ST2 10 nm | ST2:LiQ (50%:50%) 30 nm | LiQ 1 nm |

TABLE 2
Structural formulae of the materials for the OLEDs
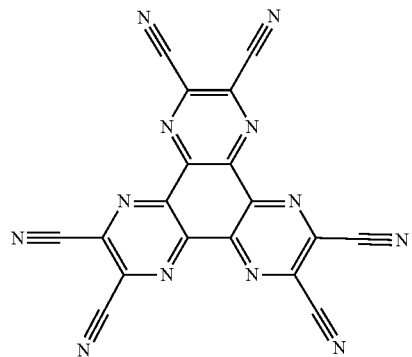 [SMILES: N#Cc1nc2c3nc(C#N)c(C#N)nc3c3nc(C#N)c(C#N)nc3c2nc1C#N]
HATCN
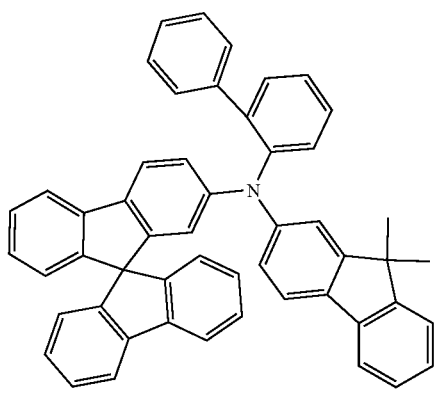 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
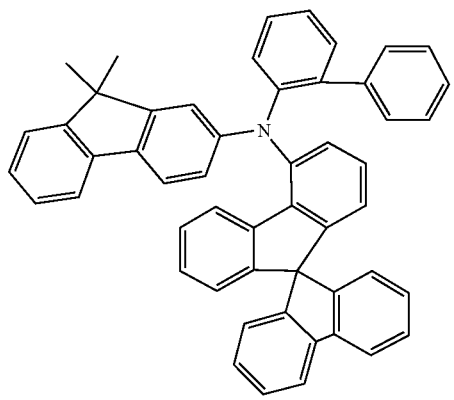 [SMILES: CC1(C)c2ccccc2-c2ccc(N(c3ccccc3-c3ccccc3)c3cccc4c3-c3ccccc3C43c4ccccc4-c4ccccc43)cc21]
SpMA3
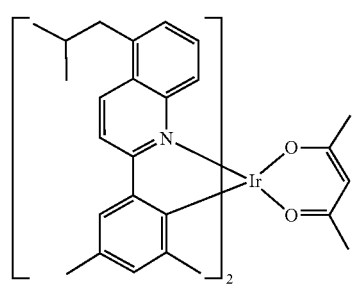
TER5
TABLE 2-continued
Structural formulae of the materials for the OLEDs
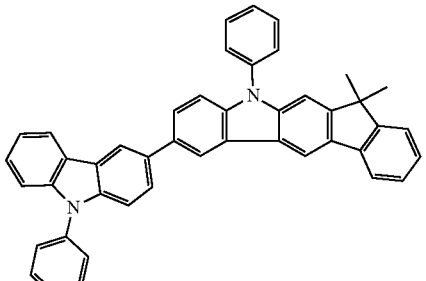
IC2
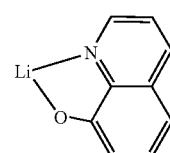
LiQ
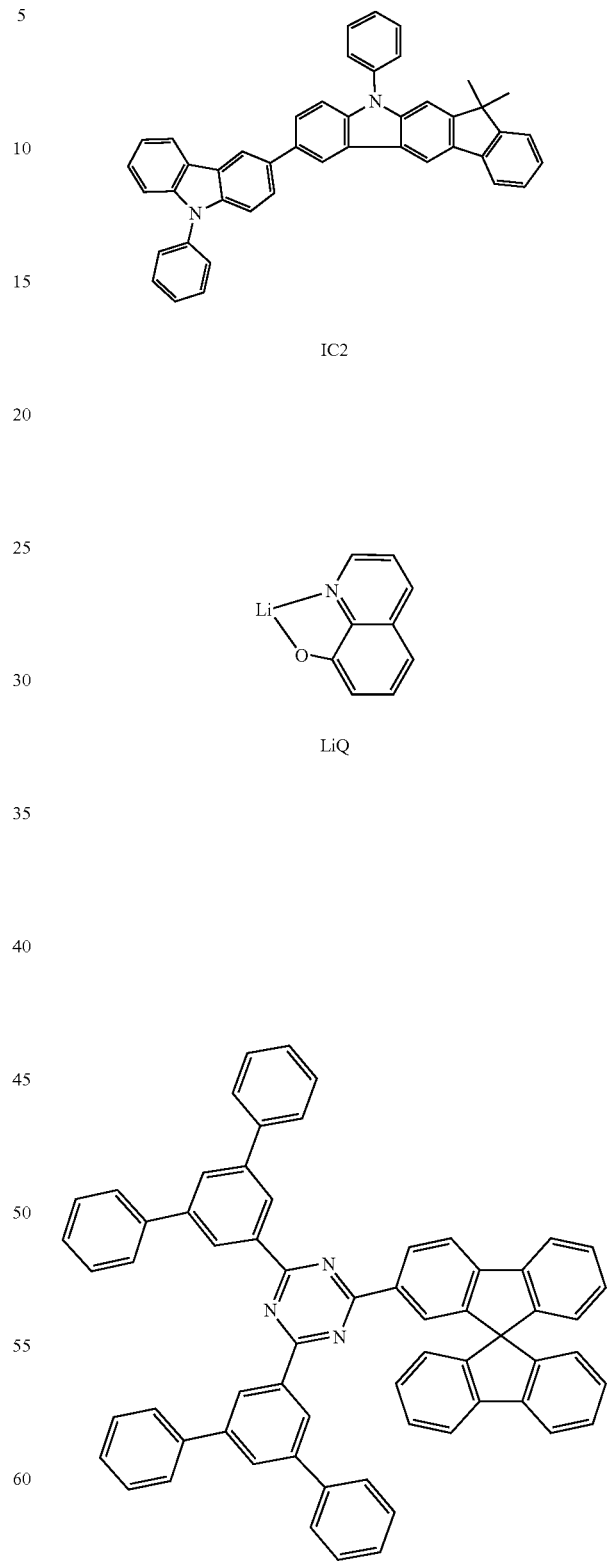
ST2

TABLE 2-continued
Structural formulae of the materials for the OLEDs
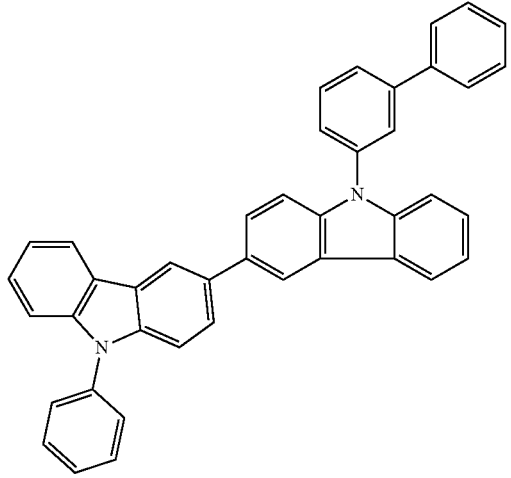 [SMILES: c1ccc(-c2cccc(-n3c4ccccc4c4cc(-c5ccc6c(c5)c5ccccc5n6-c5ccccc5)ccc43)c2)cc1]
IC3
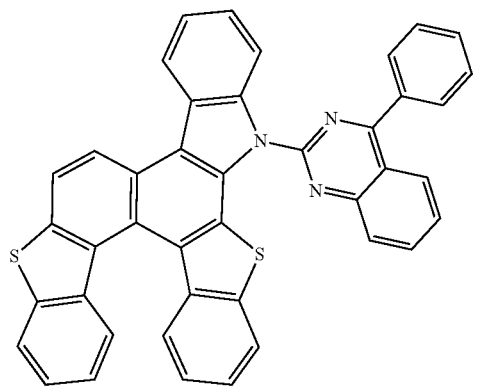 [SMILES: c1ccc(-c2nc(-n3c4ccccc4c4c5ccc6sc7ccccc7c6c5c5c6ccccc6sc5c43)nc3ccccc23)cc1]
EG1
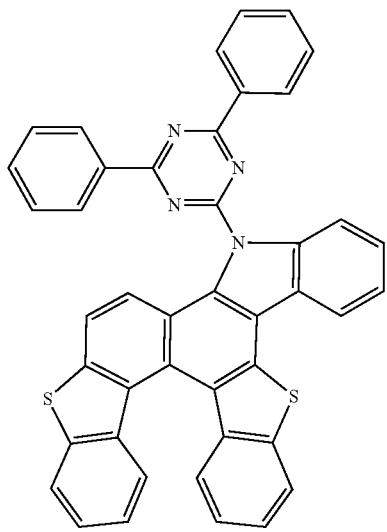 [SMILES: c1ccc(-c2nc(-c3ccccc3)nc(-n3c4ccccc4c4c5sc6ccccc6c5c5c(ccc6sc7ccccc7c65)c43)n2)cc1]
EG2
TABLE 2-continued
Structural formulae of the materials for the OLEDs
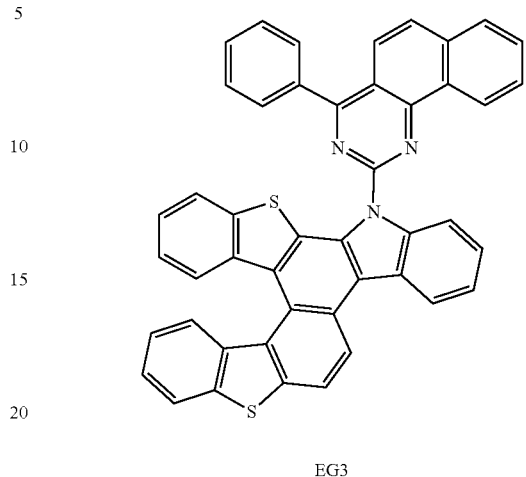
EG3
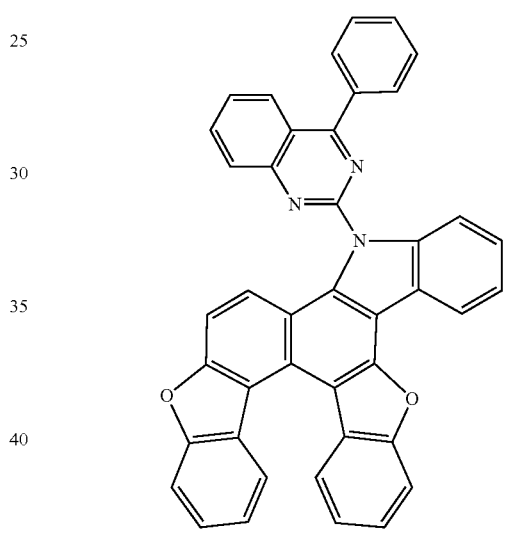
EG4
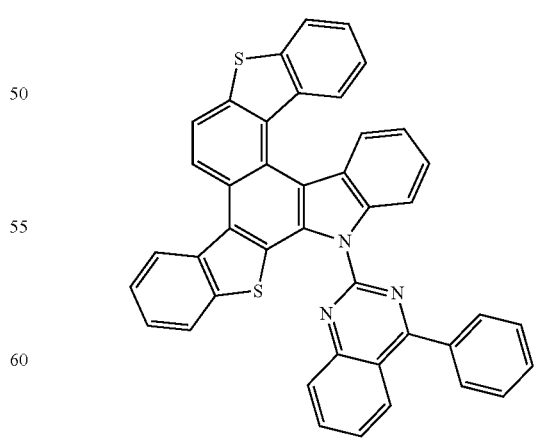
EG5

TABLE 2-continued

Structural formulae of the materials for the OLEDs

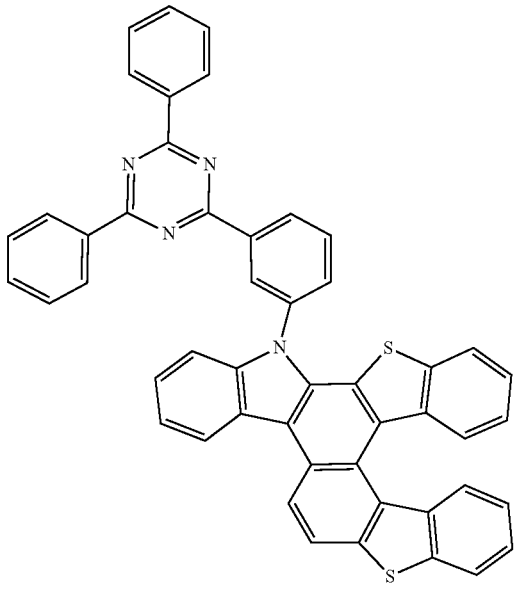 [SMILES: c1ccc(-c2nc(-c3ccccc3)nc(-c3cccc(-n4c5ccccc5c5c6ccc7sc8ccccc8c7c6c6c7ccccc7sc6c54)c3)n2)cc1]

EG6

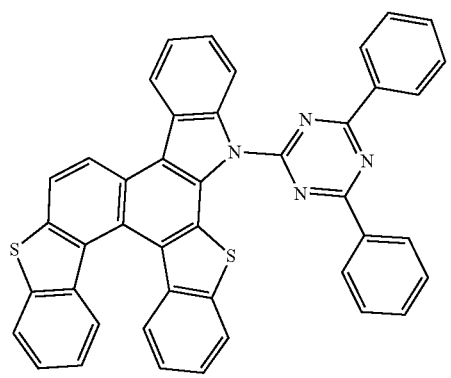 [SMILES: c1ccc(-c2nc(-c3ccccc3)nc(-n3c4ccccc4c4c5ccc6sc7ccccc7c6c5c5c6ccccc6sc5c43)n2)cc1]

EG7

TABLE 3

Data of the OLEDs

| Ex. | U1000 (V) | CIE x/y at 1000 cd/m² | j₀ (mA/cm²) | EQE 1000 % | L1 (%) | LT (h) |
|---|---|---|---|---|---|---|
| E1 | 3.3 | 0.67/0.33 | 20 | 19 | 95 | 520 |
| E2 | 3.5 | 0.67/0.34 | 20 | 20 | 95 | 410 |
| E3 | 3.4 | 0.67/0.33 | 20 | 21.2 | 95 | 375 |
| E4 | 3.3 | 0.67/0.34 | 20 | 21.1 | 95 | 400 |
| E5 | 3.3 | 0.67/0.33 | 20 | 20.5 | 95 | 337 |
| E6 | 3.4 | 0.67/0.33 | 20 | 20.3 | 95 | 391 |
| E7 | 3.3 | 0.67/0.33 | 20 | 20.1 | 95 | 430 |
| E8 | 3.3 | 0.67/0.33 | 20 | 24.0 | 95 | 220 |
| E9 | 3.4 | 0.67/0.33 | 20 | 25.6 | 95 | 230 |
| E10 | 3.1 | 0.67/0.33 | 20 | 22.7 | 95 | 300 |
| E11 | 3.2 | 0.67/0.33 | 20 | 26.3 | 95 | 490 |

Comparable results are obtained with the other compounds described in the synthesis examples in a device having an analogous structure to Examples E1 and E2.

The invention claimed is:
1. Compound of the formula (1),

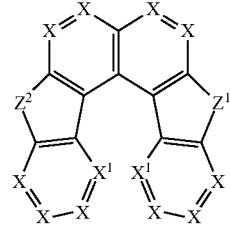

formula (1)

where the following applies to the symbols used:
X is on each occurrence, identically or differently, CR or N or two adjacent X stand for a group of the following formula (2),

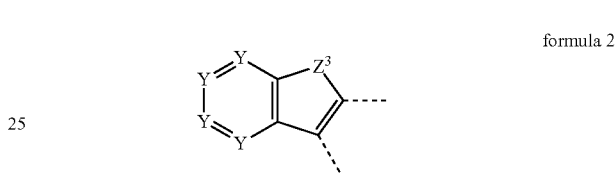

formula 2 where the dashed bonds denote the linking of this group in the formula (1), with the proviso that the compound of the formula (1) contains one or two groups of the formula (2);
$X^1$ is on each occurrence, identically or differently, CR or N;
Y is on each occurrence, identically or differently, CR or N;
$Z^1$, $Z^2$, $Z^3$ are on each occurrence, identically or differently, O, S, N—Ar or $CR_2$;
Ar is on each occurrence, identically or differently, an aromatic or heteroaromatic ring system having 5 to 40 aromatic ring atoms, which may be substituted by one or more radicals R;
R is on each occurrence, identically or differently, H, D, F, Cl, Br, I, $N(Ar')_2$, $N(R^1)_2$, OAr', SAr', CN, $NO_2$, $OR^1$, $SR^1$, $COOR^1$, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl group having 1 to 20 C atoms or an alkenyl or alkynyl group having 2 to 20 C atoms or a branched or cyclic alkyl group having 3 to 20 C atoms, where the alkyl, alkenyl or alkynyl group may in each case be substituted by one or more radicals $R^1$, where one or more non-adjacent $CH_2$ groups may be replaced by $Si(R^1)_2$, C=O, $NR^1$, O, S or $CONR^1$, or an aromatic or heteroaromatic ring system having 5 to 60 aromatic ring atoms, which may in each case be substituted by one or more radicals $R^1$; two radicals R may also form an aliphatic, heteroaliphatic, aromatic or heteroaromatic ring system with one another;
Ar' is on each occurrence, identically or differently, an aromatic or heteroaromatic ring system having 5 to 40 aromatic ring atoms, which may be substituted by one or more radicals $R^1$;
$R^1$ is on each occurrence, identically or differently, H, D, F, Cl, Br, I, $N(R^2)_2$, CN, $NO_2$, $OR^2$, $SR^2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl group having 1 to 20 C atoms or an alkenyl or alkynyl group having 2 to 20 C atoms or a branched or cyclic alkyl group having 3 to 20 C atoms, where the alkyl, alkenyl or alkynyl group may in each case be substituted by one or more radicals $R^2$, where one or more non-adjacent $CH_2$ groups may be replaced by $Si(R^2)_2$, C=O, $NR^2$, O, S or $CONR^2$ and where one or more H atoms in the alkyl, alkenyl or alkynyl group may be replaced by D, F, Cl, Br, I or CN, or an aromatic or heteroaromatic ring system having 5 to 40 aromatic ring atoms, which may in each case be substituted by one or more radicals $R^2$; two or more radicals $R^1$ may form an aliphatic ring system with one another;

$R^2$ is on each occurrence, identically or differently, H, D, F, CN or an aliphatic, aromatic or heteroaromatic organic radical, in particular a hydrocarbon radical, having 1 to 20 C atoms, in which, in addition, one or more H atoms may be replaced by F.

2. Compound according to claim 1, selected from the compounds of the formulae (3) to (8), formula (4)

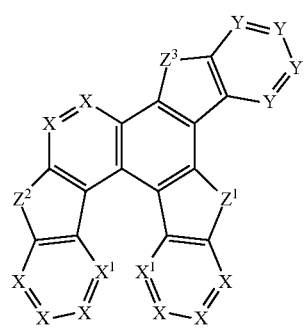

formula (3)

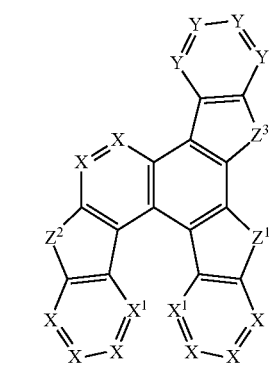

formula (5)

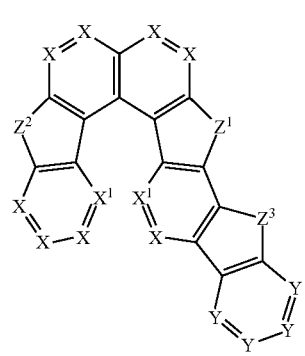

formula (6)

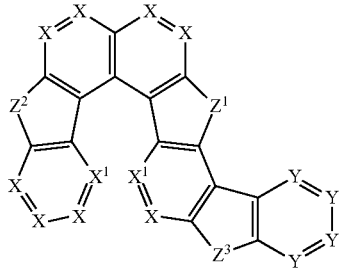

formula (7)

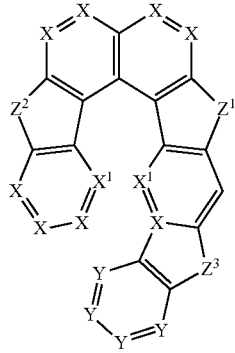

formula (8)

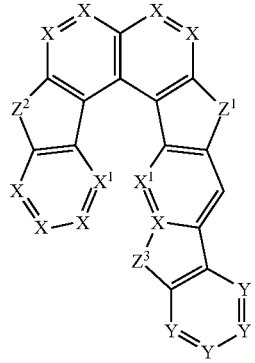

where the symbols used have the meanings given in claim 1.

3. Compound according to claim 1, wherein the compound contains precisely one group of the formula (2).

4. Compound according to claim 1, wherein the group of the formula (2) stands for a group of the formula (2a), formula (2a)

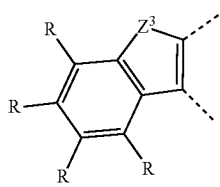

where the symbols used have the meanings given in claim 1 and the radicals R do not form an aromatic or heteroaromatic ring system with one another.

5. Compound according to claim 1, selected from the structures of the formulae (3a) to (8a),
formula (3a)
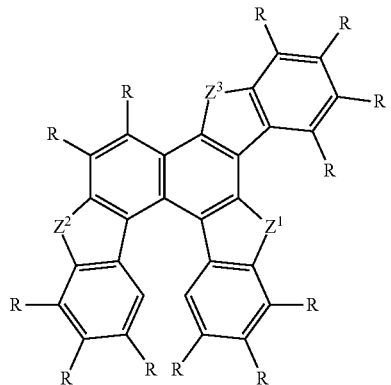
formula (4a)
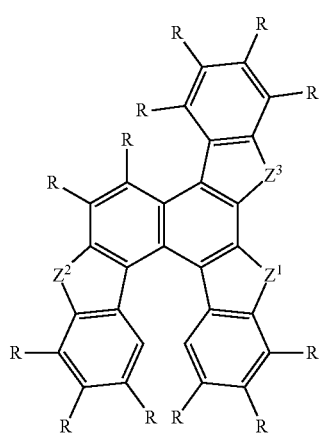
formula (5a)
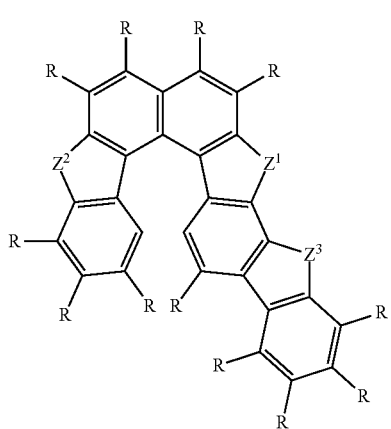
formula (6a)
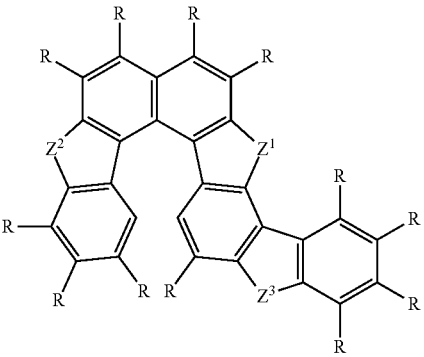
formula (8a)
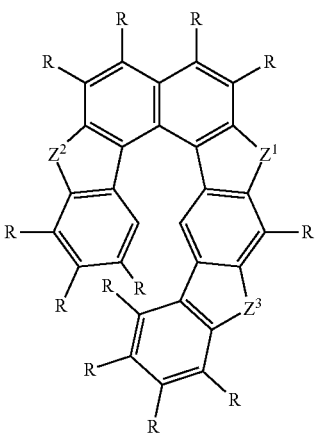
formula (7a)
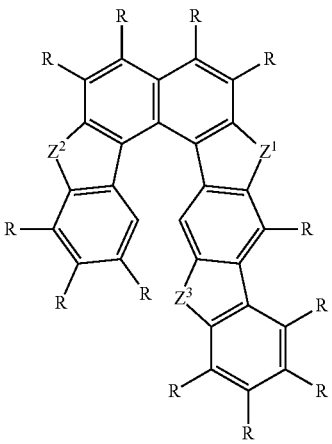
where the symbols used have the meanings given in claim 1.

6. Compound according to claim 1, selected from the structures of the formulae (3b) to (8b), formula (3b)
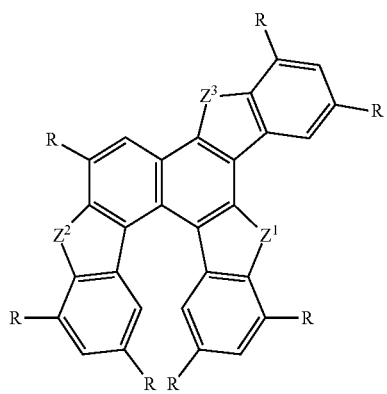

formula (4b)
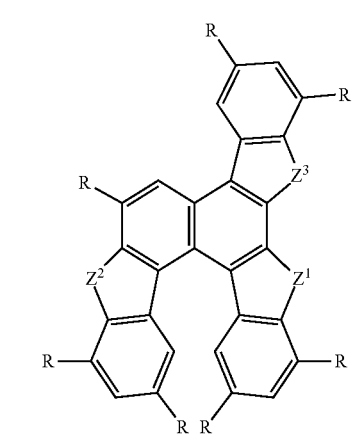

formula (5b)
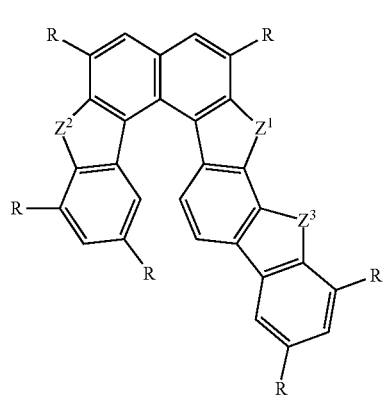

formula (6b)
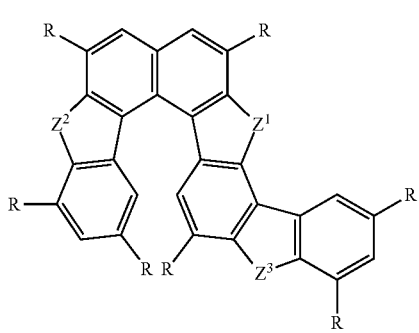

formula (7b)
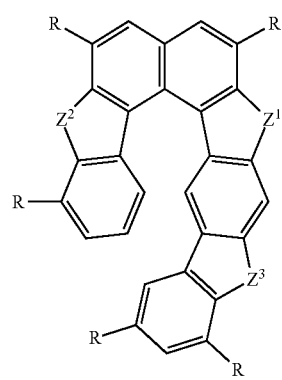

formula (8b)
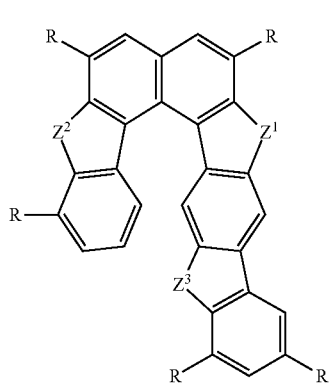

where the symbols used have the meanings given in claim 1.

7. Compound according to claim 1, wherein $Z^1$ and $Z^2$ are selected identically.

8. Compound according to claim 1, wherein at least one of the symbols $Z^1$, $Z^2$ and/or $Z^3$ stands for N—Ar.

9. Compound according to claim 1, selected from the structures of the formulae (3d) to (8d), formula (3d)
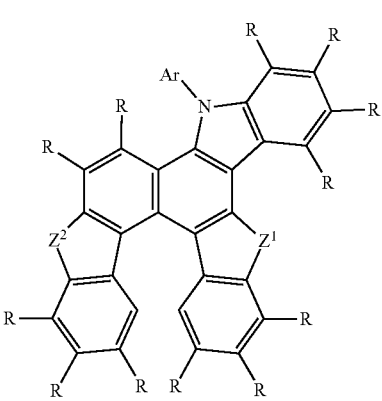

formula (4d)
formula (5d)
formula (6d)
formula (7d)
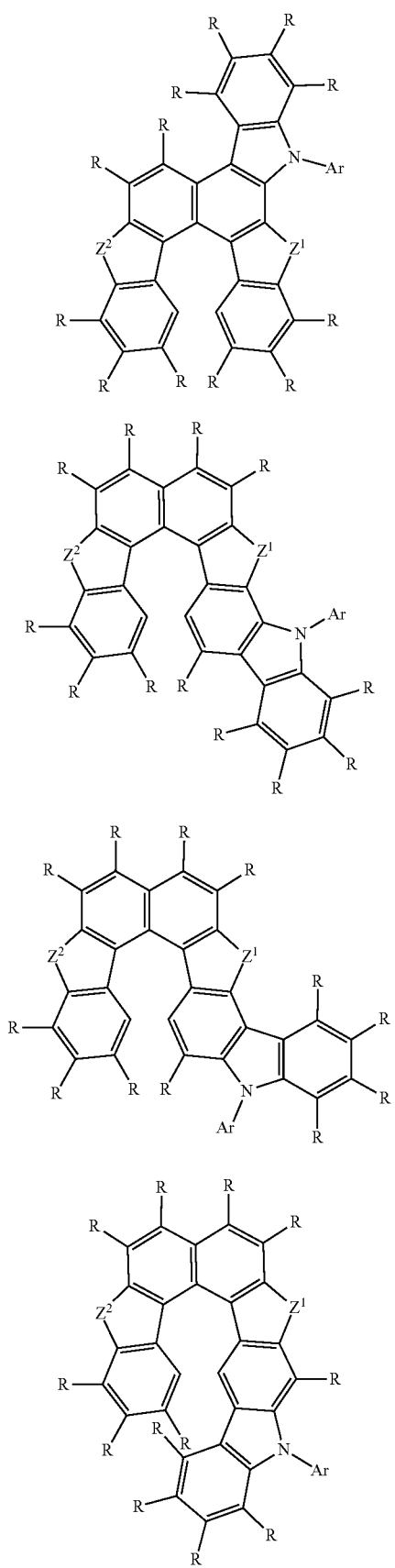
formula (8d)
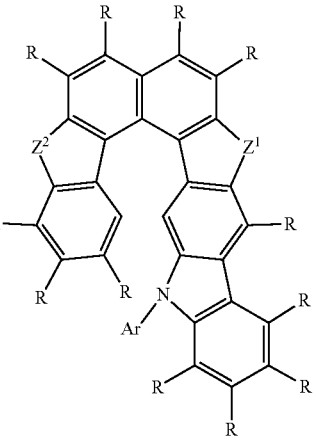
where the symbols used have the meanings given in claim 1.
10. Compound according to claim 1, selected from the structures of the formulae (3e) to (8e),
formula (3e)
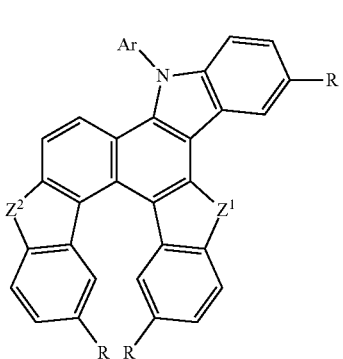
formula (4e)
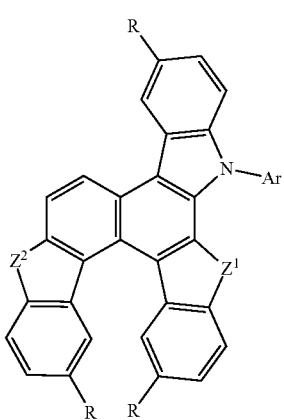

formula (5e)

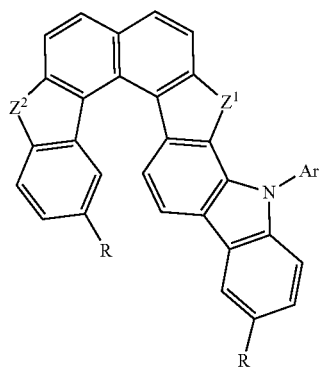

formula (6e)

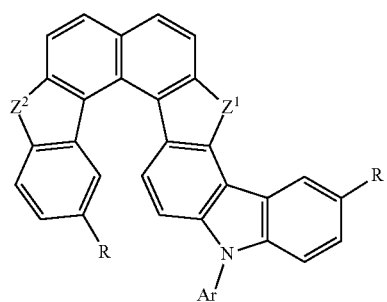

formula (7e)

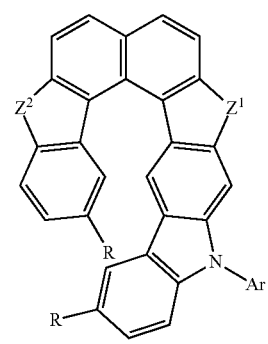

formula (8e)

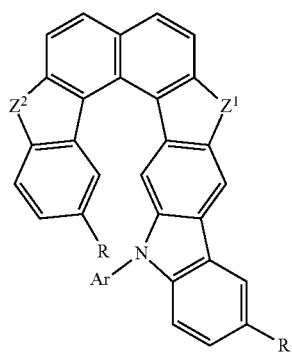

where the symbols used have the meanings given in claim 1.

11. Formulation comprising at least one compound according to claim 1 and at least one further compound and/or a solvent.

12. A method comprising including the compound according to claim 1 in an electronic device.

13. Electronic device containing at least one compound according to claim 1.

14. Electronic device according to claim 13, which is an organic electro-luminescent device, wherein the compound is employed in an emitting layer as matrix material for phosphorescent emitters or for emitters which exhibit thermally activated delayed fluorescence, and/or in an emitting layer as fluorescent emitter and/or in an electron-transport layer and/or in a hole-blocking layer and/or in a hole-transport and/or in an exciton-blocking layer.

15. Electronic device according to claim 14, wherein the compound is employed as matrix material for a phosphorescent emitter in combination with a further matrix material, where the further matrix material is selected from the group consisting of biscarbazoles, bridged carbazoles, triarylamines, dibenzofuran-carbazole derivatives, dibenzofuran-amine derivatives, carbazolamines, indenocarbazoles and indolocarbazoles.

* * * * *